US009969985B2

(12) United States Patent
Kirkwood et al.

(10) Patent No.: US 9,969,985 B2

(45) Date of Patent: May 15, 2018

(54) MODIFIED HUMAN ROTAVIRUSES AND USES THEREFOR

(71) Applicant: Murdoch Childrens Research Institute, Parkville (AU)

(72) Inventors: Carl Kirkwood, Frankston (AU); Ruth Frances Bishop, Brighton (AU); Graeme Laurence Barnes, Kew East (AU)

(73) Assignee: Murdoch Childrens Research Institute, Parkville, Victoria (AU)

( * ) Notice: Subject to any disclaimer, the term of this patent is extended or adjusted under 35 U.S.C. 154(b) by 0 days. days.

(21) Appl. No.: 14/423,660

(22) PCT Filed: Aug. 26, 2013

(86) PCT No.: PCT/PC2013/000945

§ 371 (c)(1),
(2) Date: Feb. 24, 2015

(87) PCT Pub. No.: WO2014/032082

PCT Pub. Date: Mar. 6, 2014

(65) Prior Publication Data

US 2015/0337268 A1 Nov. 26, 2015

(30) Foreign Application Priority Data

Aug. 27, 2012 (AU) ................................ 2012903702

(51) Int. Cl.

| | |
|---|---|
| ***C12N 7/04*** | (2006.01) |
| ***A61K 39/15*** | (2006.01) |
| ***C12N 7/00*** | (2006.01) |
| ***C12Q 1/70*** | (2006.01) |

(Continued)

(52) U.S. Cl.

CPC ............... *C12N 7/00* (2013.01); *A61K 39/15* (2013.01); *C07K 14/005* (2013.01); *C12Q 1/701* (2013.01); *A61K 2039/5252* (2013.01); *A61K 2039/5254* (2013.01); *A61K 2039/57* (2013.01); *C12N 2720/12321* (2013.01); *C12N 2720/12322* (2013.01); *C12N 2720/12334* (2013.01);

(Continued)

(58) Field of Classification Search

None

See application file for complete search history.

(56) References Cited

FOREIGN PATENT DOCUMENTS

| | | | |
|---|---|---|---|
| WO | 01/12797 | A2 | 2/2001 |
| WO | 2007/132480 | A2 | 11/2007 |
| WO | 2010/132561 | A2 | 11/2010 |

OTHER PUBLICATIONS

Esona et al., "Molecular characterization of human rotavirus vaccine strain CDC-9 during sequential passages in Vero cells," Hum Vaccin 6(3): 10409 (2010).*

(Continued)

*Primary Examiner* — Janet L Andres

*Assistant Examiner* — M Franco G Salvoza

(74) *Attorney, Agent, or Firm* — Mintz Levin Cohn Ferris Glovsky and Popeo, P.C.

(57) ABSTRACT

The present disclosure relates generally to the field of viral vaccines. Particularly, the present disclosure provides a modified Vero-adapted human rotavirus strain and a culturing method to produce high titer virus, a rotavirus vaccine, vaccination protocols and diagnostic and prognostic assays.

4 Claims, 58 Drawing Sheets

MA104-adapted RV3 NSP1 (SEQ ID NO:23)

```
   1 ATGGCTACTT TTAAAGATGC TTGTTATTAT TATAAGAGAA TTAACAAGTT GAATCACGCA
  61 GTCTTGAAGT TAGGAGTTAA TGATACATGG AGACCATCAC CTCCAACTAA GTATAAAGGA
 121 TGGTGTCTGG ATTGTTGCCA ACACACTGAT TTAACTTACT GTCGAGGTTG TACCATGTAT
 181 CATGTATGTC AATGGTGTAG TCAATATGGT AGATGCTTTC TTGATAGTGA ACCACATCTA
 241 TTAAGAATGA GAACTTTCAA GAATGAAGTG ACGAAAAATG ATTTAATGAA TTTAATTGAC
 301 ATGTACAATA CATTATTTCC TATAAATCAA AGAATAGTAG ATAAATTCAT TAATAGTACA
 361 AGACAACATA AATGTAGAAA TGAATGTATG ACACAGTGGT ACAATCACTT AGTACTACCA
 421 ATAACATTAC AGTCTCTATC AATCGAATTA GATGGTGATA TTTATTACGT GTTTGGATAT
 481 TATGATAGTA TGAATGACAT TAATCAAACT CCATTCTCAT TTACAAATTT AATAGATATG
 541 TATGATAAGT TGCTACTTGA TAATATAAAT TTTAACAGAA TGTCATTCTT ACCAGTAGCA
 601 TTACAACAAG AATATGCACT CAGATATTTT TCAAAATCAA GGTTTATTAG TGAAAAGAGG
 661 AAATGTATCA GTGATGTACA TTTTTCCGCT AGCGTAATAG AAAATTTACA CAATCCAAGT
 721 TTTAAGATAC AGATTACACG CAATTGTAGT GAATTATCCT CTGATTGGAA CGGAGCATGC
 781 AAACTTGTTA AAGATATGAG CGCTTATTTT GATGTCCTGA AAACATCACA TATTGAATTT
 841 TATAGTATTT CAACTAGATG TAGAGTGTTT ACGCAGTATA AACTTAAAGT AGCATCTAAG
 901 CATATAAAAC CAAATTATGT GACATCAAAT CATAGAACAT CTGCGACTGA GGTACATAAT
 961 TGTAAATGGT GCTCAATTAA TAGTAGTTAT ACTGTATGGA ATGATTTTAG AATTAAGAAG
1021 ATATATGATA ACATTTTCAA TTTTCTACGA GCTTTAGTCA AATCAAATGC TAATGTTGGA
1081 CATTGTTCGT CACAGGAAAA GATGTATGAG CATATTGAAG ATGTTCTGGA TGTATGTGAT
1141 GATGAAAAAT GGAAAATGGC GGTAACAGAA ATATTCAATT GGTTAGAACC AGTAGAACTT
1201 AATACTGTTA AATATGTTCT GTTCAATCAT GAGGTAAATT GGGATGTCAT TAATTTATTA
1261 GTTCAGAGTA TTGGTAAAGT ACCACAAATA CTGACTTTGA ATGATATTGT CATAATTATG
1321 AAATCTATCA TATATGAGTG GTTTGATATC AGATATATGA GGAACACACC AATGACTACA
1381 TTTACAGTTG ACAAATTAAG ACGGTTATGC ACAGGAGTGA AGGCTGTTGA TTATGATTCC
1441 GGCATATCTG ACGTTGAATA A
```

(51) Int. Cl.
*C07K 14/005* (2006.01)
*A61K 39/00* (2006.01)

(52) U.S. Cl.
CPC ............. *C12N 2720/12363* (2013.01); *C12N 2720/12364* (2013.01); *C12Q 2600/156* (2013.01)

(56) References Cited

OTHER PUBLICATIONS

Barnes et al., "Early phase II trial of human rotavirus vaccine candidate RV3," Vaccine 20: 2950-2956 (2002).*

Rippinger et al., "Complete Genome Sequence Analysis of Candidate Human Rotavirus Vaccine Strains RV3 and 116E," Virology 405(1): 201-213 (2010).*

International Search Report corresponding to International Application No. PCT/AU2013/000945 dated Oct. 18, 2013, 7 pages.

International Preliminary Report on Patentability—Chapter II of the PCT corresponding to International Application No. PCT/AU2013/000945 completed Dec. 3, 2014, 18 pages.

Kirkwood, C.D. et al., "Human rotavirus VP4 contains strain-specific, serotype-specific and cross-reactive neutralization sites," *Arch Virol* (1996) 141:587-600.

Kirkwood, C.D. et al., "G3P2 rotaviruses causing diarrhoeal disease in neonates differ in VP4, VP7 and NSP4 sequence from G3P2 strains causing asymptomatic neonatal infection," *Arch Virol* (1996) 141:1661-1676.

Albert, M.J. et al. (1984). "Cultivation of human rotaviruses in cell culture," *J Med Virol* 13(4):377-383.

Arnold, M. et al. (Nov. 2009). "Culturing, Storage, and Quantification of Rotaviruses," *Curr Protoc Microbio* Chapter:Unit-15C.3.

Barnes, G.L. et al. (Aug. 1997). "Phase 1 trial of a candidate rotavirus vaccine (RV3) derived from a human neonate," *J Paediatr Child Health* 33(4):300-304.

Bines, J.E. et al. (Dec. 2015, e-published Aug. 26, 2015). "Safety and immunogenicity of RV3-BB human neonatal rotavirus vaccine administered at birth or in infancy: a randomised, double-blind, placebo-controlled trial," *Lancet Infect Dis* 15(12):1389-1397.

Blackwall, J. et al. (Nov. 1, 1996). "Genetic stability of a porcine rotavirus RNA segment during repeated plaque isolation," *Virology* 225(1):181-190.

Hoshino, Y. et al. (Jun. 2000). "Rotavirus Serotypes: Classification and Importance in Epidemiology, Immunity, and Vaccine Development," *J Health Popul Nutr* 18(1):5-14.

Jenkins, G.M. et al. (Feb. 2002). "Rates of molecular evolution in RNA viruses: a quantitative phylogenetic analysis," *J Mol Evol* 54(2):156-165.

Kirkwood, C.D. et al. (Nov. 1998). "Attachment and growth of human rotaviruses RV-3 and S12/85 in Caco-2 cells depend on VP4," *J Virol* 72(11):9348-9352.

Sato, K. et al. (1981). "Isolation of human rotavirus in cell cultures: brief report," *Arch Virol* 69(2):155-160.

Wang, Y. et al. (Jul. 26, 2010). "Inactivated rotavirus vaccine induces protective immunity in gnotobiotic piglets," *Vaccine* 28(33):5432-5436.

Wu, W. et al. (Mar. 1, 2017). "Development of improved vaccine cell lines against rotavirus," *Sci Data* 4:170021.

* cited by examiner

MA104-adapted RV3 NSP1 (SEQ ID NO:23)

```
   1 ATGGCTACTT TTAAAGATGC TTGTTATTAT TATAAGAGAA TTAACAAGTT GAATCACGCA
  61 GTCTTGAAGT TAGGAGTTAA TGATACATGG AGACCATCAC CTCCAACTAA GTATAAAGGA
 121 TGGTGTCTGG ATTGTTGCCA ACACACTGAT TTAACTTACT GTCGAGGTTG TACCATGTAT
 181 CATGTATGTC AATGGTGTAG TCAATATGGT AGATGCTTTC TTGATAGTGA ACCACATCTA
 241 TTAAGAATGA GAACTTTCAA GAATGAAGTG ACGAAAAATG ATTTAATGAA TTTAATTGAC
 301 ATGTACAATA CATTATTTCC TATAAATCAA AGAATAGTAG ATAAATTCAT TAATAGTACA
 361 AGACAACATA AATGTAGAAA TGAATGTATG ACACAGTGGT ACAATCACTT AGTACTACCA
 421 ATAACATTAC AGTCTCTATC AATCGAATTA GATGGTGATA TTTATTACGT GTTTGGATAT
 481 TATGATAGTA TGAATGACAT TAATCAAACT CCATTCTCAT TTACAAATTT AATAGATATG
 541 TATGATAAGT TGCTACTTGA TAATATAAAT TTTAACAGAA TGTCATTCTT ACCAGTAGCA
 601 TTACAACAAG AATATGCACT CAGATATTTT TCAAAATCAA GGTTTATTAG TGAAAAGAGG
 661 AAATGTATCA GTGATGTACA TTTTTCCGCT AGCGTAATAG AAAATTTACA CAATCCAAGT
 721 TTTAAGATAC AGATTACACG CAATTGTAGT GAATTATCCT CTGATTGGAA CGGAGCATGC
 781 AAACTTGTTA AAGATATGAG CGCTTATTTT GATGTCCTGA AAACATCACA TATTGAATTT
 841 TATAGTATTT CAACTAGATG TAGAGTGTTT ACGCAGTATA AACTTAAAGT AGCATCTAAG
 901 CATATAAAAC CAAATTATGT GACATCAAAT CATAGAACAT CTGCGACTGA GGTACATAAT
 961 TGTAAATGGT GCTCAATTAA TAGTAGTTAT ACTGTATGGA ATGATTTTAG AATTAAGAAG
1021 ATATATGATA ACATTTTCAA TTTTCTACGA GCTTTAGTCA AATCAAATGC TAATGTTGGA
1081 CATTGTTCGT CACAGGAAAA GATGTATGAG CATATTGAAG ATGTTCTGGA TGTATGTGAT
1141 GATGAAAAAT GGAAAATGGC GGTAACAGAA ATATTCAATT GGTTAGAACC AGTAGAACTT
1201 AATACTGTTA AATATGTTCT GTTCAATCAT GAGGTAAATT GGGATGTCAT TAATTTATTA
1261 GTTCAGAGTA TTGGTAAAGT ACCACAAATA CTGACTTTGA ATGATATTGT CATAATTATG
1321 AAATCTATCA TATATGAGTG GTTTGATATC AGATATATGA GGAACACACC AATGACTACA
1381 TTTACAGTTG ACAAATTAAG ACGGTTATGC ACAGGAGTGA AGGCTGTTGA TTATGATTCC
1441 GGCATATCTG ACGTTGAATA A
```

FIG. 1

Amino acid (coding region) ADD31862 (SEQ ID NO:24)

```
  1 MATFKDACYY YKRINKLNHA VLKLGVNDTW RPSPPTKYKG WCLDCCQHTD LTYCRGCTMY
 61 HVCQWCSQYG RCFLDSEPHL LRMRTFKNEV TKNDLMNLID MYNTLFPINQ RIVDKFINST
121 RQHKCRNECM TQWYNHLVLP ITLQSLSIEL DGDIYYVFGY YDSMNDINQT PFSFTNLIDM
181 YDKLLLDNIN FNRMSFLPVA LQQEYALRYF SKSRFISEKR KCISDVHFSA SVIENLHNPS
241 FKIQITRNCS ELSSDWNGAC KLVKDMSAYF DVLKTSHIEF YSISTRCRVF TQYKLKVASK
301 HIKPNYVTSN HRTSATEVHN CKWCSINSSY TVWNDFRIKK IYDNIFNFLR ALVKSNANVG
361 HCSSQEKMYE HIEDVLDVCD DEKWKMAVTE IFNWLEPVEL NTVKYVLFNH EVNWDVINLL
421 VQSIGKVPQI LTLNDIVIIM KSIIYEWFDI RYMRNTPMTT FTVDKLRRLC TGVKAVDYDS
481 GISDVE
```

FIG. 2

Vero-adapted (Vaccine) RV3 NSP1 (SEQ ID NO:25)

```
   1 TGTAAAACGA CGGCCAGTTA TGAAAAGTCT TGTGGAAGCC ATGGCTACTT TTAAAGATGC
  61 TTGTTATTAT TATAAGAGAA TTAACAAGTT GAATCACGCA GTCTTGAAGT TAGGAGTTAA
 121 TGATACATGG AGACCATCAC CTCCAACTAA GTATAAAGGA TGGTGTCTGG ATTGTTGCCA
 181 ACACACTGAT TTAACTTACT GTCGAGGTTG TACCATGTAT CATGTATGTC AATGGTGTAG
 241 TCAATATGGT AGATGCTTTC TTGATAGTGA ACCACATCTA TTAAGAATGA GAACTTTCAA
 301 GAATGAAGTG ACGAAAAATG ATTTAATGAA TTTAATTGAC ATGTACAATA CATTATTTCC
 361 TATAAATCAA AGAATAGTAG ATAAATTCAT TAATAGTACA AGACAACATA AATGTAGAAA
 421 TGAATGTATG ACACAGTGGT ACAATCACTT AGTACTACCA ATAACATTAC AGTCTCTATC
 481 AATCGAATTA GATGGTGATA TTTATTACGT GTTTGGATAT TATGATAGTA TGAATGACAT
 541 TAATCAAACT CCATTCTCAT TTACAAATTT AATAGATATG TATGATAAGT TGCTACTTGA
 601 TAATATAAAT TTTAACAGAA TGTCATTCTT ACCAGTAGCA TTACAACAAG AATATGCACT
 661 CAGATATTTT TCAAAATCAA GGTTTATTAG TGAAAAGAGG AAATGTATCA GTGATGTACA
 721 TTTTTCCGCT AGCGTAATAG AAAATTTACA CAATCCAAGT TTTAAGATAC AGATTACACG
 781 CAATTGTAGT GAATTATCCT CTGATTGGAA CGGAGCATGC AAACTTGTTA AAGATATGAG
 841 CGCTTATTTT GATGTCCTGA AAACATCACA TATTGAATTT TATAGTATTT CAACTAGATG
 901 TAGAGTGTTT ACGCAGTATA AACTTAAAGT AGCATCTAAG CATATAAAAC CAAATTATGT
 961 GACATCAAAT CATAGAACAT CTGCGACTGA GGTACATAAT TGTAAATGGT GCTCAATTAA
1021 TAGTAGTTAT ACTGTATGGA ATGATTTTAG AATTAAGAAG ATATATGATA ACATTTTCAA
1081 TTTTCTACGA GCTTTAGTCA AATCAAATGC TAATGTTGGA CATTGTTCGT CACAGGAAAA
1141 GATGTATGAG CATATTGAAG ATGTTCTGGA TGTATGTGAT GATGAAAAAT GGAAAATGGC
1201 GGTAACAGAA ATATTCAATT GGTTAGAACC AGTAGAACTT AATACTGTTA AATATGTTCT
1261 GTTCAATCAT GAGGTAAATT GGGATGTCAT TAATTTATTA GTTCAGAGTA TTGGTAAAGT
1321 ACCACAAATA CTGACTTTGA ATGATATTGT CATAATTATG AAATCTATCA TATATGAGTG
1381 GTTTGATATC AGATATATGA GGAACACACC AATGACTACA TTTACAGTTG ACAAATTAAG
1441 ACGGTTATGC ACAGGAGTGA AGGCTGTTGA TTATGATTCC GGCATATCTG ACGTTGAATA
1501 CTGAAATAGA GGTCACATTT GCCACCGCAA GACTCCCTGC ACTAGAGTAG CGCCTAGGCA
1561 GCATAAAATG GGTCATAGCT GTTTCCTG
```

FIG. 3

Amino acid (coding region) [SEQ ID NO:26]

```
  1 MATFKDACYY YKRINKLNHA VLKLGVNDTW RPSPPTKYKG WCLDCCQHTD LTYCRGCTMY
 61 HVCQWCSQYG RCFLDSEPHL LRMRTFKNEV TKNDLMNLID MYNTLFPINQ RIVDKFINST
121 RQHKCRNECM TQWYNHLVLP ITLQSLSIEL DGDIYYVFGY YDSMNDINQT PFSFTNLIDM
181 YDKLLLDNIN FNRMSFLPVA LQQEYALRYF SKSRFISEKR KCISDVHFSA SVIENLHNPS
241 FKIQITRNCS ELSSDWNGAC KLVKDMSAYF DVLKTSHIEF YSISTRCRVF TQYKLKVASK
301 HIKPNYVTSN HRTSATEVHN CKWCSINSSY TVWNDFRIKK IYDNIFNFLR ALVKSNANVG
361 HCSSQEKMYE HIEDVLDVCD DEKWKMAVTE IFNWLEPVEL NTVKYVLFNH EVNWDVINLL
421 VQSIGKVPQI LTLNDIVIIM KSIIYEWFDI RYMRNTPMTT FTVDKLRRLC TGVKAVDYDS
481 GISDVE
```

FIG. 4 comparison of nucleotide sequences of RV3 NSP1

```
Vaccine     41 ATGGCTACTTTTAAAGATGCTTGTTATTATTATAAGAGAATTAACAAGTTGAATCACGCA  100
               ||||||||||||||||||||||||||||||||||||||||||||||||||||||||||||
MA104(JP)    1 ATGGCTACTTTTAAAGATGCTTGTTATTATTATAAGAGAATTAACAAGTTGAATCACGCA  60

Vaccine    101 GTCTTGAAGTTAGGAGTTAATGATACATGGAGACCATCACCTCCAACTAAGTATAAAGGA  160
               ||||||||||||||||||||||||||||||||||||||||||||||||||||||||||| 
MA104(JP)   61 GTCTTGAAGTTAGGAGTTAATGATACATGGAGACCATCACCTCCAACTAAGTATAAAGGA  120

Vaccine    161 TGGTGTCTGGATTGTTGCCAACACACTGATTTAACTTACTGTCGAGGTTGTACCATGTAT  220
               ||||||||||||||||||||||||||||||||||||||||||||||||||||||||||||
MA104(JP)  121 TGGTGTCTGGATTGTTGCCAACACACTGATTTAACTTACTGTCGAGGTTGTACCATGTAT  180

Vaccine    221 CATGTATGTCAATGGTGTAGTCAATATGGTAGATGCTTTCTTGATAGTGAACCACATCTA  280
               ||||||||||||||||||||||||||||||||||||||||||||||||||||||||||||
MA104(JP)  181 CATGTATGTCAATGGTGTAGTCAATATGGTAGATGCTTTCTTGATAGTGAACCACATCTA  240

Vaccine    281 TTAAGAATGAGAACTTTCAAGAATGAAGTGACGAAAAATGATTTAATGAATTTAATTGAC  340
               ||||||||||||||||||||||||||||||||||||||||||||||||||||||||||||
MA104(JP)  241 TTAAGAATGAGAACTTTCAAGAATGAAGTGACGAAAAATGATTTAATGAATTTAATTGAC  300

Vaccine    341 ATGTACAATACATTATTTCCTATAAATCAAAGAATAGTAGATAAATTCATTAATAGTACA  400
               ||||||||||||||||||||||||||||||||||||||||||||||||||||||||||||
MA104(JP)  301 ATGTACAATACATTATTTCCTATAAATCAAAGAATAGTAGATAAATTCATTAATAGTACA  360

Vaccine    401 AGACAACATAAATGTAGAAATGAATGTATGACACAGTGGTACAATCACTTAGTACTACCA  460
               ||||||||||||||||||||||||||||||||||||||||||||||||||||||||||||
MA104(JP)  361 AGACAACATAAATGTAGAAATGAATGTATGACACAGTGGTACAATCACTTAGTACTACCA  420

Vaccine    461 ATAACATTACAGTCTCTATCAATCGAATTAGATGGTGATATTTATTACGTGTTTGGATAT  520
               ||||||||||||||||||||||||||||||||||||||||||||||||||||||||||||
MA104(JP)  421 ATAACATTACAGTCTCTATCAATCGAATTAGATGGTGATATTTATTACGTGTTTGGATAT  480

Vaccine    521 TATGATAGTATGAATGACATTAATCAAACTCCATTCTCATTTACAAATTTAATAGATATG  580
               ||||||||||||||||||||||||||||||||||||||||||||||||||||||||||||
MA104(JP)  481 TATGATAGTATGAATGACATTAATCAAACTCCATTCTCATTTACAAATTTAATAGATATG  540

Vaccine    581 TATGATAAGTTGCTACTTGATAATATAAATTTTAACAGAATGTCATTCTTACCAGTAGCA  640
               ||||||||||||||||||||||||||||||||||||||||||||||||||||||||||||
MA104(JP)  541 TATGATAAGTTGCTACTTGATAATATAAATTTTAACAGAATGTCATTCTTACCAGTAGCA  600

Vaccine    641 TTACAACAAGAATATGCACTCAGATATTTTTCAAAATCAAGGTTTATTAGTGAAAAGAGG  700
               ||||||||||||||||||||||||||||||||||||||||||||||||||||||||||||
MA104(JP)  601 TTACAACAAGAATATGCACTCAGATATTTTTCAAAATCAAGGTTTATTAGTGAAAAGAGG  660

Vaccine    701 AAATGTATCAGTGATGTACATTTTTCCGCTAGCGTAATAGAAAATTTACACAATCCAAGT  760
               ||||||||||||||||||||||||||||||||||||||||||||||||||||||||||||
MA104(JP)  661 AAATGTATCAGTGATGTACATTTTTCCGCTAGCGTAATAGAAAATTTACACAATCCAAGT  720

Vaccine    761 TTTAAGATACAGATTACACGCAATTGTAGTGAATTATCCTCTGATTGGAACGGAGCATGC  820
               ||||||||||||||||||||||||||||||||||||||||||||||||||||||||||||
MA104(JP)  721 TTTAAGATACAGATTACACGCAATTGTAGTGAATTATCCTCTGATTGGAACGGAGCATGC  780

Vaccine    821 AAACTTGTTAAAGATATGAGCGCTTATTTTGATGTCCTGAAAACATCACATATTGAATTT  880
               ||||||||||||||||||||||||||||||||||||||||||||||||||||||||||||
MA104(JP)  781 AAACTTGTTAAAGATATGAGCGCTTATTTTGATGTCCTGAAAACATCACATATTGAATTT  840

Vaccine    881 TATAGTATTTCAACTAGATGTAGAGTGTTTACGCAGTATAAACTTAAAGTAGCATCTAAG  940
               ||||||||||||||||||||||||||||||||||||||||||||||||||||||||||||
MA104(JP)  841 TATAGTATTTCAACTAGATGTAGAGTGTTTACGCAGTATAAACTTAAAGTAGCATCTAAG  900

Vaccine    941 CATATAAAACCAAATTATGTGACATCAAATCATAGAACATCTGCGACTGAGGTACATAAT  1000
               ||||||||||||||||||||||||||||||||||||||||||||||||||||||||||||
```

FIG. 5A

```
MA104(JP)  901 CATATAAAACCAAATTATGTGACATCAAATCATAGAACATCTGCGACTGAGGTACATAAT  960

Vaccine   1001 TGTAAATGGTGCTCAATTAATAGTAGTTATACTGTATGGAATGATTTTAGAATTAAGAAG  1060
               ||||||||||||||||||||||||||||||||||||||||||||||||||||||||||||
MA104(JP)  961 TGTAAATGGTGCTCAATTAATAGTAGTTATACTGTATGGAATGATTTTAGAATTAAGAAG  1020

Vaccine   1061 ATATATGATAACATTTTCAATTTTCTACGAGCTTTAGTCAAATCAAATGCTAATGTTGGA  1120
               ||||||||||||||||||||||||||||||||||||||||||||||||||||||||||||
MA104(JP) 1021 ATATATGATAACATTTTCAATTTTCTACGAGCTTTAGTCAAATCAAATGCTAATGTTGGA  1080

Vaccine   1121 CATTGTTCGTCACAGGAAAAGATGTATGAGCATATTGAAGATGTTCTGGATGTATGTGAT  1180
               ||||||||||||||||||||||||||||||||||||||||||||||||||||||||||||
MA104(JP) 1081 CATTGTTCGTCACAGGAAAAGATGTATGAGCATATTGAAGATGTTCTGGATGTATGTGAT  1140

Vaccine   1181 GATGAAAAATGGAAAATGGCGGTAACAGAAATATTCAATTGGTTAGAACCAGTAGAACTT  1240
               ||||||||||||||||||||||||||||||||||||||||||||||||||||||||||||
MA104(JP) 1141 GATGAAAAATGGAAAATGGCGGTAACAGAAATATTCAATTGGTTAGAACCAGTAGAACTT  1200

Vaccine   1241 AATACTGTTAAATATGTTCTGTTCAATCATGAGGTAAATTGGGATGTCATTAATTTATTA  1300
               ||||||||||||||||||||||||||||||||||||||||||||||||||||||||||||
MA104(JP) 1201 AATACTGTTAAATATGTTCTGTTCAATCATGAGGTAAATTGGGATGTCATTAATTTATTA  1260

Vaccine   1301 GTTCAGAGTATTGGTAAAGTACCACAAATACTGACTTTGAATGATATTGTCATAATTATG  1360
               ||||||||||||||||||||||||||||||||||||||||||||||||||||||||||||
MA104(JP) 1261 GTTCAGAGTATTGGTAAAGTACCACAAATACTGACTTTGAATGATATTGTCATAATTATG  1320

Vaccine   1361 AAATCTATCATATATGAGTGGTTTGATATCAGATATATGAGGAACACACCAATGACTACA  1420
               ||||||||||||||||||||||||||||||||||||||||||||||||||||||||||||
MA104(JP) 1321 AAATCTATCATATATGAGTGGTTTGATATCAGATATATGAGGAACACACCAATGACTACA  1380

Vaccine   1421 TTTACAGTTGACAAATTAAGACGGTTATGCACAGGAGTGAAGGCTGTTGATTATGATTCC  1480
               ||||||||||||||||||||||||||||||||||||||||||||||||||||||||||||
MA104(JP) 1381 TTTACAGTTGACAAATTAAGACGGTTATGCACAGGAGTGAAGGCTGTTGATTATGATTCC  1440

Vaccine   1481 GGCATATCTGACGTTGAATA  1500
               ||||||||||||||||||||
MA104(JP) 1441 GGCATATCTGACGTTGAATA  1460
```

FIG. 5B

Comparison of amino acid (coding region) sequences of RV3 NSP1

```
Vaccine   41    MATFKDACYYYKRINKLNHAVLKLGVNDTWRPSPPTKYKGWCLDCCQHTDLTYCRGCTMY  220
                MATFKDACYYYKRINKLNHAVLKLGVNDTWRPSPPTKYKGWCLDCCQHTDLTYCRGCTMY
MA104(JP)1      MATFKDACYYYKRINKLNHAVLKLGVNDTWRPSPPTKYKGWCLDCCQHTDLTYCRGCTMY  60

Vaccine   221   HVCQWCSQYGRCFLDSEPHLLRMRTFKNEVTKNDLMNLIDMYNTLFPINQRIVDKFINST  400
                HVCQWCSQYGRCFLDSEPHLLRMRTFKNEVTKNDLMNLIDMYNTLFPINQRIVDKFINST
MA104(JP)61     HVCQWCSQYGRCFLDSEPHLLRMRTFKNEVTKNDLMNLIDMYNTLFPINQRIVDKFINST  120

Vaccine   401   RQHKCRNECMTQWYNHLVLPITLQSLSIELDGDIYYVFGYYDSMNDINQTPFSFTNLIDM  580
                RQHKCRNECMTQWYNHLVLPITLQSLSIELDGDIYYVFGYYDSMNDINQTPFSFTNLIDM
MA104(JP)121    RQHKCRNECMTQWYNHLVLPITLQSLSIELDGDIYYVFGYYDSMNDINQTPFSFTNLIDM  180

Vaccine   581   YDKLLLDNINFNRMSFLPVALQQEYALRYFSKSRFISEKRKCISDVHFSASVIENLHNPS  760
                YDKLLLDNINFNRMSFLPVALQQEYALRYFSKSRFISEKRKCISDVHFSASVIENLHNPS
MA104(JP)181    YDKLLLDNINFNRMSFLPVALQQEYALRYFSKSRFISEKRKCISDVHFSASVIENLHNPS  240

Vaccine   761   FKIQITRNCSELSSDWNGACKLVKDMSAYFDVLKTSHIEFYSISTRCRVFTQYKLKVASK  940
                FKIQITRNCSELSSDWNGACKLVKDMSAYFDVLKTSHIEFYSISTRCRVFTQYKLKVASK
MA104(JP)241    FKIQITRNCSELSSDWNGACKLVKDMSAYFDVLKTSHIEFYSISTRCRVFTQYKLKVASK  300

Vaccine   941   HIKPNYVTSNHRTSATEVHNCKWCSINSSYTVWNDFRIKKIYDNIFNFLRALVKSNANVG  1120
                HIKPNYVTSNHRTSATEVHNCKWCSINSSYTVWNDFRIKKIYDNIFNFLRALVKSNANVG
MA104(JP)301    HIKPNYVTSNHRTSATEVHNCKWCSINSSYTVWNDFRIKKIYDNIFNFLRALVKSNANVG  360

Vaccine   1121  HCSSQEKMYEHIEDVLDVCDDEKWKMAVTEIFNWLEPVELNTVKYVLFNHEVNWDVINLL  1300
                HCSSQEKMYEHIEDVLDVCDDEKWKMAVTEIFNWLEPVELNTVKYVLFNHEVNWDVINLL
MA104(JP)361    HCSSQEKMYEHIEDVLDVCDDEKWKMAVTEIFNWLEPVELNTVKYVLFNHEVNWDVINLL  420

Vaccine   1301  VQSIGKVPQILTLNDIVIIMKSIIYEWFDIRYMRNTPMTTFTVDKLRRLCTGVKAVDYDS  1480
                VQSIGKVPQILTLNDIVIIMKSIIYEWFDIRYMRNTPMTTFTVDKLRRLCTGVKAVDYDS
MA104(JP)421    VQSIGKVPQILTLNDIVIIMKSIIYEWFDIRYMRNTPMTTFTVDKLRRLCTGVKAVDYDS  480

Vaccine   1481  GISDVE  1498
                GISDVE
MA104(JP)481    GISDVE  486
```

FIG. 6

NSP2 sequence

MA104-adapted RV3 NSP2 (SEQ ID NO:31)

```
  1 ATGGCTGAGC TAGCTTGCTT TTGTTATCCT CATTTAGAGA ACGATAGCTA TAAATTTATT
 61 CCTTTCAATA GTTTGGCAAT AAAATGTATG TTGACAGCTA AAGTGGATAA GAAAGATCAA
121 GATAAATTTT ATAATTCTAT TGTATACGGA ATTGCGCCAC CACCACAATT CAAAAAACGT
181 TATAATACTA GTGATAATTC AAGAGGCATG AATTATGAAA CAACTATGTT TAATAAGGTG
241 GCTATTTTAA TTTGTGAAGC ACTTAATTCA ATTAAAGTCA CTCAATCTGA CATTGCTAAT
301 GTCCTCTCAA GAGTAGTTTC TATTAGACAT TTGGAAAATT TGGTGTTAAG AAAAGAAAAT
361 CATCAAGATG TGCTGTTTCA TTCGAAGGAG CTACTCTTAA AATCCGTTTT GATAGCTATT
421 GGTCAATCAA AAGAAATTGA AACTACTGCT ACTGCCGAGG GAGGAGAAAT AGTGTTCCAA
481 AATGCAGCTT TTACTATGTG GAAATTGACT TATTTAGATC ATAAACTAAC GCCTATTTTG
541 GACCAAAATT TTATCGAATA TAAGATTACA TTAAATGAAG ATAAACCAAT TTCAGATGTA
601 TGTGTTAAAG AACTTGTTGC TGAATTGAGA TGGCAGTATA ACAGATTTGC TGTAATAACG
661 CATGGTAAAG GTCACTATAG AGTCGTTAAA TATTCATCAG TTGCTAATCA CGCAGATAGA
721 GTATTTGTCG CATACAAAAA TAATGCTAAG AGTGGTAATG TTATTAATTT TAATTTACTG
781 GATCAAAGAA TAATTTGGCA AAATTGGTAC GCATTTACAT CTTCAATGAA ACAAGGTAAT
841 ACACTTGAAG TATGTAAGAA ACTGCTCTTT CAAAAGATGA AGCAGGAGAA GAATCCATTT
901 AAAGGACTGT CAACTGATAG AAAAATGGAT GAAGTCTCAC ATGTTGGAGT TTAG
```

FIG. 7

Amino acid (coding region) ADD31865 (SEQ ID NO:32)

```
  1 MAELACFCYP HLENDSYKFI PFNSLAIKCM LTAKVDKKDQ DKFYNSIVYG IAPPPQFKKR
 61 YNTSDNSRGM NYETTMFNKV AILICEALNS IKVTQSDIAN VLSRVVSIRH LENLVLRKEN
121 HQDVLFHSKE LLLKSVLIAI GQSKEIETTA TAEGGEIVFQ NAAFTMWKLT YLDHKLTPIL
181 DQNFIEYKIT LNEDKPISDV CVKELVAELR WQYNRFAVIT HGKGHYRVVK YSSVANHADR
241 VFVAYKNNAK SGNVINFNLL DQRIIWQNWY AFTSSMKQGN TLEVCKKLLF QKMKQEKNPF
301 KGLSTDRKMD EVSHVGV
```

FIG. 8

Vero-adapted (Vaccine) RV3 NSP2 (SEQ ID NO:33)

```
   1 GGCTTTTAAA GCGTCTCAGT CGCCGTTTGA GCCTTGCGGT GTAGCCATGG CTGAGCTAGC
  61 TTGCTTTTGT TATCCTCATT TAGAGAACGA TAGCTATAAA TTTATTCCTT TCAATAGTTT
 121 GGCAATAAAA TGTATGTTGA CAGCTAAAGT GGATAAGAAA GATCAAGATA AATTTTATAA
 181 TTCTATTGTA TACGGAATTG CGCCACCACC ACAATTCAAA AAACGTTATA ATACTAGTGA
 241 TAATTCAAGA GGCATGAATT ATGAAACAAC TATGTTTAAT AAGGTGGCTA TTTTAATTTG
 301 TGAAGCACTT AATTCAATTA AAGTCACTCA ATCTGACATT GCTAATGTCC TCTCAAGAGT
 361 AGTTTCTATT AGACATTTGG AAAATTTGGT GTTAAGAAAA GAAAATCATC AAGATGTGCT
 421 GTTTCATTCG AAAGAGCTAC TCTTAAAATC CGTTTTGATA GCTATTGGTC AATCAAAAGA
 481 AATTGAAACT ACTGCTACTG CCGAGGGAGG AGAAATAGTG TTCCAAAATG CAGCTTTTAC
 541 TATGTGGAAA TTGACTTATT TAGATCATAA ACTAACGCCT ATTTTGGACC AAAATTTTAT
 601 CGAATATAAG ATTACATTAA ATGAAGATAA ACCAATTTCA GATGTATGTG TTAAAGAACT
 661 TGTTGCTGAA TTGAGATGGC AGTATAACAG ATTTGCTGTA ATAACGCATG GTAAAGGTCA
 721 CTATAGAGTC GTTAAATATT CATCAGTTGC TAATCACGCA GATAGAGTAT TTGTCGCATA
 781 CAAAAATAAT GCTAAGAGTG GTAATGTTAT TAATTTTAAT TTACTGGATC AAAGAATAAT
 841 TTGGCAAAAT TGGTACGCAT TTACATCTTC AATGAAACAA GGTAATACAC TTGAAGTATG
 901 TAAGAAACTG CTCTTTCAAA AGATGAAGCA GGAGAAGAAT CCATTTAAAG GACTGTCAAC
 961 TGATAGAAAA ATGGATGAAG TCTCACATGT TGGAGTTTAG TTCGCTTTCG ATTTGAAAAT
1021 GATGATGACG AAGCAGGAAT AGAAAGCGCT TATGTGACC
```

FIG. 9

Amino acid (coding region) [SEQ ID NO:34]

```
   1 MAELACFCYP HLENDSYKFI PFNSLAIKCM LTAKVDKKDQ DKFYNSIVYG IAPPPQFKKR
  61 YNTSDNSRGM NYETTMFNKV AILICEALNS IKVTQSDIAN VLSRVVSIRH LENLVLRKEN
 121 HQDVLFHSKE LLLKSVLIAI GQSKEIETTA TAEGGEIVFQ NAAFTMWKLT YLDHKLTPIL
 181 DQNFIEYKIT LNEDKPISDV CVKELVAELR WQYNRFAVIT HGKGHYRVVK YSSVANHADR
 241 VFVAYKNNAK SGNVINFNLL DQRIIWQNWY AFTSSMKQGN TLEVCKKLLF QKMKQEKNPF
 301 KGLSTDRKMD EVSHVGV
```

FIG. 10

Comparisons of nucleotide sequences of RV3 NSP2

```
Vaccine   47    ATGGCTGAGCTAGCTTGCTTTTGTTATCCTCATTTAGAGAACGATAGCTATAAATTTATT  106
                ||||||||||||||||||||||||||||||||||||||||||||||||||||||||||||
MA104(JP)1      ATGGCTGAGCTAGCTTGCTTTTGTTATCCTCATTTAGAGAACGATAGCTATAAATTTATT  60

Vaccine   107   CCTTTCAATAGTTTGGCAATAAAATGTATGTTGACAGCTAAAGTGGATAAGAAAGATCAA  166
                ||||||||||||||||||||||||||||||||||||||||||||||||||||||||||||
MA104(JP)61     CCTTTCAATAGTTTGGCAATAAAATGTATGTTGACAGCTAAAGTGGATAAGAAAGATCAA  120

Vaccine   167   GATAAATTTTATAATTCTATTGTATACGGAATTGCGCCACCACCACAATTCAAAAAACGT  226
                ||||||||||||||||||||||||||||||||||||||||||||||||||||||||||||
MA104(JP)121    GATAAATTTTATAATTCTATTGTATACGGAATTGCGCCACCACCACAATTCAAAAAACGT  180

Vaccine   227   TATAATACTAGTGATAATTCAAGAGGCATGAATTATGAAACAACTATGTTTAATAAGGTG  286
                ||||||||||||||||||||||||||||||||||||||||||||||||||||||||||||
MA104(JP)181    TATAATACTAGTGATAATTCAAGAGGCATGAATTATGAAACAACTATGTTTAATAAGGTG  240

Vaccine   287   GCTATTTTAATTTGTGAAGCACTTAATTCAATTAAAGTCACTCAATCTGACATTGCTAAT  346
                ||||||||||||||||||||||||||||||||||||||||||||||||||||||||||||
MA104(JP)241    GCTATTTTAATTTGTGAAGCACTTAATTCAATTAAAGTCACTCAATCTGACATTGCTAAT  300

Vaccine   347   GTCCTCTCAAGAGTAGTTTCTATTAGACATTTGGAAAATTTGGTGTTAAGAAAAGAAAAT  406
                ||||||||||||||||||||||||||||||||||||||||||||||||||||||||||||
MA104(JP)301    GTCCTCTCAAGAGTAGTTTCTATTAGACATTTGGAAAATTTGGTGTTAAGAAAAGAAAAT  360

Vaccine   407   CATCAAGATGTGCTGTTTCATTCGAAAGAGCTACTCTTAAAATCCGTTTTGATAGCTATT  466
                |||||||||||||||||||||||||| |||||||||||||||||||||||||||||||||
MA104(JP)361    CATCAAGATGTGCTGTTTCATTCGAAGGAGCTACTCTTAAAATCCGTTTTGATAGCTATT  420

Vaccine   467   GGTCAATCAAAAGAAATTGAAACTACTGCTACTGCCGAGGGAGGAGAAATAGTGTTCCAA  526
                ||||||||||||||||||||||||||||||||||||||||||||||||||||||||||||
MA104(JP)421    GGTCAATCAAAAGAAATTGAAACTACTGCTACTGCCGAGGGAGGAGAAATAGTGTTCCAA  480

Vaccine   527   AATGCAGCTTTTACTATGTGGAAATTGACTTATTTAGATCATAAACTAACGCCTATTTTG  586
                ||||||||||||||||||||||||||||||||||||||||||||||||||||||||||||
MA104(JP)481    AATGCAGCTTTTACTATGTGGAAATTGACTTATTTAGATCATAAACTAACGCCTATTTTG  540

Vaccine   587   GACCAAAAATTTTATCGAATATAAGATTACATTAAATGAAGATAAACCAATTTCAGATGTA  646
                ||||||||||||||||||||||||||||||||||||||||||||||||||||||||||||
MA104(JP)541    GACCAAAAATTTTATCGAATATAAGATTACATTAAATGAAGATAAACCAATTTCAGATGTA  600

Vaccine   647   TGTGTTAAAGAACTTGTTGCTGAATTGAGATGGCAGTATAACAGATTTGCTGTAATAACG  706
                ||||||||||||||||||||||||||||||||||||||||||||||||||||||||||||
MA104(JP)601    TGTGTTAAAGAACTTGTTGCTGAATTGAGATGGCAGTATAACAGATTTGCTGTAATAACG  660

Vaccine   707   CATGGTAAAGGTCACTATAGAGTCGTTAAATATTCATCAGTTGCTAATCACGCAGATAGA  766
                ||||||||||||||||||||||||||||||||||||||||||||||||||||||||||||
MA104(JP)661    CATGGTAAAGGTCACTATAGAGTCGTTAAATATTCATCAGTTGCTAATCACGCAGATAGA  720

Vaccine   767   GTATTTGTCGCATACAAAAATAATGCTAAGAGTGGTAATGTTATTAATTTTAATTTACTG  826
                ||||||||||||||||||||||||||||||||||||||||||||||||||||||||||||
MA104(JP)721    GTATTTGTCGCATACAAAAATAATGCTAAGAGTGGTAATGTTATTAATTTTAATTTACTG  780

Vaccine   827   GATCAAAGAATAATTTGGCAAAATTGGTACGCATTTACATCTTCAATGAAACAAGGTAAT  886
                ||||||||||||||||||||||||||||||||||||||||||||||||||||||||||||
MA104(JP)781    GATCAAAGAATAATTTGGCAAAATTGGTACGCATTTACATCTTCAATGAAACAAGGTAAT  840

Vaccine   887   ACACTTGAAGTATGTAAGAAACTGCTCTTTCAAAAGATGAAGCAGGAGAAGAATCCATTT  946
                ||||||||||||||||||||||||||||||||||||||||||||||||||||||||||||
MA104(JP)841    ACACTTGAAGTATGTAAGAAACTGCTCTTTCAAAAGATGAAGCAGGAGAAGAATCCATTT  900

Vaccine   947   AAAGGACTGTCAACTGATAGAAAAATGGATGAAGTCTCACATGTTGGAGTTTAG  1000
                ||||||||||||||||||||||||||||||||||||||||||||||||||||||
MA104(JP)901    AAAGGACTGTCAACTGATAGAAAAATGGATGAAGTCTCACATGTTGGAGTTTAG  954
```

FIG. 11

Comparison of amino acid (coding region) sequences of RV3 NSP2

```
Vaccine   47    MAELACFCYPHLENDSYKFIPFNSLAIKCMLTAKVDKKDQDKFYNSIVYGIAPPPQFKKR  226
                MAELACFCYPHLENDSYKFIPFNSLAIKCMLTAKVDKKDQDKFYNSIVYGIAPPPQFKKR
MA104(JP)1      MAELACFCYPHLENDSYKFIPFNSLAIKCMLTAKVDKKDQDKFYNSIVYGIAPPPQFKKR  60

Vaccine   227   YNTSDNSRGMNYETTMFNKVAILICEALNSIKVTQSDIANVLSRVVSIRHLENLVLRKEN  406
                YNTSDNSRGMNYETTMFNKVAILICEALNSIKVTQSDIANVLSRVVSIRHLENLVLRKEN
MA104(JP)61     YNTSDNSRGMNYETTMFNKVAILICEALNSIKVTQSDIANVLSRVVSIRHLENLVLRKEN  120

Vaccine   407   HQDVLFHSKELLLKSVLIAIGQSKeiettataeggeiVFQNAAFTMWKLTYLDHKLTPIL  586
                HQDVLFHSKELLLKSVLIAIGQSKEIETTATAEGGEIVFQNAAFTMWKLTYLDHKLTPIL
MA104(JP)121    HQDVLFHSKELLLKSVLIAIGQSKEIETTATAEGGEIVFQNAAFTMWKLTYLDHKLTPIL  180

Vaccine   587   DQNFIEYKITLNEDKPISDVCVKELVAELRWQYNRFAVITHGKGHYRVVKYSSVANHADR  766
                DQNFIEYKITLNEDKPISDVCVKELVAELRWQYNRFAVITHGKGHYRVVKYSSVANHADR
MA104(JP)181    DQNFIEYKITLNEDKPISDVCVKELVAELRWQYNRFAVITHGKGHYRVVKYSSVANHADR  240

Vaccine   767   VFVAYKNNAKSGNVINFNLLDQRIIWQNWYAFTSSMKQGNTLEVCKKLLFQKMKQEKNPF  946
                VFVAYKNNAKSGNVINFNLLDQRIIWQNWYAFTSSMKQGNTLEVCKKLLFQKMKQEKNPF
MA104(JP)241    VFVAYKNNAKSGNVINFNLLDQRIIWQNWYAFTSSMKQGNTLEVCKKLLFQKMKQEKNPF  300

Vaccine   947   KGLSTDRKMDEVSHVGV  997
                KGLSTDRKMDEVSHVGV
MA104(JP)301    KGLSTDRKMDEVSHVGV  317
```

FIG. 12

MA104-adapted RV3 NSP3 (SEQ ID NO:43)

```
  1 TTTTAATGCT TTTCAGTGGT TGCTGCTCAA GATGGAGTCT ACTCAGCAGA TGGTAAGCTC
 61 TATTATTAAC ACTTCTTTTG AAGCTGCAGT TGTTGCTGCC ACTTCAACAT TAGAATTAAT
121 GGGTATTCAA TATGATTACA ATGAAGTATT TACTAGAGTT AAAAGTAAAT TTGATTATGT
181 GATGGATGAC TCTGGTGTTA AAAACAATCT TTTGGGTAAA GCTATAACTA TTGATCAGGC
241 GTTAAATGGA AAGTTTGGCT CAGCTATTAG AAATAGAAAT TGGATGACTG ATTCTAAAAC
301 GGTTGCTAAA TTAGATGAAG ACGTGAATAA ACTTAGAATG ACATTATCTT CTAAAGGAAT
361 CGACCAAAAG ATGAGAGTAC TTAATGCTTG TTTTAGTGTA AAAAGAATAC CAGGAAAATC
421 ATCATCAATA ATTAAATGCT CTAGACTTAT GAAGGATAAA ATAGAACGTG GAGAAGTTGA
481 GGTTGATGAT TCATATGTTG ATGAGAAAAT GGAAATTGAT ACTATTGATT GGAAATCTCG
541 TTATGATCAG TTAGAAAAAA GATTTGAGTC ACTAAAACAA AGAGTTAATG AGAAATACAA
601 TACTTGGGTA CAAAAAGCGA AGAAAGTAAA TGAAAATATG TACTCTCTTC AGAATGTCAT
661 TTCACAACAG CAAAACCAAA TAGCAGATCT TCAACAATAT TGTAATAAAT TGGAAGCTGA
721 TTTGCAAGGC AAATTTAGTT CATTAGTGTC ATCAGTTGAG TGGTATCTAA GGTCTATGGA
781 ATTGCCAAAT GATGTAAAGA ATGATATTGA ACAGCAGTTA AATTCAATTG ATTTAATTAA
841 TCCCATTAAT GCTATAGATG ATATCGAATC ATTGATTAGA AATTTAATTC AAGATTATGA
901 CAGAACATTT TTAATGTTAA AAGGACTGTT GAAGCAATGC AACTATGAAT ATACATATGA
961 GTAG
```

FIG. 13

Amino acid (coding region) ADD31864 (SEQ ID NO:44)

```
  1 MESTQQMVSS IINTSFEAAV VAATSTLELM GIQYDYNEVF TRVKSKFDYV MDDSGVKNNL
 61 LGKAITIDQA LNGKFGSAIR NRNWMTDSKT VAKLDEDVNK LRMTLSSKGI DQKMRVLNAC
121 FSVKRIPGKS SSIIKCSRLM KDKIERGEVE VDDSYVDEKM EIDTIDWKSR YDQLEKRFES
181 LKQRVNEKYN TWVQKAKKVN ENMYSLQNVI SQQQNQIADL QQYCNKLEAD LQGKFSSLVS
241 SVEWYLRSME LPNDVKNDIE QQLNSIDLIN PINAIDDIES LIRNLIQDYD RTFLMLKGLL
301 KQCNYEYTYE
```

FIG. 14

Vero-adapted (Vaccine) RV3 NSP3 (SEQ ID NO:45)

```
   1 GGCTTTTAAT GCTTTTCAGT GGTTGCTGCT CAAGATGGAG TCTACTCAGC AGATGGTAAG
  61 CTCTATTATT AACACTTCTT TTGAAGCTGC AGTTGTTGCT GCCACTTCAA CATTAGAATT
 121 AATGGGTATT CAATATGATT ACAATGAAGT ATTTACTAGA GTTAAAAGTA AATTTGATTA
 181 TGTGATGGAT GACTCTGGTG TTAAAAACAA TCTTTTGGGT AAAGCTATAA CTATTGATCA
 241 GGCGTTAAAT GGAAAGTTTG GCTCAGCTAT TAGAAATAGA AATTGGATGA CTGATTCTAA
 301 AACGGTTGCT AAATTAGATG AAGACGTGAA TAAACTTAGA ATGACATTAT CTTCTAAAGG
 361 AATCGACCAA AAGATGAGAG TACTTAATGC TTGTTTTAGT GTAAAAAGAA TACCAGGAAA
 421 ATCATCATCA ATAATTAAAT GCTCTAGACT TATGAAGGAT AAAATAGAAC GTGGAGAAGT
 481 TGAGGTTGAT GATTCATATG TTGATGAGAA AATGGAAATT GATACTATTG ATTGGAAATC
 541 TCGTTATGAT CAGTTAGAAA AAAGATTTGA GTCACTAAAA CAAAGAGTTA ATGAGAAATA
 601 CAATACTTGG GTACAAAAAG CGAAGAAAGT AAATGAAAAT ATGTACTCTC TTCAGAATGT
 661 CATTTCACAA CAGCAAAACC AAATAGCAGA TCTTCAACAA TATTGTAATA AATTGGAAGC
 721 TGATTTGCAA GGCAAATTTA GTTCATTAGT GTCATCAGTT GAGTGGTATC TAAGGTCTAT
 781 GGAATTGCCA AATGATGTAA AGAATGATAT TGAACAGCAG TTAAATTCAA TTGATTTAAT
 841 TAATCCCATT AATGCTATAG ATGATATCGA ATCATTGATT AGAAATTTAA TTCAAGATTA
 901 TGACAGAACA TTTTTAATGT TAAAAGGACT GTTGAAGCAA TGCAACTATG AATATACATA
 961 TGAGTAGTCA CATAATTAAA AGTATTAACC ATCTACACAT GACCCTCTAT GAGCACAATA
1021 GTTAAAAGCT AACACTGTCA AAAACCTAAA TGGCTATAGG GGCGTTATGT
```

FIG. 15

Amino acid (coding region) [SEQ ID NO:46]

```
  1 MESTQQMVSS IINTSFEAAV VAATSTLELM GIQYDYNEVF TRVKSKFDYV MDDSGVKNNL
 61 LGKAITIDQA LNGKFGSAIR NRNWMTDSKT VAKLDEDVNK LRMTLSSKGI DQKMRVLNAC
121 FSVKRIPGKS SSIIKCSRLM KDKIERGEVE VDDSYVDEKM EIDTIDWKSR YDQLEKRFES
181 LKQRVNEKYN TWVQKAKKVN ENMYSLQNVI SQQQNQIADL QQYCNKLEAD LQGKFSSLVS
241 SVEWYLRSME LPNDVKNDIE QQLNSIDLIN PINAIDDIES LIRNLIQDYD RTFLMLKGLL
301 KQCNYEYTYE
```

FIG. 16

Comparison of nucleotide sequences of RV3 NSP3

```
Vaccine   4    TTTTAATGCTTTTCAGTGGTTGCTGCTCAAGATGGAGTCTACTCAGCAGATGGTAAGCTC  63
               ||||||||||||||||||||||||||||||||||||||||||||||||||||||||||||
MA104(JP)1     TTTTAATGCTTTTCAGTGGTTGCTGCTCAAGATGGAGTCTACTCAGCAGATGGTAAGCTC  60

Vaccine   64   TATTATTAACACTTCTTTTGAAGCTGCAGTTGTTGCTGCCACTTCAACATTAGAATTAAT  123
               ||||||||||||||||||||||||||||||||||||||||||||||||||||||||||||
MA104(JP)61    TATTATTAACACTTCTTTTGAAGCTGCAGTTGTTGCTGCCACTTCAACATTAGAATTAAT  120

Vaccine   124  GGGTATTCAATATGATTACAATGAAGTATTTACTAGAGTTAAAAGTAAATTTGATTATGT  183
               ||||||||||||||||||||||||||||||||||||||||||||||||||||||||||||
MA104(JP)121   GGGTATTCAATATGATTACAATGAAGTATTTACTAGAGTTAAAAGTAAATTTGATTATGT  180

Vaccine   184  GATGGATGACTCTGGTGTTAAAAACAATCTTTTGGGTAAAGCTATAACTATTGATCAGGC  243
               ||||||||||||||||||||||||||||||||||||||||||||||||||||||||||||
MA104(JP)181   GATGGATGACTCTGGTGTTAAAAACAATCTTTTGGGTAAAGCTATAACTATTGATCAGGC  240

Vaccine   244  GTTAAATGGAAAGTTTGGCTCAGCTATTAGAAATAGAAATTGGATGACTGATTCTAAAAC  303
               ||||||||||||||||||||||||||||||||||||||||||||||||||||||||||||
MA104(JP)241   GTTAAATGGAAAGTTTGGCTCAGCTATTAGAAATAGAAATTGGATGACTGATTCTAAAAC  300

Vaccine   304  GGTTGCTAAATTAGATGAAGACGTGAATAAACTTAGAATGACATTATCTTCTAAAGGAAT  363
               ||||||||||||||||||||||||||||||||||||||||||||||||||||||||||||
MA104(JP)301   GGTTGCTAAATTAGATGAAGACGTGAATAAACTTAGAATGACATTATCTTCTAAAGGAAT  360

Vaccine   364  CGACCAAAAGATGAGAGTACTTAATGCTTGTTTTAGTGTAAAAAGAATACCAGGAAAATC  423
               ||||||||||||||||||||||||||||||||||||||||||||||||||||||||||||
MA104(JP)361   CGACCAAAAGATGAGAGTACTTAATGCTTGTTTTAGTGTAAAAAGAATACCAGGAAAATC  420

Vaccine   424  ATCATCAATAATTAAATGCTCTAGACTTATGAAGGATAAAATAGAACGTGGAGAAGTTGA  483
               ||||||||||||||||||||||||||||||||||||||||||||||||||||||||||||
MA104(JP)421   ATCATCAATAATTAAATGCTCTAGACTTATGAAGGATAAAATAGAACGTGGAGAAGTTGA  480

Vaccine   484  GGTTGATGATTCATATGTTGATGAGAAAATGGAAATTGATACTATTGATTGGAAATCTCG  543
               ||||||||||||||||||||||||||||||||||||||||||||||||||||||||||||
MA104(JP)481   GGTTGATGATTCATATGTTGATGAGAAAATGGAAATTGATACTATTGATTGGAAATCTCG  540

Vaccine   544  TTATGATCAGTTAGAAAAAAGATTTGAGTCACTAAAACAAAGAGTTAATGAGAAATACAA  603
               ||||||||||||||||||||||||||||||||||||||||||||||||||||||||||||
MA104(JP)541   TTATGATCAGTTAGAAAAAAGATTTGAGTCACTAAAACAAAGAGTTAATGAGAAATACAA  600

Vaccine   604  TACTTGGGTACAAAAAGCGAAGAAAGTAAATGAAAATATGTACTCTCTTCAGAATGTCAT  663
               ||||||||||||||||||||||||||||||||||||||||||||||||||||||||||||
MA104(JP)601   TACTTGGGTACAAAAAGCGAAGAAAGTAAATGAAAATATGTACTCTCTTCAGAATGTCAT  660

Vaccine   664  TTCACAACAGCAAAACCAAATAGCAGATCTTCAACAATATTGTAATAAATTGGAAGCTGA  723
               ||||||||||||||||||||||||||||||||||||||||||||||||||||||||||||
MA104(JP)661   TTCACAACAGCAAAACCAAATAGCAGATCTTCAACAATATTGTAATAAATTGGAAGCTGA  720


Vaccine   724  TTTGCAAGGCAAATTTAGTTCATTAGTGTCATCAGTTGAGTGGTATCTAAGGTCTATGGA  783
               ||||||||||||||||||||||||||||||||||||||||||||||||||||||||||||
MA104(JP)721   TTTGCAAGGCAAATTTAGTTCATTAGTGTCATCAGTTGAGTGGTATCTAAGGTCTATGGA  780

Vaccine   784  ATTGCCAAATGATGTAAAGAATGATATTGAACAGCAGTTAAATTCAATTGATTTAATTAA  843
               ||||||||||||||||||||||||||||||||||||||||||||||||||||||||||||
MA104(JP)781   ATTGCCAAATGATGTAAAGAATGATATTGAACAGCAGTTAAATTCAATTGATTTAATTAA  840

Vaccine   844  TCCCATTAATGCTATAGATGATATCGAATCATTGATTAGAAATTTAATTCAAGATTATGA  903
               ||||||||||||||||||||||||||||||||||||||||||||||||||||||||||||
MA104(JP)841   TCCCATTAATGCTATAGATGATATCGAATCATTGATTAGAAATTTAATTCAAGATTATGA  900

Vaccine   904  CAGAACATTTTTAATGTTAAAAGGACTGTTGAAGCAATGCAACTATGAATATACATATGA  963
               ||||||||||||||||||||||||||||||||||||||||||||||||||||||||||||
MA104(JP)901   CAGAACATTTTTAATGTTAAAAGGACTGTTGAAGCAATGCAACTATGAATATACATATGA  960

Vaccine   964  GTAG  967
               ||||
MA104(JP)961   GTAG  964
```

FIG. 17

Comparison of amino acid (coding region) sequences of RV3 NSP3

```
Vaccine   35     MESTQQMVSSIINTSFEAAVVAATSTLELMGIQYDYNEVFTRVKSKFDYVMDDSGVKNNL  214
                 MESTQQMVSSIINTSFEAAVVAATSTLELMGIQYDYNEVFTRVKSKFDYVMDDSGVKNNL
MA104(JP)1       MESTQQMVSSIINTSFEAAVVAATSTLELMGIQYDYNEVFTRVKSKFDYVMDDSGVKNNL  60

Vaccine   215    LGKAITIDQALNGKFGSAIRNRNWMTDSKTVAKLDEDVNKLRMTLSSKGIDQKMRVLNAC  394
                 LGKAITIDQALNGKFGSAIRNRNWMTDSKTVAKLDEDVNKLRMTLSSKGIDQKMRVLNAC
MA104(JP)61      LGKAITIDQALNGKFGSAIRNRNWMTDSKTVAKLDEDVNKLRMTLSSKGIDQKMRVLNAC  120

Vaccine   395    FSVKRIPGKSSSIIKCSRLMKDKIERGEVEVDDSYVDEKMEIDTIDWKSRYDQLEKRFES  574
                 FSVKRIPGKSSSIIKCSRLMKDKIERGEVEVDDSYVDEKMEIDTIDWKSRYDQLEKRFES
MA104(JP)121     FSVKRIPGKSSSIIKCSRLMKDKIERGEVEVDDSYVDEKMEIDTIDWKSRYDQLEKRFES  180

Vaccine   575    LKQRVNEKYNTWVQKAKKVNENMYSLQNVISQQQNQIADLQQYCNKLEADLQGKFSSLVS  754
                 LKQRVNEKYNTWVQKAKKVNENMYSLQNVISQQQNQIADLQQYCNKLEADLQGKFSSLVS
MA104(JP)181     LKQRVNEKYNTWVQKAKKVNENMYSLQNVISQQQNQIADLQQYCNKLEADLQGKFSSLVS  240

Vaccine   755    SVEWYLRSMELPNDVKNDIEQQLNSIDLINPINAIDDIESLIRNLIQDYDRTFLMLKGLL  934
                 SVEWYLRSMELPNDVKNDIEQQLNSIDLINPINAIDDIESLIRNLIQDYDRTFLMLKGLL
MA104(JP)241     SVEWYLRSMELPNDVKNDIEQQLNSIDLINPINAIDDIESLIRNLIQDYDRTFLMLKGLL  300

Vaccine   935    KQCNYEYTYE  964
                 KQCNYEYTYE
MA104(JP)301     KQCNYEYTYE  310
```

FIG. 18

NSP4 sequence (Seq ID NO:35)

```
  1 ATGGATAAGC TTGCCGACCT CAACTACACA TTGAGTGTAA TCACTTTAAT GAATGACACA
 61 TTGCATTCTA TAATTCAAGA TCCTGGAATG GCGTATTTTA CATATATTGC ATCTGTTCTA
121 ACAGTTTTGT TCACATTACA CAAAGCTTCA ATTCCAGCCA TGAAAATAGC ATTGAAAACA
181 TCAAAATGTT CATATAAAGT AATTAAATAT TGTATAGTCA CGATAATTAA TACTCTTTTA
241 AAATTGGCTG GATGTAAAGA GCAGGTTACT ACAAAAGACG AAATTGAGCA ACAGATGGAC
301 AGAATTGTTA AAGAGATGAG ACGTCAGCTG GAGATGATTG ATAAACTAAC TACTCGTGAA
361 ATTGAACAGG TTGAATTGCT TAAATGTATA TATGACAACC TGATAACTAG ACCAGTTAAC
421 GTTATAGATA TGTCGAAGGA ATTCAATCAA AAAAACATCA AAACGCTAGA TGAATGGGAG
481 AGTGTAAAAA ATCCATATGA ACCGTCAGAA GTGACTGCAT CCATGTAA
```

FIG. 19

Amino acid (coding region) ADD31867 (SEQ ID NO:36)

```
  1 MDKLADLNYT LSVITLMNDT LHSIIQDPGM AYFTYIASVL TVLFTLHKAS IPAMKIALKT
 61 SKCSYKVIKY CIVTIINTLL KLAGCKEQVT TKDEIEQQMD RIVKEMRRQL EMIDKLTTRE
121 IEQVELLKCI YDNLITRPVN VIDMSKEFNQ KNIKTLDEWE SVKNPYEPSE VTASM
```

FIG. 20

Vero-adapted (Vaccine) RV3 NSP4 (SEQ ID NO:37)

```
  1 GGCTTTTAAA AGTTCTGTCC GAGAGAGCGC GTGCGGAAAG ATGGATAAGC TTGCCGACCT
 61 CAACTACACA TTGAGTGTAA TCACTTTAAT GAATGACACA TTGCATTCTA TAATTCAAGA
121 TCCTGGAATG GCGTATTTTA CATATATTGC ATCTGTTCTA ACAGTTTTGT TCACATTACA
181 CAAAGCTTCA ATTCCAACCA TGAAAATAGC ATTGAAAACA TCAAAATGTT CATATAAAGT
241 AATTAAATAT TGTATAGTCA CGATAACTAA TACTCTTTTA AAATTGGCTG GATATAAAGA
301 GCAGGTTACT ACAAAAGACG AAATTGAGCA ACAGATGGAC AGAATTGTTA AAGAGATGAG
361 ACGTCAGCTG GAGATGATTG ATAAACTAAC TACTCGTGAA ATTGAACAGG TTGAATTGCT
421 TAAATGTATA TATGACAACC TGATAACTAG ACCAGTTAAC GTTATAGATA TGTCGAAGGA
481 ATTCAATCAA AAAAACATCA AAACGCTAGA TGAATGGGAG AGTGGAAAAA ATCTATATGA
541 ACCGTCAGAA GTGACTGCAT CCATGTAAGA GGTTGAGTTG CCGTCGTCTG TCTTCGGAAG
601 CGGCGGAACT CTTCACCGCA AGCCCCATTA GACCTGATGA TTGACTGAGA AGCCACAGTC
661 AATCATATCG CGTGTGGCTC AGCCTTAATC CCGTTTAACC AATCCAGCGA GTGTTGGACG
721 TTAATGGAAG GAATGGTCTT AGTGTGACC
```

FIG. 21

Amino acid (coding region) [SEQ ID NO:38]

```
  1 MDKLADLNYT LSVITLMNDT LHSIIQDPGM AYFTYIASVL TVLFTLHKAS IPTMKIALKT
 61 SKCSYKVIKY CIVTITNTLL KLAGYKEQVT TKDEIEQQMD RIVKEMRRQL EMIDKLTTRE
121 IEQVELLKCI YDNLITRPVN VIDMSKEFNQ KNIKTLDEWE SGKNLYEPSE VTASM
```

FIG. 22

Comparison of nucleotide sequences of RV3 NSP4

Vaccine 197 A to MA104(JP) 157 G
Vaccine 267 C to MA104(JP) 227 T
Vaccine 294 A to MA104(JP) 254 G
Vaccine 525 G to MA104(JP) 485 T
Vaccine 534 T to MA104(JP) 494 C

```
Vaccine   41   ATGGATAAGCTTGCCGACCTCAACTACACATTGAGTGTAATCACTTTAATGAATGACACA  100
               ||||||||||||||||||||||||||||||||||||||||||||||||||||||||||||
MA104(JP)1     ATGGATAAGCTTGCCGACCTCAACTACACATTGAGTGTAATCACTTTAATGAATGACACA  60

Vaccine   101  TTGCATTCTATAATTCAAGATCCTGGAATGGCGTATTTTACATATATTGCATCTGTTCTA  160
               ||||||||||||||||||||||||||||||||||||||||||||||||||||||||||||
MA104(JP)61    TTGCATTCTATAATTCAAGATCCTGGAATGGCGTATTTTACATATATTGCATCTGTTCTA  120

Vaccine   161  ACAGTTTTGTTCACATTACACAAAGCTTCAATTCCAACCATGAAAATAGCATTGAAAACA  220
               |||||||||||||||||||||||||||||||||||| |||||||||||||||||||||||
MA104(JP)121   ACAGTTTTGTTCACATTACACAAAGCTTCAATTCCAGCCATGAAAATAGCATTGAAAACA  180

Vaccine   221  TCAAAATGTTCATATAAAGTAATTAAATATTGTATAGTCACGATAACTAATACTCTTTTA  280
               |||||||||||||||||||||||||||||||||||||||||||||| |||||||||||||
MA104(JP)181   TCAAAATGTTCATATAAAGTAATTAAATATTGTATAGTCACGATAATTAATACTCTTTTA  240

Vaccine   281  AAATTGGCTGGATATAAAGAGCAGGTTACTACAAAAGACGAAATTGAGCAACAGATGGAC  340
               ||||||||||||| ||||||||||||||||||||||||||||||||||||||||||||||
MA104(JP)241   AAATTGGCTGGATGTAAAGAGCAGGTTACTACAAAAGACGAAATTGAGCAACAGATGGAC  300

Vaccine   341  AGAATTGTTAAAGAGATGAGACGTCAGCTGGAGATGATTGATAAACTAACTACTCGTGAA  400
               ||||||||||||||||||||||||||||||||||||||||||||||||||||||||||||
MA104(JP)301   AGAATTGTTAAAGAGATGAGACGTCAGCTGGAGATGATTGATAAACTAACTACTCGTGAA  360

Vaccine   401  ATTGAACAGGTTGAATTGCTTAAATGTATATATGACAACCTGATAACTAGACCAGTTAAC  460
               ||||||||||||||||||||||||||||||||||||||||||||||||||||||||||||
MA104(JP)361   ATTGAACAGGTTGAATTGCTTAAATGTATATATGACAACCTGATAACTAGACCAGTTAAC  420

Vaccine   461  GTTATAGATATGTCGAAGGAATTCAATCaaaaaaaCATCAAAACGCTAGATGAATGGGAG  520
               ||||||||||||||||||||||||||||||||||||||||||||||||||||||||||||
MA104(JP)421   GTTATAGATATGTCGAAGGAATTCAATCAAAAAAACATCAAAACGCTAGATGAATGGGAG  480

Vaccine   521  AGTGGAAAAAATCTATATGAACCGTCAGAAGTGACTGCATCCATGTAA  568
               |||| |||||||| ||||||||||||||||||||||||||||||||||
MA104(JP)481   AGTGTAAAAAATCCATATGAACCGTCAGAAGTGACTGCATCCATGTAA  528
```

FIG. 23

Comparison of amino acid (coding region) sequences of RV3 NSP4

Vaccine 53 T to MA104(JP) 53 A
Vaccine 76 T to MA104(JP) 76 I
Vaccine 85 Y to MA104(JP) 85 C
Vaccine 162 G to MA104(JP) 162 V
Vaccine 165 L to MA104(JP) 165 P

```
Vaccine  41    MDKLADLNYTLSVITLMNDTLHSIIQDPGMAYFTYIASVLTVLFTLHKASIPTMKIALKT  220
               MDKLADLNYTLSVITLMNDTLHSIIQDPGMAYFTYIASVLTVLFTLHKASIP MKIALKT
MA104(JP)1     MDKLADLNYTLSVITLMNDTLHSIIQDPGMAYFTYIASVLTVLFTLHKASIPAMKIALKT  60

Vaccine  221   SKCSYKVIKYCIVTITNTLLKLAGYKEQVTTKDEIEQQMDRIVKEMRRQLEMIDKLTTRE  400
               SKCSYKVIKYCIVTI NTLLKLAG KEQVTTKDEIEQQMDRIVKEMRRQLEMIDKLTTRE
MA104(JP)61    SKCSYKVIKYCIVTIINTLLKLAGCKEQVTTKDEIEQQMDRIVKEMRRQLEMIDKLTTRE  120

Vaccine  401   IEQVELLKCIYDNLITRPVNVIDMSKEFNQKNIKTLDEWESGKNLYEPSEVTASM  565
               IEQVELLKCIYDNLITRPVNVIDMSKEFNQKNIKTLDEWES KN YEPSEVTASM
MA104(JP)121   IEQVELLKCIYDNLITRPVNVIDMSKEFNQKNIKTLDEWESVKNPYEPSEVTASM  175
```

FIG. 24

MA104-adapted RV3 NSP5/6

```
  1 ATGTCTCTCA GCATTGACGT AGCAAGTCTT CCCTCAATTT CTTCTAGTAT CTTTAAAAAT
 61 GAATCGTCTT CTACAACGTC AACTCTTTCT GGAAAATCTA TTGGTAGGAG TGAACAGTAC
121 ATTTCACCAG ATGCAGGAGC ATTTAATAAA TACATGTTGT CGAAGTCTCC AGAGGATATT
181 GGACCGTCTG ATTCTGCTTC AAACGATCCA CTCACCAGCT TTTCGATTAG ATCGAATGCA
241 GTTAAAACAA ATGCAGACGC TGGCGTGTCT ATGGATTCAT CGACGCAATC ACGACCTTCA
301 AGCAACGTTG GGTGCGATCA ATTGGATTTC TCCTTAACTA AAGGTATTAA TGTTAGTGCT
361 AATCTTGATT CATGTATATC AATTTCAACT GATCATAAGA AGGAGAAATC CAAGAAAGAT
421 AAAAGTAGGA AACACTACCC GAGAATTGAA GCAGATTCTG ATTCTGAAGA TTATGTTTTG
481 GATGATTCAG ATAGTGATGA CGGTAAATGT AAGAATTGTA AATATAAGAA AAAATATTTC
541 GCACTAAGAA TGAGGATGAA GCGAGTCGCA ATGCAATTGA TCGAGGATTT GTAA
```

FIG. 25

Amino acid (coding region) ADD31868 (SEQ ID NO:28)

```
  1 MSLSIDVASL PSISSSIFKN ESSSTTSTLS GKSIGRSEQY ISPDAGAFNK YMLSKSPEDI
 61 GPSDSASNDP LTSFSIRSNA VKTNADAGVS MDSSTQSRPS SNVGCDQLDF SLTKGINVSA
121 NLDSCISIST DHKKEKSKKD KSRKHYPRIE ADSDSEDYVL DDSDSDDGKC KNCKYKKKYF
181 ALRMRMKRVA MQLIEDL
```

FIG. 26

Vero-adapted (Vaccine) RV3 NSP5/6 (SEQ ID NO:29)

```
  1 GGCTTTTAAA GCGCTACAGT GATGTCTCTC AGCATTGACG TAGCAAGTCT TCCCTCAATT
 61 TCTTCTAGTA TCTTTAAAAA TGAATCGTCT TCTACAACGT CAACTCTTTC TGGAAAATCT
121 ATTGGTAGGA GTGAACAGTA CATTTCACCA GATGCAGAAG CATTCAATAA ATACATGTTG
181 TCGAAGTCTC CAGAGGATAT TGGACCGTCT GATTCTGCTT CAAACGATCC ACTCACCAGC
241 TTTTCGATTA GATCGAATGC AGTTAAAACA AATGCAGACG CTGGCGTGTC TATGGATTCA
301 TCGACGCAAT CACGACCTTC AAGCAACGTT GGGTGCGATC AATTGGATTT CTCCATAACT
361 AAAGGTATTA ATGTTAGTGC TAATCTTGAT TCATGTATAT CAATTTCAAC TGATCATAAG
421 AAGGAGAAAT CCAAGAAAGA TAAAAGTAGG AAACACTACC CGAGAATTGA AGCAGATTCT
481 GATTCTGAAG ATTATGTTTT GGATGATTCA GATAGTGATG ACGGTAAATG TAAGAATTGT
541 AAATATAAGA AAAAATATTT CGCACTAAGA ATGAGGATGA AGCGAGTCGC AATGCAATTG
601 ATCGAGGATT TGTAATGTCA ACCTGAGAGC ACACTAGGGA GCTCCCCACT CCCGTTTTGT
661 GACC
```

FIG. 27

Amino acid (coding region) [SEQ ID NO:30]

```
  1 MSLSIDVASL PSISSSIFKN ESSSTTSTLS GKSIGRSEQY ISPDAEAFNK YMLSKSPEDI
 61 GPSDSASNDP LTSFSIRSNA VKTNADAGVS MDSSTQSRPS SNVGCDQLDF SITKGINVSA
121 NLDSCISIST DHKKEKSKKD KSRKHYPRIE ADSDSEDYVL DDSDSDDGKC KNCKYKKKYF
181 ALRMRMKRVA MQLIEDL
```

FIG. 28

Comparison of nucleotide sequences of RV3 NSP5/6

Vaccine 158 A to MA104(JP) 137 G
Vaccine 165 C to MA104(JP) 144 T
Vaccine 355 A to MA104(JP) 334 T

```
Vaccine   22   ATGTCTCTCAGCATTGACGTAGCAAGTCTTCCCTCAATTTCTTCTAGTATCTTTAAAAAT  81
               ||||||||||||||||||||||||||||||||||||||||||||||||||||||||||||
MA104(JP)1     ATGTCTCTCAGCATTGACGTAGCAAGTCTTCCCTCAATTTCTTCTAGTATCTTTAAAAAT  60

Vaccine   82   GAATCGTCTTCTACAACGTCAACTCTTTCTGGAAAATCTATTGGTAGGAGTGAACAGTAC  141
               ||||||||||||||||||||||||||||||||||||||||||||||||||||||||||||
MA104(JP)61    GAATCGTCTTCTACAACGTCAACTCTTTCTGGAAAATCTATTGGTAGGAGTGAACAGTAC  120

Vaccine   142  ATTTCACCAGATGCAGAAGCATTCAATAAATACATGTTGTCGAAGTCTCCAGAGGATATT  201
               |||||||||||||||| |||||| ||||||||||||||||||||||||||||||||||||
MA104(JP)121   ATTTCACCAGATGCAGGAGCATTTAATAAATACATGTTGTCGAAGTCTCCAGAGGATATT  180

Vaccine   202  GGACCGTCTGATTCTGCTTCAAACGATCCACTCACCAGCTTTTCGATTAGATCGAATGCA  261
               ||||||||||||||||||||||||||||||||||||||||||||||||||||||||||||
MA104(JP)181   GGACCGTCTGATTCTGCTTCAAACGATCCACTCACCAGCTTTTCGATTAGATCGAATGCA  240

Vaccine   262  GTTAAAACAAATGCAGACGCTGGCGTGTCTATGGATTCATCGACGCAATCACGACCTTCA  321
               ||||||||||||||||||||||||||||||||||||||||||||||||||||||||||||
MA104(JP)241   GTTAAAACAAATGCAGACGCTGGCGTGTCTATGGATTCATCGACGCAATCACGACCTTCA  300

Vaccine   322  AGCAACGTTGGGTGCGATCAATTGGATTTCTCCATAACTAAAGGTATTAATGTTAGTGCT  381
               |||||||||||||||||||||||||||||||||| |||||||||||||||||||||||||
MA104(JP)301   AGCAACGTTGGGTGCGATCAATTGGATTTCTCCTTAACTAAAGGTATTAATGTTAGTGCT  360

Vaccine   382  AATCTTGATTCATGTATATCAATTTCAACTGATCATAAGAAGGAGAAATCCAAGAAAGAT  441
               ||||||||||||||||||||||||||||||||||||||||||||||||||||||||||||
MA104(JP)361   AATCTTGATTCATGTATATCAATTTCAACTGATCATAAGAAGGAGAAATCCAAGAAAGAT  420

Vaccine   442  AAAAGTAGGAAACACTACCCGAGAATTGAAGCAGATTCTGATTCTGAAGATTATGTTTTG  501
               ||||||||||||||||||||||||||||||||||||||||||||||||||||||||||||
MA104(JP)421   AAAAGTAGGAAACACTACCCGAGAATTGAAGCAGATTCTGATTCTGAAGATTATGTTTTG  480

Vaccine   502  GATGATTCAGATAGTGATGACGGTAAATGTAAGAATTGTAAATATAAGAAAAAATATTTC  561
               ||||||||||||||||||||||||||||||||||||||||||||||||||||||||||||
MA104(JP)481   GATGATTCAGATAGTGATGACGGTAAATGTAAGAATTGTAAATATAAGAAAAAATATTTC  540

Vaccine   562  GCACTAAGAATGAGGATGAAGCGAGTCGCAATGCAATTGATCGAGGATTTGTAA  615
               ||||||||||||||||||||||||||||||||||||||||||||||||||||||
MA104(JP)541   GCACTAAGAATGAGGATGAAGCGAGTCGCAATGCAATTGATCGAGGATTTGTAA  594
```

FIG. 29

Comparison of amino acid (coding region) sequences of RV3 NSP5

Vaccine 46 E to MA104(JP) 46 G
Vaccine 112 I to MA104(JP) 112 L

```
Vaccine    22      MSLSIDVASLPsisssifknesssttstlsGKSIGRSEQYISPDAEAFNKYMLSKSPEDI
201
               MSLSIDVASLPSISSSIFKNESSSTTSTLSGKSIGRSEQYISPDA AFNKYMLSKSPEDI
MA104(JP)1         MSLSIDVASLPSISSSIFKNESSSTTSTLSGKSIGRSEQYISPDAGAFNKYMLSKSPEDI
60

Vaccine    202     GPSDSASNDPLTSFSIRSNAVKTNADAGVSMDSSTQSRPSSNVGCDQLDFSITKGINVSA
381
               GPSDSASNDPLTSFSIRSNAVKTNADAGVSMDSSTQSRPSSNVGCDQLDFS+TKGINVSA
MA104(JP)61        GPSDSASNDPLTSFSIRSNAVKTNADAGVSMDSSTQSRPSSNVGCDQLDFSLTKGINVSA
120

Vaccine    382     NLDSCISISTdhkkekskkdksrkhYPRIEAdsdsedyvlddsdsddGkcknckykkkyF
561
               NLDSCISISTDHKKEKSKKDKSRKHYPRIEADSDSEDYVLDDSDSDDGKCKNCKYKKKYF
MA104(JP)121       NLDSCISISTDHKKEKSKKDKSRKHYPRIEADSDSEDYVLDDSDSDDGKCKNCKYKKKYF
180

Vaccine   562  ALRMRMKRVAMQLIEDL  612
               ALRMRMKRVAMQLIEDL
MA104(JP)181   ALRMRMKRVAMQLIEDL  197
```

FIG. 30

VP1 Sequence
MA104-adapted RV3 VP1 (SEQ ID NO:47)

```
   1 ATGGGGAAGT ACAATCTAAT CTTGTCAGAA TATTTATCAT TTGTTTATAA TTCACAATCT
  61 GCAGTTCAAA TACCAATTTA TTATTCTTCC AATTCAGAAT TAGAAAAAAG ATGTATTGAA
 121 TTTCATGCTA AATGTGTTGA CAGTTCAAAA AAAGGTCTAT CATTAAAACC TTTATTCGAA
 181 AAATATAAAG ATGTAATAGA TAATGCAACT TTACTATCTC TATTATCATA TTCTTATGAT
 241 AAATACAACG CTGTAGAAAG GAAACTAGTC AATTATGCTA AAGGTAAACC ATTAGAGGCT
 301 GATTTAACGG CAAACGAGCT TGATTATGAA AATAATAAAA TAACTTCTGA ATTGTTTCAA
 361 TCAGCTGAAG AATATACTGA TTCATTAATG GATCCTGCTA TATTAACTTC GTTATCTTCA
 421 AATCTAAATG CAGTCATGTT TGGTTAGAA CGACACTCAA ATGACGTTGC TGATGCAAAC
 481 AAAATTTATA AACGTAGACT GGATCTATTT ACCATAGTAG CATCTACAAT AAATAAATAT
 541 GGAGTACCTA GACATAATGA AAAATATAGA TATGAATACG AGGTGATGAA GGATAAACCG
 601 TACTACTTAG TAACCTGGGC CAACTCATCT ATAGAAATGC TTATGTCAGT GTTTTCCCAT
 661 GAAGATTATT TAATAGCAAA AGAGTTAATA ATCTTATCAT ATTCAAATAG ATCAACGTTA
 721 GCAAAACTAG TTTCATCTCC AATGTCGATA TTGGTTGCAT TAATAGATAT CAATGGTACG
 781 TTTATTACAA ATGAAGAGTT AGAACTCGAG TTTTCAGATA AATATGTTAA GGCAATTGTG
 841 CCTGATCAAA TTTTCGATGA ATTACAGGAA ATGATCGACA ATATGAGGAA AGTTGGTTTA
 901 GTAGATATAC CAAAAATGAT TCAAGAATGG TTAATTGATT GTTCATTAGA GAAATTTACA
 961 TTGATGTCAA AAATTTATTC TTGGTCATTT CATGTTGGTT TTAGAAAAACA AAAGATGATT
1021 GATGCAGCAT TAGACCAATT GAAAACAGAG TACACTGAAG ATGTAGATAA TGAGATGTAT
1081 AATGAGTATA CGATGTTAAT TAGAGATGAA ATAGTTAAAA TGCTAGAAGT ACCAGTTAAA
1141 CATGATGATC ATCTACTTCG CGATTCAGAA TTAGCCGGAT TGTTATCAAT GTCATCAGCT
1201 TCAAATGGTG AATCAAGGCA ACTTAAATTT GGTCGTAAAA CAATATTTTC AACTAAGAAA
1261 AATATGCATG TCATGGATGA TATCGCACAT GGAAAATATA CTCCGGGTGT CATTCCTCCA
1321 GTAAATGTAG ATAGACCAAT TCCACTAGGT CGTAGAGATG TTCCTGGACG AAGAACAAGA
1381 ATTATATTCA TATTACCATA TGAATACTTT ATTGCGCAGC ACGCTGTCGT AGAAAAAATG
1441 TTATCATACG CAAAGCATAC TAGAGAGTAC GCAGAATTTT ATTCGCAGTC AAATCAATTG
1501 CTATCATATG GTGATGTTAC AAGATTCTTA TCCAATAATT CTATGGTATT ATACACAGAC
1561 GTTTCACAAT GGGATTCGTC ACAACATAAC ACACAACCAT TTAGAAAAGG AATAATTATG
1621 GGTTTAGATA TGCTATCCAA TATGACTAAT GATCCAAAAG TAGTACAAAC GCTAAATTTA
1681 TATAAACAAA CACAAATTAA TCTCATGGAT TCATATGTTC AAATACCTGA CGGTAATGTA
1741 ATAAAAAAGA TTCAGTATGG TGCTGTTGCT TCAGGAGAAA AACAAACCAA GGCAGCTAAT
1801 TCTATAGCTA ATTTGGCACT CATTAAAACG GTATTGTCAA GAATTGCAAA TAAATATTCT
1861 TTTATAACCA AAATAATCAG AGTCGATGGT GATGATAATT ATGCAGTACT ACAATTTAAT
1921 ACCGATGTCA CTAAACAAAT GGTCCAAGAT GTGTCAAACG ATGTGAGGTA TATATATTCT
1981 AGAATGAATG CTAAAGTTAA AGCACTGGTA TCTACAGTCG GTATCGAAAT AGCAAAAAGA
2041 TATATAGCAG GAGGAAAAAT ATTTTTCAGA GCTGGTATAA ACTTATTAAA TAATGAGAAA
2101 CGTGGACAAA GTACACAATG GGATCAAGCA GCTATTTTAT ACTCAAACTA CATTGTTAAC
2161 AAATTACGAG GATTTGAGAC TGATAGAGAA TTTGTACTAA CTAAAATTAT ACAAATGACA
2221 TCTATAGCTA TTACTGGATC ACTAAGGCTA TTTCCGTCAG AACGAGTGTT AACTACTAAT
2281 TCTACATTCA AAGTATTTGA CTCAGAAGAT TTCATTATAG AGTATGGAAC AACTGACGAT
2341 GAAGTATATA TACAAAGAGC ATTTATGTCA TTATCTAGTC AAAAGTCAGG AATAGCTGAT
2401 GAAATTGCTT CTTCACAAAC ATTTAAAAAT TATGTCAATA AATTATCTGA CCAACTATTA
2461 GTATCAAAAA ACGTAATTGT ATCTAAAGGT ATAGCTGTAA CAGAAAAGGC GAAATTGAAT
2521 TCATATGCAC CAGTTTATTT AGAAAAACGT CGTGCACAAA TATCAGCGCT ATTAACTATG
2581 TTGCAGAAAC CAGTGTCATT TAAATCAAAT AAAATTACTA TTAATGACAT TTTGCGTGAC
2641 ATAAAACCAT TTTTTGTCAC TTCTGAAGCT AATTTGTCAA TTCAATACAG AAAATTTATG
2701 CCAACACTAC CTGATAATGT CCAATATGTT ATACAATGTA TAGGATCGAG GACGTACCAG
2761 ATAGAAGATA GTGGGTCAAA ATCATCGATT TCGAAGTTAA TATCAAAATA TTCAGTTTAC
2821 AAACCATCGA TTGAAGAACT ATATAAAGTT ATATCTTTAA GAGAACAAGA AATACAGTTG
2881 TATTTAGTTT CATTAGGAGT TCCGCTAGTT GATGCAAGCA CGTACGTCGG GTCAAGAATA
2941 TATTCGCAAG ATAAATATAA AATATTAGAA TCTTACGTAT ATAATTTATT ATCAATTAAT
3001 TATGGATGTT ATCAATTATT CGATTTTAAT TCTCCAGATT TAGAGAGACT TATACGAATT
3061 CCTTTTAAAG GTAAGATACC AGCTGTAACA TTTATATTAC ATCTTTACGC TAAACTTGAA
3121 ATAATAAACT ATGCTATTAA GAACGGAGCT TGGATCAGCT TGTTTTGTAA CTATCCAAAA
3181 TCTGAGATGA TTAAATTATG GAAGAAAATG TGGAATATAA CAGCATTACG GTCTCCCTAT
3241 ACTAGTGCGA ATTTCTTTCA AGATTAG
```

FIG. 31

Amino acid (coding region) transeq (SEQ ID NO:48)

```
   1 MGKYNLILSE YLSFVYNSQS AVQIPIYYSS NSELEKRCIE FHAKCVDSSK KGLSLKPLFE
  61 KYKDVIDNAT LLSLLSYSYD KYNAVERKLV NYAKGKPLEA DLTANELDYE NNKITSELFQ
 121 SAEEYTDSLM DPAILTSLSS NLNAVMFWLE RHSNDVADAN KIYKRRLDLF TIVASTINKY
 181 GVPRHNEKYR YEYEVMKDKP YYLVTWANSS IEMLMSVFSH EDYLIAKELI ILSYSNRSTL
 241 AKLVSSPMSI LVALIDINGT FITNEELELE FSDKYVKAIV PDQIFDELQE MIDNMRKVGL
 301 VDIPKMIQEW LIDCSLEKFT LMSKIYSWSF HVGFRKQKMI DAALDQLKTE YTEDVDNEMY
 361 NEYTMLIRDE IVKMLEVPVK HDDHLLRDSE LAGLLSMSSA SNGESRQLKF GRKTIFSTKK
 421 NMHVMDDIAH GKYTPGVIPP VNVDRPIPLG RRDVPGRRTR IIFILPYEYF IAQHAVVEKM
 481 LSYAKHTREY AEFYSQSNQL LSYGDVTRFL SNNSMVLYTD VSQWDSSQHN TQPFRKGIIM
 541 GLDMLSNMTN DPKVVQTLNL YKQTQINLMD SYVQIPDGNV IKKIQYGAVA SGEKQTKAAN
 601 SIANLALIKT VLSRIANKYS FITKIIRVDG DDNYAVLQFN TDVTKQMVQD VSNDVRYIYS
 661 RMNAKVKALV STVGIEIAKR YIAGGKIFFR AGINLLNNEK RGQSTQWDQA AILYSNYIVN
 721 KLRGFETDRE FVLTKIIQMT SIAITGSLRL FPSERVLTTN STFKVFDSED FIIEYGTTDD
 781 EVYIQRAFMS LSSQKSGIAD EIASSQTFKN YVNKLSDQLL VSKNVIVSKG IAVTEKAKLN
 841 SYAPVYLEKR RAQISALLTM LQKPVSFKSN KITINDILRD IKPFFVTSEA NLSIQYRKFM
 901 PTLPDNVQYV IQCIGSRTYQ IEDSGSKSSI SKLISKYSVY KPSIEELYKV ISLREQEIQL
 961 YLVSLGVPLV DASTYVGSRI YSQDKYKILE SYVYNLLSIN YGCYQLFDFN SPDLERLIRI
1021 PFKGKIPAVT FILHLYAKLE IINYAIKNGA WISLFCNYPK SEMIKLWKKM WNITALRSPY
1081 TSANFFQD
```

FIG. 32

Vero-adapted (Vaccine) RV3 VP1 (SEQ ID NO:49)

```
   1 TGTAAAACGA CGGCCAGTGG CTATTAAAGC TGTACAATGG GGAAGTACAA TCTAATCTTG
  61 TCAGAATATT TATCATTTGT TTATAATTCA CAATCTGCAG TTCAAATACC AATTTATTAT
 121 TCTTCCAATT CAGAATTAGA AAAAAGATGT ATTGAATTTC ATGCTAAATG TGTTGACAGT
 181 TCAAAAAAAG GTCTATCATT AAAACCTTTA TTCGAAAAAT ATAAAGATGT AATAGATAAT
 241 GCAACTTTAC TATCTCTATT ATCATATTCT TATGATAAAT ACAACGCTGT AGAAAGGAAA
 301 CTAGTCAATT ATGCTAAAGG TAAACCATTA GAGGCTGATT TAACGGCAAA CGAGCTTGAT
 361 TATGAAAATA ATAAAATAAC TTCTGAATTG TTTCAATCAG CTGAAGAATA TACTGATTCA
 421 TTAATGGATC CTGCTATATT AACTTCGTTA TCTTCAAATC TAAATGCAGT CATGTTTTGG
 481 TTAGAACGAC ACTCAAATGA CGTTGCTGAT GCAAACAAAA TTTATAAACG TAGACTGGAT
 541 CTATTTACCA TAGTAGCATC TACAATAAAT AAATATGGAG TACCTAGACA TAATGAAAAA
 601 TATAGATATG AATACGAGGT GATGAAGGAT AAACCGTACT ACTTAGTAAC CTGGGCCAAC
 661 TCATCTATAG AAATGCTTAT GTCAGTGTTT TCCCATGAAG ATTATTTAAT AGCAAAAGAG
 721 TTAATAATCT TATCATATTC AAATAGATCA ACGTTAGCAA AACTAGTTTC ATCTCCAATG
 781 TCGATATTGG TTGCATTAAT AGATATCAAT GGTACGTTTA TTACAAATGA AGAGTTAGAA
 841 CTCGAGTTTT CAGATAAATA TGTTAAGGCA ATTGTGCCTG ATCAAATTTT CGATGAATTA
 901 CAGGAAATGA TCGACAATAT GAGGAAAGTT GGTTTAGTAG ATATACCAAA AATGATTCAA
 961 GAATGGTTAA TTGATTGTTC ATTAGAGAAA TTTACATTGA TGTCAAAAAT TTATTCTTGG
1021 TCATTTCATG TTGGTTTTAG AAAACAAAAG ATGATTGATG CAGCATTAGA CCAATTGAAA
1081 ACAGAGTACA CTGAAGATGT AGATAATGAG ATGTATAATG AGTATACGAT GTTAATTAGA
1141 GATGAAATAG TTAAAATGCT AGAAGTACCA GTTAAACATG ATGATCATCT ACTTCGCGAT
1201 TCAGAATTAG CCGGATTGTT ATCAATGTCA TCAGCTTCAA ATGGTGAATC AAGGCAACTT
1261 AAATTTGGTC GTAAAACAAT ATTTTCAACT AAGAAAAATA TGCATGTCAT GGATGATATC
1321 GCACATGGAA AATATACTCC GGGTGTCATT CCTCCAGTAA ATGTAGATAG ACCAATTCCA
1381 CTAGGTCGTA GAGATGTTCC TGGACGAAGA ACAAGAATTA TATTCATATT ACCATATGAA
1441 TACTTTATTG CGCAGCACGC TGTCGTAGAA AAAATGTTAT CATACGCAAA GCATACTAGA
1501 GAGTACGCAG AATTTTATTC GCAGTCAAAT CAATTGCTAT CATATGGTGA TGTTACAAGA
1561 TTCTTATCCA ATAATTCTAT GGTATTATAC ACAGACGTTT CACAATGGGA TTCGTCACAA
1621 CATAACACAC AACCATTTAG AAAAGGAATA ATTATGGGTT TAGATATGCT ATCCAATATG
1681 ACTAATGATC CAAAAGTAGT ACAAACGCTA AATTTATATA AACAAACACA AATTAATCTC
1741 ATGGATTCAT ATGTTCAAAT ACCTGACGGT AATGTAATAA AAAAGATTCA GTATGGTGCT
1801 GTTGCTTCAG GAGAAAAACA AACCAAGGCA GCTAATTCTA TAGCTAATTT GGCACTCATT
1861 AAAACGGTAT TGTCAAGAAT TGCAAATAAA TATTCTTTTA TAACCAAAAT AATCAGAGTC
1921 GATGGTGATG ATAATTATGC AGTACTACAA TTTAATACCG ATGTCACTAA ACAAATGGTC
1981 CAAGATGTGT CAAACGATGT GAGGTATATA TATTCTAGAA TGAATGCTAA AGTTAAAGCA
2041 CTGGTATCTA CAGTCGGTAT CGAAATAGCA AAAAGATATA TAGCAGGAGG AAAAATATTT
2101 TTCAGAGCTG GTATAAACTT ATTAAATAAT GAGAAACGTG GACAAAGTAC ACAATGGGAT
2161 CAAGCAGCTA TTTTATACTC AAACTACATT GTTAACAAAT TACGAGGATT TGAGACTGAT
2221 AGAGAATTTG TACTAACTAA AATTATACAA ATGACATCTA TAGCTATTAC TGGATCACTA
2281 AGGCTATTTC CGTCAGAACG AGTGTTAACT ACTAATTCTA CATTCAAAGT ATTTGACTCA
2341 GAAGATTTCA TTATAGAGTA TGGAACAACT GACGATGAAG TATATATACA AAGAGCATTT
2401 ATGTCATTAT CTAGTCAAAA GTCAGGAATA GCTGATGAAA TTGCTTCTTC ACAAACATTT
2461 AAAAATTATG TCAATAAATT ATCTGACCAA CTATTAGTAT CAAAAAACGT AATTGTATCT
2521 AAAGGTATAG CTGTAACAGA AAAGGCGAAA TTGAATTCAT ATGCACCAGT TTATTTAGAA
2581 AAACGTCGTG CACAAATATC AGCGCTATTA ACTATGTTGC AGAAACCAGT GTCATTTAAA
2641 TCAAATAAAA TTACTATTAA TGACATTTTG CGTGACATAA AACCATTTTT TTTCACTTCT
2701 GAAGCTAATT TGTCAATTCA ATACAGAAAA TTTATGCCAA CACTACCTGA TAATGTCCAA
2761 TATGTTATAC AATGTATAGG ATCGAGGACG TACCAGATAG AAGATAGTGG GTCAAAATCA
2821 TCGATTTCGA AGTTAATATC AAAATATTCA GTTTACAAAC CATCGATTGA AGAACTATAT
2881 AAAGTTATAT CTTTAAGAGA ACAAGAAATA CAGTTGTATT TAGTTTCATT AGGAGTTCCG
2941 CTAGTTGATG CAAGCACGTA CGTCGGGTCA AGAATATATT CGCAAGATAA ATATAAAATA
3001 TTAGAATCTT ACGTATATAA TTTATTATCA ATTAATTATG GATGTTATCA ATTATTCGAT
3061 TTTAATTCTC CAGATTTAGA GAGACTTATA CGAATTCCTT TTAAAGGTAA GATACCAGCT
3121 GTAACATTTA TATTACATCT TTACGCTAAA CTTGAAATAA TAAACTATGC TATTAAGAAC
3181 GGAGCTTGGA TCAGCTTGTT TTGTAACTAT CCAAAATCTG AGATGATTAA ATTATGGAAG
3241 AAAATGTGGA ATATAACAGC ATTACGGTCT CCCTATACTA GTGCGAATTT CTTTCAAGAT
3301 TAGAGCGGCT TAGGATGTGA CC
```

FIG. 33

Amino acid (coding region) [SEQ ID NO:50]

```
   1 MGKYNLILSE YLSFVYNSQS AVQIPIYYSS NSELEKRCIE FHAKCVDSSK KGLSLKPLFE
  61 KYKDVIDNAT LLSLLSYSYD KYNAVERKLV NYAKGKPLEA DLTANELDYE NNKITSELFQ
 121 SAEEYTDSLM DPAILTSLSS NLNAVMFWLE RHSNDVADAN KIYKRRLDLF TIVASTINKY
 181 GVPRHNEKYR YEYEVMKDKP YYLVTWANSS IEMLMSVFSH EDYLIAKELI ILSYSNRSTL
 241 AKLVSSPMSI LVALIDINGT FITNEELELE FSDKYVKAIV PDQIFDELQE MIDNMRKVGL
 301 VDIPKMIQEW LIDCSLEKFT LMSKIYSWSF HVGFRKQKMI DAALDQLKTE YTEDVDNEMY
 361 NEYTMLIRDE IVKMLEVPVK HDDHLLRDSE LAGLLSMSSA SNGESRQLKF GRKTIFSTKK
 421 NMHVMDDIAH GKYTPGVIPP VNVDRPIPLG RRDVPGRRTR IIFILPYEYF IAQHAVVEKM
 481 LSYAKHTREY AEFYSQSNQL LSYGDVTRFL SNNSMVLYTD VSQWDSSQHN TQPFRKGIIM
 541 GLDMLSNMTN DPKVVQTLNL YKQTQINLMD SYVQIPDGNV IKKIQYGAVA SGEKQTKAAN
 601 SIANLALIKT VLSRIANKYS FITKIIRVDG DDNYAVLQFN TDVTKQMVQD VSNDVRYIYS
 661 RMNAKVKALV STVGIEIAKR YIAGGKIFFR AGINLLNNEK RGQSTQWDQA AILYSNYIVN
 721 KLRGFETDRE FVLTKIIQMT SIAITGSLRL FPSERVLTTN STFKVFDSED FIIEYGTTDD
 781 EVYIQRAFMS LSSQKSGIAD EIASSQTFKN YVNKLSDQLL VSKNVIVSKG IAVTEKAKLN
 841 SYAPVYLEKR RAQISALLTM LQKPVSFKSN KITINDILRD IKPFFFTSEA NLSIQYRKFM
 901 PTLPDNVQYV IQCIGSRTYQ IEDSGSKSSI SKLISKYSVY KPSIEELYKV ISLREQEIQL
 961 YLVSLGVPLV DASTYVGSRI YSQDKYKILE SYVYNLLSIN YGCYQLFDFN SPDLERLIRI
1021 PFKGKIPAVT FILHLYAKLE IINYAIKNGA WISLFCNYPK SEMIKLWKKM WNITALRSPY
1081 TSANFFQD
```

FIG. 34

Comparison of nucleotide sequences of RV3 VP1

Vaccine 2692 T to MA104(JP) 2656 G

```
Vaccine   37   ATGGGGAAGTACAATCTAATCTTGTCAGAATATTTATCATTTGTTTATAATTCACAATCT  96
               ||||||||||||||||||||||||||||||||||||||||||||||||||||||||||||
MA104(JP)1     ATGGGGAAGTACAATCTAATCTTGTCAGAATATTTATCATTTGTTTATAATTCACAATCT  60

Vaccine   97   GCAGTTCAAATACCAATTTATTATTCTTCCAATTCAGAATTAGAAAAAGATGTATTGAA  156
               ||||||||||||||||||||||||||||||||||||||||||||||||||||||||||||
MA104(JP)61    GCAGTTCAAATACCAATTTATTATTCTTCCAATTCAGAATTAGAAAAAGATGTATTGAA  120

Vaccine   157  TTTCATGCTAAATGTGTTGACAGTTCaaaaaaaGGTCTATCATTAAAACCTTTATTCGAA  216
               ||||||||||||||||||||||||||||||||||||||||||||||||||||||||||||
MA104(JP)121   TTTCATGCTAAATGTGTTGACAGTTCAAAAAAAGGTCTATCATTAAAACCTTTATTCGAA  180

Vaccine   217  AAATATAAAGATGTAATAGATAATGCAACTTTACTATCTCTATTATCATATTCTTATGAT  276
               ||||||||||||||||||||||||||||||||||||||||||||||||||||||||||||
MA104(JP)181   AAATATAAAGATGTAATAGATAATGCAACTTTACTATCTCTATTATCATATTCTTATGAT  240

Vaccine   277  AAATACAACGCTGTAGAAAGGAAACTAGTCAATTATGCTAAAGGTAAACCATTAGAGGCT  336
               ||||||||||||||||||||||||||||||||||||||||||||||||||||||||||||
MA104(JP)241   AAATACAACGCTGTAGAAAGGAAACTAGTCAATTATGCTAAAGGTAAACCATTAGAGGCT  300

Vaccine   337  GATTTAACGGCAAACGAGCTTGATTATGAAAATAATAAAATAACTTCTGAATTGTTTCAA  396
               ||||||||||||||||||||||||||||||||||||||||||||||||||||||||||||
MA104(JP)301   GATTTAACGGCAAACGAGCTTGATTATGAAAATAATAAAATAACTTCTGAATTGTTTCAA  360

Vaccine   397  TCAGCTGAAGAATATACTGATTCATTAATGGATCCTGCTATATTAACTTCGTTATCTTCA  456
               ||||||||||||||||||||||||||||||||||||||||||||||||||||||||||||
MA104(JP)361   TCAGCTGAAGAATATACTGATTCATTAATGGATCCTGCTATATTAACTTCGTTATCTTCA  420

Vaccine   457  AATCTAAATGCAGTCATGTTTTGGTTAGAACGACACTCAAATGACGTTGCTGATGCAAAC  516
               ||||||||||||||||||||||||||||||||||||||||||||||||||||||||||||
MA104(JP)421   AATCTAAATGCAGTCATGTTTTGGTTAGAACGACACTCAAATGACGTTGCTGATGCAAAC  480

Vaccine   517  AAAATTTATAAACGTAGACTGGATCTATTTACCATAGTAGCATCTACAATAAATAAATAT  576
               ||||||||||||||||||||||||||||||||||||||||||||||||||||||||||||
MA104(JP)481   AAAATTTATAAACGTAGACTGGATCTATTTACCATAGTAGCATCTACAATAAATAAATAT  540

Vaccine   577  GGAGTACCTAGACATAATGAAAAATATAGATATGAATACGAGGTGATGAAGGATAAACCG  636
               ||||||||||||||||||||||||||||||||||||||||||||||||||||||||||||
MA104(JP)541   GGAGTACCTAGACATAATGAAAAATATAGATATGAATACGAGGTGATGAAGGATAAACCG  600

Vaccine   637  TACTACTTAGTAACCTGGGCCAACTCATCTATAGAAATGCTTATGTCAGTGTTTTCCCAT  696
               ||||||||||||||||||||||||||||||||||||||||||||||||||||||||||||
MA104(JP)601   TACTACTTAGTAACCTGGGCCAACTCATCTATAGAAATGCTTATGTCAGTGTTTTCCCAT  660

Vaccine   697  GAAGATTATTTAATAGCAAAAGAGTTAATAATCTTATCATATTCAAATAGATCAACGTTA  756
               ||||||||||||||||||||||||||||||||||||||||||||||||||||||||||||
MA104(JP)661   GAAGATTATTTAATAGCAAAAGAGTTAATAATCTTATCATATTCAAATAGATCAACGTTA  720

Vaccine   757  GCAAAACTAGTTTCATCTCCAATGTCGATATTGGTTGCATTAATAGATATCAATGGTACG  816
               ||||||||||||||||||||||||||||||||||||||||||||||||||||||||||||
MA104(JP)721   GCAAAACTAGTTTCATCTCCAATGTCGATATTGGTTGCATTAATAGATATCAATGGTACG  780

Vaccine   817  TTTATTACAAATGAAGAGTTAGAACTCGAGTTTTCAGATAAATATGTTAAGGCAATTGTG  876
               ||||||||||||||||||||||||||||||||||||||||||||||||||||||||||||
MA104(JP)781   TTTATTACAAATGAAGAGTTAGAACTCGAGTTTTCAGATAAATATGTTAAGGCAATTGTG  840

Vaccine   877  CCTGATCAAATTTTCGATGAATTACAGGAAATGATCGACAATATGAGGAAAGTTGGTTTA  936
               ||||||||||||||||||||||||||||||||||||||||||||||||||||||||||||
MA104(JP)841   CCTGATCAAATTTTCGATGAATTACAGGAAATGATCGACAATATGAGGAAAGTTGGTTTA  900
```

FIG. 35A

```
Vaccine   937   GTAGATATACCAAAAATGATTCAAGAATGGTTAATTGATTGTTCATTAGAGAAATTTACA   996
                ||||||||||||||||||||||||||||||||||||||||||||||||||||||||||||
MA104(JP)901    GTAGATATACCAAAAATGATTCAAGAATGGTTAATTGATTGTTCATTAGAGAAATTTACA   960

Vaccine   997   TTGATGTCAAAAATTTATTCTTGGTCATTTCATGTTGGTTTTAGAAAACAAAAGATGATT   1056
                ||||||||||||||||||||||||||||||||||||||||||||||||||||||||||||
MA104(JP)961    TTGATGTCAAAAATTTATTCTTGGTCATTTCATGTTGGTTTTAGAAAACAAAAGATGATT   1020

Vaccine   1057  GATGCAGCATTAGACCAATTGAAAACAGAGTACACTGAAGATGTAGATAATGAGATGTAT   1116
                ||||||||||||||||||||||||||||||||||||||||||||||||||||||||||||
MA104(JP)1021   GATGCAGCATTAGACCAATTGAAAACAGAGTACACTGAAGATGTAGATAATGAGATGTAT   1080

Vaccine   1117  AATGAGTATACGATGTTAATTAGAGATGAAATAGTTAAAATGCTAGAAGTACCAGTTAAA   1176
                ||||||||||||||||||||||||||||||||||||||||||||||||||||||||||||
MA104(JP)1081   AATGAGTATACGATGTTAATTAGAGATGAAATAGTTAAAATGCTAGAAGTACCAGTTAAA   1140

Vaccine   1177  CATGATGATCATCTACTTCGCGATTCAGAATTAGCCGGATTGTTATCAATGTCATCAGCT   1236
                ||||||||||||||||||||||||||||||||||||||||||||||||||||||||||||
MA104(JP)1141   CATGATGATCATCTACTTCGCGATTCAGAATTAGCCGGATTGTTATCAATGTCATCAGCT   1200

Vaccine   1237  TCAAATGGTGAATCAAGGCAACTTAAATTTGGTCGTAAAACAATATTTTCAACTAAGAAA   1296
                ||||||||||||||||||||||||||||||||||||||||||||||||||||||||||||
MA104(JP)1201   TCAAATGGTGAATCAAGGCAACTTAAATTTGGTCGTAAAACAATATTTTCAACTAAGAAA   1260

Vaccine   1297  AATATGCATGTCATGGATGATATCGCACATGGAAAATATACTCCGGGTGTCATTCCTCCA   1356
                ||||||||||||||||||||||||||||||||||||||||||||||||||||||||||||
MA104(JP)1261   AATATGCATGTCATGGATGATATCGCACATGGAAAATATACTCCGGGTGTCATTCCTCCA   1320

Vaccine   1357  GTAAATGTAGATAGACCAATTCCACTAGGTCGTAGAGATGTTCCTGGACGAAGAACAAGA   1416
                ||||||||||||||||||||||||||||||||||||||||||||||||||||||||||||
MA104(JP)1321   GTAAATGTAGATAGACCAATTCCACTAGGTCGTAGAGATGTTCCTGGACGAAGAACAAGA   1380

Vaccine   1417  ATTATATTCATATTACCATATGAATACTTTATTGCGCAGCACGCTGTCGTAGAAAAAATG   1476
                ||||||||||||||||||||||||||||||||||||||||||||||||||||||||||||
MA104(JP)1381   ATTATATTCATATTACCATATGAATACTTTATTGCGCAGCACGCTGTCGTAGAAAAAATG   1440

Vaccine   1477  TTATCATACGCAAAGCATACTAGAGAGTACGCAGAATTTTATTCGCAGTCAAATCAATTG   1536
                ||||||||||||||||||||||||||||||||||||||||||||||||||||||||||||
MA104(JP)1441   TTATCATACGCAAAGCATACTAGAGAGTACGCAGAATTTTATTCGCAGTCAAATCAATTG   1500

Vaccine   1537  CTATCATATGGTGATGTTACAAGATTCTTATCCAATAATTCTATGGTATTATACACAGAC   1596
                ||||||||||||||||||||||||||||||||||||||||||||||||||||||||||||
MA104(JP)1501   CTATCATATGGTGATGTTACAAGATTCTTATCCAATAATTCTATGGTATTATACACAGAC   1560

Vaccine   1597  GTTTCACAATGGGATTCGTCACAACATAACACACAACCATTTAGAAAAGGAATAATTATG   1656
                ||||||||||||||||||||||||||||||||||||||||||||||||||||||||||||
MA104(JP)1561   GTTTCACAATGGGATTCGTCACAACATAACACACAACCATTTAGAAAAGGAATAATTATG   1620

Vaccine   1657  GGTTTAGATATGCTATCCAATATGACTAATGATCCAAAAGTAGTACAAACGCTAAATTTA   1716
                ||||||||||||||||||||||||||||||||||||||||||||||||||||||||||||
MA104(JP)1621   GGTTTAGATATGCTATCCAATATGACTAATGATCCAAAAGTAGTACAAACGCTAAATTTA   1680

Vaccine   1717  TATAAACAAACACAAATTAATCTCATGGATTCATATGTTCAAATACCTGACGGTAATGTA   1776
                ||||||||||||||||||||||||||||||||||||||||||||||||||||||||||||
MA104(JP)1681   TATAAACAAACACAAATTAATCTCATGGATTCATATGTTCAAATACCTGACGGTAATGTA   1740

Vaccine   1777  ATAAAAAAGATTCAGTATGGTGCTGTTGCTTCAGGAGAAAAACAAACCAAGGCAGCTAAT   1836
                ||||||||||||||||||||||||||||||||||||||||||||||||||||||||||||
MA104(JP)1741   ATAAAAAAGATTCAGTATGGTGCTGTTGCTTCAGGAGAAAAACAAACCAAGGCAGCTAAT   1800

Vaccine   1837  TCTATAGCTAATTTGGCACTCATTAAAACGGTATTGTCAAGAATTGCAAATAAATATTCT   1896
                ||||||||||||||||||||||||||||||||||||||||||||||||||||||||||||
MA104(JP)1801   TCTATAGCTAATTTGGCACTCATTAAAACGGTATTGTCAAGAATTGCAAATAAATATTCT   1860
```

FIG. 35B

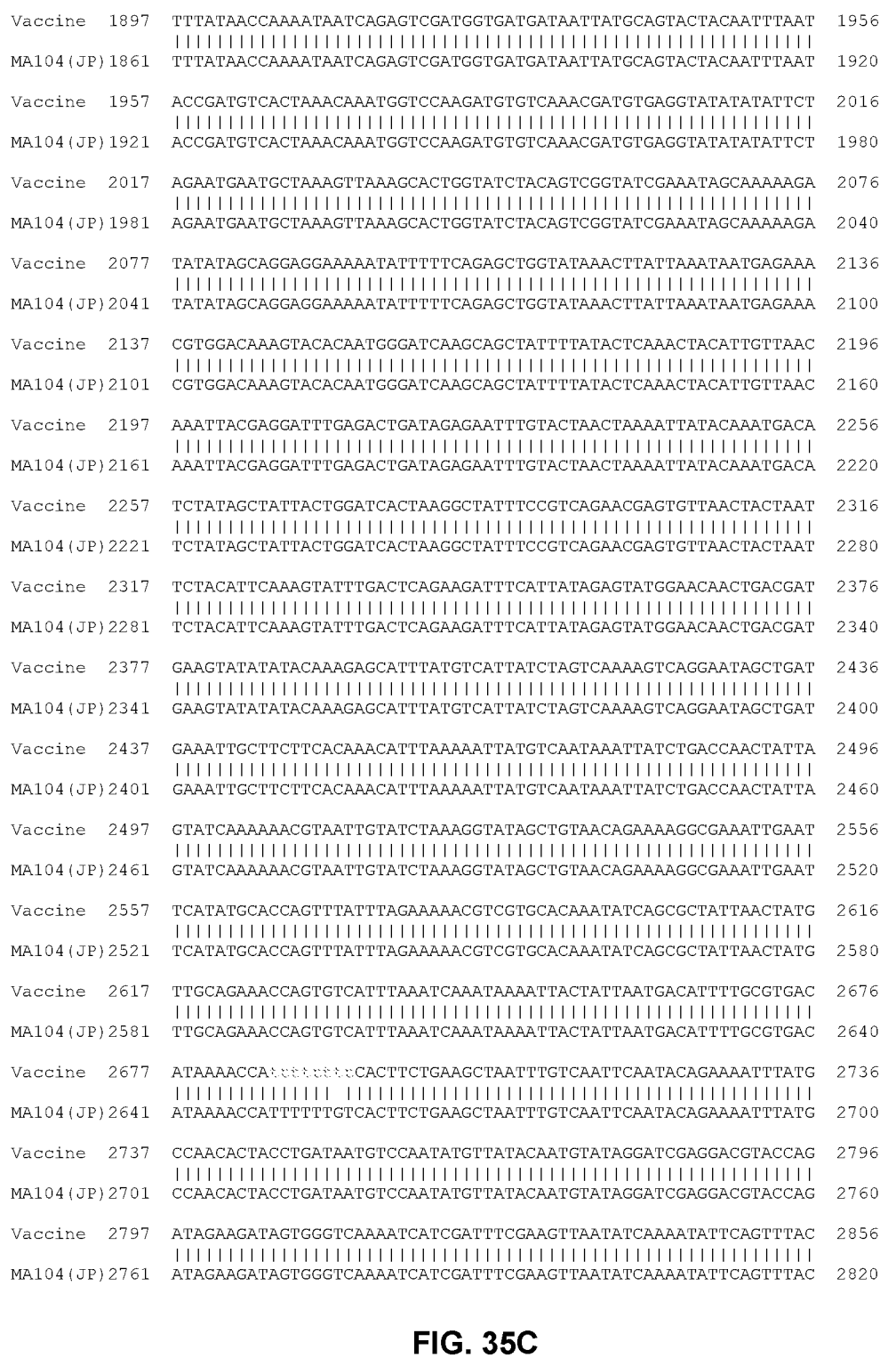

```
Vaccine   1897  TTTATAACCAAAATAATCAGAGTCGATGGTGATGATAATTATGCAGTACTACAATTTAAT  1956
                ||||||||||||||||||||||||||||||||||||||||||||||||||||||||||||
MA104(JP)1861   TTTATAACCAAAATAATCAGAGTCGATGGTGATGATAATTATGCAGTACTACAATTTAAT  1920

Vaccine   1957  ACCGATGTCACTAAACAAATGGTCCAAGATGTGTCAAACGATGTGAGGTATATATATTCT  2016
                ||||||||||||||||||||||||||||||||||||||||||||||||||||||||||||
MA104(JP)1921   ACCGATGTCACTAAACAAATGGTCCAAGATGTGTCAAACGATGTGAGGTATATATATTCT  1980

Vaccine   2017  AGAATGAATGCTAAAGTTAAAGCACTGGTATCTACAGTCGGTATCGAAATAGCAAAAAGA  2076
                ||||||||||||||||||||||||||||||||||||||||||||||||||||||||||||
MA104(JP)1981   AGAATGAATGCTAAAGTTAAAGCACTGGTATCTACAGTCGGTATCGAAATAGCAAAAAGA  2040

Vaccine   2077  TATATAGCAGGAGGAAAAATATTTTTCAGAGCTGGTATAAACTTATTAAATAATGAGAAA  2136
                ||||||||||||||||||||||||||||||||||||||||||||||||||||||||||||
MA104(JP)2041   TATATAGCAGGAGGAAAAATATTTTTCAGAGCTGGTATAAACTTATTAAATAATGAGAAA  2100

Vaccine   2137  CGTGGACAAAGTACACAATGGGATCAAGCAGCTATTTTATACTCAAACTACATTGTTAAC  2196
                ||||||||||||||||||||||||||||||||||||||||||||||||||||||||||||
MA104(JP)2101   CGTGGACAAAGTACACAATGGGATCAAGCAGCTATTTTATACTCAAACTACATTGTTAAC  2160

Vaccine   2197  AAATTACGAGGATTTGAGACTGATAGAGAATTTGTACTAACTAAAATTATACAAATGACA  2256
                ||||||||||||||||||||||||||||||||||||||||||||||||||||||||||||
MA104(JP)2161   AAATTACGAGGATTTGAGACTGATAGAGAATTTGTACTAACTAAAATTATACAAATGACA  2220

Vaccine   2257  TCTATAGCTATTACTGGATCACTAAGGCTATTTCCGTCAGAACGAGTGTTAACTACTAAT  2316
                ||||||||||||||||||||||||||||||||||||||||||||||||||||||||||||
MA104(JP)2221   TCTATAGCTATTACTGGATCACTAAGGCTATTTCCGTCAGAACGAGTGTTAACTACTAAT  2280

Vaccine   2317  TCTACATTCAAAGTATTTGACTCAGAAGATTTCATTATAGAGTATGGAACAACTGACGAT  2376
                ||||||||||||||||||||||||||||||||||||||||||||||||||||||||||||
MA104(JP)2281   TCTACATTCAAAGTATTTGACTCAGAAGATTTCATTATAGAGTATGGAACAACTGACGAT  2340

Vaccine   2377  GAAGTATATATACAAAGAGCATTTATGTCATTATCTAGTCAAAAGTCAGGAATAGCTGAT  2436
                ||||||||||||||||||||||||||||||||||||||||||||||||||||||||||||
MA104(JP)2341   GAAGTATATATACAAAGAGCATTTATGTCATTATCTAGTCAAAAGTCAGGAATAGCTGAT  2400

Vaccine   2437  GAAATTGCTTCTTCACAAACATTTAAAAATTATGTCAATAAATTATCTGACCAACTATTA  2496
                ||||||||||||||||||||||||||||||||||||||||||||||||||||||||||||
MA104(JP)2401   GAAATTGCTTCTTCACAAACATTTAAAAATTATGTCAATAAATTATCTGACCAACTATTA  2460

Vaccine   2497  GTATCAAAAAAACGTAATTGTATCTAAAGGTATAGCTGTAACAGAAAAGGCGAAATTGAAT  2556
                ||||||||||||||||||||||||||||||||||||||||||||||||||||||||||||
MA104(JP)2461   GTATCAAAAAAACGTAATTGTATCTAAAGGTATAGCTGTAACAGAAAAGGCGAAATTGAAT  2520

Vaccine   2557  TCATATGCACCAGTTTATTTAGAAAAACGTCGTGCACAAATATCAGCGCTATTAACTATG  2616
                ||||||||||||||||||||||||||||||||||||||||||||||||||||||||||||
MA104(JP)2521   TCATATGCACCAGTTTATTTAGAAAAACGTCGTGCACAAATATCAGCGCTATTAACTATG  2580

Vaccine   2617  TTGCAGAAACCAGTGTCATTTAAATCAAATAAAATTACTATTAATGACATTTTGCGTGAC  2676
                ||||||||||||||||||||||||||||||||||||||||||||||||||||||||||||
MA104(JP)2581   TTGCAGAAACCAGTGTCATTTAAATCAAATAAAATTACTATTAATGACATTTTGCGTGAC  2640

Vaccine   2677  ATAAAACCA[illegible]CACTTCTGAAGCTAATTTGTCAATTCAATACAGAAAATTTATG  2736
                |||||||||||||||| |||||||||||||||||||||||||||||||||||||||||||
MA104(JP)2641   ATAAAACCATTTTTTGTCACTTCTGAAGCTAATTTGTCAATTCAATACAGAAAATTTATG  2700

Vaccine   2737  CCAACACTACCTGATAATGTCCAATATGTTATACAATGTATAGGATCGAGGACGTACCAG  2796
                ||||||||||||||||||||||||||||||||||||||||||||||||||||||||||||
MA104(JP)2701   CCAACACTACCTGATAATGTCCAATATGTTATACAATGTATAGGATCGAGGACGTACCAG  2760

Vaccine   2797  ATAGAAGATAGTGGGTCAAAATCATCGATTTCGAAGTTAATATCAAAATATTCAGTTTAC  2856
                ||||||||||||||||||||||||||||||||||||||||||||||||||||||||||||
MA104(JP)2761   ATAGAAGATAGTGGGTCAAAATCATCGATTTCGAAGTTAATATCAAAATATTCAGTTTAC  2820
```

FIG. 35C

```
Vaccine   2857  AAACCATCGATTGAAGAACTATATAAAGTTATATCTTTAAGAGAACAAGAAATACAGTTG  2916
                ||||||||||||||||||||||||||||||||||||||||||||||||||||||||||||
MA104(JP)2821  AAACCATCGATTGAAGAACTATATAAAGTTATATCTTTAAGAGAACAAGAAATACAGTTG  2880

Vaccine   2917  TATTTAGTTTCATTAGGAGTTCCGCTAGTTGATGCAAGCACGTACGTCGGGTCAAGAATA  2976
                ||||||||||||||||||||||||||||||||||||||||||||||||||||||||||||
MA104(JP)2881  TATTTAGTTTCATTAGGAGTTCCGCTAGTTGATGCAAGCACGTACGTCGGGTCAAGAATA  2940

Vaccine   2977  TATTCGCAAGATAAATATAAAATATTAGAATCTTACGTATATAATTTATTATCAATTAAT  3036
                ||||||||||||||||||||||||||||||||||||||||||||||||||||||||||||
MA104(JP)2941  TATTCGCAAGATAAATATAAAATATTAGAATCTTACGTATATAATTTATTATCAATTAAT  3000

Vaccine   3037  TATGGATGTTATCAATTATTCGATTTTAATTCTCCAGATTTAGAGAGACTTATACGAATT  3096
                ||||||||||||||||||||||||||||||||||||||||||||||||||||||||||||
MA104(JP)3001  TATGGATGTTATCAATTATTCGATTTTAATTCTCCAGATTTAGAGAGACTTATACGAATT  3060

Vaccine   3097  CCTTTTAAAGGTAAGATACCAGCTGTAACATTTATATTACATCTTTACGCTAAACTTGAA  3156
                ||||||||||||||||||||||||||||||||||||||||||||||||||||||||||||
MA104(JP)3061  CCTTTTAAAGGTAAGATACCAGCTGTAACATTTATATTACATCTTTACGCTAAACTTGAA  3120

Vaccine   3157  ATAATAAACTATGCTATTAAGAACGGAGCTTGGATCAGCTTGTTTTGTAACTATCCAAAA  3216
                ||||||||||||||||||||||||||||||||||||||||||||||||||||||||||||
MA104(JP)3121  ATAATAAACTATGCTATTAAGAACGGAGCTTGGATCAGCTTGTTTTGTAACTATCCAAAA  3180

Vaccine   3217  TCTGAGATGATTAAATTATGGAAGAAAATGTGGAATATAACAGCATTACGGTCTCCCTAT  3276
                ||||||||||||||||||||||||||||||||||||||||||||||||||||||||||||
MA104(JP)3181  TCTGAGATGATTAAATTATGGAAGAAAATGTGGAATATAACAGCATTACGGTCTCCCTAT  3240

Vaccine   3277  ACTAGTGCGAATTTCTTTCAAGATTAG  3303
                |||||||||||||||||||||||||||
MA104(JP)3241  ACTAGTGCGAATTTCTTTCAAGATTAG  3267
```

FIG. 35D

Comparison of amino acid (coding region) sequences of RV3 VP1

```
Vaccine   37     MGKYNLILSEYLSFVYNSQSAVQIPIYYSSNSELEKRCIEFHAKCVDSSKKGLSLKPLFE  216
                 MGKYNLILSEYLSFVYNSQSAVQIPIYYSSNSELEKRCIEFHAKCVDSSKKGLSLKPLFE
MA104(JP)1       MGKYNLILSEYLSFVYNSQSAVQIPIYYSSNSELEKRCIEFHAKCVDSSKKGLSLKPLFE  60

Vaccine   217    KYKDVIDNATllsllsysyDKYNAVERKLVNYAKGKPLEADLTANELDYENNKITSELFQ  396
                 KYKDVIDNATLLSLLSYSYDKYNAVERKLVNYAKGKPLEADLTANELDYENNKITSELFQ
MA104(JP)61      KYKDVIDNATLLSLLSYSYDKYNAVERKLVNYAKGKPLEADLTANELDYENNKITSELFQ  120

Vaccine   397    SAEEYTDSLMDPAILTSLSSNLNAVMFWLERHSNDVADANKIYKRRLDLFTIVASTINKY  576
                 SAEEYTDSLMDPAILTSLSSNLNAVMFWLERHSNDVADANKIYKRRLDLFTIVASTINKY
MA104(JP)121     SAEEYTDSLMDPAILTSLSSNLNAVMFWLERHSNDVADANKIYKRRLDLFTIVASTINKY  180

Vaccine   577    GVPRHNEKYRYEYEVMKDKPYYLVTWANSSIEMLMSVFSHEDYLIAKELIILSYSNRSTL  756
                 GVPRHNEKYRYEYEVMKDKPYYLVTWANSSIEMLMSVFSHEDYLIAKELIILSYSNRSTL
MA104(JP)181     GVPRHNEKYRYEYEVMKDKPYYLVTWANSSIEMLMSVFSHEDYLIAKELIILSYSNRSTL  240

Vaccine   757    AKLVSSPMSILVALIDINGTFITNEELELEFSDKYVKAIVPDQIFDELQEMIDNMRKVGL  936
                 AKLVSSPMSILVALIDINGTFITNEELELEFSDKYVKAIVPDQIFDELQEMIDNMRKVGL
MA104(JP)241     AKLVSSPMSILVALIDINGTFITNEELELEFSDKYVKAIVPDQIFDELQEMIDNMRKVGL  300

Vaccine   937    VDIPKMIQEWLIDCSLEKFTLMSKIYSWSFHVGFRKQKMIDAALDQLKTEYTEDVDNEMY  1116
                 VDIPKMIQEWLIDCSLEKFTLMSKIYSWSFHVGFRKQKMIDAALDQLKTEYTEDVDNEMY
MA104(JP)301     VDIPKMIQEWLIDCSLEKFTLMSKIYSWSFHVGFRKQKMIDAALDQLKTEYTEDVDNEMY  360

Vaccine   1117   NEYTMLIRDEIVKMLEVPVKHDDHLLRDSELAGLLSMSSASNGESRQLKFGRKTIFSTKK  1296
                 NEYTMLIRDEIVKMLEVPVKHDDHLLRDSELAGLLSMSSASNGESRQLKFGRKTIFSTKK
MA104(JP)361     NEYTMLIRDEIVKMLEVPVKHDDHLLRDSELAGLLSMSSASNGESRQLKFGRKTIFSTKK  420

Vaccine   1297   NMHVMDDIAHGKYTPGVIPPVNVDRPIPLGRRDVPGRRTRIIFILPYEYFIAQHAVVEKM  1476
                 NMHVMDDIAHGKYTPGVIPPVNVDRPIPLGRRDVPGRRTRIIFILPYEYFIAQHAVVEKM
MA104(JP)421     NMHVMDDIAHGKYTPGVIPPVNVDRPIPLGRRDVPGRRTRIIFILPYEYFIAQHAVVEKM  480

Vaccine   1477   LSYAKHTREYAEFYSQSNQLLSYGDVTRFLSNNSMVLYTDVSQWDSSQHNTQPFRKGIIM  1656
                 LSYAKHTREYAEFYSQSNQLLSYGDVTRFLSNNSMVLYTDVSQWDSSQHNTQPFRKGIIM
MA104(JP)481     LSYAKHTREYAEFYSQSNQLLSYGDVTRFLSNNSMVLYTDVSQWDSSQHNTQPFRKGIIM  540

Vaccine   1657   GLDMLSNMTNDPKVVQTLNLYKQTQINLMDSYVQIPDGNVIKKIQYGAVASGEKQTKAAN  1836
                 GLDMLSNMTNDPKVVQTLNLYKQTQINLMDSYVQIPDGNVIKKIQYGAVASGEKQTKAAN
MA104(JP)541     GLDMLSNMTNDPKVVQTLNLYKQTQINLMDSYVQIPDGNVIKKIQYGAVASGEKQTKAAN  600

Vaccine   1837   SIANLALIKTVLSRIANKYSFITKIIRVDGDDNYAVLQFNTDVTKQMVQDVSNDVRYIYS  2016
                 SIANLALIKTVLSRIANKYSFITKIIRVDGDDNYAVLQFNTDVTKQMVQDVSNDVRYIYS
MA104(JP)601     SIANLALIKTVLSRIANKYSFITKIIRVDGDDNYAVLQFNTDVTKQMVQDVSNDVRYIYS  660

Vaccine   2017   RMNAKVKALVSTVGIEIAKRYIAGGKIFFRAGINLLNNEKRGQSTQWDQAAILYSNYIVN  2196
                 RMNAKVKALVSTVGIEIAKRYIAGGKIFFRAGINLLNNEKRGQSTQWDQAAILYSNYIVN
MA104(JP)661     RMNAKVKALVSTVGIEIAKRYIAGGKIFFRAGINLLNNEKRGQSTQWDQAAILYSNYIVN  720

Vaccine   2197   KLRGFETDREFVLTKIIQMTSIAITGSLRLFPSERVLTTNSTFKVFDSEDFIIEYGTTDD  2376
                 KLRGFETDREFVLTKIIQMTSIAITGSLRLFPSERVLTTNSTFKVFDSEDFIIEYGTTDD
MA104(JP)721     KLRGFETDREFVLTKIIQMTSIAITGSLRLFPSERVLTTNSTFKVFDSEDFIIEYGTTDD  780

Vaccine   2377   EVYIQRAFMSLSSQKSGIADEIASSQTFKNYVNKLSDQLLVSKNVIVSKGIAVTEKAKLN  2556
                 EVYIQRAFMSLSSQKSGIADEIASSQTFKNYVNKLSDQLLVSKNVIVSKGIAVTEKAKLN
MA104(JP)781     EVYIQRAFMSLSSQKSGIADEIASSQTFKNYVNKLSDQLLVSKNVIVSKGIAVTEKAKLN  840
Vaccine   2557   SYAPVYLEKRRAQISALLTMLQKPVSFKSNKITINDILRDIKPFFFTSEANLSIQYRKFM  2736
                 SYAPVYLEKRRAQISALLTMLQKPVSFKSNKITINDILRDIKPFF TSEANLSIQYRKFM
MA104(JP)841     SYAPVYLEKRRAQISALLTMLQKPVSFKSNKITINDILRDIKPFFVTSEANLSIQYRKFM  900
Vaccine   2737   PTLPDNVQYVIQCIGSRTYQIEDsgskssiskliskysvykPSIEELYKVISLREQEIQL  2916
                 PTLPDNVQYVIQCIGSRTYQIEDSGSKSSISKLISKYSVYKPSIEELYKVISLREQEIQL
MA104(JP)901     PTLPDNVQYVIQCIGSRTYQIEDSGSKSSISKLISKYSVYKPSIEELYKVISLREQEIQL  960
Vaccine   2917   YLVSLGVPLVDASTYVGSRIYSQDKYKILESYVYNLLSINYGCYQLFDFNSPDLERLIRI  3096
                 YLVSLGVPLVDASTYVGSRIYSQDKYKILESYVYNLLSINYGCYQLFDFNSPDLERLIRI
MA104(JP)961     YLVSLGVPLVDASTYVGSRIYSQDKYKILESYVYNLLSINYGCYQLFDFNSPDLERLIRI  1020
Vaccine   3097   PFKGKIPAVTFILHLYAKLEIINYAIKNGAWISLFCNYPKSEMIKLWKKMWNITALRSPY  3276
                 PFKGKIPAVTFILHLYAKLEIINYAIKNGAWISLFCNYPKSEMIKLWKKMWNITALRSPY
MA104(JP)1021    PFKGKIPAVTFILHLYAKLEIINYAIKNGAWISLFCNYPKSEMIKLWKKMWNITALRSPY  1080
Vaccine   3277   TSANFFQD  3302
                 TSANFFQD
MA104(JP)1081    TSANFFQD  1088
```

FIG. 36

VP2 sequence
MA104-adapted RV3 VP2 (SEQ ID NO:51)

```
   1 ATGGCGTACA GGAAGCGCGG AGTTAAACGT GAAAACTTAC CACAACAAAA TGAACGTCTG
  61 CAAGAAAAAG AAACTGAAAA TAATACAGAC GTAACCATGG AAAATAAAAA TAACAATAGA
 121 AGGCAGCAAT TATCTGACAA AGTGTTATCA CAAAAAGAGG AAATAATAAC TGATGTACAA
 181 GATGACATTA AAATAGCTGA TGAGGTTAAA AAATCATCAA AAGAAGAGTC AAAACAGTTA
 241 CTTGAAATAT TAAAAACGAA AGAAGATCAT CAGAAAGAAG TACAGTACGA AATTCTACAA
 301 AAAACAATAC CGACTTTTGA ACCAAAAGAA TCAATTTTGA AAAAATTAGA AGATATAAGA
 361 CCAGAACAAG CTAAGAAGCA AATGAAATTG TTTAGAATAT TTGAACCAAG ACAATTACCA
 421 ATCTATCGAG CAAATGGTGA GAAAGAGTTA AGGAATAGAT GGTATTGGAA ATTGAAAAAG
 481 GATACACTGC CGGACGGAGA TTATGACGTA CGAGAGTATT TTTTAAATTT ATATGATCAA
 541 ATACTGATAG AAATGCCAGA TTATTTATTA CTAAAAGATA TGGCTGTAGA AAATAAAAAC
 601 TCTAGAGATG CTGGTAAAGT TGTAGATTCT GAGACTGCAA GTATTTGTGA TGCTATATTT
 661 CAAGATGAGG AGACAGAGGG AGTTATTAGA AGATTCATCG CAGATATGAG ACAACAAGTT
 721 CAAGCTGATA GAAATATTGT CAATTATCCA TCAATTTTGC ATCCGATTGA TCACGCATTT
 781 AATGAATACT TTTTGAATCA TCAATTAGTT GAACCATTGA ATAACGAAAT TATTTTTAAT
 841 TATATACCAG AAAGAATAAG GAATGATGTT AACTATATTT TGAATATGGA TATGAATTTG
 901 CCATCAACAG CGCGATATAT TAGACCAAAT CTATTGCAAG ATAGACTAAA TTTACATGAT
 961 AATTTTGAAT CATTATGGGA CACGATAACT ACATCAAATT ACATATTAGC AAGATCAGTC
1021 GTGCCTGATT TGAAGGAAAA AGAATTAGTT TCAACTGAAG CTCAGATCCA GAAAATGTCT
1081 CAAGATTTGC AGCTTGAAGC TTTAACAATA CAATCTGAAA CGCAGTTTCT GGCCGGTATA
1141 AATTCACAAG CAGCGAATGA TTGTTTTAAA ACACTGATAG CAGCTATGTT AAGCCAACGT
1201 ACAATGTCAT TAGATTTTGT AACTACGAAT TATATGTCAC TTATATCTGG CATGTGGCTA
1261 TTGACTGTTA TACCAAATGA TATGTTTCTT CGTGAGTCGC TAGTCGCATG CGAATTGGCT
1321 ATAATAAATA CTATAGTTTA TCCAGCATTT GGAATGCAAA GAATGCATTA TAGAAATGGC
1381 GATCCTCAGA CTCCATTTCA AATAGCAGAA CAACAGATAC AAAATTTTCA AGTAGCTAAT
1441 TGGTTACATT TTATTAACAA TAATAGATTT AGGCAAGTTG TTATTGATGG AGTGTTAAAT
1501 CAAACACTTA ATGACAACAT TAGGAATGGA CAAGTTATTA ATCAATTAAT GGAAGCATTA
1561 ATGCAGTTAT CTAGACAACA ATTTCCGACC ATGCCAGTTG ATTATAAAAG ATCAATCCAG
1621 AGAGGAATAT TGTTATTATC TAACAGATTA GGTCAGTTGG TTGATTTAAC AAGATTATTA
1681 TCATACAATT ATGAAACTCT AATGGCTTGT ATAACTATGA ACATGCAACA TGTTCAAACT
1741 CTCACTACCG AAAAATTACA ATTAACTTCT GTCACATCTT TATGTATGTT AATTGGAAAT
1801 ACCACAGTAA TTCCAGGTCC ACAAACACTA TTTCACTATT ATAACGTAAA TGTAAATTTT
1861 CATTCAAATT ATAACGAACG AATTAATGAT GCTGTGGCTA TTATTACGGC TGCTAATAGA
1921 TTAAACTTAT ATCAGAAAAA AATGAAATCA ATAGTTGAGG ATTTTTTGAA AAGATTGCAA
1981 ATTTTTGATG TACCACGAGT GCCAGATGAC CAAACGTACA GGTTGAGAGA CAGACTTAGA
2041 TTATTGCCAG TTGAAAGACG AAGACTTGAT ATATTTAACT TAATATTAAT GAATATGGAG
2101 CAGATCGAAC GAGCTTCAGA CAAAATTGCT CAAGGAGTAA TAATTGCTTA CAGAGATATG
2161 CAGCTAGAAA GAGATGAGAT GTATGGGTTT GTTAACATCG CTAGGAACCT CGATGGATAT
2221 CAACAAATCA ATTTGGAAGA GTTGATGAGA ACTGGGGACT ATGGTCAAAT TACTAATATG
2281 CTATTAAACA ACCAGCCTGT AGCTTTAGTA GGAGCATTAC CATTTGTGAC AGATTCATCA
2341 GTTATATCGC TCATTGCAAA ATTGGATGCC ACAGTTTTTG CTCAAATAGT TAAACTTAGA
2401 AAAGTGGACA CTTTAAAACC AATATTGTAT AAAATAAATT CTGATTCTAA TGATTTCTAT
2461 TTAGTTGCAA ATTATGATTG GATACCAACT TCAACCACAA AAGTTTATAA GCAAGTACCA
2521 CAACCTTTTG ATTTCAGAGC GTCAATGCAT ATGTTAACGT CTAATTTAAC TTTTACTGTT
2581 TATTCCGATT TGCTATCTTT CGTTTCTGCA GACACGGTTG AACCTATTAA CGCAATTGCT
2641 TTTGACAATA TGCGCATTAT GAACGAACTG TAA
```

FIG. 37

Amino acid (coding region) ADD31859 (SEQ ID NO:52)

```
  1 MAYRKRGVKR ENLPQQNERL QEKETENNTD VTMENKNNNR RQQLSDKVLS QKEEIITDVQ
 61 DDIKIADEVK KSSKEESKQL LEILKTKEDH QKEVQYEILQ KTIPTFEPKE SILKKLEDIR
121 PEQAKKQMKL FRIFEPRQLP IYRANGEKEL RNRWYWKLKK DTLPDGDYDV REYFLNLYDQ
181 ILIEMPDYLL LKDMAVENKN SRDAGKVVDS ETASICDAIF QDEETEGVIR RFIADMRQQV
241 QADRNIVNYP SILHPIDHAF NEYFLNHQLV EPLNNEIIFN YIPERIRNDV NYILNMDMNL
301 PSTARYIRPN LLQDRLNLHD NFESLWDTIT TSNYILARSV VPDLKEKELV STEAQIQKMS
361 QDLQLEALTI QSETQFLAGI NSQAANDCFK TLIAAMLSQR TMSLDFVTTN YMSLISGMWL
421 LTVIPNDMFL RESLVACELA IINTIVYPAF GMQRMHYRNG DPQTPFQIAE QQIQNFQVAN
481 WLHFINNNRF RQVVIDGVLN QTLNDNIRNG QVINQLMEAL MQLSRQQFPT MPVDYKRSIQ
541 RGILLLSNRL GQLVDLTRLL SYNYETLMAC ITMNMQHVQT LTTEKLQLTS VTSLCMLIGN
601 TTVIPGPQTL FHYYNVNVNF HSNYNERIND AVAIITAANR LNLYQKKMKS IVEDFLKRLQ
661 IFDVPRVPDD QTYRLRDRLR LLPVERRRLD IFNLILMNME QIERASDKIA QGVIIAYRDM
721 QLERDEMYGF VNIARNLDGY QQINLEELMR TGDYGQITNM LLNNQPVALV GALPFVTDSS
781 VISLIAKLDA TVFAQIVKLR KVDTLKPILY KINSDSNDFY LVANYDWIPT STTKVYKQVP
841 QPFDFRASMH MLTSNLTFTV YSDLLSFVSA DTVEPINAIA FDNMRIMNEL
```

FIG. 38

Vero-adapted (Vaccine) RV3 VP2 (SEQ ID NO:53)

```
   1 GGCTATTAAA GGTTCAATGG CGTACAGGAA GCGCGGAGTT AAACGTGAAA ACTTACCACA
  61 ACAAAATGAA CGTCTGCAAG AAAAAGAAAC TGAAAATAAT ACAGACGTAA CCATGGAAAA
 121 TAAAAATAAC AATAGAAGGC AGCAATTATC TGACAAAGTG TTATCACAAA AAGAGGAAAT
 181 AATAACTGAT GTACAAGATG ACATTAAAAT AGCTGATGAG GTTAAAAAAT CATCAAAAGA
 241 AGAGTCAAAA CAGTTACTTG AAATATTAAA AACGAAAGAA GATCATCAGA AAGAAGTACA
 301 GTACGAAATT CTACAAAAAA CAATACCGAC TTTTGAACCA AAAGAATCAA TTTTGAAAAA
 361 ATTAGAAGAT ATAAGACCAG AACAAGCTAA GAAGCAAATG AAATTGTTTA GAATATTTGA
 421 ACCAAGACAA TTACCAATCT ATCGAGCAAA TGGTGAGAAA GAGTTAAGGA ATAGATGGTA
 481 TTGGAAATTG AAAAAGGATA CACTGCCGGA CGGAGATTAT GACGTACGAG AGTATTTTTT
 541 AAATTTATAT GATCAAATAC TGATAGAAAT GCCAGATTAT TTATTACTAA AAGATATGGC
 601 TGTAGAAAAT AAAAACTCTA GAGATGCTGG TAAAGTTGTA GATTCTGAGA CTGCAAGTAT
 661 TTGTGATGCT ATATTTCAAG ATGAGGAGAC AGAGGGAGTT ATTAGAAGAT TCATCGCAGA
 721 TATGAGACAA CAAGTTCAAG CTGATAGAAA TATTGTCAAT TATCCATCAA TTTTGCATCC
 781 GATTGATCAC GCATTTAATG AATACTTTTT GAATCATCAA TTAGTTGAAC CATTGAATAA
 841 CGAAATTATT TTTAATTATA TACCAGAAAG AATAAGGAAT GATGTTAACT ATATTTTGAA
 901 TATGGATATG AATTTGCCAT CAACAGCGCG ATATATTAGA CCAAATCTAT TGCAAGATAG
 961 ACTAAATTTA CATGATAATT TTGAATCATT ATGGGACACG ATAACTACAT CAAATTACAT
1021 ATTAGCAAGA TCAGTCGTGC CTGATTTGAA GGAAAAAGAA TTAGTTTCAA CTGAAGCTCA
1081 GATCCAGAAA ATGTCTCAAG ATTTGCAGCT TGAAGCTTTA ACAATACAAT CTGAAACGCA
1141 GTTTCTGGCC GGTATAAATT CACAAGCAGC GAATGATTGT TTTAAAACAC TGATAGCAGC
1201 TATGTTAAGC CAACGTACAA TGTCATTAGA TTTTGTAACT ACGAATTATA TGTCACTTAT
1261 ATCTGGCATG TGGCTATTGA CTGTTATACC AAATGATATG TTTCTTCGTG AGTCGCTAGT
1321 CGCATGCGAA TTGGCTATAA TAAATACTAT AGTTTATCCA GCATTTGGAA TGCAAAGAAT
1381 GCATTATAGA AATGGCGATC CTCAGACTCC ATTTCAAATA GCAGAACAAC AGATACAAAA
1441 TTTTCAAGTA GCTAATTGGT TACATTTTAT TAACAATAAT AGATTTAGGC AAGTTGTTAT
1501 TGATGGAGTG TTAAATCAAA CACTTAATGA CAACATTAGG AATGGACAAG TTATTAATCA
1561 ATTAATGGAA GCATTAATGC AGTTATCTAG ACAACAATTT CCGACCATGC CAGTTGATTA
1621 TAAAAGATCA ATCCAGAGAG GAATATTGTT ATTATCTAAC AGATTAGGTC AGTTGGTTGA
1681 TTTAACAAGA TTATTATCAT ACAATTATGA AACTCTAATG GCTTGTATAA CTATGAACAT
1741 GCAACATGTT CAAACTCTCA CTACCGAAAA ATTACAATTA ACTTCTGTCA CATCTTTATG
1801 TATGTTAATT GGAAATACCA CAGTAATTCC AGGTCCACAA ACACTATTTC ACTATTATAA
1861 CGTAAATGTA AATTTTCATT CAAATTATAA CGAACGAATT AATGATGCTG TGGCTATTAT
1921 TACGGCTGCT AATAGATTAA ACTTATATCA GAAAAAAATG AAATCAATAG TTGAGGATTT
1981 TTTGAAAAGA TTGCAAATTT TTGATGTACC ACGAGTGCCA GATGACCAAA CGTACAGGTT
2041 GAGAGACAGA CTTAGATTAT TGCCAGTTGA AAGACGAAGA CTTGATATAT TTAACTTAAT
2101 ATTAATGAAT ATGGAGCAGA TCGAACGAGC TTCAGACAAA ATTGCTCAAG GAGTAATAAT
2161 TGCTTACAGA GATATGCAGC TAGAAAGAGA TGAGATGTAT GGGTTTGTTA ACATCGCTAG
2221 GAACCTCGAT GGATATCAAC AAATCAATTT GGAAGAGTTG ATGAGAACTG GGGACTATGG
2281 TCAAATTACT AATATGCTAT TAAACAACCA GCCTGTAGCT TTAGTAGGAG CATTACCATT
2341 TGTGACAGAT TCATCAGTTA TATCGCTCAT TGCAAAATTG GATGCCACAG TTTTTGCTCA
2401 AATAGTTAAA CTTAGAAAAG TGGACACTTT AAAACCAATA TTGTATAAAA TAAATTCTGA
2461 TTCTAATGAT TTCTATTTAG TTGCAAATTA TGATTGGATA CCAACTTCAA CCACAAAAGT
2521 TTATAAGCAA GTACCACAAC CTTTTGATTT CAGAGCGTCA ATGCATATGT TAACGTCTAA
2581 TTTAACTTTT ACTGTTTATT CCGATTTGCT ATCTTTCGTT TCTGCAGACA CGGTTGAACC
2641 TATTAACGCA ATTGCTTTTG ACAATATGCG CATTATGAAC GAACTGTAAA CGCCAACCGC
2701 ACTGTGGAGA TATGACC
```

FIG. 39

Amino acid (coding region) [SEQ ID NO:54]

```
  1 MAYRKRGVKR ENLPQQNERL QEKETENNTD VTMENKNNNR RQQLSDKVLS QKEEIITDVQ
 61 DDIKIADEVK KSSKEESKQL LEILKTKEDH QKEVQYEILQ KTIPTFEPKE SILKKLEDIR
121 PEQAKKQMKL FRIFEPRQLP IYRANGEKEL RNRWYWKLKK DTLPDGDYDV REYFLNLYDQ
181 ILIEMPDYLL LKDMAVENKN SRDAGKVVDS ETASICDAIF QDEETEGVIR RFIADMRQQV
241 QADRNIVNYP SILHPIDHAF NEYFLNHQLV EPLNNEIIFN YIPERIRNDV NYILNMDMNL
301 PSTARYIRPN LLQDRLNLHD NFESLWDTIT TSNYILARSV VPDLKEKELV STEAQIQKMS
361 QDLQLEALTI QSETQFLAGI NSQAANDCFK TLIAAMLSQR TMSLDFVTTN YMSLISGMWL
421 LTVIPNDMFL RESLVACELA IINTIVYPAF GMQRMHYRNG DPQTPFQIAE QQIQNFQVAN
481 WLHFINNNRF RQVVIDGVLN QTLNDNIRNG QVINQLMEAL MQLSRQQFPT MPVDYKRSIQ
541 RGILLLSNRL GQLVDLTRLL SYNYETLMAC ITMNMQHVQT LTTEKLQLTS VTSLCMLIGN
601 TTVIPGPQTL FHYYNVNVNF HSNYNERIND AVAIITAANR LNLYQKKMKS IVEDFLKRLQ
661 IFDVPRVPDD QTYRLRDRLR LLPVERRRLD IFNLILMNME QIERASDKIA QGVIIAYRDM
721 QLERDEMYGF VNIARNLDGY QQINLEELMR TGDYGQITNM LLNNQPVALV GALPFVTDSS
781 VISLIAKLDA TVFAQIVKLR KVDTLKPILY KINSDSNDFY LVANYDWIPT STTKVYKQVP
841 QPFDFRASMH MLTSNLTFTV YSDLLSFVSA DTVEPINAIA FDNMRIMNEL
```

FIG. 40

Comparison of nucleotide sequences of RV3 VP2

```
Vaccine   17    ATGGCGTACAGGAAGCGCGGAGTTAAACGTGAAAACTTACCACAACAAAATGAACGTCTG   76
                ||||||||||||||||||||||||||||||||||||||||||||||||||||||||||||
MA104(JP)1      ATGGCGTACAGGAAGCGCGGAGTTAAACGTGAAAACTTACCACAACAAAATGAACGTCTG   60

Vaccine   77    CAAGAAAAAGAAACTGAAAATAATACAGACGTAACCATGGAAAATAAAAATAACAATAGA   136
                ||||||||||||||||||||||||||||||||||||||||||||||||||||||||||||
MA104(JP)61     CAAGAAAAAGAAACTGAAAATAATACAGACGTAACCATGGAAAATAAAAATAACAATAGA   120

Vaccine   137   AGGCAGCAATTATCTGACAAAGTGTTATCACAAAAAGAGGAAATAATAACTGATGTACAA   196
                ||||||||||||||||||||||||||||||||||||||||||||||||||||||||||||
MA104(JP)121    AGGCAGCAATTATCTGACAAAGTGTTATCACAAAAAGAGGAAATAATAACTGATGTACAA   180

Vaccine   197   GATGACATTAAAATAGCTGATGAGGTTAAAAAATCATCAAAAGAAGAGTCAAAACAGTTA   256
                ||||||||||||||||||||||||||||||||||||||||||||||||||||||||||||
MA104(JP)181    GATGACATTAAAATAGCTGATGAGGTTAAAAAATCATCAAAAGAAGAGTCAAAACAGTTA   240

Vaccine   257   CTTGAAATATTAAAAACGAAAGAAGATCATCAGAAAGAAGTACAGTACGAAATTCTACAA   316
                ||||||||||||||||||||||||||||||||||||||||||||||||||||||||||||
MA104(JP)241    CTTGAAATATTAAAAACGAAAGAAGATCATCAGAAAGAAGTACAGTACGAAATTCTACAA   300

Vaccine   317   AAAACAATACCGACTTTTGAACCAAAAGAATCAATTTTGAAAAAATTAGAAGATATAAGA   376
                ||||||||||||||||||||||||||||||||||||||||||||||||||||||||||||
MA104(JP)301    AAAACAATACCGACTTTTGAACCAAAAGAATCAATTTTGAAAAAATTAGAAGATATAAGA   360

Vaccine   377   CCAGAACAAGCTAAGAAGCAAATGAAATTGTTTAGAATATTTGAACCAAGACAATTACCA   436
                ||||||||||||||||||||||||||||||||||||||||||||||||||||||||||||
MA104(JP)361    CCAGAACAAGCTAAGAAGCAAATGAAATTGTTTAGAATATTTGAACCAAGACAATTACCA   420

Vaccine   437   ATCTATCGAGCAAATGGTGAGAAAGAGTTAAGGAATAGATGGTATTGGAAATTGAAAAAG   496
                ||||||||||||||||||||||||||||||||||||||||||||||||||||||||||||
MA104(JP)421    ATCTATCGAGCAAATGGTGAGAAAGAGTTAAGGAATAGATGGTATTGGAAATTGAAAAAG   480

Vaccine   497   GATACACTGCCGGACGGAGATTATGACGTACGAGAGTATTTTTTAAATTTATATGATCAA   556
                ||||||||||||||||||||||||||||||||||||||||||||||||||||||||||||
MA104(JP)481    GATACACTGCCGGACGGAGATTATGACGTACGAGAGTATTTTTTAAATTTATATGATCAA   540

Vaccine   557   ATACTGATAGAAATGCCAGATTATTTATTACTAAAAGATATGGCTGTAGAAAATAAAAAC   616
                ||||||||||||||||||||||||||||||||||||||||||||||||||||||||||||
MA104(JP)541    ATACTGATAGAAATGCCAGATTATTTATTACTAAAAGATATGGCTGTAGAAAATAAAAAC   600

Vaccine   617   TCTAGAGATGCTGGTAAAGTTGTAGATTCTGAGACTGCAAGTATTTGTGATGCTATATTT   676
                ||||||||||||||||||||||||||||||||||||||||||||||||||||||||||||
MA104(JP)601    TCTAGAGATGCTGGTAAAGTTGTAGATTCTGAGACTGCAAGTATTTGTGATGCTATATTT   660

Vaccine   677   CAAGATGAGGAGACAGAGGGAGTTATTAGAAGATTCATCGCAGATATGAGACAACAAGTT   736
                ||||||||||||||||||||||||||||||||||||||||||||||||||||||||||||
MA104(JP)661    CAAGATGAGGAGACAGAGGGAGTTATTAGAAGATTCATCGCAGATATGAGACAACAAGTT   720

Vaccine   737   CAAGCTGATAGAAATATTGTCAATTATCCATCAATTTTGCATCCGATTGATCACGCATTT   796
                ||||||||||||||||||||||||||||||||||||||||||||||||||||||||||||
MA104(JP)721    CAAGCTGATAGAAATATTGTCAATTATCCATCAATTTTGCATCCGATTGATCACGCATTT   780

Vaccine   797   AATGAATACTTTTTGAATCATCAATTAGTTGAACCATTGAATAACGAAATTATTTTTAAT   856
                ||||||||||||||||||||||||||||||||||||||||||||||||||||||||||||
MA104(JP)781    AATGAATACTTTTTGAATCATCAATTAGTTGAACCATTGAATAACGAAATTATTTTTAAT   840

Vaccine   857   TATATACCAGAAAGAATAAGGAATGATGTTAACTATATTTTGAATATGGATATGAATTTG   916
                ||||||||||||||||||||||||||||||||||||||||||||||||||||||||||||
MA104(JP)841    TATATACCAGAAAGAATAAGGAATGATGTTAACTATATTTTGAATATGGATATGAATTTG   900

Vaccine   917   CCATCAACAGCGCGATATATTAGACCAAATCTATTGCAAGATAGACTAAATTTACATGAT   976
                ||||||||||||||||||||||||||||||||||||||||||||||||||||||||||||
MA104(JP)901    CCATCAACAGCGCGATATATTAGACCAAATCTATTGCAAGATAGACTAAATTTACATGAT   960

Vaccine   977   AATTTTGAATCATTATGGGACACGATAACTACATCAAATTACATATTAGCAAGATCAGTC   1036
                ||||||||||||||||||||||||||||||||||||||||||||||||||||||||||||
MA104(JP)961    AATTTTGAATCATTATGGGACACGATAACTACATCAAATTACATATTAGCAAGATCAGTC   1020
```

FIG. 41A

```
Vaccine    1037  GTGCCTGATTTGAAGGAAAAAGAATTAGTTTCAACTGAAGCTCAGATCCAGAAAATGTCT  1096
                 ||||||||||||||||||||||||||||||||||||||||||||||||||||||||||||
MA104(JP)  1021  GTGCCTGATTTGAAGGAAAAAGAATTAGTTTCAACTGAAGCTCAGATCCAGAAAATGTCT  1080

Vaccine    1097  CAAGATTTGCAGCTTGAAGCTTTAACAATACAATCTGAAACGCAGTTTCTGGCCGGTATA  1156
                 ||||||||||||||||||||||||||||||||||||||||||||||||||||||||||||
MA104(JP)  1081  CAAGATTTGCAGCTTGAAGCTTTAACAATACAATCTGAAACGCAGTTTCTGGCCGGTATA  1140

Vaccine    1157  AATTCACAAGCAGCGAATGATTGTTTTAAAACACTGATAGCAGCTATGTTAAGCCAACGT  1216
                 ||||||||||||||||||||||||||||||||||||||||||||||||||||||||||||
MA104(JP)  1141  AATTCACAAGCAGCGAATGATTGTTTTAAAACACTGATAGCAGCTATGTTAAGCCAACGT  1200

Vaccine    1217  ACAATGTCATTAGATTTTGTAACTACGAATTATATGTCACTTATATCTGGCATGTGGCTA  1276
                 ||||||||||||||||||||||||||||||||||||||||||||||||||||||||||||
MA104(JP)  1201  ACAATGTCATTAGATTTTGTAACTACGAATTATATGTCACTTATATCTGGCATGTGGCTA  1260

Vaccine    1277  TTGACTGTTATACCAAATGATATGTTTCTTCGTGAGTCGCTAGTCGCATGCGAATTGGCT  1336
                 ||||||||||||||||||||||||||||||||||||||||||||||||||||||||||||
MA104(JP)  1261  TTGACTGTTATACCAAATGATATGTTTCTTCGTGAGTCGCTAGTCGCATGCGAATTGGCT  1320

Vaccine    1337  ATAATAAATACTATAGTTTATCCAGCATTTGGAATGCAAAGAATGCATTATAGAAATGGC  1396
                 ||||||||||||||||||||||||||||||||||||||||||||||||||||||||||||
MA104(JP)  1321  ATAATAAATACTATAGTTTATCCAGCATTTGGAATGCAAAGAATGCATTATAGAAATGGC  1380

Vaccine    1397  GATCCTCAGACTCCATTTCAAATAGCAGAACAACAGATACAAAATTTTCAAGTAGCTAAT  1456
                 ||||||||||||||||||||||||||||||||||||||||||||||||||||||||||||
MA104(JP)  1381  GATCCTCAGACTCCATTTCAAATAGCAGAACAACAGATACAAAATTTTCAAGTAGCTAAT  1440

Vaccine    1457  TGGTTACATTTTATTAACAATAATAGATTTAGGCAAGTTGTTATTGATGGAGTGTTAAAT  1516
                 ||||||||||||||||||||||||||||||||||||||||||||||||||||||||||||
MA104(JP)  1441  TGGTTACATTTTATTAACAATAATAGATTTAGGCAAGTTGTTATTGATGGAGTGTTAAAT  1500

Vaccine    1517  CAAACACTTAATGACAACATTAGGAATGGACAAGTTATTAATCAATTAATGGAAGCATTA  1576
                 ||||||||||||||||||||||||||||||||||||||||||||||||||||||||||||
MA104(JP)  1501  CAAACACTTAATGACAACATTAGGAATGGACAAGTTATTAATCAATTAATGGAAGCATTA  1560

Vaccine    1577  ATGCAGTTATCTAGACAACAATTTCCGACCATGCCAGTTGATTATAAAAGATCAATCCAG  1636
                 ||||||||||||||||||||||||||||||||||||||||||||||||||||||||||||
MA104(JP)  1561  ATGCAGTTATCTAGACAACAATTTCCGACCATGCCAGTTGATTATAAAAGATCAATCCAG  1620

Vaccine    1637  AGAGGAATATTGTTATTATCTAACAGATTAGGTCAGTTGGTTGATTTAACAAGATTATTA  1696
                 ||||||||||||||||||||||||||||||||||||||||||||||||||||||||||||
MA104(JP)  1621  AGAGGAATATTGTTATTATCTAACAGATTAGGTCAGTTGGTTGATTTAACAAGATTATTA  1680

Vaccine    1697  TCATACAATTATGAAACTCTAATGGCTTGTATAACTATGAACATGCAACATGTTCAAACT  1756
                 ||||||||||||||||||||||||||||||||||||||||||||||||||||||||||||
MA104(JP)  1681  TCATACAATTATGAAACTCTAATGGCTTGTATAACTATGAACATGCAACATGTTCAAACT  1740

Vaccine    1757  CTCACTACCGAAAAATTACAATTAACTTCTGTCACATCTTTATGTATGTTAATTGGAAAT  1816
                 ||||||||||||||||||||||||||||||||||||||||||||||||||||||||||||
MA104(JP)  1741  CTCACTACCGAAAAATTACAATTAACTTCTGTCACATCTTTATGTATGTTAATTGGAAAT  1800

Vaccine    1817  ACCACAGTAATTCCAGGTCCACAAACACTATTTCACTATTATAACGTAAATGTAAATTTT  1876
                 ||||||||||||||||||||||||||||||||||||||||||||||||||||||||||||
MA104(JP)  1801  ACCACAGTAATTCCAGGTCCACAAACACTATTTCACTATTATAACGTAAATGTAAATTTT  1860

Vaccine    1877  CATTCAAATTATAACGAACGAATTAATGATGCTGTGGCTATTATTACGGCTGCTAATAGA  1936
                 ||||||||||||||||||||||||||||||||||||||||||||||||||||||||||||
MA104(JP)  1861  CATTCAAATTATAACGAACGAATTAATGATGCTGTGGCTATTATTACGGCTGCTAATAGA  1920

Vaccine    1937  TTAAACTTATATCAGaaaaaaaaTGAAATCAATAGTTGAGGATTTTTTGAAAAGATTGCAA  1996
                 ||||||||||||||||||||||||||||||||||||||||||||||||||||||||||||
MA104(JP)  1921  TTAAACTTATATCAGAAAAAAAATGAAATCAATAGTTGAGGATTTTTTGAAAAGATTGCAA  1980

Vaccine    1997  ATTTTTGATGTACCACGAGTGCCAGATGACCAAACGTACAGGTTGAGAGACAGACTTAGA  2056
                 ||||||||||||||||||||||||||||||||||||||||||||||||||||||||||||
MA104(JP)  1981  ATTTTTGATGTACCACGAGTGCCAGATGACCAAACGTACAGGTTGAGAGACAGACTTAGA  2040

Vaccine    2057  TTATTGCCAGTTGAAAGACGAAGACTTGATATATTTAACTTAATATTAATGAATATGGAG  2116
                 ||||||||||||||||||||||||||||||||||||||||||||||||||||||||||||
MA104(JP)  2041  TTATTGCCAGTTGAAAGACGAAGACTTGATATATTTAACTTAATATTAATGAATATGGAG  2100
```

FIG. 41B

```
Vaccine    2117  CAGATCGAACGAGCTTCAGACAAAATTGCTCAAGGAGTAATAATTGCTTACAGAGATATG  2176
                 ||||||||||||||||||||||||||||||||||||||||||||||||||||||||||||
MA104(JP)2101    CAGATCGAACGAGCTTCAGACAAAATTGCTCAAGGAGTAATAATTGCTTACAGAGATATG  2160

Vaccine    2177  CAGCTAGAAAGAGATGAGATGTATGGGTTTGTTAACATCGCTAGGAACCTCGATGGATAT  2236
                 ||||||||||||||||||||||||||||||||||||||||||||||||||||||||||||
MA104(JP)2161    CAGCTAGAAAGAGATGAGATGTATGGGTTTGTTAACATCGCTAGGAACCTCGATGGATAT  2220

Vaccine    2237  CAACAAATCAATTTGGAAGAGTTGATGAGAACTGGGGACTATGGTCAAATTACTAATATG  2296
                 ||||||||||||||||||||||||||||||||||||||||||||||||||||||||||||
MA104(JP)2221    CAACAAATCAATTTGGAAGAGTTGATGAGAACTGGGGACTATGGTCAAATTACTAATATG  2280

Vaccine    2297  CTATTAAACAACCAGCCTGTAGCTTTAGTAGGAGCATTACCATTTGTGACAGATTCATCA  2356
                 ||||||||||||||||||||||||||||||||||||||||||||||||||||||||||||
MA104(JP)2281    CTATTAAACAACCAGCCTGTAGCTTTAGTAGGAGCATTACCATTTGTGACAGATTCATCA  2340

Vaccine    2357  GTTATATCGCTCATTGCAAAATTGGATGCCACAGTTTTTGCTCAAATAGTTAAACTTAGA  2416
                 ||||||||||||||||||||||||||||||||||||||||||||||||||||||||||||
MA104(JP)2341    GTTATATCGCTCATTGCAAAATTGGATGCCACAGTTTTTGCTCAAATAGTTAAACTTAGA  2400

Vaccine    2417  AAAGTGGACACTTTAAAACCAATATTGTATAAAATAAATTCTGATTCTAATGATTTCTAT  2476
                 ||||||||||||||||||||||||||||||||||||||||||||||||||||||||||||
MA104(JP)2401    AAAGTGGACACTTTAAAACCAATATTGTATAAAATAAATTCTGATTCTAATGATTTCTAT  2460

Vaccine    2477  TTAGTTGCAAATTATGATTGGATACCAACTTCAACCACAAAAGTTTATAAGCAAGTACCA  2536
                 ||||||||||||||||||||||||||||||||||||||||||||||||||||||||||||
MA104(JP)2461    TTAGTTGCAAATTATGATTGGATACCAACTTCAACCACAAAAGTTTATAAGCAAGTACCA  2520

Vaccine    2537  CAACCTTTTGATTTCAGAGCGTCAATGCATATGTTAACGTCTAATTTAACTTTTACTGTT  2596
                 ||||||||||||||||||||||||||||||||||||||||||||||||||||||||||||
MA104(JP)2521    CAACCTTTTGATTTCAGAGCGTCAATGCATATGTTAACGTCTAATTTAACTTTTACTGTT  2580

Vaccine    2597  TATTCCGATTTGCTATCTTTCGTTTCTGCAGACACGGTTGAACCTATTAACGCAATTGCT  2656
                 ||||||||||||||||||||||||||||||||||||||||||||||||||||||||||||
MA104(JP)2581    TATTCCGATTTGCTATCTTTCGTTTCTGCAGACACGGTTGAACCTATTAACGCAATTGCT  2640

Vaccine    2657  TTTGACAATATGCGCATTATGAACGAACTGTAA  2689
                 |||||||||||||||||||||||||||||||||
MA104(JP)2641    TTTGACAATATGCGCATTATGAACGAACTGTAA  2673
```

FIG. 41C

Comparison of amino acid (coding region) sequecnes of RV3 VP2

```
Vaccine   17     MAYRKRGVKRENLPQQNERLQEKETENNTDVTMENKNNNRRQQLSDKVLSQKEEIITDVQ  196
                 MAYRKRGVKRENLPQQNERLQEKETENNTDVTMENKNNNRRQQLSDKVLSQKEEIITDVQ
MA104(JP)1       MAYRKRGVKRENLPQQNERLQEKETENNTDVTMENKNNNRRQQLSDKVLSQKEEIITDVQ  60

Vaccine   197    DDIKIADEVkksskeeskqlleilkTKEDHQKEVQYEILQKTIPTFEPKESILKKLEDIR  376
                 DDIKIADEVKKSSKEESKQLLEILKTKEDHQKEVQYEILQKTIPTFEPKESILKKLEDIR
MA104(JP)61      DDIKIADEVKKSSKEESKQLLEILKTKEDHQKEVQYEILQKTIPTFEPKESILKKLEDIR  120

Vaccine   377    PEQAKKQMKLFRIFEPRQLPIYRANGEKELRNRWYWKLKKDTLPDGDYDVREYFLNLYDQ  556
                 PEQAKKQMKLFRIFEPRQLPIYRANGEKELRNRWYWKLKKDTLPDGDYDVREYFLNLYDQ
MA104(JP)121     PEQAKKQMKLFRIFEPRQLPIYRANGEKELRNRWYWKLKKDTLPDGDYDVREYFLNLYDQ  180

Vaccine   557    ILIEMPDYLLLKDMAVENKNSRDAGKVVDSETASICDAIFQDEETEGVIRRFIADMRQQV  736
                 ILIEMPDYLLLKDMAVENKNSRDAGKVVDSETASICDAIFQDEETEGVIRRFIADMRQQV
MA104(JP)181     ILIEMPDYLLLKDMAVENKNSRDAGKVVDSETASICDAIFQDEETEGVIRRFIADMRQQV  240

Vaccine   737    QADRNIVNYPSILHPIDHAFNEYFLNHQLVEPLNNEIIFNYIPERIRNDVNYILNMDMNL  916
                 QADRNIVNYPSILHPIDHAFNEYFLNHQLVEPLNNEIIFNYIPERIRNDVNYILNMDMNL
MA104(JP)241     QADRNIVNYPSILHPIDHAFNEYFLNHQLVEPLNNEIIFNYIPERIRNDVNYILNMDMNL  300

Vaccine   917    PSTARYIRPNLLQDRLNLHDNFESLWDTITTSNYILARSVVPDLKEKELVSTEAQIQKMS  1096
                 PSTARYIRPNLLQDRLNLHDNFESLWDTITTSNYILARSVVPDLKEKELVSTEAQIQKMS
MA104(JP)301     PSTARYIRPNLLQDRLNLHDNFESLWDTITTSNYILARSVVPDLKEKELVSTEAQIQKMS  360

Vaccine   1097   QDLQLEALTIQSETQFLAGINSQAANDCFKTLIAAMLSQRTMSLDFVTTNYMSLISGMWL  1276
                 QDLQLEALTIQSETQFLAGINSQAANDCFKTLIAAMLSQRTMSLDFVTTNYMSLISGMWL
MA104(JP)361     QDLQLEALTIQSETQFLAGINSQAANDCFKTLIAAMLSQRTMSLDFVTTNYMSLISGMWL  420

Vaccine   1277   LTVIPNDMFLRESLVACELAIINTIVYPAFGMQRMHYRNGDPQTPFQIAEQQIQNFQVAN  1456
                 LTVIPNDMFLRESLVACELAIINTIVYPAFGMQRMHYRNGDPQTPFQIAEQQIQNFQVAN
MA104(JP)421     LTVIPNDMFLRESLVACELAIINTIVYPAFGMQRMHYRNGDPQTPFQIAEQQIQNFQVAN  480

Vaccine   1457   WLHFINNNRFRQVVIDGVLNQTLNDNIRNGQVINQLMEALMQLSRQQFPTMPVDYKRSIQ  1636
                 WLHFINNNRFRQVVIDGVLNQTLNDNIRNGQVINQLMEALMQLSRQQFPTMPVDYKRSIQ
MA104(JP)481     WLHFINNNRFRQVVIDGVLNQTLNDNIRNGQVINQLMEALMQLSRQQFPTMPVDYKRSIQ  540

Vaccine   1637   RGILLLSNRLGQLVDLTRLLSYNYETLMACITMNMQHVQTLTTEKLQLTSVTSLCMLIGN  1816
                 RGILLLSNRLGQLVDLTRLLSYNYETLMACITMNMQHVQTLTTEKLQLTSVTSLCMLIGN
MA104(JP)541     RGILLLSNRLGQLVDLTRLLSYNYETLMACITMNMQHVQTLTTEKLQLTSVTSLCMLIGN  600

Vaccine   1817   TTVIPGPQTLFHYYNVNVNFHSNYNERINDAVAIITAANRLNLYQKKMKSIVEDFLKRLQ  1996
                 TTVIPGPQTLFHYYNVNVNFHSNYNERINDAVAIITAANRLNLYQKKMKSIVEDFLKRLQ
MA104(JP)601     TTVIPGPQTLFHYYNVNVNFHSNYNERINDAVAIITAANRLNLYQKKMKSIVEDFLKRLQ  660

Vaccine   1997   IFDVPRVPDDQTYrlrdrlrllpverrrlDIFNLILMNMEQIERASDKIAQGVIIAYRDM  2176
                 IFDVPRVPDDQTYRLRDRLRLLPVERRRLDIFNLILMNMEQIERASDKIAQGVIIAYRDM
MA104(JP)661     IFDVPRVPDDQTYRLRDRLRLLPVERRRLDIFNLILMNMEQIERASDKIAQGVIIAYRDM  720

Vaccine   2177   QLERDEMYGFVNIARNLDGYQQINLEELMRTGDYGQITNMLLNNQPVALVGALPFVTDSS  2356
                 QLERDEMYGFVNIARNLDGYQQINLEELMRTGDYGQITNMLLNNQPVALVGALPFVTDSS
MA104(JP)721     QLERDEMYGFVNIARNLDGYQQINLEELMRTGDYGQITNMLLNNQPVALVGALPFVTDSS  780

Vaccine   2357   VISLIAKLDATVFAQIVKLRKVDTLKPILYKINSDSNDFYLVANYDWIPTSTTKVYKQVP  2536
                 VISLIAKLDATVFAQIVKLRKVDTLKPILYKINSDSNDFYLVANYDWIPTSTTKVYKQVP
MA104(JP)781     VISLIAKLDATVFAQIVKLRKVDTLKPILYKINSDSNDFYLVANYDWIPTSTTKVYKQVP  840

Vaccine   2537   QPFDFRASMHMLTSNLTFTVYSDLLSFVSADTVEPINAIAFDNMRIMNEL  2686
                 QPFDFRASMHMLTSNLTFTVYSDLLSFVSADTVEPINAIAFDNMRIMNEL
MA104(JP)841     QPFDFRASMHMLTSNLTFTVYSDLLSFVSADTVEPINAIAFDNMRIMNEL  890
```

FIG. 42

VP3 sequence
MA104-adapted RV3 VP3 (SEQ ID NO:55)

```
   1 ATGAAAGTAT TAGCTTTAAG ACACAGTGTG GCTCAGGTGT ATGCAGATAC TCAAACCTAT
  61 TTGCATGATG ATTCAAAAGA TGAGTATGAA AATGCATTTC TCATTTCTAA TCTAACTACA
 121 CATAATATAT TATACCTGAA TTACAGCCTT AAAACATTAA AAATATTAAA TGAATCAGGT
 181 ATAGCAGCAG TTGAAGTACA GTCTCCAGAT GAATTATTTG CGTTAATAAG GTGTAATTTT
 241 ACGTACGATT ATGAGAATAA CATAGTTTAT TTACATGATT ATTCATATTA TACTAACAAT
 301 GAAATAAGAA CAGATCAACA TTGGATAACT AAAACTGATA TAATTGACTA TCTATTACCT
 361 GGATGGAAAT TAACATATGT AGGCTATAAT GGAAAGAACA CACGAGGTCA CTATGATTTT
 421 TCATTTTATAT GTCAAAATGC AGCTACAGAT GATGATATAA TAATTGAATA TATATACTCC
 481 AATGAGTTAG ACTTTCAAAA CTTTCTGTTA AGAAAAATTA AAGAGAGAAT GACCACATCT
 541 CTTCCAATTG CTAGATTATC AAATCGTGTG TTTAGAGATA AATTATTTCC ATCTATTGTA
 601 AACATACATA AAAAAGTGAT AAACGTTGGG CCAAGGAATG AATCTATGTT CACATTCTTA
 661 AATTTTCCAA CTATTAAGCA ATTTTCAAAC GGTGCGTATA TTGTGAAGCA TACTATTAAA
 721 TTGAAGCAGG AGAAATGGTT GGGTAAAAGA GTATCACAAT TTGACATCGG ACAATATAAA
 781 AACATGTTAA ATGTGGTTAC TACTATTTAC TATTACTATA ATTTATACTA TTCGAAACCT
 841 ATAATATACA TGCTTGGTTC AGCTCCATCT TATTGGATTT ATGATATTAA ACAGTATTCT
 901 GATTTTACAT TTGAAACATG GGATCCATTA GATACTCCAT ATTCTACAAC ACATCATAAA
 961 GAATTATTTT TTGATAAGGA TGTCAATAAG CTTAAAGATA ATTCAGTTTT ATATATAGAC
1021 ATAAGAACTG ATAGAGGTAA TATGGATTGG AAAGAGTGGA GAAAAATAGT AGAACAACAA
1081 ACTGTTAGCA ATCTAAATAT TGCGTATAAA TATCTATCAA CAGGAAAAGC AAAGGTGTGT
1141 TGTGTTAAAT TAACTGCTAT GGACCTAGAA TTACCAATAA CAGCAAAATT ACTTCATCAT
1201 CCAACTACTG AAGTTAGATC AGAATTTTAT GCAATATTGG ATGTATGGGA TATTATTACC
1261 ATTAAAAGAT TTATACCAAA AGGTGTATTT TATGCTTTTA TAAATAATGT AACCACAGAG
1321 AATGTGTTTA TACAACCTCC TTTCAAATTA AAAACGTCAC CTACTGATTA CATAGTGGCA
1381 TTGTATGCTT TATCCAATGA CTTCAACTCG AGGCAAGATG TTATTAATTT GATTAATAAA
1441 CAAAAACAAT CACTCATTAC TGTTCGTATA AATAATACTT TAAAGACGA ACCAAAAGTA
1501 AATTTTAAAA ATATTTATGA TTGGACGTTT CTGCCAACAG ATTTTGAACT TAAAGATTCG
1561 ATAATTACAT CATATGATGG TTGTTTAGGC ATATTCGGAT TATCGATATC TTTATCGTCT
1621 AAACCCACTG GAAATAATCA TTTATTTATA ATAAATGGAA CTGACAAATA TGATAAACTA
1681 GACCAATATG CAAATCATAT GGGTATTTCT AGAAGATCGC ATCAAATTAG ATTCTCAGAG
1741 TCTGCGACAT CATATTCGGG ATACATTTTT AGAGATCTTT CAAATAATAA TTTCAATCTA
1801 ATAGGTACTA ATGTGGAGAA TTCAGTTTCA GGACATGTCT ATAATGCATT AATTTACTAT
1861 AGATATAATT ATGCGTTTGA TCTTAAAAGA TGGATTTATC TACATTCAAT TGGGAAAGTC
1921 GCTGTAGAGG GTGGAAGATA TTATGAACAT GCACCAATCG AACTGATATA TGCATGCCGA
1981 TCAGCTAAAG AATTTGCTAT ATTACAAGAT GACTTAACGG TATTGAGATA CGCTAATGAA
2041 ATTGAAGGGT ATATAAGCAA AGTGTACAGT ATAACCTATG CTGACGATCC CAATTACTTT
2101 ATAGGAATTA AATTTAATAG TATACCTTAT GAATACGATG TTAAAATTCC ACATTTGACG
2161 CTAGGAGTAT TATTTATATC TGATAATATG ATACATGATG TAATCACAGT GTTGAAGAAA
2221 ATGAAGACAG AGCTATTTAA AATGGAAATT AGTACTAGTT ATACTTATAT GCTATCTGAT
2281 AATACGTATG TAGCAAATGC TAGTGGTGTG TTATCAACTT ATTTTAAATT ATATAATATG
2341 TTCTATAGAA ATTATATCAC GTTTGGACAA TCACGAATGT TTATCCCACA CATTACGCTT
2401 AGTTTTAGCA ACAAACAGAC GGTTAGAATA GAAAGTACAA AACTCAGAAT CAATTCAATT
2461 TACTTAAGAA AGATTAAAGG TGAAACCGTA TTTGATATGT CTGAGTGA
```

FIG. 43

Amino acid (coding region) ADD31860 (SEQ ID NO:56)

```
  1 MKVLALRHSV AQVYADTQTY LHDDSKDEYE NAFLISNLTT HNILYLNYSL KTLKILNESG
 61 IAAVEVQSPD ELFALIRCNF TYDYENNIVY LHDYSYYTNN EIRTDQHWIT KTDIIDYLLP
121 GWKLTYVGYN GKNTRGHYDF SFICQNAATD DDIIIEYIYS NELDFQNFLL RKIKERMTTS
181 LPIARLSNRV FRDKLFPSIV NIHKKVINVG PRNESMFTFL NFPTIKQFSN GAYIVKHTIK
241 LKQEKWLGKR VSQFDIGQYK NMLNVVTTIY YYYNLYYSKP IIYMLGSAPS YWIYDIKQYS
301 DFTFETWDPL DTPYSTTHHK ELFFDKDVNK LKDNSVLYID IRTDRGNMDW KEWRKIVEQQ
361 TVSNLNIAYK YLSTGKAKVC CVKLTAMDLE LPITAKLLHH PTTEVRSEFY AILDVWDIIT
421 IKRFIPKGVF YAFINNVTTE NVFIQPPFKL KTSPTDYIVA LYALSNDFNS RQDVINLINK
481 QKQSLITVRI NNTFKDEPKV NFKNIYDWTF LPTDFELKDS IITSYDGCLG IFGLSISLSS
541 KPTGNNHLFI INGTDKYDKL DQYANHMGIS RRSHQIRFSE SATSYSGYIF RDLSNNNFNL
601 IGTNVENSVS GHVYNALIYY RYNYAFDLKR WIYLHSIGKV AVEGGRYYEH APIELIYACR
661 SAKEFAILQD DLTVLRYANE IEGYISKVYS ITYADDPNYF IGIKFNSIPY EYDVKIPHLT
721 LGVLFISDNM IHDVITVLKK MKTELFKMEI STSYTYMLSD NTYVANASGV LSTYFKLYNM
781 FYRNYITFGQ SRMFIPHITL SFSNKQTVRI ESTKLRINSI YLRKIKGETV FDMSE
```

FIG. 44

Vero-adapted (Vaccine) RV3 VP3 (SEQ ID NO:57)

```
   1 GGCTATTAAA GCAGTACCAG TAGTGTGTTT TACCTCTGAT GGTGTAAGCA TGAAAGTATT
  61 AGCTTTAAGA CACAGTGTGG CTCAGGTGTA TGCAGATACT CAAACCTATT TGCATGATGA
 121 TTCAAAAGAT GAGTATGAAA ATGCATTTCT CATTTCTAAT CTAACTACAC ATAATATATT
 181 ATACCTGAAT TACAGCCTTA AAACATTAAA AATATTAAAT GAATCAGGTA TAGCAGCAGT
 241 TGAAGTACAG TCTCCAGATG AATTATTTGC GTTAATAAGG TGTAATTTTA CGTACGATTA
 301 TGAGAATAAC ATAGTTTATT TACATGATTA TTCATATTAT ACCAACAATG AAATAAGAAC
 361 AGATCAACAT TGGATAACTA AAACTGATAT AATTGACTAT CTATTACCTG GATGGAAATT
 421 AACATATGTA GGCTATAATG GAAAGAACAC ACGAGGTCAC TATGATTTTT CATTTATATG
 481 TCAAAATGCA GCTACAGATG ATGATATAAT AATTGAATAT ATATACTCCA ATGAGTTAGA
 541 CTTTCAAAAC TTTCTGTTAA GAAAAATTAA AGAGAGAATG ACCACATCTC TTCCAATTGC
 601 TAGATTATCA AATCGTGTGT TTAGAGATAA ATTATTTCCA TCTATTGTAA ACATACATAA
 661 AAAAGTGATA AACGTTGGGC CAAGGAATGA ATCTATGTTC ACATTCTTAA ATTTTCCAAC
 721 TATTAAGCAA TTTTCAAACG GTGCGTATAT TGTGAAGCAT ACTATTAAAT TGAAGCAGGA
 781 GAAATGGTTG GGTAAAAGAG TATCACAATT TGACATCGGA CAATATAAAA ACATGTTAAA
 841 TGTGGTTACT ACTATTTACT ATTACTATAA TTTATACTAT TCGAAACCTA TAATATACAT
 901 GCTTGGTTCA GCTCCATCTT ATTGGATTTA TGATATTAAA CAGTATTCTG ATTTTACATT
 961 TGAAACATGG GATCCATTAG ATACTCCATA TTCTACAACA CATCATAAAG AATTATTTTT
1021 TGATAAGGAT GTCAATAAGC TTAAAGATAA TTCAGTTTTA TATATAGACA TAAGAACTGA
1081 TAGAGGTAAT ATGGATTGGA AAGAGTGGAG AAAAATAGTA GAACAACAAA CTGTTAGCAA
1141 TCTAAATATT GCGTATAAAT ATCTATCAAC AGGAAAAGCA AAGGTGTGTT GTGTTAAATT
1201 AACTGCTATG GACCTAGAAT TACCAATAAC AGCAAAATTA CTTCATCATC CAACTACTGA
1261 AGTTAGATCA GAATTTTATG CAATATTGGA TGTATGGGAT ATTATTACCA TTAAAAGATT
1321 TATACCAAAA GGTGTATTTT ATGCTTTTAT AAATAATGTA ACCACGGAGA ATGTGTTTAT
1381 ACAACCTCCT TTCAAATTAA AAACGTCACC TACTGATTAC ATAGTGGCAT TGTATGCTTT
1441 ATCCAATGAC TTCAACTCGA GGCAAGATGT TATTAATTTG ATTAATAAAC AAAAACAATC
1501 ACTCATTACT GTTCGTATAA ATAATACTTT TAAAGACGAA CCAAAAGTAA ATTTTAAAAA
1561 TATTTATGAT TGGACGTTTC TGCCAACAGA TTTTGAACTT AAAGATTCGA TAATTACATC
1621 ATATGATGGT TGTTTAGGCA TATTCGGATT ATCGATATCT TTATCGTCTA AACCCACTGG
1681 AAATAATCAT TTATTTATAA TAAATGGAAC TGACAAATAT GATAAACTAG ACCAATATGC
1741 AAACCATATG GGTATTTCTA GAAGATCGCA TCAAATTAGA TTCTCAGAGT CTGCGACATC
1801 ATATTCGGGA TACATTTTTA GAGATCTTTC AAATAATAAT TTCAATCTAA TAGGTACTAA
1861 TGTGGAGAAT TCAGTTTCAG GACATGTCTA TAATGCATTA ATTTACTATA GATATAATTA
1921 TGCGTTTGAT CTTAAAAGAT GGATTTATCT ACATTCAATT GGGAAAGTCG CTGTAAAGGG
1981 TGGAAGATAT TATGAACATG CACCAATCGA ACTGATATAT GCATGCCGAT CAGCTAAAGA
2041 ATTTGCTATA TTACAAGATG ACTTAACGGT ATTGAGATAC GCTAATGAAA TTGAAGGGTA
2101 TATAAGCAAA GTGTACAGTA TAACCTATGC TGACGATCCC AATTACTTTA TAGGAATTAA
2161 ATTTAATAGT ATACCTTATG AATACGATGT TAAAATTCCA CATTTGACGC TAGGAGTATT
2221 ATTTATATCT GATAATATGA TACATGATGT AATCACAGTG TTGAAGAAAA TGAAGACAGA
2281 GCTATTTAAA ATGGAAATTA GTACTAGTTA TACTTATATG CTATCTGATA ATACGTATGT
2341 AGCAAATGCT AGTGGTGTGT TATCAACTTA TTTTAAATTA TATAATATGT TCTATAGAAA
2401 TCATATCACG TTTGGACAAT CACGAATGTT TATCCCACAC ATTACGCTTA GTTTTAGCAA
2461 CAAACAGACG GTTAGAATAG AAAGTACAAA ACTCAGAATC AATTCAATTT ACTTAAGAAA
2521 GATTAAAGGT GAAACCGTAT TTGATATGTC TGAGTGAGCT AGAAACTTAA CACACTAGTC
2581 ATGATGTGAC C
```

FIG. 45

Amino acid (coding region) [SEQ ID NO:58]

```
  1 MKVLALRHSV AQVYADTQTY LHDDSKDEYE NAFLISNLTT HNILYLNYSL KTLKILNESG
 61 IAAVEVQSPD ELFALIRCNF TYDYENNIVY LHDYSYYTNN EIRTDQHWIT KTDIIDYLLP
121 GWKLTYVGYN GKNTRGHYDF SFICQNAATD DDIIIEYIYS NELDFQNFLL RKIKERMTTS
181 LPIARLSNRV FRDKLFPSIV NIHKKVINVG PRNESMFTFL NFPTIKQFSN GAYIVKHTIK
241 LKQEKWLGKR VSQFDIGQYK NMLNVVTTIY YYYNLYYSKP IIYMLGSAPS YWIYDIKQYS
301 DFTFETWDPL DTPYSTTHHK ELFFDKDVNK LKDNSVLYID IRTDRGNMDW KEWRKIVEQQ
361 TVSNLNIAYK YLSTGKAKVC CVKLTAMDLE LPITAKLLHH PTTEVRSEFY AILDVWDIIT
421 IKRFIPKGVF YAFINNVTTE NVFIQPPFKL KTSPTDYIVA LYALSNDFNS RQDVINLINK
481 QKQSLITVRI NNTFKDEPKV NFKNIYDWTF LPTDFELKDS IITSYDGCLG IFGLSISLSS
541 KPTGNNHLFI INGTDKYDKL DQYANHMGIS RRSHQIRFSE SATSYSGYIF RDLSNNNFNL
601 IGTNVENSVS GHVYNALIYY RYNYAFDLKR WIYLHSIGKV AVKGGRYYEH APIELIYACR
661 SAKEFAILQD DLTVLRYANE IEGYISKVYS ITYADDPNYF IGIKFNSIPY EYDVKIPHLT
721 LGVLFISDNM IHDVITVLKK MKTELFKMEI STSYTYMLSD NTYVANASGV LSTYFKLYNM
781 FYRNHITFGQ SRMFIPHITL SFSNKQTVRI ESTKLRINSI YLRKIKGETV FDMSE
```

FIG. 46

Comparison of nucleotide sequences of RV3 VP3

Vaccine 343 C to MA104(JP) 294 T
Vaccine 1366 G to MA104(JP) 1317 A
Vaccine 1744 C to MA104(JP) 1695 T
Vaccine 1976 A to MA104(JP) 1927 G
Vaccine 2402 C to MA104(JP) 2353 T

```
Vaccine  50    ATGAAAGTATTAGCTTTAAGACACAGTGTGGCTCAGGTGTATGCAGATACTCAAACCTAT  109
               ||||||||||||||||||||||||||||||||||||||||||||||||||||||||||||
MA104(JP)1     ATGAAAGTATTAGCTTTAAGACACAGTGTGGCTCAGGTGTATGCAGATACTCAAACCTAT  60

Vaccine  110   TTGCATGATGATTCAAAAGATGAGTATGAAAATGCATTTCTCATTTCTAATCTAACTACA  169
               ||||||||||||||||||||||||||||||||||||||||||||||||||||||||||||
MA104(JP)61    TTGCATGATGATTCAAAAGATGAGTATGAAAATGCATTTCTCATTTCTAATCTAACTACA  120

Vaccine  170   CATAATATATTATACCTGAATTACAGCCTTAAAACATTAAAAATATTAAATGAATCAGGT  229
               ||||||||||||||||||||||||||||||||||||||||||||||||||||||||||||
MA104(JP)121   CATAATATATTATACCTGAATTACAGCCTTAAAACATTAAAAATATTAAATGAATCAGGT  180

Vaccine  230   ATAGCAGCAGTTGAAGTACAGTCTCCAGATGAATTATTTGCGTTAATAAGGTGTAATTTT  289
               ||||||||||||||||||||||||||||||||||||||||||||||||||||||||||||
MA104(JP)181   ATAGCAGCAGTTGAAGTACAGTCTCCAGATGAATTATTTGCGTTAATAAGGTGTAATTTT  240

Vaccine  290   ACGTACGATTATGAGAATAACATAGTTTATTTACATGATTATTCATATTATACCAACAAT  349
               ||||||||||||||||||||||||||||||||||||||||||||||||||||| ||||||
MA104(JP)241   ACGTACGATTATGAGAATAACATAGTTTATTTACATGATTATTCATATTATACTAACAAT  300

Vaccine  350   GAAATAAGAACAGATCAACATTGGATAACTAAAACTGATATAATTGACTATCTATTACCT  409
               ||||||||||||||||||||||||||||||||||||||||||||||||||||||||||||
MA104(JP)301   GAAATAAGAACAGATCAACATTGGATAACTAAAACTGATATAATTGACTATCTATTACCT  360

Vaccine  410   GGATGGAAATTAACATATGTAGGCTATAATGGAAAGAACACACGAGGTCACTATGATTTT  469
               ||||||||||||||||||||||||||||||||||||||||||||||||||||||||||||
MA104(JP)361   GGATGGAAATTAACATATGTAGGCTATAATGGAAAGAACACACGAGGTCACTATGATTTT  420

Vaccine  470   TCATTTATATGTCAAAATGCAGCTACAGATGATGATATAATAATTGAATATATATACTCC  529
               ||||||||||||||||||||||||||||||||||||||||||||||||||||||||||||
MA104(JP)421   TCATTTATATGTCAAAATGCAGCTACAGATGATGATATAATAATTGAATATATATACTCC  480

Vaccine  530   AATGAGTTAGACTTTCAAAACTTTCTGTTAAGAAAAATTAAAGAGAGAATGACCACATCT  589
               ||||||||||||||||||||||||||||||||||||||||||||||||||||||||||||
MA104(JP)481   AATGAGTTAGACTTTCAAAACTTTCTGTTAAGAAAAATTAAAGAGAGAATGACCACATCT  540

Vaccine  590   CTTCCAATTGCTAGATTATCAAATCGTGTGTTTAGAGATAAATTATTTCCATCTATTGTA  649
               ||||||||||||||||||||||||||||||||||||||||||||||||||||||||||||
MA104(JP)541   CTTCCAATTGCTAGATTATCAAATCGTGTGTTTAGAGATAAATTATTTCCATCTATTGTA  600

Vaccine  650   AACATACATAAAAAAGTGATAAACGTTGGGCCAAGGAATGAATCTATGTTCACATTCTTA  709
               ||||||||||||||||||||||||||||||||||||||||||||||||||||||||||||
MA104(JP)601   AACATACATAAAAAAGTGATAAACGTTGGGCCAAGGAATGAATCTATGTTCACATTCTTA  660

Vaccine  710   AATTTTCCAACTATTAAGCAATTTTCAAACGGTGCGTATATTGTGAAGCATACTATTAAA  769
               ||||||||||||||||||||||||||||||||||||||||||||||||||||||||||||
MA104(JP)661   AATTTTCCAACTATTAAGCAATTTTCAAACGGTGCGTATATTGTGAAGCATACTATTAAA  720

Vaccine  770   TTGAAGCAGGAGAAATGGTTGGGTAAAAGAGTATCACAATTTGACATCGGACAATATAAA  829
               ||||||||||||||||||||||||||||||||||||||||||||||||||||||||||||
MA104(JP)721   TTGAAGCAGGAGAAATGGTTGGGTAAAAGAGTATCACAATTTGACATCGGACAATATAAA  780

Vaccine  830   AACATGTTAAATGTGGTTACTACTATTTACTATTACTATAATTTATACTATTCGAAACCT  889
               ||||||||||||||||||||||||||||||||||||||||||||||||||||||||||||
MA104(JP)781   AACATGTTAAATGTGGTTACTACTATTTACTATTACTATAATTTATACTATTCGAAACCT  840

Vaccine  890   ATAATATACATGCTTGGTTCAGCTCCATCTTATTGGATTTATGATATTAAACAGTATTCT  949
               ||||||||||||||||||||||||||||||||||||||||||||||||||||||||||||
MA104(JP)841   ATAATATACATGCTTGGTTCAGCTCCATCTTATTGGATTTATGATATTAAACAGTATTCT  900
```

FIG. 47A

```
Vaccine    950    GATTTTACATTTGAAACATGGGATCCATTAGATACTCCATATTCTACAACACATCATAAA  1009
                  ||||||||||||||||||||||||||||||||||||||||||||||||||||||||||||
MA104(JP)901      GATTTTACATTTGAAACATGGGATCCATTAGATACTCCATATTCTACAACACATCATAAA  960

Vaccine    1010   GAATTATTTTTTGATAAGGATGTCAATAAGCTTAAAGATAATTCAGTTTTATATATAGAC  1069
                  ||||||||||||||||||||||||||||||||||||||||||||||||||||||||||||
MA104(JP)961      GAATTATTTTTTGATAAGGATGTCAATAAGCTTAAAGATAATTCAGTTTTATATATAGAC  1020

Vaccine    1070   ATAAGAACTGATAGAGGTAATATGGATTGGAAAGAGTGGAGAAAAATAGTAGAACAACAA  1129
                  ||||||||||||||||||||||||||||||||||||||||||||||||||||||||||||
MA104(JP)1021     ATAAGAACTGATAGAGGTAATATGGATTGGAAAGAGTGGAGAAAAATAGTAGAACAACAA  1080

Vaccine    1130   ACTGTTAGCAATCTAAATATTGCGTATAAATATCTATCAACAGGAAAAGCAAAGGTGTGT  1189
                  ||||||||||||||||||||||||||||||||||||||||||||||||||||||||||||
MA104(JP)1081     ACTGTTAGCAATCTAAATATTGCGTATAAATATCTATCAACAGGAAAAGCAAAGGTGTGT  1140

Vaccine    1190   TGTGTTAAATTAACTGCTATGGACCTAGAATTACCAATAACAGCAAAATTACTTCATCAT  1249
                  ||||||||||||||||||||||||||||||||||||||||||||||||||||||||||||
MA104(JP)1141     TGTGTTAAATTAACTGCTATGGACCTAGAATTACCAATAACAGCAAAATTACTTCATCAT  1200

Vaccine    1250   CCAACTACTGAAGTTAGATCAGAATTTTATGCAATATTGGATGTATGGGATATTATTACC  1309
                  ||||||||||||||||||||||||||||||||||||||||||||||||||||||||||||
MA104(JP)1201     CCAACTACTGAAGTTAGATCAGAATTTTATGCAATATTGGATGTATGGGATATTATTACC  1260

Vaccine    1310   ATTAAAAGATTTATACCAAAAGGTGTATTTTATGCTTTTATAAATAATGTAACCACGGAG  1369
                  |||||||||||||||||||||||||||||||||||||||||||||||||||||||| |||
MA104(JP)1261     ATTAAAAGATTTATACCAAAAGGTGTATTTTATGCTTTTATAAATAATGTAACCACAGAG  1320

Vaccine    1370   AATGTGTTTATACAACCTCCTTTCAAATTAAAAACGTCACCTACTGATTACATAGTGGCA  1429
                  ||||||||||||||||||||||||||||||||||||||||||||||||||||||||||||
MA104(JP)1321     AATGTGTTTATACAACCTCCTTTCAAATTAAAAACGTCACCTACTGATTACATAGTGGCA  1380

Vaccine    1430   TTGTATGCTTTATCCAATGACTTCAACTCGAGGCAAGATGTTATTAATTTGATTAATAAA  1489
                  ||||||||||||||||||||||||||||||||||||||||||||||||||||||||||||
MA104(JP)1381     TTGTATGCTTTATCCAATGACTTCAACTCGAGGCAAGATGTTATTAATTTGATTAATAAA  1440

Vaccine    1490   CAAAAACAATCACTCATTACTGTTCGTATAAATAATACTTTTAAAGACGAACCAAAAGTA  1549
                  ||||||||||||||||||||||||||||||||||||||||||||||||||||||||||||
MA104(JP)1441     CAAAAACAATCACTCATTACTGTTCGTATAAATAATACTTTTAAAGACGAACCAAAAGTA  1500

Vaccine    1550   AATTTTAAAAATATTTATGATTGGACGTTTCTGCCAACAGATTTTGAACTTAAAGATTCG  1609
                  ||||||||||||||||||||||||||||||||||||||||||||||||||||||||||||
MA104(JP)1501     AATTTTAAAAATATTTATGATTGGACGTTTCTGCCAACAGATTTTGAACTTAAAGATTCG  1560

Vaccine    1610   ATAATTACATCATATGATGGTTGTTTAGGCATATTCGGATTATCGATATCTTTATCGTCT  1669
                  ||||||||||||||||||||||||||||||||||||||||||||||||||||||||||||
MA104(JP)1561     ATAATTACATCATATGATGGTTGTTTAGGCATATTCGGATTATCGATATCTTTATCGTCT  1620

Vaccine    1670   AAACCCACTGGAAATAATCATTTATTTATAATAAATGGAACTGACAAATATGATAAACTA  1729
                  ||||||||||||||||||||||||||||||||||||||||||||||||||||||||||||
MA104(JP)1621     AAACCCACTGGAAATAATCATTTATTTATAATAAATGGAACTGACAAATATGATAAACTA  1680

Vaccine    1730   GACCAATATGCAAACCATATGGGTATTTCTAGAAGATCGCATCAAATTAGATTCTCAGAG  1789
                  |||||||||||||| |||||||||||||||||||||||||||||||||||||||||||||
MA104(JP)1681     GACCAATATGCAAATCATATGGGTATTTCTAGAAGATCGCATCAAATTAGATTCTCAGAG  1740

Vaccine    1790   TCTGCGACATCATATTCGGGATACATTTTTAGAGATCTTTCAAATAATAATTTCAATCTA  1849
                  ||||||||||||||||||||||||||||||||||||||||||||||||||||||||||||
MA104(JP)1741     TCTGCGACATCATATTCGGGATACATTTTTAGAGATCTTTCAAATAATAATTTCAATCTA  1800

Vaccine    1850   ATAGGTACTAATGTGGAGAATTCAGTTTCAGGACATGTCTATAATGCATTAATTTACTAT  1909
                  ||||||||||||||||||||||||||||||||||||||||||||||||||||||||||||
MA104(JP)1801     ATAGGTACTAATGTGGAGAATTCAGTTTCAGGACATGTCTATAATGCATTAATTTACTAT  1860

Vaccine    1910   AGATATAATTATGCGTTTGATCTTAAAAGATGGATTTATCTACATTCAATTGGGAAAGTC  1969
                  ||||||||||||||||||||||||||||||||||||||||||||||||||||||||||||
MA104(JP)1861     AGATATAATTATGCGTTTGATCTTAAAAGATGGATTTATCTACATTCAATTGGGAAAGTC  1920

Vaccine    1970   GCTGTAAAGGGTGGAAGATATTATGAACATGCACCAATCGAACTGATATATGCATGCCGA  2029
                  |||||| |||||||||||||||||||||||||||||||||||||||||||||||||||||
MA104(JP)1921     GCTGTAGAGGGTGGAAGATATTATGAACATGCACCAATCGAACTGATATATGCATGCCGA  1980
```

FIG. 47B

```
Vaccine    2030  TCAGCTAAAGAATTTGCTATATTACAAGATGACTTAACGGTATTGAGATACGCTAATGAA  2089
                 ||||||||||||||||||||||||||||||||||||||||||||||||||||||||||||
MA104(JP)1981  TCAGCTAAAGAATTTGCTATATTACAAGATGACTTAACGGTATTGAGATACGCTAATGAA  2040

Vaccine    2090  ATTGAAGGGTATATAAGCAAAGTGTACAGTATAACCTATGCTGACGATCCCAATTACTTT  2149
                 ||||||||||||||||||||||||||||||||||||||||||||||||||||||||||||
MA104(JP)2041  ATTGAAGGGTATATAAGCAAAGTGTACAGTATAACCTATGCTGACGATCCCAATTACTTT  2100

Vaccine    2150  ATAGGAATTAAATTTAATAGTATACCTTATGAATACGATGTTAAAATTCCACATTTGACG  2209
                 ||||||||||||||||||||||||||||||||||||||||||||||||||||||||||||
MA104(JP)2101  ATAGGAATTAAATTTAATAGTATACCTTATGAATACGATGTTAAAATTCCACATTTGACG  2160

Vaccine    2210  CTAGGAGTATTATTTATATCTGATAATATGATACATGATGTAATCACAGTGTTGAAGAAA  2269
                 ||||||||||||||||||||||||||||||||||||||||||||||||||||||||||||
MA104(JP)2161  CTAGGAGTATTATTTATATCTGATAATATGATACATGATGTAATCACAGTGTTGAAGAAA  2220

Vaccine    2270  ATGAAGACAGAGCTATTTAAAATGGAAATTAGTACTAGTTATACTTATATGCTATCTGAT  2329
                 ||||||||||||||||||||||||||||||||||||||||||||||||||||||||||||
MA104(JP)2221  ATGAAGACAGAGCTATTTAAAATGGAAATTAGTACTAGTTATACTTATATGCTATCTGAT  2280

Vaccine    2330  AATACGTATGTAGCAAATGCTAGTGGTGTGTTATCAACTTATTTTAAATTATATAATATG  2389
                 ||||||||||||||||||||||||||||||||||||||||||||||||||||||||||||
MA104(JP)2281  AATACGTATGTAGCAAATGCTAGTGGTGTGTTATCAACTTATTTTAAATTATATAATATG  2340

Vaccine    2390  TTCTATAGAAATCATATCACGTTTGGACAATCACGAATGTTTATCCCACACATTACGCTT  2449
                 |||||||||||| |||||||||||||||||||||||||||||||||||||||||||||||
MA104(JP)2341  TTCTATAGAAATTATATCACGTTTGGACAATCACGAATGTTTATCCCACACATTACGCTT  2400

Vaccine    2450  AGTTTTAGCAACAAACAGACGGTTAGAATAGAAAGTACAAAACTCAGAATCAATTCAATT  2509
                 ||||||||||||||||||||||||||||||||||||||||||||||||||||||||||||
MA104(JP)2401  AGTTTTAGCAACAAACAGACGGTTAGAATAGAAAGTACAAAACTCAGAATCAATTCAATT  2460


Vaccine    2510  TACTTAAGAAAGATTAAAGGTGAAACCGTATTTGATATGTCTGAGTGA  2557
                 ||||||||||||||||||||||||||||||||||||||||||||||||
MA104(JP)2461  TACTTAAGAAAGATTAAAGGTGAAACCGTATTTGATATGTCTGAGTGA  2508
```

FIG. 47C

Comparison of amino acid (coding region) sequences of RV3 VP3

Vaccine 643 K to MA104(JP) 643 E
Vaccine 785 H to MA104(JP) 785 Y

```
Vaccine   50    MKVLALRHSVAQVYADTQTYLHDDSKDEYENAFLISNLTTHNILYLNYSLKTLKILNESG  229
                MKVLALRHSVAQVYADTQTYLHDDSKDEYENAFLISNLTTHNILYLNYSLKTLKILNESG
MA104(JP)1      MKVLALRHSVAQVYADTQTYLHDDSKDEYENAFLISNLTTHNILYLNYSLKTLKILNESG  60

Vaccine   230   IAAVEVQSPDELFALIRCNFTYDYENNIVYLHDYSYYTNNEIRTDQHWITKTDIIDYLLP  409
                IAAVEVQSPDELFALIRCNFTYDYENNIVYLHDYSYYTNNEIRTDQHWITKTDIIDYLLP
MA104(JP)61     IAAVEVQSPDELFALIRCNFTYDYENNIVYLHDYSYYTNNEIRTDQHWITKTDIIDYLLP  120

Vaccine   410   GWKLTYVGYNGKNTRGHYDFSFICQNAATDDDIIIEYIYSNELDFQNFLLRKIKERMTTS  589
                GWKLTYVGYNGKNTRGHYDFSFICQNAATDDDIIIEYIYSNELDFQNFLLRKIKERMTTS
MA104(JP)121    GWKLTYVGYNGKNTRGHYDFSFICQNAATDDDIIIEYIYSNELDFQNFLLRKIKERMTTS  180

Vaccine   590   LPIARLSNRVFRDKLFPSIVNIHKKVINVGPRNESMFTFLNFPTIKQFSNGAYIVKHTIK  769
                LPIARLSNRVFRDKLFPSIVNIHKKVINVGPRNESMFTFLNFPTIKQFSNGAYIVKHTIK
MA104(JP)181    LPIARLSNRVFRDKLFPSIVNIHKKVINVGPRNESMFTFLNFPTIKQFSNGAYIVKHTIK  240

Vaccine   770   LKQEKWLGKRVSQFDIGQYKNMlnvvttiyyyynlyySKPIIYMLGSAPSYWIYDIKQYS  949
                LKQEKWLGKRVSQFDIGQYKNMLNVVTTIYYYYNLYYSKPIIYMLGSAPSYWIYDIKQYS
MA104(JP)241    LKQEKWLGKRVSQFDIGQYKNMLNVVTTIYYYYNLYYSKPIIYMLGSAPSYWIYDIKQYS  300

Vaccine   950   DFTFETWDPLDTPYSTTHHKELFFDKDVNKLKDNSVLYIDIRTDRGNMDWKEWRKIVEQQ  1129
                DFTFETWDPLDTPYSTTHHKELFFDKDVNKLKDNSVLYIDIRTDRGNMDWKEWRKIVEQQ
MA104(JP)301    DFTFETWDPLDTPYSTTHHKELFFDKDVNKLKDNSVLYIDIRTDRGNMDWKEWRKIVEQQ  360

Vaccine   1130  TVSNLNIAYKYLSTGKAKVCCVKLTAMDLELPITAKLLHHPTTEVRSEFYAILDVWDIIT  1309
                TVSNLNIAYKYLSTGKAKVCCVKLTAMDLELPITAKLLHHPTTEVRSEFYAILDVWDIIT
MA104(JP)361    TVSNLNIAYKYLSTGKAKVCCVKLTAMDLELPITAKLLHHPTTEVRSEFYAILDVWDIIT  420

Vaccine   1310  IKRFIPKGVFYAFINNVTTENVFIQPPFKLKTSPTDYIVALYALSNDFNSRQDVINLINK  1489
                IKRFIPKGVFYAFINNVTTENVFIQPPFKLKTSPTDYIVALYALSNDFNSRQDVINLINK
MA104(JP)421    IKRFIPKGVFYAFINNVTTENVFIQPPFKLKTSPTDYIVALYALSNDFNSRQDVINLINK  480

Vaccine   1490  QKQSLITVRINNTFKDEPKVNFKNIYDWTFLPTDFELKDSIITSYDGClgifglsislss  1669
                QKQSLITVRINNTFKDEPKVNFKNIYDWTFLPTDFELKDSIITSYDGCLGIFGLSISLSS
MA104(JP)481    QKQSLITVRINNTFKDEPKVNFKNIYDWTFLPTDFELKDSIITSYDGCLGIFGLSISLSS  540

Vaccine   1670  KPTGNNHLFIINGTDKYDKLDQYANHMGISRRSHQIRFSESATSYSGYIFRDLSNNNFNL  1849
                KPTGNNHLFIINGTDKYDKLDQYANHMGISRRSHQIRFSESATSYSGYIFRDLSNNNFNL
MA104(JP)541    KPTGNNHLFIINGTDKYDKLDQYANHMGISRRSHQIRFSESATSYSGYIFRDLSNNNFNL  600

Vaccine   1850  IGTNVENSVSGHVYNALIYYRYNYAFDLKRWIYLHSIGKVAVKGGRYYEHAPIELIYACR  2029
                IGTNVENSVSGHVYNALIYYRYNYAFDLKRWIYLHSIGKVAV+GGRYYEHAPIELIYACR
MA104(JP)601    IGTNVENSVSGHVYNALIYYRYNYAFDLKRWIYLHSIGKVAVEGGRYYEHAPIELIYACR  660

Vaccine   2030  SAKEFAILQDDLTVLRYANEIEGYISKVYSITYADDPNYFIGIKFNSIPYEYDVKIPHLT  2209
                SAKEFAILQDDLTVLRYANEIEGYISKVYSITYADDPNYFIGIKFNSIPYEYDVKIPHLT
MA104(JP)661    SAKEFAILQDDLTVLRYANEIEGYISKVYSITYADDPNYFIGIKFNSIPYEYDVKIPHLT  720

Vaccine   2210  LGVLFISDNMIHDVITVLKKMKTELFKMEISTSYTYMLSDNTYVANASGVLSTYFKLYNM  2389
                LGVLFISDNMIHDVITVLKKMKTELFKMEISTSYTYMLSDNTYVANASGVLSTYFKLYNM
MA104(JP)721    LGVLFISDNMIHDVITVLKKMKTELFKMEISTSYTYMLSDNTYVANASGVLSTYFKLYNM  780

Vaccine   2390  FYRNHITFGQSRMFIPHITLSFSNKQTVRIESTKLRINSIYLRKIKGETVFDMSE  2554
                FYRN+ITFGQSRMFIPHITLSFSNKQTVRIESTKLRINSIYLRKIKGETVFDMSE
MA104(JP)781    FYRNYITFGQSRMFIPHITLSFSNKQTVRIESTKLRINSIYLRKIKGETVFDMSE  835
```

FIG. 48

VP4 sequence
MA104-adapted RV3 VP4 (SEQ ID NO:59)

```
   1 ATGGCTTCAC TCATTTATAG ACAGCTACTC ACTAATTCAT ACACAGTTGA ATTATCAGAT
  61 GAGATTAATA CGATTGGATC AGAAAAAAGT CAAAATGTAA CGATTAATCC CGGACCGTTT
 121 GCTCAACCAA ATTATGCACG AGTAACTTGG AGTCATGGGG AAGTGAATGA TTCGACAACA
 181 ATAGAGCCAG TACTTGATGG CCCTTATCAA TCAACAAGTT TTAAGCCACC AAGCGATTAC
 241 TGGATATTAT TGAATCCAAC TAATCAACAA GTTGTATTAG AGGGTACCAA TAAAACTGAT
 301 ATTTGGGTTG CCTTATTACT TGTTGAACCA AACGTAACCA ATCAAAGTAG ACAATACACA
 361 TTATTTGGAG AAACGAAACA AATTACTGTA GAAAATAACA CAAACAAATG GAAATTCTTC
 421 GAAATGTTCA GAAGCAGTGT TAGTGCCGAA TTTCAACATA AGCGCACTTT AACATCAGAC
 481 ACTAAATTAG CTGGGTTTTT AAAACATTAT AACAGTGTTT GGACTTTCCA CGGTGAAACG
 541 CCACATGCTA CAACTGATTA CTCATCAACT TCAAATTTAT CTGAAGTAGA AACTACAATA
 601 CATGTTGAGT TTTATATAAT ACCAAGATCG CAGGAATCTA AGTGTGTTGA ATATATAAAT
 661 ACTGGATTGC CACCAATGCA GAATACAAGG AATATAGTTC CAGTTGCACT ATCATCTAGA
 721 GCAGTGACTT ATCAACGTGC TCAGGTTAAT GAAGATATCA TCATATCAAA GACATCGTTG
 781 TGGAAGGAAA TGCAATATAA CAGAGACATC GTAATAAGGT TTAAATTTAA TAATAGTATA
 841 GTAAAACTTG GTGGGCTAGG TTATAAATGG TCAGAAATTT CGTTTAAAGC TGCTAATTAT
 901 CAGTACAATT ACTTGCGAGA TGGAGAACAA GTTACGGCAC ATACTACTTG TTCAGTCAAT
 961 GGTGTGAATA ACTTCAGTTA TAATGGAGGA TCACTGCCAA CTGATTTTAG TGTATCAAGA
1021 TATGAAGTGA TTAAGGAGAA TTCTTATGTC TATGTTGATT ATTGGGATGA TTCACAAGCA
1081 TTTAGGAACA TGGTATACGT CAGGTCATTG GCAGCAAATT TAAATTCAGT AAAGTGTAGT
1141 GGAGGAAATT ATGATTTTCA AATACCAGTT GGTGCATGGC CAGTGATGAG TGGAGGTGCG
1201 GTATCTTTGC ATTTTGCGGG AGTCACCTTA TCCACTCAAT TTACTGACTT TGTATCACTT
1261 AATTCGTTAA GATTTAGATT CAGTTTGACC GTTGAAGATC CACCTTTTTC AATTTCACGC
1321 ACACGTGTGT CAGGATTATA CGGGCTACCA GCATTTAATC CGAATAGCGG ACATGAATAT
1381 TATGAAATAG CTGGGGGATT TTCTCTTATT TCATTAGTAC CGTCTAATGA CGATTATCAA
1441 ACTCCAATCA TGAATTCAGT TACAGTGCGA CAAGATCTTG AACGTCAACT AGGTGATTTA
1501 AGGGAGGAAT TCAATTCTCT ATCACAAGAA ATAGCGATGA CGCAATTGAT AGATTTAGCA
1561 TTATTACCGT TAGATATGTT TTCTATGTTC TCAGGTATTA AAAGCACAAT TGACGCAGCT
1621 AAATCAATGG CCACAAAGGT GATGAAAAAG TTTAAGAGAT CGGGATTAGC TACATCAATC
1681 TCTGAATTAA CTGGATCATT ATCAAACGCT GCTTCATCAG TTTCCAGAAG TTCATCTATT
1741 AGATCTAACA TATCATCCAT TTCAGTGTGG ACGGATGTTT CCGAACAGAT AGCGGGTTCG
1801 TCAGACTCTG TCAGGAATAT TTCCACGCAA ACGTCAGCTA TTAGTAGAAG ATTGCGACTA
1861 CGCGAAATTA CTACACAAAC TGAAGGTATG AATTTTGATG ATATTTCAGC GGCAGTTCTT
1921 AAAACTAAGA TAGATAAATC AACTCATATA AGCCCAGATA CATTACCAGA CATAATAACT
1981 GAGTCATCTG AAAAATTCAT ACCAAAACGA GCTTATAGAG TTCTAAAAGA TGATGAAGTG
2041 ATGGAAGCTG ACGTGGATGG GAAGTTCTTT GCATATAAGG TTGACACTTT TGAAGAAGTG
2101 CCATTTGACG TAGATAAATT TGTCGATTTG GTAACTGATT CTCCTGTAAT TTCAGCTATA
2161 ATCGATTTTA AGACGTTGAA GAATTTAAAC GACAATTATG GTATAACGCG ATCTCAAGCG
2221 TTAGACTTAA TCAGATCTGA TCCCAGAGTT TTACGCGATT TTATCAATCA GAATAATCCA
2281 ATTATTAAAA ATAGAATTGA ACAGCTAATA CTGCAATGTA GACTGTGA
```

FIG. 49

Amino acid (coding region) ADD31861 (SEQ ID NO:60)

```
  1 MASLIYRQLL TNSYTVELSD EINTIGSEKS QNVTINPGPF AQPNYARVTW SHGEVNDSTT
 61 IEPVLDGPYQ STSFKPPSDY WILLNPTNQQ VVLEGTNKTD IWVALLLVEP NVTNQSRQYT
121 LFGETKQITV ENNTNKWKFF EMFRSSVSAE FQHKRTLTSD TKLAGFLKHY NSVWTFHGET
181 PHATTDYSST SNLSEVETTI HVEFYIIPRS QESKCVEYIN TGLPPMQNTR NIVPVALSSR
241 AVTYQRAQVN EDIIISKTSL WKEMQYNRDI VIRFKFNNSI VKLGGLGYKW SEISFKAANY
301 QYNYLRDGEQ VTAHTTCSVN GVNNFSYNGG SLPTDFSVSR YEVIKENSYV YVDYWDDSQA
361 FRNMVYVRSL AANLNSVKCS GGNYDFQIPV GAWPVMSGGA VSLHFAGVTL STQFTDFVSL
421 NSLRFRFSLT VEDPPFSISR TRVSGLYGLP AFNPNSGHEY YEIAGGFSLI SLVPSNDDYQ
481 TPIMNSVTVR QDLERQLGDL REEFNSLSQE IAMTQLIDLA LLPLDMFSMF SGIKSTIDAA
541 KSMATKVMKK FKRSGLATSI SELTGSLSNA ASSVSRSSSI RSNISSISVW TDVSEQIAGS
601 SDSVRNISTQ TSAISRRLRL REITTQTEGM NFDDISAAVL KTKIDKSTHI SPDTLPDIIT
661 ESSEKFIPKR AYRVLKDDEV MEADVDGKFF AYKVDTFEEV PFDVDKFVDL VTDSPVISAI
721 IDFKTLKNLN DNYGITRSQA LDLIRSDPRV LRDFINQNNP IIKNRIEQLI LQCRL
```

FIG. 50

Vero-adapted (Vaccine) RV3 VP4 (SEQ ID NO:61)

```
   1 GGCTATAAAA TGGCTTCACT CATTTATAGA CAGCTACTCA CTAATTCATA CACAGTTGAA
  61 TTATCAGATG AGATTAATAC GATTGGATCA GAAAAAAGTC AAAATGTAAC GATTAATCCC
 121 GGACCGTTTG CTCAAACAAA TTATGCACGA GTAACTTGGA GTCATGGGGA AGTGAATGAT
 181 TCGACAACAA TAGAGCCAGT ACTTGATGGC CCTTATCAAT CAACAAGTTT TAAGCCACCA
 241 AGCGATTACT GGATATTATT GAATCCAACT AATCAACAAG TTGTATTAGA GGGTACCAAT
 301 AAAACTGATA TTTGGGTTGC CTTATTACTT GTTGAACCAA ACGTAACCAA TCAAAGTAGA
 361 CAATACACGT TATTTGGAGA AACGAAACAA ATTACTGTAG AAAATAACAC AAACAAATGG
 421 AAATTCTTCG AAATGTTCAG AAGCAGTGTT AGTGCCGAAT TTCAACATAA GCGCACTTTA
 481 ACATCAGACA CTAAATTAGC TGGGTTTTTA AAACATTATA ACAGTGTTTG GACTTTCCAC
 541 GGTGAAACGC CACATGCTAC AACTGATTAC TCATCAACTT CAAATTTATC TGAAGTAGAA
 601 ACTACAATAC ATGTTGAGTT TTATATAATA CCAAGATCGC AGGAATCTAA GTGTGTTGAA
 661 TATATAAATA CTGGATTGCC ACCAATGCAG AATACAAGGA ATATAGTTCC AGTTGCACTA
 721 TCATCTAGAG CAGTGACTTA TCAACGTGCT CAGGTTAATG AAGATATCAT CATATCAAAG
 781 ACATCGTTGT GGAAGGAAAT GCAATATAAC AGAGACATCG TAATAAGGTT TAAATTTAAT
 841 AATAGTATAG TAAAACTTGG TGGGCTAGGT TATAAATGGT CAGAAATTTC GTTTAAAGCT
 901 GCTAATTATC AGTACAATTA CTTGCGAGAT GGAGAACAAG TTACGGCACA TACTACTTGT
 961 TCAGTCAATG GTGTGAATAA CTTCAGTTAT AATGGAGGAT CACTGCCAAC TGATTTTAGT
1021 GTATCAAGAT ATGAAGTGAT TAAGGAGAAT TCTTATGTCT ATGTTGATTA TTGGGATGAT
1081 TCACAAGCAT TTAGGAACAT GGTATACGTC AGGTCATTGG CAGCAAATTC AAATTCAGTA
1141 AAGTGTAGTG GAGGAAATTA TAATTTTCAA CTACCAGTTG GTGCATGGCC AGTGATGAGT
1201 GGAGGTGCGG TATCTTTGCA TTTTGCGGGA GTCACCTTAT CCACTCAATT TACTGACTTT
1261 GTATCACTTA ATTCGTTAAG ATTTAGATTC AGTTTGACCG TTGAAGATCC ACCTTTTTCA
1321 ATTTCACGCA CACATGTGTC AGGATTATAC GGGCTACCAG CATTTAATCC GAATAGCGGA
1381 CATGAATATT ATGAAATAGC TGGGGGATTT TCTCTTATTT CATTAGTACC GTCTAATGAC
1441 GATTATCAAA CTCCAATCAT GAATTCAGTT ACAGTGCGAC AAGATCTTGA ACGTCAACTA
1501 GGTGATTTAA GGGAGGAATT CAATTCTCTA TCACAAGAAA TAGCGATGAC GCAATTGATA
1561 GATTTAGCAT TATTACCGTT AGATATGTTT TCTATGTTCT CAGGTATTAA AAGCACAATT
1621 GACGCAGCTA AATCAATGGC CACAAAGGTG ATGAAAAAGT TTAAGAGATC GGGATTAGCT
1681 ACATCAATCT CTGAATTAAC TGGATCATTA TCAAACGCTG CTTCATCAGT TTCCAGAAGT
1741 TCATCTATTA GATCTAACAT ATCATCCATT TCAGTGTGGA CGGATGTTTC CGAACAGATA
1801 GCGGGTTCGT CAGACTCTGT CAGGAATATT TCCACGCAAA CGTCAGCTAT TAGTAGAAGA
1861 TTGCGACTAC GCGAAATTAC TACACAAACT GAAGGTATGA ATTTTGATGA TATTTCAGCG
1921 GCAGTTCTTA AAACTAAGAT AGATAAATCA ACTCATATAA GCCCAGATAC ATTACCAGAC
1981 ATAATAACTG AGTCATCTGA AAAATTCATA CCAAAACGAG CTTATAGAGT TCTAAAAGAT
2041 GATGAAGTGA TGGAAGCTGA CGTGGATGGG AAGTTCTTTG CATATAAGGT TGACACTTTT
2101 GAAGAAGTGC CATTTGACGT AGATAAATTT GTCGATTTGG TAACTGATTC TCCTGTAATT
2161 TCAGCTATAA TCGATTTTAA GACGTTGAAG AATTTAAACG ACAATTATGG TATAACGCGA
2221 TCTCAAGCGT TAGACTTAAT CAGATCTGAT CCCAGAGTTT TACGCGATTT TATCATTCAG
2281 AATAATCCAA TTATTAAAAA TAGAATTGAA CAGCTAATAC TGCAATGTAG ACTGTGAGAG
2341 CTCCATCGAG GAATGTGACC GGTCATAGCT GTTTCCTG
```

FIG. 51

Amino acid (coding region) [SEQ ID NO:62]

```
  1 MASLIYRQLL TNSYTVELSD EINTIGSEKS QNVTINPGPF AQTNYARVTW SHGEVNDSTT
 61 IEPVLDGPYQ STSFKPPSDY WILLNPTNQQ VVLEGTNKTD IWVALLLVEP NVTNQSRQYT
121 LFGETKQITV ENNTNKWKFF EMFRSSVSAE FQHKRTLTSD TKLAGFLKHY NSVWTFHGET
181 PHATTDYSST SNLSEVETTI HVEFYIIPRS QESKCVEYIN TGLPPMQNTR NIVPVALSSR
241 AVTYQRAQVN EDIIISKTSL WKEMQYNRDI VIRFKFNNSI VKLGGLGYKW SEISFKAANY
301 QYNYLRDGEQ VTAHTTCSVN GVNNFSYNGG SLPTDFSVSR YEVIKENSYV YVDYWDDSQA
361 FRNMVYVRSL AANSNSVKCS GGNYNFQLPV GAWPVMSGGA VSLHFAGVTL STQFTDFVSL
421 NSLRFRFSLT VEDPPFSISR THVSGLYGLP AFNPNSGHEY YEIAGGFSLI SLVPSNDDYQ
481 TPIMNSVTVR QDLERQLGDL REEFNSLSQE IAMTQLIDLA LLPLDMFSMF SGIKSTIDAA
541 KSMATKVMKK FKRSGLATSI SELTGSLSNA ASSVSRSSSI RSNISSISVW TDVSEQIAGS
601 SDSVRNISTQ TSAISRRLRL REITTQTEGM NFDDISAAVL KTKIDKSTHI SPDTLPDIIT
661 ESSEKFIPKR AYRVLKDDEV MEADVDGKFF AYKVDTFEEV PFDVDKFVDL VTDSPVISAI
721 IDFKTLKNLN DNYGITRSQA LDLIRSDPRV LRDFIIQNNPI IKNRIEQLI LQCRL
```

FIG. 52

Comparison of nucleotide sequences of RV3 VP4

Vaccine 136 A to MA104(JP) 127 C
Vaccine 369 G to MA104(JP) 360 A
Vaccine 1130 C to MA104(JP) 1121 T
Vaccine 1162 A to MA104(JP) 1153 G
Vaccine 1171 C to MA104(JP) 1162 A
Vaccine 1334 A to MA104(JP) 1325 G
Vaccine 2276 T to MA104(JP) 2267 A

```
Vaccine   10     ATGGCTTCACTCATTTATAGACAGCTACTCACTAATTCATACACAGTTGAATTATCAGAT  69
                 ||||||||||||||||||||||||||||||||||||||||||||||||||||||||||||
MA104(JP)1       ATGGCTTCACTCATTTATAGACAGCTACTCACTAATTCATACACAGTTGAATTATCAGAT  60

Vaccine   70     GAGATTAATACGATTGGATCAGAAAAAAGTCAAAATGTAACGATTAATCCCGGACCGTTT  129
                 ||||||||||||||||||||||||||||||||||||||||||||||||||||||||||||
MA104(JP)61      GAGATTAATACGATTGGATCAGAAAAAAGTCAAAATGTAACGATTAATCCCGGACCGTTT  120

Vaccine   130    GCTCAAACAAATTATGCACGAGTAACTTGGAGTCATGGGGAAGTGAATGATTCGACAACA  189
                 |||||| |||||||||||||||||||||||||||||||||||||||||||||||||||||
MA104(JP)121     GCTCAACCAAATTATGCACGAGTAACTTGGAGTCATGGGGAAGTGAATGATTCGACAACA  180

Vaccine   190    ATAGAGCCAGTACTTGATGGCCCTTATCAATCAACAAGTTTTAAGCCACCAAGCGATTAC  249
                 ||||||||||||||||||||||||||||||||||||||||||||||||||||||||||||
MA104(JP)181     ATAGAGCCAGTACTTGATGGCCCTTATCAATCAACAAGTTTTAAGCCACCAAGCGATTAC  240

Vaccine   250    TGGATATTATTGAATCCAACTAATCAACAAGTTGTATTAGAGGGTACCAATAAAACTGAT  309
                 ||||||||||||||||||||||||||||||||||||||||||||||||||||||||||||
MA104(JP)241     TGGATATTATTGAATCCAACTAATCAACAAGTTGTATTAGAGGGTACCAATAAAACTGAT  300

Vaccine   310    ATTTGGGTTGCCTTATTACTTGTTGAACCAAACGTAACCAATCAAAGTAGACAATACACG  369
                 ||||||||||||||||||||||||||||||||||||||||||||||||||||||||||| 
MA104(JP)301     ATTTGGGTTGCCTTATTACTTGTTGAACCAAACGTAACCAATCAAAGTAGACAATACACA  360

Vaccine   370    TTATTTGGAGAAACGAAACAAATTACTGTAGAAAATAACACAAACAAATGGAAATTCTTC  429
                 ||||||||||||||||||||||||||||||||||||||||||||||||||||||||||||
MA104(JP)361     TTATTTGGAGAAACGAAACAAATTACTGTAGAAAATAACACAAACAAATGGAAATTCTTC  420

Vaccine   430    GAAATGTTCAGAAGCAGTGTTAGTGCCGAATTTCAACATAAGCGCACTTTAACATCAGAC  489
                 ||||||||||||||||||||||||||||||||||||||||||||||||||||||||||||
MA104(JP)421     GAAATGTTCAGAAGCAGTGTTAGTGCCGAATTTCAACATAAGCGCACTTTAACATCAGAC  480

Vaccine   490    ACTAAATTAGCTGGGTTTTTAAAACATTATAACAGTGTTTGGACTTTCCACGGTGAAACG  549
                 ||||||||||||||||||||||||||||||||||||||||||||||||||||||||||||
MA104(JP)481     ACTAAATTAGCTGGGTTTTTAAAACATTATAACAGTGTTTGGACTTTCCACGGTGAAACG  540

Vaccine   550    CCACATGCTACAACTGATTACTCATCAACTTCAAATTTATCTGAAGTAGAAACTACAATA  609
                 ||||||||||||||||||||||||||||||||||||||||||||||||||||||||||||
MA104(JP)541     CCACATGCTACAACTGATTACTCATCAACTTCAAATTTATCTGAAGTAGAAACTACAATA  600

Vaccine   610    CATGTTGAGTTTTATATAATACCAAGATCGCAGGAATCTAAGTGTGTTGAATATATAAAT  669
                 ||||||||||||||||||||||||||||||||||||||||||||||||||||||||||||
MA104(JP)601     CATGTTGAGTTTTATATAATACCAAGATCGCAGGAATCTAAGTGTGTTGAATATATAAAT  660

Vaccine   670    ACTGGATTGCCACCAATGCAGAATACAAGGAATATAGTTCCAGTTGCACTATCATCTAGA  729
                 ||||||||||||||||||||||||||||||||||||||||||||||||||||||||||||
MA104(JP)661     ACTGGATTGCCACCAATGCAGAATACAAGGAATATAGTTCCAGTTGCACTATCATCTAGA  720

Vaccine   730    GCAGTGACTTATCAACGTGCTCAGGTTAATGAAGATATCATCATATCAAAGACATCGTTG  789
                 ||||||||||||||||||||||||||||||||||||||||||||||||||||||||||||
MA104(JP)721     GCAGTGACTTATCAACGTGCTCAGGTTAATGAAGATATCATCATATCAAAGACATCGTTG  780

Vaccine   790    TGGAAGGAAATGCAATATAACAGAGACATCGTAATAAGGTTTAAATTTAATAATAGTATA  849
                 ||||||||||||||||||||||||||||||||||||||||||||||||||||||||||||
MA104(JP)781     TGGAAGGAAATGCAATATAACAGAGACATCGTAATAAGGTTTAAATTTAATAATAGTATA  840
```

FIG. 53A

```
Vaccine   850   GTAAAACTTGGTGGGCTAGGTTATAAATGGTCAGAAATTTCGTTTAAAGCTGCTAATTAT  909
                ||||||||||||||||||||||||||||||||||||||||||||||||||||||||||||
MA104(JP)841    GTAAAACTTGGTGGGCTAGGTTATAAATGGTCAGAAATTTCGTTTAAAGCTGCTAATTAT  900

Vaccine   910   CAGTACAATTACTTGCGAGATGGAGAACAAGTTACGGCACATACTACTTGTTCAGTCAAT  969
                ||||||||||||||||||||||||||||||||||||||||||||||||||||||||||||
MA104(JP)901    CAGTACAATTACTTGCGAGATGGAGAACAAGTTACGGCACATACTACTTGTTCAGTCAAT  960

Vaccine   970   GGTGTGAATAACTTCAGTTATAATGGAGGATCACTGCCAACTGATTTTAGTGTATCAAGA  1029
                ||||||||||||||||||||||||||||||||||||||||||||||||||||||||||||
MA104(JP)961    GGTGTGAATAACTTCAGTTATAATGGAGGATCACTGCCAACTGATTTTAGTGTATCAAGA  1020

Vaccine   1030  TATGAAGTGATTAAGGAGAATTCTTATGTCTATGTTGATTATTGGGATGATTCACAAGCA  1089
                ||||||||||||||||||||||||||||||||||||||||||||||||||||||||||||
MA104(JP)1021   TATGAAGTGATTAAGGAGAATTCTTATGTCTATGTTGATTATTGGGATGATTCACAAGCA  1080

Vaccine   1090  TTTAGGAACATGGTATACGTCAGGTCATTGGCAGCAAATTCAAATTCAGTAAAGTGTAGT  1149
                |||||||||||||||||||||||||||||||||||||||| |||||||||||||||||||
MA104(JP)1081   TTTAGGAACATGGTATACGTCAGGTCATTGGCAGCAAATTTAAATTCAGTAAAGTGTAGT  1140

Vaccine   1150  GGAGGAAATTATAATTTTCAACTACCAGTTGGTGCATGGCCAGTGATGAGTGGAGGTGCG  1209
                |||||||||||| |||||||| ||||||||||||||||||||||||||||||||||||||
MA104(JP)1141   GGAGGAAATTATGATTTTCAAATACCAGTTGGTGCATGGCCAGTGATGAGTGGAGGTGCG  1200

Vaccine   1210  GTATCTTTGCATTTTGCGGGAGTCACCTTATCCACTCAATTTACTGACTTTGTATCACTT  1269
                ||||||||||||||||||||||||||||||||||||||||||||||||||||||||||||
MA104(JP)1201   GTATCTTTGCATTTTGCGGGAGTCACCTTATCCACTCAATTTACTGACTTTGTATCACTT  1260

Vaccine   1270  AATTCGTTAAGATTTAGATTCAGTTTGACCGTTGAAGATCCACCTTTTTCAATTTCACGC  1329
                ||||||||||||||||||||||||||||||||||||||||||||||||||||||||||||
MA104(JP)1261   AATTCGTTAAGATTTAGATTCAGTTTGACCGTTGAAGATCCACCTTTTTCAATTTCACGC  1320

Vaccine   1330  ACACATGTGTCAGGATTATACGGGCTACCAGCATTTAATCCGAATAGCGGACATGAATAT  1389
                |||| |||||||||||||||||||||||||||||||||||||||||||||||||||||||
MA104(JP)1321   ACACGTGTGTCAGGATTATACGGGCTACCAGCATTTAATCCGAATAGCGGACATGAATAT  1380

Vaccine   1390  TATGAAATAGCTGGGGGATTTTCTCTTATTTCATTAGTACCGTCTAATGACGATTATCAA  1449
                ||||||||||||||||||||||||||||||||||||||||||||||||||||||||||||
MA104(JP)1381   TATGAAATAGCTGGGGGATTTTCTCTTATTTCATTAGTACCGTCTAATGACGATTATCAA  1440

Vaccine   1450  ACTCCAATCATGAATTCAGTTACAGTGCGACAAGATCTTGAACGTCAACTAGGTGATTTA  1509
                ||||||||||||||||||||||||||||||||||||||||||||||||||||||||||||
MA104(JP)1441   ACTCCAATCATGAATTCAGTTACAGTGCGACAAGATCTTGAACGTCAACTAGGTGATTTA  1500

Vaccine   1510  AGGGAGGAATTCAATTCTCTATCACAAGAAATAGCGATGACGCAATTGATAGATTTAGCA  1569
                ||||||||||||||||||||||||||||||||||||||||||||||||||||||||||||
MA104(JP)1501   AGGGAGGAATTCAATTCTCTATCACAAGAAATAGCGATGACGCAATTGATAGATTTAGCA  1560

Vaccine   1570  TTATTACCGTTAGATATGTTTTCTATGTTCTCAGGTATTAAAAGCACAATTGACGCAGCT  1629
                ||||||||||||||||||||||||||||||||||||||||||||||||||||||||||||
MA104(JP)1561   TTATTACCGTTAGATATGTTTTCTATGTTCTCAGGTATTAAAAGCACAATTGACGCAGCT  1620

Vaccine   1630  AAATCAATGGCCACAAAGGTGATGAAAAAGTTTAAGAGATCGGGATTAGCTACATCAATC  1689
                ||||||||||||||||||||||||||||||||||||||||||||||||||||||||||||
MA104(JP)1621   AAATCAATGGCCACAAAGGTGATGAAAAAGTTTAAGAGATCGGGATTAGCTACATCAATC  1680

Vaccine   1690  TCTGAATTAACTGGATCATTATCAAACGCTGCTTCATCAGTTTCCAGAAGTTCATCTATT  1749
                ||||||||||||||||||||||||||||||||||||||||||||||||||||||||||||
MA104(JP)1681   TCTGAATTAACTGGATCATTATCAAACGCTGCTTCATCAGTTTCCAGAAGTTCATCTATT  1740

Vaccine   1750  AGATCTAACATATCATCCATTTCAGTGTGGACGGATGTTTCCGAACAGATAGCGGGTTCG  1809
                ||||||||||||||||||||||||||||||||||||||||||||||||||||||||||||
MA104(JP)1741   AGATCTAACATATCATCCATTTCAGTGTGGACGGATGTTTCCGAACAGATAGCGGGTTCG  1800

Vaccine   1810  TCAGACTCTGTCAGGAATATTTCCACGCAAACGTCAGCTATTAGTAGAAGATTGCGACTA  1869
                ||||||||||||||||||||||||||||||||||||||||||||||||||||||||||||
MA104(JP)1801   TCAGACTCTGTCAGGAATATTTCCACGCAAACGTCAGCTATTAGTAGAAGATTGCGACTA  1860

Vaccine   1870  CGCGAAATTACTACACAAACTGAAGGTATGAATTTTGATGATATTTCAGCGGCAGTTCTT  1929
                ||||||||||||||||||||||||||||||||||||||||||||||||||||||||||||
MA104(JP)1861   CGCGAAATTACTACACAAACTGAAGGTATGAATTTTGATGATATTTCAGCGGCAGTTCTT  1920
```

FIG. 53B

```
Vaccine    1930  AAAACTAAGATAGATAAATCAACTCATATAAGCCCAGATACATTACCAGACATAATAACT  1989
                 ||||||||||||||||||||||||||||||||||||||||||||||||||||||||||||
MA104(JP)1921    AAAACTAAGATAGATAAATCAACTCATATAAGCCCAGATACATTACCAGACATAATAACT  1980

Vaccine    1990  GAGTCATCTGAAAAATTCATACCAAAACGAGCTTATAGAGTTCTAAAAGATGATGAAGTG  2049
                 ||||||||||||||||||||||||||||||||||||||||||||||||||||||||||||
MA104(JP)1981    GAGTCATCTGAAAAATTCATACCAAAACGAGCTTATAGAGTTCTAAAAGATGATGAAGTG  2040

Vaccine    2050  ATGGAAGCTGACGTGGATGGGAAGTTCTTTGCATATAAGGTTGACACTTTTGAAGAAGTG  2109
                 ||||||||||||||||||||||||||||||||||||||||||||||||||||||||||||
MA104(JP)2041    ATGGAAGCTGACGTGGATGGGAAGTTCTTTGCATATAAGGTTGACACTTTTGAAGAAGTG  2100

Vaccine    2110  CCATTTGACGTAGATAAATTTGTCGATTTGGTAACTGATTCTCCTGTAATTTCAGCTATA  2169
                 ||||||||||||||||||||||||||||||||||||||||||||||||||||||||||||
MA104(JP)2101    CCATTTGACGTAGATAAATTTGTCGATTTGGTAACTGATTCTCCTGTAATTTCAGCTATA  2160

Vaccine    2170  ATCGATTTTAAGACGTTGAAGAATTTAAACGACAATTATGGTATAACGCGATCTCAAGCG  2229
                 ||||||||||||||||||||||||||||||||||||||||||||||||||||||||||||
MA104(JP)2161    ATCGATTTTAAGACGTTGAAGAATTTAAACGACAATTATGGTATAACGCGATCTCAAGCG  2220

Vaccine    2230  TTAGACTTAATCAGATCTGATCCCAGAGTTTTACGCGATTTTATCATTCAGAATAATCCA  2289
                 |||||||||||||||||||||||||||||||||||||||||||||| |||||||||||||
MA104(JP)2221    TTAGACTTAATCAGATCTGATCCCAGAGTTTTACGCGATTTTATCAATCAGAATAATCCA  2280

Vaccine    2290  ATTATTAAAAATAGAATTGAACAGCTAATACTGCAATGTAGACTGTGA  2337
                 ||||||||||||||||||||||||||||||||||||||||||||||||
MA104(JP)2281    ATTATTAAAAATAGAATTGAACAGCTAATACTGCAATGTAGACTGTGA  2328
```

FIG. 53C

Comparison of amino acid (coding region) sequences of RV3 VP4

Vaccine 43 T to MA104(JP) 43 P
Vaccine 374 S to MA104(JP) 374 L
Vaccine 385 N to MA104(JP) 385 D
Vaccine 388 L to MA104(JP) 388 I
Vaccine 442 H to MA104(JP) 442 R
Vaccine 756 I to MA104(JP) 756 N

```
Vaccine   10    MASLIYRQLLTNSYTVELSDEINTIGSEKSQNVTINPGPFAQTNYARVTWSHGEVNDSTT  189
                MASLIYRQLLTNSYTVELSDEINTIGSEKSQNVTINPGPFAQ NYARVTWSHGEVNDSTT
MA104(JP)1      MASLIYRQLLTNSYTVELSDEINTIGSEKSQNVTINPGPFAQPNYARVTWSHGEVNDSTT  60

Vaccine   190   IEPVLDGPYQSTSFKPPSDYWILLNPTNQQVVLEGTNKTDIWVALLLVEPNVTNQSRQYT  369
                IEPVLDGPYQSTSFKPPSDYWILLNPTNQQVVLEGTNKTDIWVALLLVEPNVTNQSRQYT
MA104(JP)61     IEPVLDGPYQSTSFKPPSDYWILLNPTNQQVVLEGTNKTDIWVALLLVEPNVTNQSRQYT  120

Vaccine   370   LFGETKQITVENNTNKWKFFEMFRSSVSAEFQHKRTLTSDTKLAGFLKHYNSVWTFHGET  549
                LFGETKQITVENNTNKWKFFEMFRSSVSAEFQHKRTLTSDTKLAGFLKHYNSVWTFHGET
MA104(JP)121    LFGETKQITVENNTNKWKFFEMFRSSVSAEFQHKRTLTSDTKLAGFLKHYNSVWTFHGET  180

Vaccine   550   PHATTDYSSTSNLSEVETTIHVEFYIIPRSQESKCVEYINTGLPPMQNTRNIVPVALSSR  729
                PHATTDYSSTSNLSEVETTIHVEFYIIPRSQESKCVEYINTGLPPMQNTRNIVPVALSSR
MA104(JP)181    PHATTDYSSTSNLSEVETTIHVEFYIIPRSQESKCVEYINTGLPPMQNTRNIVPVALSSR  240

Vaccine   730   AVTYQRAQVNEDIIISKTSLWKEMQYNRDIVIRFKFNNSIVKLGGLGYKWSEISFKAANY  909
                AVTYQRAQVNEDIIISKTSLWKEMQYNRDIVIRFKFNNSIVKLGGLGYKWSEISFKAANY
MA104(JP)241    AVTYQRAQVNEDIIISKTSLWKEMQYNRDIVIRFKFNNSIVKLGGLGYKWSEISFKAANY  300

Vaccine   910   QYNYLRDGEQVTAHTTCSVNGVNNFSYNGGSLPTDFSVSRYEVIKENSYVYVDYWDDSQA  1089
                QYNYLRDGEQVTAHTTCSVNGVNNFSYNGGSLPTDFSVSRYEVIKENSYVYVDYWDDSQA
MA104(JP)301    QYNYLRDGEQVTAHTTCSVNGVNNFSYNGGSLPTDFSVSRYEVIKENSYVYVDYWDDSQA  360

Vaccine   1090  FRNMVYVRSLAANSNSVKCSGGNYNFQLPVGAWPVMSGGAVSLHFAGVTLSTQFTDFVSL  1269
                FRNMVYVRSLAAN NSVKCSGGNY+FQ+PVGAWPVMSGGAVSLHFAGVTLSTQFTDFVSL
MA104(JP)361    FRNMVYVRSLAANLNSVKCSGGNYDFQIPVGAWPVMSGGAVSLHFAGVTLSTQFTDFVSL  420

Vaccine   1270  NSLRFRFSLTVEDPPFSISRTHVSGLYGLPAFNPNSGHEYYEIAGGFSLISLVPSNDDYQ  1449
                NSLRFRFSLTVEDPPFSISRT VSGLYGLPAFNPNSGHEYYEIAGGFSLISLVPSNDDYQ
MA104(JP)421    NSLRFRFSLTVEDPPFSISRTRVSGLYGLPAFNPNSGHEYYEIAGGFSLISLVPSNDDYQ  480

Vaccine   1450  TPIMNSVTVRQDLERQLGDLREEFNSLSQEIAMTQLIDLALLPLDMFSMFSGIKSTIDAA  1629
                TPIMNSVTVRQDLERQLGDLREEFNSLSQEIAMTQLIDLALLPLDMFSMFSGIKSTIDAA
MA104(JP)481    TPIMNSVTVRQDLERQLGDLREEFNSLSQEIAMTQLIDLALLPLDMFSMFSGIKSTIDAA  540

Vaccine   1630  KSMATKVMKKFKRSGLATSISELTGSLsnaassvsrsssirsnissisvWTDVSEQIAGS  1809
                KSMATKVMKKFKRSGLATSISELTGSLSNAASSVSRSSSIRSNISSISVWTDVSEQIAGS
MA104(JP)541    KSMATKVMKKFKRSGLATSISELTGSLSNAASSVSRSSSIRSNISSISVWTDVSEQIAGS  600

Vaccine   1810  SDSVRNISTQTSAISRRLRLREITTQTEGMNFDDISAAVLKTKIDKSTHISPDTLPDIIT  1989
                SDSVRNISTQTSAISRRLRLREITTQTEGMNFDDISAAVLKTKIDKSTHISPDTLPDIIT
MA104(JP)601    SDSVRNISTQTSAISRRLRLREITTQTEGMNFDDISAAVLKTKIDKSTHISPDTLPDIIT  660

Vaccine   1990  ESSEKFIPKRAYRVLKDDEVMEADVDGKFFAYKVDTFEEVPFDVDKFVDLVTDSPVISAI  2169
                ESSEKFIPKRAYRVLKDDEVMEADVDGKFFAYKVDTFEEVPFDVDKFVDLVTDSPVISAI
MA104(JP)661    ESSEKFIPKRAYRVLKDDEVMEADVDGKFFAYKVDTFEEVPFDVDKFVDLVTDSPVISAI  720

Vaccine   2170  IDFKTLKNLNDNYGITRSQALDLIRSDPRVLRDFIIQNNPIIKNRIEQLILQCRL  2334
                IDFKTLKNLNDNYGITRSQALDLIRSDPRVLRDFI QNNPIIKNRIEQLILQCRL
MA104(JP)721    IDFKTLKNLNDNYGITRSQALDLIRSDPRVLRDFINQNNPIIKNRIEQLILQCRL  775
```

FIG. 54

VP6 sequence
MA104-adapted RV3 VP6 (SEQ ID NO:39)

```
   1 ATGGAGGTTC TGTATTCATT GTCAAAAACT CTTAAAGATG CTAGGGATAA GATTGTTGAA
  61 GGTACATTAT ATTCTAATGT TAGTGATCTC ATTCAGCAAT TTAATCAAAT GATAGTAACC
 121 ATGAATGGAA ATGACTTTCA AACTGGAGGA ATTGGCAATT TACCTATTAG AAATTGGACA
 181 TTTGACTTTG GTCTACTAGG TACTACGCTG TTAAACCTTG ATGCTAATTA CGTTGAGACC
 241 GCAAGAACTA CAATTAAGTA TTTTATTGAC TTTATTGATA ATGTATGTAT GGATGAAATG
 301 GCAAGAGAGT CTCAAAGAAA TGGAGTAGCT CCACAATCTG AGGCATTGAG GAAGCTAGCC
 361 GGTATTAAAT TTAAAAGAAT AAATTTTAAT AATTCATCAG AATATATAGA AAATTGGAAT
 421 TTACAAAATA GAAGACAGCG TACCGGATTT GTTTTCCATA AACCTAATAT ATTTCCATAC
 481 TCAGCATCAT TTACTTTAAA TAGGTCTCAA CCAATGCATG ACAATTTAAT GGGAACCATG
 541 TGGCTTAACG CTGGATCAGA AATTCAAGTG GCTGGATTTG ACTACTCGTG TGCCCTAAAT
 601 GCTCCAGCAA ATATTCAGCA GTTTGAACAT ATTGTCCAGC TTAGGCGTGC GCTAACTACA
 661 GCTACTATAA CTTTGCTACC TGATGCAGAA AGATTTAGTT TTCCAAGAGT TATTAATTCA
 721 GCAGATGGCG CAACCACATG GTTCTTTAAT CCAATTATCC TAAGACCAAA CAATGTAGAG
 781 GTAGAATTTT TACTGAATGG ACAAATTATT AATACATATC AAGCTAGATT TGGCACTATT
 841 ATCGCAAGAA ATTTTGATAC AATTCGTCTA TCATTCCAAT TAATGCGTCC ACCAAACATG
 901 ACGCCAGCCG TAAATGCATT ATTTCCGCAA GCACAACCTT TTCAACATCA TGCAACAGTT
 961 GGACTTACGT TACGTATTGA GTCTGCAGTT TGTGAATCAG TGCTTGCGGA TGCAAATGAA
1021 ACTTTATTGG CGAATGTTAC TGCAGTACGT CAAGAGTATG CTATACCGGT TGGACCAGTA
1081 TTTCCACCAG GCATGAATTG GACTGAGCTG ATTACTAACT ATTCACCATC CAGGGAAGAT
1141 AATTTGCAAC GTGTCTTTAC AGTAGCCTCT ATCAGAAGCA TGTTAATTAA GTGA
```

FIG. 55

Amino acid (coding region) ADD31863 (SEQ ID NO:40)

```
   1 MEVLYSLSKT LKDARDKIVE GTLYSNVSDL IQQFNQMIVT MNGNDFQTGG IGNLPIRNWT
  61 FDFGLLGTTL LNLDANYVET ARTTIKYFID FIDNVCMDEM ARESQRNGVA PQSEALRKLA
 121 GIKFKRINFN NSSEYIENWN LQNRRQRTGF VFHKPNIFPY SASFTLNRSQ PMHDNLMGTM
 181 WLNAGSEIQV AGFDYSCALN APANIQQFEH IVQLRRALTT ATITLLPDAE RFSFPRVINS
 241 ADGATTWFFN PIILRPNNVE VEFLLNGQII NTYQARFGTI IARNFDTIRL SFQLMRPPNM
 301 TPAVNALFPQ AQPFQHHATV GLTLRIESAV CESVLADANE TLLANVTAVR QEYAIPVGPV
 361 FPPGMNWTEL ITNYSPSRED NLQRVFTVAS IRSMLIK
```

FIG. 56

Vero-adapted (Vaccine) RV3 VP6 (SEQ ID NO:41)

```
   1 GGCTTTTAAA CGAAGAAGTC TTCGACATGG AGGTTCTGTA TTCATTGTCA AAAACTCTTA
  61 AAGATGCTAG GGATAAGATT GTTGAAGGTA CATTATATTC TAATGTTAGT GATCTCATTC
 121 AGCAATTTAA TCAAATGATA GTAACCATGA ATGGAAATGA CTTTCAAACT GGAGGAATTG
 181 GCAATTTACC TATTAGAAAT TGGACATTTG ACTTTGGTCT ACTAGGTACT ACGCTGTTAA
 241 ACCTTGATGC TAATTACGTT GAGACCGCAA GAACTACAAT TAAGTATTTT ATTGACTTTA
 301 TTGATAATGT ATGTATGGAT GAAATGGCAA GAGAGTCTCA AAGAAATGGA GTAGCTCCAC
 361 AATCTGAGGC ATTGAGGAAG CTAGCCGGTA TTAAATTTAA AAGAATAAAT TTTAATAATT
 421 CATCAGAATA TATAGAAAAT TGGAATTTAC AAAATAGAAG ACAGCGTACC GGATTTGTTT
 481 TCCATAAACC TAATATATTT CCATACTCAG CATCATTTAC TTTAAATAGG TCTCAACCAA
 541 TGCATGACAA TTTAATGGGA ACCATGTGGC TTAACGCTGG ATCAGAAATT CAAGTGGCTG
 601 GATTTGACTA CTCGTGTGCC CTAAATGCTC CAGCAAATAT TCAGCAGTTT GAACATATTG
 661 TCCAGCTTAG GCGTGCGCTA ACTACAGCTA CTATAACTTT GCTACCTGAT GCAGAAAGAT
 721 TTAGTTTTCC AAGAGTTATT AATTCAGCAG ATGGCGCAAC CACATGGTTC TTTAATCCAA
 781 TTATCCTAAG ACCAAACAAT GTAGAGGTAG AATTTTTACT GAATGGACAA ATTATTAATA
 841 CATATCAAGC TAGATTTGGC ACTATTATCG CAAGAAATTT TGATACAATT CGTCTATCAT
 901 TCCAATTAAT GCGTCCACCA AACATGACGC CAGCCGTAAA TGCATTATTT CCGCAAGCAC
 961 AACCTTTTCA ACATCATGCA ACAGTTGGAC TTACGTTACG TATTGAGTCT GCAGTTTGTG
1021 AATCAGTGCT TGCGGATGCA AATGAAACTT TATTGGCGAA TGTTACTGCA GTACGTCAAG
1081 AGTATGCTAT ACCGGTTGGA CCAGTATTTC CACCAGGCAT GAATTGGACT GAGCTGATTA
1141 CTAACTATTC ACCATCCAGG GAAGATAATT TGCAACGTGT CTTTACAGTA GCCTCTATCA
1201 GAAGCATGTT AATTAAGTGA GGACCAGACT AACCATCTGG TATCCAATCT TAATTAGCAT
1261 GTAGCTATGT CAAGTCATTC AGACTCTACA AGTAAGGACA TGATTTCATG TTCGCTACGT
1321 AGAGTAACTG CATGAATGAT GTAGTGAGAG GATGTGACC
```

FIG. 57

Amino acid (coding region) [SEQ ID NO:42]

```
   1 MEVLYSLSKT LKDARDKIVE GTLYSNVSDL IQQFNQMIVT MNGNDFQTGG IGNLPIRNWT
  61 FDFGLLGTTL LNLDANYVET ARTTIKYFID FIDNVCMDEM ARESQRNGVA PQSEALRKLA
 121 GIKFKRINFN NSSEYIENWN LQNRRQRTGF VFHKPNIFPY SASFTLNRSQ PMHDNLMGTM
 181 WLNAGSEIQV AGFDYSCALN APANIQQFEH IVQLRRALTT ATITLLPDAE RFSFPRVINS
 241 ADGATTWFFN PIILRPNNVE VEFLLNGQII NTYQARFGTI IARNFDTIRL SFQLMRPPNM
 301 TPAVNALFPQ AQPFQHHATV GLTLRIESAV CESVLADANE TLLANVTAVR QEYAIPVGPV
 361 FPPGMNWTEL ITNYSPSRED NLQRVFTVAS IRSMLIK
```

FIG. 58

Comparison of nucleotide sequences of RV3 VP6

```
Vaccine   27    ATGGAGGTTCTGTATTCATTGTCAAAAACTCTTAAAGATGCTAGGGATAAGATTGTTGAA  86
                ||||||||||||||||||||||||||||||||||||||||||||||||||||||||||||
MA104(JP)1      ATGGAGGTTCTGTATTCATTGTCAAAAACTCTTAAAGATGCTAGGGATAAGATTGTTGAA  60

Vaccine   87    GGTACATTATATTCTAATGTTAGTGATCTCATTCAGCAATTTAATCAAATGATAGTAACC  146
                ||||||||||||||||||||||||||||||||||||||||||||||||||||||||||||
MA104(JP)61     GGTACATTATATTCTAATGTTAGTGATCTCATTCAGCAATTTAATCAAATGATAGTAACC  120

Vaccine   147   ATGAATGGAAATGACTTTCAAACTGGAGGAATTGGCAATTTACCTATTAGAAATTGGACA  206
                ||||||||||||||||||||||||||||||||||||||||||||||||||||||||||||
MA104(JP)121    ATGAATGGAAATGACTTTCAAACTGGAGGAATTGGCAATTTACCTATTAGAAATTGGACA  180

Vaccine   207   TTTGACTTTGGTCTACTAGGTACTACGCTGTTAAACCTTGATGCTAATTACGTTGAGACC  266
                ||||||||||||||||||||||||||||||||||||||||||||||||||||||||||||
MA104(JP)181    TTTGACTTTGGTCTACTAGGTACTACGCTGTTAAACCTTGATGCTAATTACGTTGAGACC  240

Vaccine   267   GCAAGAACTACAATTAAGTATTTTATTGACTTTATTGATAATGTATGTATGGATGAAATG  326
                ||||||||||||||||||||||||||||||||||||||||||||||||||||||||||||
MA104(JP)241    GCAAGAACTACAATTAAGTATTTTATTGACTTTATTGATAATGTATGTATGGATGAAATG  300

Vaccine   327   GCAAGAGAGTCTCAAAGAAATGGAGTAGCTCCACAATCTGAGGCATTGAGGAAGCTAGCC  386
                ||||||||||||||||||||||||||||||||||||||||||||||||||||||||||||
MA104(JP)301    GCAAGAGAGTCTCAAAGAAATGGAGTAGCTCCACAATCTGAGGCATTGAGGAAGCTAGCC  360

Vaccine   387   GGTATTAAATTTAAAAGAATAAATTTTAATAATTCATCAGAATATATAGAAAATTGGAAT  446
                ||||||||||||||||||||||||||||||||||||||||||||||||||||||||||||
MA104(JP)361    GGTATTAAATTTAAAAGAATAAATTTTAATAATTCATCAGAATATATAGAAAATTGGAAT  420

Vaccine   447   TTACAAAATAGAAGACAGCGTACCGGATTTGTTTTCCATAAACCTAATATATTTCCATAC  506
                ||||||||||||||||||||||||||||||||||||||||||||||||||||||||||||
MA104(JP)421    TTACAAAATAGAAGACAGCGTACCGGATTTGTTTTCCATAAACCTAATATATTTCCATAC  480

Vaccine   507   TCAGCATCATTTACTTTAAATAGGTCTCAACCAATGCATGACAATTTAATGGGAACCATG  566
                ||||||||||||||||||||||||||||||||||||||||||||||||||||||||||||
MA104(JP)481    TCAGCATCATTTACTTTAAATAGGTCTCAACCAATGCATGACAATTTAATGGGAACCATG  540

Vaccine   567   TGGCTTAACGCTGGATCAGAAATTCAAGTGGCTGGATTTGACTACTCGTGTGCCCTAAAT  626
                ||||||||||||||||||||||||||||||||||||||||||||||||||||||||||||
MA104(JP)541    TGGCTTAACGCTGGATCAGAAATTCAAGTGGCTGGATTTGACTACTCGTGTGCCCTAAAT  600

Vaccine   627   GCTCCAGCAAATATTCAGCAGTTTGAACATATTGTCCAGCTTAGGCGTGCGCTAACTACA  686
                ||||||||||||||||||||||||||||||||||||||||||||||||||||||||||||
MA104(JP)601    GCTCCAGCAAATATTCAGCAGTTTGAACATATTGTCCAGCTTAGGCGTGCGCTAACTACA  660

Vaccine   687   GCTACTATAACTTTGCTACCTGATGCAGAAAGATTTAGTTTTCCAAGAGTTATTAATTCA  746
                ||||||||||||||||||||||||||||||||||||||||||||||||||||||||||||
MA104(JP)661    GCTACTATAACTTTGCTACCTGATGCAGAAAGATTTAGTTTTCCAAGAGTTATTAATTCA  720

Vaccine   747   GCAGATGGCGCAACCACATGGTTCTTTAATCCAATTATCCTAAGACCAAACAATGTAGAG  806
                ||||||||||||||||||||||||||||||||||||||||||||||||||||||||||||
MA104(JP)721    GCAGATGGCGCAACCACATGGTTCTTTAATCCAATTATCCTAAGACCAAACAATGTAGAG  780

Vaccine   807   GTAGAATTTTTACTGAATGGACAAATTATTAATACATATCAAGCTAGATTTGGCACTATT  866
                ||||||||||||||||||||||||||||||||||||||||||||||||||||||||||||
MA104(JP)781    GTAGAATTTTTACTGAATGGACAAATTATTAATACATATCAAGCTAGATTTGGCACTATT  840

Vaccine   867   ATCGCAAGAAATTTTGATACAATTCGTCTATCATTCCAATTAATGCGTCCACCAAACATG  926
                ||||||||||||||||||||||||||||||||||||||||||||||||||||||||||||
MA104(JP)841    ATCGCAAGAAATTTTGATACAATTCGTCTATCATTCCAATTAATGCGTCCACCAAACATG  900

Vaccine   927   ACGCCAGCCGTAAATGCATTATTTCCGCAAGCACAACCTTTTCAACATCATGCAACAGTT  986
                ||||||||||||||||||||||||||||||||||||||||||||||||||||||||||||
MA104(JP)901    ACGCCAGCCGTAAATGCATTATTTCCGCAAGCACAACCTTTTCAACATCATGCAACAGTT  960
```

FIG. 59A

```
Vaccine   987   GGACTTACGTTACGTATTGAGTCTGCAGTTTGTGAATCAGTGCTTGCGGATGCAAATGAA  1046
                ||||||||||||||||||||||||||||||||||||||||||||||||||||||||||||
MA104(JP)961    GGACTTACGTTACGTATTGAGTCTGCAGTTTGTGAATCAGTGCTTGCGGATGCAAATGAA  1020

Vaccine   1047  ACTTTATTGGCGAATGTTACTGCAGTACGTCAAGAGTATGCTATACCGGTTGGACCAGTA  1106
                ||||||||||||||||||||||||||||||||||||||||||||||||||||||||||||
MA104(JP)1021   ACTTTATTGGCGAATGTTACTGCAGTACGTCAAGAGTATGCTATACCGGTTGGACCAGTA  1080

Vaccine   1107  TTTCCACCAGGCATGAATTGGACTGAGCTGATTACTAACTATTCACCATCCAGGGAAGAT  1166
                ||||||||||||||||||||||||||||||||||||||||||||||||||||||||||||
MA104(JP)1081   TTTCCACCAGGCATGAATTGGACTGAGCTGATTACTAACTATTCACCATCCAGGGAAGAT  1140

Vaccine   1167  AATTTGCAACGTGTCTTTACAGTAGCCTCTATCAGAAGCATGTTAATTAAGTGA  1220
                ||||||||||||||||||||||||||||||||||||||||||||||||||||||
MA104(JP)1141   AATTTGCAACGTGTCTTTACAGTAGCCTCTATCAGAAGCATGTTAATTAAGTGA  1194
```

FIG. 59B

Comparison of amino acid (coding region) sequences of RV3 VP6

```
Vaccine    27     MEVLYSLSKTLKDARDKIVEGTLYSNVSDLIQQFNQMIVTMNGNDFQTGGIGNLPIRNWT
206
                MEVLYSLSKTLKDARDKIVEGTLYSNVSDLIQQFNQMIVTMNGNDFQTGGIGNLPIRNWT
MA104(JP)1        MEVLYSLSKTLKDARDKIVEGTLYSNVSDLIQQFNQMIVTMNGNDFQTGGIGNLPIRNWT
60

Vaccine    207    fdfgllgttllnldanYVETARTTIKYFIDFIDNVCMDEMARESQRNGVAPQSEALRKLA
386
                FDFGLLGTTLLNLDANYVETARTTIKYFIDFIDNVCMDEMARESQRNGVAPQSEALRKLA
MA104(JP)61       FDFGLLGTTLLNLDANYVETARTTIKYFIDFIDNVCMDEMARESQRNGVAPQSEALRKLA
120

Vaccine    387    GIKFKRINFNNSSEYIENWNLQNRRQRTGFVFHKPNIFPYSASFTLNRSQPMHDNLMGTM
566
                GIKFKRINFNNSSEYIENWNLQNRRQRTGFVFHKPNIFPYSASFTLNRSQPMHDNLMGTM
MA104(JP)121      GIKFKRINFNNSSEYIENWNLQNRRQRTGFVFHKPNIFPYSASFTLNRSQPMHDNLMGTM
180

Vaccine    567    WLNAGSEIQVAGFDYSCALNAPANIQQFEHIVQlrralttatitllPDAERFSFPRVINS
746
                WLNAGSEIQVAGFDYSCALNAPANIQQFEHIVQLRRALTTATITLLPDAERFSFPRVINS
MA104(JP)181      WLNAGSEIQVAGFDYSCALNAPANIQQFEHIVQLRRALTTATITLLPDAERFSFPRVINS
240

Vaccine    747    ADGATTWFFNPIILRPNNVEVEFLLNGQIINTYQARFGTIIARNFDTIRLSFQLMRPPNM
926
                ADGATTWFFNPIILRPNNVEVEFLLNGQIINTYQARFGTIIARNFDTIRLSFQLMRPPNM
MA104(JP)241      ADGATTWFFNPIILRPNNVEVEFLLNGQIINTYQARFGTIIARNFDTIRLSFQLMRPPNM
300

Vaccine    927    TPAVNALFPQAQPFQHHATVGLTLRIESAVCESVLADANETLLANVTAVRQEYAIPVGPV
1106
                TPAVNALFPQAQPFQHHATVGLTLRIESAVCESVLADANETLLANVTAVRQEYAIPVGPV
MA104(JP)301      TPAVNALFPQAQPFQHHATVGLTLRIESAVCESVLADANETLLANVTAVRQEYAIPVGPV
360

Vaccine    1107 FPPGMNWTELITNYSPSREDNLQRVFTVASIRSMLIK  1217
                FPPGMNWTELITNYSPSREDNLQRVFTVASIRSMLIK
MA104(JP)361    FPPGMNWTELITNYSPSREDNLQRVFTVASIRSMLIK  397
```

FIG. 60

VP7 sequence
MA104-adapted RV3 VP7 (SEQ ID NO:63)

```
  1 ATGTATGGTA TTGAATATAC CACAGTTTTG ACCTTTTTGA TATCAATTAT ATTGTTGAAT
 61 TACGTACTCA AATCATTAAC TAGAATAATG GACTTTATTA TCTACAGATT TCTTTTGATT
121 ATAGTTATAC TGTCACCACT CCTTAATGCA CAAAATTATG GAATAAATCT TCCGATTACT
181 GGATCAATGG ACACACCATA TACGAACTCA ACGCGAGAGG AAGTATTCCT AACTTCGACT
241 TTATGTTTGT ATTACCCAAC CGAAGCAGCA ACAGAAATAA ATGATAATGC ATGGAAGGAT
301 ACACTTTCTC AACTATTTTT AACTAAAGGA TGGCCGACAG GATCTATTTA TTTTAAAGAT
361 TATACTGATA TTGCCTCGTT TTCAGTTGAT CCACAACTGT ACTGTGATTA TAATTTGGTA
421 TTAATGAAAT ACGACGCTAC ACTACAACTG GACATGTCTG AACTAGCAGA TTTGTTACTT
481 AATGAGTGGT TATGTAATCC TATGGATATT ACTTTGTATT ATTATCAACA AACTGATGAG
541 GCAAATAAAT GGATTTCAAT GGGATCATCT TGTACCATAA AGGTATGTCC ACTAAATACG
601 CAAACATTAG GAATTGGGTG TCTAACTACT GATACAAACA CGTTCGAAGA AGTTGCAACA
661 GCTGAAAAAT TAGTGATTAC TGACGTTGTA GATGGGGTCA ATCATAAATT GAACGTGACG
721 ACAAACACTT GTACGATTAG AAATTGTAAA AAATTAGGAC CAAGGGAAAA CGTAGCAGTT
781 ATACAGGTTG GTGGCTCAGA TGTACTTGAC ATAACAGCTG ATCCTACGAC AGCGCCACGA
841 ACAGAAAGAA TGATGCGAGT GAATTGGAAG AAATGGTGGC AAGTATTTTA TACAATAGTT
901 GACTACGTGA ATCAAATTGT GCAAGCGATG TCCAAAAGAT CGAGATCGTT AAATTCTGCT
961 GCATTTTACT ACAGGGTATA G
```

FIG. 61

Amino acid (coding region) ADD31866 (SEQ ID NO:64)

```
  1 MYGIEYTTVL TFLISIILLN YVLKSLTRIM DFIIYRFLLI IVILSPLLNA QNYGINLPIT
 61 GSMDTPYTNS TREEVFLTST LCLYYPTEAA TEINDNAWKD TLSQLFLTKG WPTGSIYFKD
121 YTDIASFSVD PQLYCDYNLV LMKYDATLQL DMSELADLLL NEWLCNPMDI TLYYYQQTDE
181 ANKWISMGSS CTIKVCPLNT QTLGIGCLTT DTNTFEEVAT AEKLVITDVV DGVNHKLNVT
241 TNTCTIRNCK KLGPRENVAV IQVGGSDVLD ITADPTTAPR TERMMRVNWK KWWQVFYTIV
301 DYVNQIVQAM SKRSRSLNSA AFYYRV
```

FIG. 62

Vero-adapted (Vaccine) RV3 VP7 (SEQ ID NO:65)

```
   1 GGCTTTAAAA GAGAGAATTT CCGTCTGGCT AGCGGTTAGC TCCTTTTAAT GTATGGTATT
  61 GAATATACCA CAGTTTTGAC CTTTTTGATA TCAATTATAT TGTTGAATTA CGTACTCAAA
 121 TCATTAACTA GAATAATGGA CTTTATTATC TACAGATTTC TTTTGATTAT AGTTATACTG
 181 TCACCACTCC TTAATGCACA AAATTATGGA ATAAATCTTC CGATTACTGG ATCAATGGAC
 241 ACACCATATA CGAACTCAAC GCGAGAGGAA GTATTCCTAA CTTCGACTTT ATGTTTGTAT
 301 TACCCAACCG AAGCAGCAAC AGAAATAAAT GATAATGCAT GGAAGGATAC ACTTTCTCAA
 361 CTATTTTTAA CTAAAGGATG GCCGACAGGA TCTATTTATT TTAAAGATTA TACTGATATT
 421 GCCTCGTTTT CAGTTGATCC ACAACTGTAC TGTGATTATA ATTTGGTATT AATGAAATAC
 481 GACGCTACAC TACAACTGGA CATGTCTGAA CTAGCAGATT TGTTACTTAA TGAGTGGTTA
 541 TGTAATCCTA TGGATATTAC TTTGTATTAT TATCAACAAA CTGATGAGGC AAATAAATGG
 601 ATTTCAATGG GATCATCTTG TACCATAAAG GTATGTCCAC TAAATACGCA AACATTAGGA
 661 ATTGGGTGTC TAACTACTGA TACAAACACG TTCGAAGAAG TTGCAACAGC TGAAAAATTA
 721 GTGATTACTG ACGTTGTAGA TGGGGTCAAT CATAAATTGA ACGTGACGAC AAACACTTGT
 781 ACGATTAGAA ATTGTAAAAA ATTAGGACCA AGGGAAAACG TAGCAGTTAT ACAGGTTGGT
 841 GGCTCAGATG TACTTGACAT AACAGCTGAT CCTACGACAG CGCCACGAAC AGAAAGAATG
 901 ATGCGAGTGA ATTGGAAGAA ATGGTGGCAA GTATTTTATA CAATAGTTGA CTACGTGAAT
 961 CAAATTGTGC AAGCGATGTC CAAAAGATCG AGATCGTTAA ATTCTGCTGC ATTTTACTAC
1021 AGGGTATAGG TATAGCTTAG ATTAGAATTG TATGATGTGA CC
```

FIG. 63

Amino acid (coding region) [SEQ ID NO:66]

```
   1 MYGIEYTTVL TFLISIILLN YVLKSLTRIM DFIIYRFLLI IVILSPLLNA QNYGINLPIT
  61 GSMDTPYTNS TREEVFLTST LCLYYPTEAA TEINDNAWKD TLSQLFLTKG WPTGSIYFKD
 121 YTDIASFSVD PQLYCDYNLV LMKYDATLQL DMSELADLLL NEWLCNPMDI TLYYYQQTDE
 181 ANKWISMGSS CTIKVCPLNT QTLGIGCLTT DTNTFEEVAT AEKLVITDVV DGVNHKLNVT
 241 TNTCTIRNCK KLGPRENVAV IQVGGSDVLD ITADPTTAPR TERMMRVNWK KWWQVFYTIV
 301 DYVNQIVQAM SKRSRSLNSA AFYYRV
```

FIG. 64

Comparison of nucleotide sequences of RV3 VP7

```
Vaccine   49    ATGTATGGTATTGAATATACCACAGTTTTGACCTTTTTGATATCAATTATATTGTTGAAT  108
                ||||||||||||||||||||||||||||||||||||||||||||||||||||||||||||
MA104(JP)1      ATGTATGGTATTGAATATACCACAGTTTTGACCTTTTTGATATCAATTATATTGTTGAAT  60

Vaccine   109   TACGTACTCAAATCATTAACTAGAATAATGGACTTTATTATCTACAGATTTCTTTTGATT  168
                ||||||||||||||||||||||||||||||||||||||||||||||||||||||||||||
MA104(JP)61     TACGTACTCAAATCATTAACTAGAATAATGGACTTTATTATCTACAGATTTCTTTTGATT  120

Vaccine   169   ATAGTTATACTGTCACCACTCCTTAATGCACAAAATTATGGAATAAATCTTCCGATTACT  228
                ||||||||||||||||||||||||||||||||||||||||||||||||||||||||||||
MA104(JP)121    ATAGTTATACTGTCACCACTCCTTAATGCACAAAATTATGGAATAAATCTTCCGATTACT  180

Vaccine   229   GGATCAATGGACACACCATATACGAACTCAACGCGAGAGGAAGTATTCCTAACTTCGACT  288
                ||||||||||||||||||||||||||||||||||||||||||||||||||||||||||||
MA104(JP)181    GGATCAATGGACACACCATATACGAACTCAACGCGAGAGGAAGTATTCCTAACTTCGACT  240

Vaccine   289   TTATGTTTGTATTACCCAACCGAAGCAGCAACAGAAATAAATGATAATGCATGGAAGGAT  348
                ||||||||||||||||||||||||||||||||||||||||||||||||||||||||||||
MA104(JP)241    TTATGTTTGTATTACCCAACCGAAGCAGCAACAGAAATAAATGATAATGCATGGAAGGAT  300

Vaccine   349   ACACTTTCTCAACTATTTTTAACTAAAGGATGGCCGACAGGATCTATTTATTTTAAAGAT  408
                ||||||||||||||||||||||||||||||||||||||||||||||||||||||||||||
MA104(JP)301    ACACTTTCTCAACTATTTTTAACTAAAGGATGGCCGACAGGATCTATTTATTTTAAAGAT  360

Vaccine   409   TATACTGATATTGCCTCGTTTTCAGTTGATCCACAACTGTACTGTGATTATAATTTGGTA  468
                ||||||||||||||||||||||||||||||||||||||||||||||||||||||||||||
MA104(JP)361    TATACTGATATTGCCTCGTTTTCAGTTGATCCACAACTGTACTGTGATTATAATTTGGTA  420

Vaccine   469   TTAATGAAATACGACGCTACACTACAACTGGACATGTCTGAACTAGCAGATTTGTTACTT  528
                ||||||||||||||||||||||||||||||||||||||||||||||||||||||||||||
MA104(JP)421    TTAATGAAATACGACGCTACACTACAACTGGACATGTCTGAACTAGCAGATTTGTTACTT  480

Vaccine   529   AATGAGTGGTTATGTAATCCTATGGATATTACTTTGTATTATTATCAACAAACTGATGAG  588
                ||||||||||||||||||||||||||||||||||||||||||||||||||||||||||||
MA104(JP)481    AATGAGTGGTTATGTAATCCTATGGATATTACTTTGTATTATTATCAACAAACTGATGAG  540

Vaccine   589   GCAAATAAATGGATTTCAATGGGATCATCTTGTACCATAAAGGTATGTCCACTAAATACG  648
                ||||||||||||||||||||||||||||||||||||||||||||||||||||||||||||
MA104(JP)541    GCAAATAAATGGATTTCAATGGGATCATCTTGTACCATAAAGGTATGTCCACTAAATACG  600

Vaccine   649   CAAACATTAGGAATTGGGTGTCTAACTACTGATACAAACACGTTCGAAGAAGTTGCAACA  708
                ||||||||||||||||||||||||||||||||||||||||||||||||||||||||||||
MA104(JP)601    CAAACATTAGGAATTGGGTGTCTAACTACTGATACAAACACGTTCGAAGAAGTTGCAACA  660

Vaccine   709   GCTGAAAAATTAGTGATTACTGACGTTGTAGATGGGGTCAATCATAAATTGAACGTGACG  768
                ||||||||||||||||||||||||||||||||||||||||||||||||||||||||||||
MA104(JP)661    GCTGAAAAATTAGTGATTACTGACGTTGTAGATGGGGTCAATCATAAATTGAACGTGACG  720

Vaccine   769   ACAAACACTTGTACGATTAGAAATTGTAAAAAATTAGGACCAAGGGAAAACGTAGCAGTT  828
                ||||||||||||||||||||||||||||||||||||||||||||||||||||||||||||
MA104(JP)721    ACAAACACTTGTACGATTAGAAATTGTAAAAAATTAGGACCAAGGGAAAACGTAGCAGTT  780

Vaccine   829   ATACAGGTTGGTGGCTCAGATGTACTTGACATAACAGCTGATCCTACGACAGCGCCACGA  888
                ||||||||||||||||||||||||||||||||||||||||||||||||||||||||||||
MA104(JP)781    ATACAGGTTGGTGGCTCAGATGTACTTGACATAACAGCTGATCCTACGACAGCGCCACGA  840

Vaccine   889   ACAGAAAGAATGATGCGAGTGAATTGGAAGAAATGGTGGCAAGTATTTTATACAATAGTT  948
                ||||||||||||||||||||||||||||||||||||||||||||||||||||||||||||
MA104(JP)841    ACAGAAAGAATGATGCGAGTGAATTGGAAGAAATGGTGGCAAGTATTTTATACAATAGTT  900

Vaccine   949   GACTACGTGAATCAAATTGTGCAAGCGATGTCCAAAAGATCGAGATCGTTAAATTCTGCT  1008
                ||||||||||||||||||||||||||||||||||||||||||||||||||||||||||||
MA104(JP)901    GACTACGTGAATCAAATTGTGCAAGCGATGTCCAAAAGATCGAGATCGTTAAATTCTGCT  960

Vaccine   1009  GCATTTTACTACAGGGTATAG  1029
                |||||||||||||||||||||
MA104(JP)961    GCATTTTACTACAGGGTATAG  981
```

FIG. 65

Comparison of amino acid (coding region) sequences of RV3 VP7

```
Vaccine   49     MYGIEYTTVLTFLISIILLNYVLKSLTRIMDFIIYRFLLIIVILSPLLNAQNYGINLPIT  228
                 MYGIEYTTVLTFLISIILLNYVLKSLTRIMDFIIYRFLLIIVILSPLLNAQNYGINLPIT
MA104(JP)1       MYGIEYTTVLTFLISIILLNYVLKSLTRIMDFIIYRFLLIIVILSPLLNAQNYGINLPIT  60

Vaccine   229    GSMDTPYTNSTREEVFLTSTLCLYYPTEAATEINDNAWKDTLSQLFLTKGWPTGSIYFKD  408
                 GSMDTPYTNSTREEVFLTSTLCLYYPTEAATEINDNAWKDTLSQLFLTKGWPTGSIYFKD
MA104(JP)61      GSMDTPYTNSTREEVFLTSTLCLYYPTEAATEINDNAWKDTLSQLFLTKGWPTGSIYFKD  120

Vaccine   409    YTDIASFSVDPQLYCDYNLVLMKYDATLQLDMSELADLLLNEWLCNPMDITLYYYQQTDE  588
                 YTDIASFSVDPQLYCDYNLVLMKYDATLQLDMSELADLLLNEWLCNPMDITLYYYQQTDE
MA104(JP)121     YTDIASFSVDPQLYCDYNLVLMKYDATLQLDMSELADLLLNEWLCNPMDITLYYYQQTDE  180

Vaccine   589    ANKWISMGSSCTIKVCPLNTQTLGIGCLTTDTNTFEEVATAEKLVITDVVDGVNHKLNVT  768
                 ANKWISMGSSCTIKVCPLNTQTLGIGCLTTDTNTFEEVATAEKLVITDVVDGVNHKLNVT
MA104(JP)181     ANKWISMGSSCTIKVCPLNTQTLGIGCLTTDTNTFEEVATAEKLVITDVVDGVNHKLNVT  240

Vaccine   769    TNTCTIRNCKKLGPRENVAVIQVGGSDVLDITADPTTAPRTERMMRVNWKKWWQVFYTIV  948
                 TNTCTIRNCKKLGPRENVAVIQVGGSDVLDITADPTTAPRTERMMRVNWKKWWQVFYTIV
MA104(JP)241     TNTCTIRNCKKLGPRENVAVIQVGGSDVLDITADPTTAPRTERMMRVNWKKWWQVFYTIV  300

Vaccine   949    DYVNQIVQAMSKRSRSLNSAAFYYRV  1026
                 DYVNQIVQAMSKRSRSLNSAAFYYRV
MA104(JP)301     DYVNQIVQAMSKRSRSLNSAAFYYRV  326
```

FIG. 66

SEQUENCE LISTING

<160> NUMBER OF SEQ ID NOS: 66

<210> SEQ ID NO 1
<211> LENGTH: 35
<212> TYPE: DNA
<213> ORGANISM: artificial
<220> FEATURE:
<223> OTHER INFORMATION: Primer - JCV1 VP1 5'UTR

<400> SEQUENCE: 1
tgtaaaacga cggccagtgg ctattaaagc tgtac 35

<210> SEQ ID NO 2
<211> LENGTH: 18
<212> TYPE: DNA
<213> ORGANISM: artificial
<220> FEATURE:
<223> OTHER INFORMATION: Primer - GEN-VP1R

<400> SEQUENCE: 2
ggtcacatct aagcgytc 18

<210> SEQ ID NO 3
<211> LENGTH: 20
<212> TYPE: DNA
<213> ORGANISM: artificial
<220> FEATURE:
<223> OTHER INFORMATION: Primer - GEN-VP2F

<400> SEQUENCE: 3
ggctattraa ggytcaatgg 20

<210> SEQ ID NO 4
<211> LENGTH: 19
<212> TYPE: DNA
<213> ORGANISM: artificial
<220> FEATURE:
<223> OTHER INFORMATION: Primer - GEN-VP2R

<400> SEQUENCE: 4
ggtcatatct ccacartgg 19

<210> SEQ ID NO 5
<211> LENGTH: 19
<212> TYPE: DNA
<213> ORGANISM: artificial
<220> FEATURE:
<223> OTHER INFORMATION: Primer - GEN-VP3F

<400> SEQUENCE: 5
ggctwttaaa gcagtacca 19

<210> SEQ ID NO 6
<211> LENGTH: 19
<212> TYPE: DNA
<213> ORGANISM: artificial
<220> FEATURE:
<223> OTHER INFORMATION: Primer - GEN-VP3R

<400> SEQUENCE: 6
ggycacatca tgactagtg 19

<210> SEQ ID NO 7
<211> LENGTH: 21
<212> TYPE: DNA
<213> ORGANISM: artificial

<220> FEATURE:
<223> OTHER INFORMATION: Primer - JP 1 for g4 RV3

<400> SEQUENCE: 7
ggctataaaa tggcttcact c 21

<210> SEQ ID NO 8
<211> LENGTH: 35
<212> TYPE: DNA
<213> ORGANISM: artificial
<220> FEATURE:
<223> OTHER INFORMATION: Primer - JCV1 VP4 3'UTR

<400> SEQUENCE: 8
caggaaacag ctatgaccgg tcacatycct cratr 35

<210> SEQ ID NO 9
<211> LENGTH: 22
<212> TYPE: DNA
<213> ORGANISM: artificial
<220> FEATURE:
<223> OTHER INFORMATION: Primer - GEN VP6F

<400> SEQUENCE: 9
ggctttwaaa cgaagaagtc tt 22

<210> SEQ ID NO 10
<211> LENGTH: 17
<212> TYPE: DNA
<213> ORGANISM: artificial
<220> FEATURE:
<223> OTHER INFORMATION: Primer - GEN VP6R

<400> SEQUENCE: 10
ggtcacatcc tctcact 17

<210> SEQ ID NO 11
<211> LENGTH: 28
<212> TYPE: DNA
<213> ORGANISM: artificial
<220> FEATURE:
<223> OTHER INFORMATION: Primer - Beg9

<400> SEQUENCE: 11
ggctttaaaa gagagaattt ccgtctgg 28

<210> SEQ ID NO 12
<211> LENGTH: 27
<212> TYPE: DNA
<213> ORGANISM: artificial
<220> FEATURE:
<223> OTHER INFORMATION: Primer - End9

<400> SEQUENCE: 12
ggtcacatca tacaattcta atctaag 27

<210> SEQ ID NO 13
<211> LENGTH: 39
<212> TYPE: DNA
<213> ORGANISM: artificial
<220> FEATURE:
<223> OTHER INFORMATION: Primer - JCV1 NSP1 5'UTR

<400> SEQUENCE: 13
tgtaaaacga cggccagtta tgaaaagtct tgtggaagc 39

<210> SEQ ID NO 14
<211> LENGTH: 38
<212> TYPE: DNA
<213> ORGANISM: artificial
<220> FEATURE:
<223> OTHER INFORMATION: Primer - JCV1 NSP1 3'UTR

<400> SEQUENCE: 14
caggaaacag ctatgaccca ttttatgctg cctaggcg 38

<210> SEQ ID NO 15
<211> LENGTH: 19
<212> TYPE: DNA
<213> ORGANISM: artificial
<220> FEATURE:
<223> OTHER INFORMATION: Primer - GEN-NSP2F

<400> SEQUENCE: 15
ggcttttaaa gcgtctcag 19

<210> SEQ ID NO 16
<211> LENGTH: 18
<212> TYPE: DNA
<213> ORGANISM: artificial
<220> FEATURE:
<223> OTHER INFORMATION: Primer - GEN-NSP2R

<400> SEQUENCE: 16
ggtcacataa gcgctttc 18

<210> SEQ ID NO 17
<211> LENGTH: 21
<212> TYPE: DNA
<213> ORGANISM: artificial
<220> FEATURE:
<223> OTHER INFORMATION: Prinmer - GEN-NSP3F

<400> SEQUENCE: 17
ggcttttaat gcttttcagt g 21

<210> SEQ ID NO 18
<211> LENGTH: 18
<212> TYPE: DNA
<213> ORGANISM: artificial
<220> FEATURE:
<223> OTHER INFORMATION: Primer - GEN-NSP3R

<400> SEQUENCE: 18
acataacgcc cctatagc 18

<210> SEQ ID NO 19
<211> LENGTH: 21
<212> TYPE: DNA
<213> ORGANISM: artificial
<220> FEATURE:
<223> OTHER INFORMATION: Primer - 10.1

<400> SEQUENCE: 19
ggcttttaaa agttctgttc c 21

<210> SEQ ID NO 20
<211> LENGTH: 20
<212> TYPE: DNA
<213> ORGANISM: artificial
<220> FEATURE:
<223> OTHER INFORMATION: Primer - 10.2

<400> SEQUENCE: 20
ggtcacacta agaccattcc 20

<210> SEQ ID NO 21
<211> LENGTH: 18
<212> TYPE: DNA
<213> ORGANISM: artificial
<220> FEATURE:
<223> OTHER INFORMATION: Primer - GEN-NSP5F

<400> SEQUENCE: 21
ggctttaaag cgctacag 18

<210> SEQ ID NO 22
<211> LENGTH: 17
<212> TYPE: DNA
<213> ORGANISM: artificial
<220> FEATURE:
<223> OTHER INFORMATION: Primer - GEN-NSP5R

<400> SEQUENCE: 22
ggtcacaaaa cgggagt 17

<210> SEQ ID NO 23
<211> LENGTH: 1461
<212> TYPE: DNA
<213> ORGANISM: artificial
<220> FEATURE:
<223> OTHER INFORMATION: MA104-RV3 NSP1

<400> SEQUENCE: 23
atggctactt ttaaagatgc ttgttattat tataagagaa ttaacaagtt gaatcacgca 60
gtcttgaagt taggagttaa tgatacatgg agaccatcac ctccaactaa gtataaagga 120
tggtgtctgg attgttgcca acacactgat ttaacttact gtcgaggttg taccatgtat 180
catgtatgtc aatggtgtag tcaatatggt agatgctttc ttgatagtga accacatcta 240
ttaagaatga gaactttcaa gaatgaagtg acgaaaaatg atttaatgaa tttaattgac 300
atgtacaata cattatttcc tataaatcaa agaatagtag ataaattcat taatagtaca 360
agacaacata aatgtagaaa tgaatgtatg acacagtggt acaatcactt agtactacca 420
ataacattac agtctctatc aatcgaatta gatggtgata tttattacgt gtttggatat 480
tatgatagta tgaatgacat taatcaaact ccattctcat ttacaaattt aatagatatg 540
tatgataagt tgctacttga taatataaat tttaacagaa tgtcattctt accagtagca 600
ttacaacaag aatatgcact cagatatttt tcaaaatcaa ggtttattag tgaaaagagg 660
aaatgtatca gtgatgtaca tttttccgct agcgtaatag aaaatttaca caatccaagt 720
tttaagatac agattacacg caattgtagt gaattatcct ctgattggaa cggagcatgc 780
aaacttgtta aagatatgag cgcttatttt gatgtcctga aaacatcaca tattgaattt 840
tatagtattt caactagatg tagagtgttt acgcagtata aacttaaagt agcatctaag 900
catataaaac caaattatgt gacatcaaat catagaacat ctgcgactga ggtacataat 960
tgtaaatggt gctcaattaa tagtagttat actgtatgga atgattttag aattaagaag 1020
atatatgata acattttcaa ttttctacga gctttagtca aatcaaatgc taatgttgga 1080
cattgttcgt cacaggaaaa gatgtatgag catattgaag atgttctgga tgtatgtgat 1140
gatgaaaaat ggaaaatggc ggtaacagaa atattcaatt ggttagaacc agtagaactt 1200

```
aatactgtta aatatgttct gttcaatcat gaggtaaatt gggatgtcat taatttatta   1260

gttcagagta ttggtaaagt accacaaata ctgactttga atgatattgt cataattatg   1320

aaatctatca tatatgagtg gtttgatatc agatatatga ggaacacacc aatgactaca   1380

tttacagttg acaaattaag acggttatgc acaggagtga aggctgttga ttatgattcc   1440

ggcatatctg acgttgaata a                                             1461
```

```
<210> SEQ ID NO 24
<211> LENGTH: 486
<212> TYPE: PRT
<213> ORGANISM: artificial
<220> FEATURE:
<223> OTHER INFORMATION: MA104-adapted RV3 NSP1

<400> SEQUENCE: 24

Met Ala Thr Phe Lys Asp Ala Cys Tyr Tyr Tyr Lys Arg Ile Asn Lys
1               5                   10                  15

Leu Asn His Ala Val Leu Lys Leu Gly Val Asn Asp Thr Trp Arg Pro
            20                  25                  30

Ser Pro Pro Thr Lys Tyr Lys Gly Trp Cys Leu Asp Cys Cys Gln His
        35                  40                  45

Thr Asp Leu Thr Tyr Cys Arg Gly Cys Thr Met Tyr His Val Cys Gln
    50                  55                  60

Trp Cys Ser Gln Tyr Gly Arg Cys Phe Leu Asp Ser Glu Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Thr Leu Phe Pro Ile Asn Gln Arg Ile
            100                 105                 110

Val Asp Lys Phe Ile Asn Ser Thr Arg Gln His Lys Cys Arg Asn Glu
        115                 120                 125

Cys Met Thr Gln Trp Tyr Asn His Leu Val Leu Pro Ile Thr Leu Gln
    130                 135                 140

Ser Leu Ser Ile Glu Leu Asp Gly Asp Ile Tyr Tyr Val Phe Gly Tyr
145                 150                 155                 160

Tyr Asp Ser Met Asn Asp Ile Asn Gln Thr Pro Phe Ser Phe Thr Asn
                165                 170                 175

Leu Ile Asp Met Tyr Asp Lys Leu Leu Leu Asp Asn Ile Asn Phe Asn
            180                 185                 190

Arg Met Ser Phe Leu Pro Val Ala Leu Gln Gln Glu Tyr Ala Leu Arg
        195                 200                 205

Tyr Phe Ser Lys Ser Arg Phe Ile Ser Glu Lys Arg Lys Cys Ile Ser
    210                 215                 220

Asp Val His Phe Ser Ala Ser Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Ala Tyr Phe Asp Val
            260                 265                 270

Leu Lys Thr Ser His Ile Glu Phe Tyr Ser Ile Ser Thr Arg Cys Arg
        275                 280                 285

Val Phe Thr Gln Tyr Lys Leu Lys Val Ala Ser Lys His Ile Lys Pro
    290                 295                 300

Asn Tyr Val Thr Ser Asn His Arg Thr Ser Ala Thr Glu Val His Asn
305                 310                 315                 320
```

```
Cys Lys Trp Cys Ser Ile Asn Ser Ser Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ala Asn Val Gly His Cys Ser Ser Gln Glu Lys Met
        355                 360                 365

Tyr Glu His Ile Glu Asp Val Leu Asp Val Cys Asp Asp Glu Lys Trp
    370                 375                 380

Lys Met Ala Val Thr Glu Ile Phe Asn Trp Leu Glu Pro Val Glu Leu
385                 390                 395                 400

Asn Thr Val Lys Tyr Val Leu Phe Asn His Glu Val Asn Trp Asp Val
                405                 410                 415

Ile Asn Leu Leu Val Gln Ser Ile Gly Lys Val Pro Gln Ile Leu Thr
            420                 425                 430

Leu Asn Asp Ile Val Ile Ile Met Lys Ser Ile Ile Tyr Glu Trp Phe
        435                 440                 445

Asp Ile Arg Tyr Met Arg Asn Thr Pro Met Thr Thr Phe Thr Val Asp
    450                 455                 460

Lys Leu Arg Arg Leu Cys Thr Gly Val Lys Ala Val Asp Tyr Asp Ser
465                 470                 475                 480

Gly Ile Ser Asp Val Glu
                485
```

```
<210> SEQ ID NO 25
<211> LENGTH: 1588
<212> TYPE: DNA
<213> ORGANISM: artificial
<220> FEATURE:
<223> OTHER INFORMATION: RV3-Vero NSP1

<400> SEQUENCE: 25

tgtaaaacga cggccagtta tgaaaagtct tgtggaagcc atggctactt ttaaagatgc     60

ttgttattat tataagagaa ttaacaagtt gaatcacgca gtcttgaagt taggagttaa    120

tgatacatgg agaccatcac ctccaactaa gtataaagga tggtgtctgg attgttgcca    180

acacactgat ttaacttact gtcgaggttg taccatgtat catgtatgtc aatggtgtag    240

tcaatatggt agatgctttc ttgatagtga accacatcta ttaagaatga gaactttcaa    300

gaatgaagtg acgaaaaatg atttaatgaa tttaattgac atgtacaata cattatttcc    360

tataaatcaa agaatagtag ataaattcat taatagtaca agacaacata aatgtagaaa    420

tgaatgtatg acacagtggt acaatcactt agtactacca ataacattac agtctctatc    480

aatcgaatta gatggtgata tttattacgt gtttggatat tatgatagta tgaatgacat    540

taatcaaact ccattctcat ttacaaattt aatagatatg tatgataagt tgctacttga    600

taatataaat tttaacagaa tgtcattctt accagtagca ttacaacaag aatatgcact    660

cagatatttt tcaaaatcaa ggtttattag tgaaaagagg aaatgtatca gtgatgtaca    720

tttttccgct agcgtaatag aaaatttaca caatccaagt tttaagatac agattacacg    780

caattgtagt gaattatcct ctgattggaa cggagcatgc aaacttgtta aagatatgag    840

cgcttatttt gatgtcctga aacatcaca tattgaattt tatagtattt caactagatg    900

tagagtgttt acgcagtata aacttaaagt agcatctaag catataaaac caaattatgt    960

gacatcaaat catagaacat ctgcgactga ggtacataat tgtaaatggt gctcaattaa   1020

tagtagttat actgtatgga atgattttag aattaagaag atatatgata acattttcaa   1080
```

```
ttttctacga gctttagtca aatcaaatgc taatgttgga cattgttcgt cacaggaaaa   1140

gatgtatgag catattgaag atgttctgga tgtatgtgat gatgaaaaat ggaaaatggc   1200

ggtaacagaa atattcaatt ggttagaacc agtagaactt aatactgtta aatatgttct   1260

gttcaatcat gaggtaaatt gggatgtcat taatttatta gttcagagta ttggtaaagt   1320

accacaaata ctgactttga atgatattgt cataattatg aaatctatca tatatgagtg   1380

gtttgatatc agatatatga ggaacacacc aatgactaca tttacagttg acaaattaag   1440

acggttatgc acaggagtga aggctgttga ttatgattcc ggcatatctg acgttgaata   1500

ctgaaataga ggtcacattt gccaccgcaa gactccctgc actagagtag cgcctaggca   1560

gcataaaatg ggtcatagct gtttcctg                                      1588
```

```
<210> SEQ ID NO 26
<211> LENGTH: 486
<212> TYPE: PRT
<213> ORGANISM: artificial
<220> FEATURE:
<223> OTHER INFORMATION: RV3-Vero NSP1

<400> SEQUENCE: 26

Met Ala Thr Phe Lys Asp Ala Cys Tyr Tyr Tyr Lys Arg Ile Asn Lys
1               5                   10                  15

Leu Asn His Ala Val Leu Lys Leu Gly Val Asn Asp Thr Trp Arg Pro
            20                  25                  30

Ser Pro Pro Thr Lys Tyr Lys Gly Trp Cys Leu Asp Cys Cys Gln His
        35                  40                  45

Thr Asp Leu Thr Tyr Cys Arg Gly Cys Thr Met Tyr His Val Cys Gln
    50                  55                  60

Trp Cys Ser Gln Tyr Gly Arg Cys Phe Leu Asp Ser Glu Pro His Leu
65                  70                  75                  80

Leu Arg Met Arg Thr Phe Lys Asn Glu Val Thr Lys Asn Asp Leu Met
                85                  90                  95

Asn Leu Ile Asp Met Tyr Asn Thr Leu Phe Pro Ile Asn Gln Arg Ile
            100                 105                 110

Val Asp Lys Phe Ile Asn Ser Thr Arg Gln His Lys Cys Arg Asn Glu
        115                 120                 125

Cys Met Thr Gln Trp Tyr Asn His Leu Val Leu Pro Ile Thr Leu Gln
    130                 135                 140

Ser Leu Ser Ile Glu Leu Asp Gly Asp Ile Tyr Tyr Val Phe Gly Tyr
145                 150                 155                 160

Tyr Asp Ser Met Asn Asp Ile Asn Gln Thr Pro Phe Ser Phe Thr Asn
                165                 170                 175

Leu Ile Asp Met Tyr Asp Lys Leu Leu Leu Asp Asn Ile Asn Phe Asn
            180                 185                 190

Arg Met Ser Phe Leu Pro Val Ala Leu Gln Gln Glu Tyr Ala Leu Arg
        195                 200                 205

Tyr Phe Ser Lys Ser Arg Phe Ile Ser Glu Lys Arg Lys Cys Ile Ser
    210                 215                 220

Asp Val His Phe Ser Ala Ser Val Ile Glu Asn Leu His Asn Pro Ser
225                 230                 235                 240

Phe Lys Ile Gln Ile Thr Arg Asn Cys Ser Glu Leu Ser Ser Asp Trp
                245                 250                 255

Asn Gly Ala Cys Lys Leu Val Lys Asp Met Ser Ala Tyr Phe Asp Val
            260                 265                 270
```

```
Leu Lys Thr Ser His Ile Glu Phe Tyr Ser Ile Ser Thr Arg Cys Arg
        275                 280                 285

Val Phe Thr Gln Tyr Lys Leu Lys Val Ala Ser Lys His Ile Lys Pro
    290                 295                 300

Asn Tyr Val Thr Ser Asn His Arg Thr Ser Ala Thr Glu Val His Asn
305                 310                 315                 320

Cys Lys Trp Cys Ser Ile Asn Ser Ser Tyr Thr Val Trp Asn Asp Phe
                325                 330                 335

Arg Ile Lys Lys Ile Tyr Asp Asn Ile Phe Asn Phe Leu Arg Ala Leu
            340                 345                 350

Val Lys Ser Asn Ala Asn Val Gly His Cys Ser Ser Gln Glu Lys Met
        355                 360                 365

Tyr Glu His Ile Glu Asp Val Leu Asp Val Cys Asp Asp Glu Lys Trp
    370                 375                 380

Lys Met Ala Val Thr Glu Ile Phe Asn Trp Leu Glu Pro Val Glu Leu
385                 390                 395                 400

Asn Thr Val Lys Tyr Val Leu Phe Asn His Glu Val Asn Trp Asp Val
                405                 410                 415

Ile Asn Leu Leu Val Gln Ser Ile Gly Lys Val Pro Gln Ile Leu Thr
            420                 425                 430

Leu Asn Asp Ile Val Ile Ile Met Lys Ser Ile Ile Tyr Glu Trp Phe
        435                 440                 445

Asp Ile Arg Tyr Met Arg Asn Thr Pro Met Thr Thr Phe Thr Val Asp
    450                 455                 460

Lys Leu Arg Arg Leu Cys Thr Gly Val Lys Ala Val Asp Tyr Asp Ser
465                 470                 475                 480

Gly Ile Ser Asp Val Glu
                485
```

<210> SEQ ID NO 27
<211> LENGTH: 594
<212> TYPE: DNA
<213> ORGANISM: artificial
<220> FEATURE:
<223> OTHER INFORMATION: MA104 RV3 NSP5/6

<400> SEQUENCE: 27

```
atgtctctca gcattgacgt agcaagtctt ccctcaattt cttctagtat ctttaaaaat      60

gaatcgtctt ctacaacgtc aactctttct ggaaaatcta ttggtaggag tgaacagtac     120

atttcaccag atgcaggagc atttaataaa tacatgttgt cgaagtctcc agaggatatt     180

ggaccgtctg attctgcttc aaacgatcca ctcaccagct tttcgattag atcgaatgca     240

gttaaaacaa atgcagacgc tggcgtgtct atggattcat cgacgcaatc acgaccttca     300

agcaacgttg ggtgcgatca attggatttc tccttaacta aaggtattaa tgttagtgct     360

aatcttgatt catgtatatc aatttcaact gatcataaga aggagaaatc caagaaagat     420

aaaagtagga aacactaccc gagaattgaa gcagattctg attctgaaga ttatgttttg     480

gatgattcag atagtgatga cggtaaatgt aagaattgta aatataagaa aaaatatttc     540

gcactaagaa tgaggatgaa gcgagtcgca atgcaattga tcgaggattt gtaa           594
```

<210> SEQ ID NO 28
<211> LENGTH: 197
<212> TYPE: PRT
<213> ORGANISM: artificial
<220> FEATURE:

<223> OTHER INFORMATION: MA104-adapted RV3 NSP5

<400> SEQUENCE: 28

```
Met Ser Leu Ser Ile Asp Val Ala Ser Leu Pro Ser Ile Ser Ser Ser
1               5                   10                  15

Ile Phe Lys Asn Glu Ser Ser Ser Thr Thr Ser Thr Leu Ser Gly Lys
            20                  25                  30

Ser Ile Gly Arg Ser Glu Gln Tyr Ile Ser Pro Asp Ala Gly Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Leu Asp Phe Ser Leu
            100                 105                 110

Thr Lys Gly Ile Asn Val Ser Ala Asn Leu Asp Ser Cys Ile Ser Ile
        115                 120                 125

Ser Thr Asp His Lys Lys Glu Lys Ser Lys Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Asp Gly Lys Cys Lys Asn Cys Lys Tyr Lys
                165                 170                 175

Lys Lys Tyr Phe Ala Leu Arg Met Arg Met Lys Arg Val Ala Met Gln
            180                 185                 190

Leu Ile Glu Asp Leu
        195
```

<210> SEQ ID NO 29
<211> LENGTH: 664
<212> TYPE: DNA
<213> ORGANISM: artificial
<220> FEATURE:
<223> OTHER INFORMATION: RV3-Vero NSP5/6

<400> SEQUENCE: 29

```
ggcttttaaa gcgctacagt gatgtctctc agcattgacg tagcaagtct tccctcaatt     60

tcttctagta tctttaaaaa tgaatcgtct tctacaacgt caactctttc tggaaaatct    120

attggtagga gtgaacagta catttcacca gatgcagaag cattcaataa atacatgttg    180

tcgaagtctc cagaggatat tggaccgtct gattctgctt caaacgatcc actcaccagc    240

ttttcgatta gatcgaatgc agttaaaaca aatgcagacg ctggcgtgtc tatggattca    300

tcgacgcaat cacgaccttc aagcaacgtt gggtgcgatc aattggattt ctccataact    360

aaaggtatta atgttagtgc taatcttgat tcatgtatat caatttcaac tgatcataag    420

aaggagaaat ccaagaaaga taaaagtagg aaacactacc cgagaattga agcagattct    480

gattctgaag attatgtttt ggatgattca gatagtgatg acggtaaatg taagaattgt    540

aaatataaga aaaaatattt cgcactaaga atgaggatga agcgagtcgc aatgcaattg    600

atcgaggatt tgtaatgtca acctgagagc acactaggga gctccccact cccgttttgt    660

gacc                                                                 664
```

<210> SEQ ID NO 30

<211> LENGTH: 197
<212> TYPE: PRT
<213> ORGANISM: artificial
<220> FEATURE:
<223> OTHER INFORMATION: RV3-Vero NSP5

<400> SEQUENCE: 30

```
Met Ser Leu Ser Ile Asp Val Ala Ser Leu Pro Ser Ile Ser Ser Ser
1               5                   10                  15

Ile Phe Lys Asn Glu Ser Ser Ser Thr Thr Ser Thr Leu Ser Gly Lys
            20                  25                  30

Ser Ile Gly Arg Ser Glu Gln Tyr Ile Ser Pro Asp Ala Glu Ala Phe
        35                  40                  45

Asn Lys Tyr Met Leu Ser Lys Ser Pro Glu Asp Ile Gly Pro Ser Asp
    50                  55                  60

Ser Ala Ser Asn Asp Pro Leu Thr Ser Phe Ser Ile Arg Ser Asn Ala
65                  70                  75                  80

Val Lys Thr Asn Ala Asp Ala Gly Val Ser Met Asp Ser Ser Thr Gln
                85                  90                  95

Ser Arg Pro Ser Ser Asn Val Gly Cys Asp Gln Leu Asp Phe Ser Ile
            100                 105                 110

Thr Lys Gly Ile Asn Val Ser Ala Asn Leu Asp Ser Cys Ile Ser Ile
        115                 120                 125

Ser Thr Asp His Lys Lys Glu Lys Ser Lys Lys Asp Lys Ser Arg Lys
    130                 135                 140

His Tyr Pro Arg Ile Glu Ala Asp Ser Asp Ser Glu Asp Tyr Val Leu
145                 150                 155                 160

Asp Asp Ser Asp Ser Asp Asp Gly Lys Cys Lys Asn Cys Lys Tyr Lys
                165                 170                 175

Lys Lys Tyr Phe Ala Leu Arg Met Arg Met Lys Arg Val Ala Met Gln
            180                 185                 190

Leu Ile Glu Asp Leu
        195
```

<210> SEQ ID NO 31
<211> LENGTH: 954
<212> TYPE: DNA
<213> ORGANISM: artificial
<220> FEATURE:
<223> OTHER INFORMATION: MA104 RV3 NSP2

<400> SEQUENCE: 31

```
atggctgagc tagcttgctt ttgttatcct catttagaga acgatagcta taaatttatt     60

cctttcaata gtttggcaat aaaatgtatg ttgacagcta aagtggataa gaaagatcaa    120

gataaatttt ataattctat tgtatacgga attgcgccac caccacaatt caaaaaacgt    180

tataatacta gtgataattc aagaggcatg aattatgaaa caactatgtt taataaggtg    240

gctattttaa tttgtgaagc acttaattca attaaagtca ctcaatctga cattgctaat    300

gtcctctcaa gagtagtttc tattagacat ttggaaaatt tggtgttaag aaaagaaaat    360

catcaagatg tgctgtttca ttcgaaggag ctactcttaa aatccgtttt gatagctatt    420

ggtcaatcaa aagaaattga aactactgct actgccgagg gaggagaaat agtgttccaa    480

aatgcagctt ttactatgtg gaaattgact tatttagatc ataaactaac gcctattttg    540

gaccaaaatt ttatcgaata taagattaca ttaaatgaag ataaaccaat ttcagatgta    600

tgtgttaaag aacttgttgc tgaattgaga tggcagtata acagatttgc tgtaataacg    660
```

```
catggtaaag gtcactatag agtcgttaaa tattcatcag ttgctaatca cgcagataga    720

gtatttgtcg catacaaaaa taatgctaag agtggtaatg ttattaattt taatttactg    780

gatcaaagaa taatttggca aaattggtac gcatttacat cttcaatgaa acaaggtaat    840

acacttgaag tatgtaagaa actgctcttt caaaagatga agcaggagaa gaatccattt    900

aaaggactgt caactgatag aaaaatggat gaagtctcac atgttggagt ttag          954


<210> SEQ ID NO 32
<211> LENGTH: 317
<212> TYPE: PRT
<213> ORGANISM: artificial
<220> FEATURE:
<223> OTHER INFORMATION: MA104-adapted RV3 NSP2

<400> SEQUENCE: 32

Met Ala Glu Leu Ala Cys Phe Cys Tyr Pro His Leu Glu Asn Asp Ser
1               5                   10                  15

Tyr Lys Phe Ile Pro Phe Asn Ser Leu Ala Ile Lys Cys Met Leu Thr
            20                  25                  30

Ala Lys Val Asp Lys Lys Asp Gln Asp Lys Phe Tyr Asn Ser Ile Val
        35                  40                  45

Tyr Gly Ile Ala Pro Pro Pro Gln Phe Lys Lys Arg Tyr Asn Thr Ser
    50                  55                  60

Asp Asn Ser Arg Gly Met Asn Tyr Glu Thr Thr Met Phe Asn Lys Val
65                  70                  75                  80

Ala Ile Leu Ile Cys Glu Ala Leu Asn Ser Ile Lys Val Thr Gln Ser
                85                  90                  95

Asp Ile Ala Asn Val Leu Ser Arg Val Val Ser Ile Arg His Leu Glu
            100                 105                 110

Asn Leu Val Leu Arg Lys Glu Asn His Gln Asp Val Leu Phe His Ser
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Asp His Lys Leu
                165                 170                 175

Thr Pro Ile Leu Asp Gln Asn Phe Ile Glu Tyr Lys Ile Thr Leu Asn
            180                 185                 190

Glu Asp Lys Pro Ile Ser Asp Val Cys Val Lys Glu Leu Val Ala Glu
        195                 200                 205

Leu Arg Trp Gln Tyr Asn Arg Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Phe Val Ala Tyr Lys Asn Asn Ala Lys Ser Gly Asn Val Ile Asn
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Glu Val Cys Lys Lys Leu
        275                 280                 285

Leu Phe Gln Lys Met Lys Gln Glu Lys Asn Pro Phe Lys Gly Leu Ser
    290                 295                 300

Thr Asp Arg Lys Met Asp Glu Val Ser His Val Gly Val
305                 310                 315
```

<210> SEQ ID NO 33
<211> LENGTH: 1059
<212> TYPE: DNA
<213> ORGANISM: artificial
<220> FEATURE:
<223> OTHER INFORMATION: RV3-Vero NSP2

<400> SEQUENCE: 33

```
ggcttttaaa gcgtctcagt cgccgtttga gccttgcggt gtagccatgg ctgagctagc     60

ttgcttttgt tatcctcatt tagagaacga tagctataaa tttattcctt tcaatagttt    120

ggcaataaaa tgtatgttga cagctaaagt ggataagaaa gatcaagata aattttataa    180

ttctattgta tacggaattg cgccaccacc acaattcaaa aaacgttata atactagtga    240

taattcaaga ggcatgaatt atgaaacaac tatgtttaat aaggtggcta ttttaatttg    300

tgaagcactt aattcaatta aagtcactca atctgacatt gctaatgtcc tctcaagagt    360

agtttctatt agacatttgg aaaatttggt gttaagaaaa gaaaatcatc aagatgtgct    420

gtttcattcg aaagagctac tcttaaaatc cgttttgata gctattggtc aatcaaaaga    480

aattgaaact actgctactg ccgagggagg agaaatagtg ttccaaaatg cagcttttac    540

tatgtggaaa ttgacttatt tagatcataa actaacgcct attttggacc aaaattttat    600

cgaatataag attacattaa atgaagataa accaatttca gatgtatgtg ttaaagaact    660

tgttgctgaa ttgagatggc agtataacag atttgctgta ataacgcatg gtaaaggtca    720

ctatagagtc gttaaatatt catcagttgc taatcacgca gatagagtat ttgtcgcata    780

caaaaataat gctaagagtg gtaatgttat taattttaat ttactggatc aaagaataat    840

ttggcaaaat tggtacgcat ttacatcttc aatgaaacaa ggtaatacac ttgaagtatg    900

taagaaactg ctctttcaaa agatgaagca ggagaagaat ccatttaaag gactgtcaac    960

tgatagaaaa atggatgaag tctcacatgt tggagtttag ttcgctttcg atttgaaaat   1020

gatgatgacg aagcaggaat agaaagcgct tatgtgacc                         1059
```

<210> SEQ ID NO 34
<211> LENGTH: 317
<212> TYPE: PRT
<213> ORGANISM: artificial
<220> FEATURE:
<223> OTHER INFORMATION: RV3-Vero NSP2

<400> SEQUENCE: 34

```
Met Ala Glu Leu Ala Cys Phe Cys Tyr Pro His Leu Glu Asn Asp Ser
1               5                   10                  15

Tyr Lys Phe Ile Pro Phe Asn Ser Leu Ala Ile Lys Cys Met Leu Thr
            20                  25                  30

Ala Lys Val Asp Lys Lys Asp Gln Asp Lys Phe Tyr Asn Ser Ile Val
        35                  40                  45

Tyr Gly Ile Ala Pro Pro Pro Gln Phe Lys Lys Arg Tyr Asn Thr Ser
    50                  55                  60

Asp Asn Ser Arg Gly Met Asn Tyr Glu Thr Thr Met Phe Asn Lys Val
65                  70                  75                  80

Ala Ile Leu Ile Cys Glu Ala Leu Asn Ser Ile Lys Val Thr Gln Ser
                85                  90                  95

Asp Ile Ala Asn Val Leu Ser Arg Val Val Ser Ile Arg His Leu Glu
            100                 105                 110

Asn Leu Val Leu Arg Lys Glu Asn His Gln Asp Val Leu Phe His Ser
```

```
        115                 120                 125

Lys Glu Leu Leu Leu Lys Ser Val Leu Ile Ala Ile Gly Gln Ser Lys
    130                 135                 140

Glu Ile Glu Thr Thr Ala Thr Ala Glu Gly Gly Glu Ile Val Phe Gln
145                 150                 155                 160

Asn Ala Ala Phe Thr Met Trp Lys Leu Thr Tyr Leu Asp His Lys Leu
                165                 170                 175

Thr Pro Ile Leu Asp Gln Asn Phe Ile Glu Tyr Lys Ile Thr Leu Asn
            180                 185                 190

Glu Asp Lys Pro Ile Ser Asp Val Cys Val Lys Glu Leu Val Ala Glu
        195                 200                 205

Leu Arg Trp Gln Tyr Asn Arg Phe Ala Val Ile Thr His Gly Lys Gly
    210                 215                 220

His Tyr Arg Val Val Lys Tyr Ser Ser Val Ala Asn His Ala Asp Arg
225                 230                 235                 240

Val Phe Val Ala Tyr Lys Asn Asn Ala Lys Ser Gly Asn Val Ile Asn
                245                 250                 255

Phe Asn Leu Leu Asp Gln Arg Ile Ile Trp Gln Asn Trp Tyr Ala Phe
            260                 265                 270

Thr Ser Ser Met Lys Gln Gly Asn Thr Leu Glu Val Cys Lys Lys Leu
        275                 280                 285

Leu Phe Gln Lys Met Lys Gln Glu Lys Asn Pro Phe Lys Gly Leu Ser
    290                 295                 300

Thr Asp Arg Lys Met Asp Glu Val Ser His Val Gly Val
305                 310                 315


<210> SEQ ID NO 35
<211> LENGTH: 528
<212> TYPE: DNA
<213> ORGANISM: artificial
<220> FEATURE:
<223> OTHER INFORMATION: MA104-derived RV3 NSP4

<400> SEQUENCE: 35

atggataagc ttgccgacct caactacaca ttgagtgtaa tcactttaat gaatgacaca     60

ttgcattcta taattcaaga tcctggaatg gcgtatttta catatattgc atctgttcta    120

acagttttgt tcacattaca caaagcttca attccagcca tgaaaatagc attgaaaaca    180

tcaaaatgtt catataaagt aattaaatat tgtatagtca cgataattaa tactctttta    240

aaattggctg gatgtaaaga gcaggttact acaaaagacg aaattgagca acagatggac    300

agaattgtta aagagatgag acgtcagctg gagatgattg ataaactaac tactcgtgaa    360

attgaacagg ttgaattgct taaatgtata tatgacaacc tgataactag accagttaac    420

gttatagata tgtcgaagga attcaatcaa aaaaacatca aaacgctaga tgaatgggag    480

agtgtaaaaa atccatatga accgtcagaa gtgactgcat ccatgtaa                 528


<210> SEQ ID NO 36
<211> LENGTH: 175
<212> TYPE: PRT
<213> ORGANISM: artificial
<220> FEATURE:
<223> OTHER INFORMATION: RV3 NSP4

<400> SEQUENCE: 36

Met Asp Lys Leu Ala Asp Leu Asn Tyr Thr Leu Ser Val Ile Thr Leu
1               5                   10                  15
```

```
Met Asn Asp Thr Leu His Ser Ile Ile Gln Asp Pro Gly Met Ala Tyr
            20                  25                  30

Phe Thr Tyr Ile Ala Ser Val Leu Thr Val Leu Phe Thr Leu His Lys
        35                  40                  45

Ala Ser Ile Pro Ala Met Lys Ile Ala Leu Lys Thr Ser Lys Cys Ser
    50                  55                  60

Tyr Lys Val Ile Lys Tyr Cys Ile Val Thr Ile Ile Asn Thr Leu Leu
65                  70                  75                  80

Lys Leu Ala Gly Cys Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Cys Ile Tyr Asp Asn Leu Ile Thr Arg Pro Val Asn Val Ile Asp Met
    130                 135                 140

Ser Lys Glu Phe Asn Gln Lys Asn Ile Lys Thr Leu Asp Glu Trp Glu
145                 150                 155                 160

Ser Val Lys Asn Pro Tyr Glu Pro Ser Glu Val Thr Ala Ser Met
                165                 170                 175


<210> SEQ ID NO 37
<211> LENGTH: 749
<212> TYPE: DNA
<213> ORGANISM: artificial
<220> FEATURE:
<223> OTHER INFORMATION: RV3-Vero NSP4

<400> SEQUENCE: 37

ggcttttaaa agttctgtcc gagagagcgc gtgcggaaag atggataagc ttgccgacct     60

caactacaca ttgagtgtaa tcactttaat gaatgacaca ttgcattcta taattcaaga    120

tcctggaatg gcgtatttta catatattgc atctgttcta acagttttgt tcacattaca    180

caaagcttca attccaacca tgaaaatagc attgaaaaca tcaaaatgtt catataaagt    240

aattaaatat tgtatagtca cgataactaa tactctttta aaattggctg gatataaaga    300

gcaggttact acaaaagacg aaattgagca acagatggac agaattgtta aagagatgag    360

acgtcagctg gagatgattg ataaactaac tactcgtgaa attgaacagg ttgaattgct    420

taaatgtata tatgacaacc tgataactag accagttaac gttatagata tgtcgaagga    480

attcaatcaa aaaaacatca aaacgctaga tgaatgggag agtggaaaaa atctatatga    540

accgtcagaa gtgactgcat ccatgtaaga ggttgagttg ccgtcgtctg tcttcggaag    600

cggcggaact cttcaccgca agccccatta gacctgatga ttgactgaga agccacagtc    660

aatcatatcg cgtgtggctc agccttaatc ccgtttaacc aatccagcga gtgttggacg    720

ttaatggaag gaatggtctt agtgtgacc                                      749


<210> SEQ ID NO 38
<211> LENGTH: 175
<212> TYPE: PRT
<213> ORGANISM: artificial
<220> FEATURE:
<223> OTHER INFORMATION: RV3-Vero NSP4

<400> SEQUENCE: 38

Met Asp Lys Leu Ala Asp Leu Asn Tyr Thr Leu Ser Val Ile Thr Leu
1               5                   10                  15
```

```
Met Asn Asp Thr Leu His Ser Ile Ile Gln Asp Pro Gly Met Ala Tyr
            20                  25                  30

Phe Thr Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Ile Val Thr Ile Thr Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Val Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Cys Ile Tyr Asp Asn Leu Ile Thr Arg Pro Val Asn Val Ile Asp Met
    130                 135                 140

Ser Lys Glu Phe Asn Gln Lys Asn Ile Lys Thr Leu Asp Glu Trp Glu
145                 150                 155                 160

Ser Gly Lys Asn Leu Tyr Glu Pro Ser Glu Val Thr Ala Ser Met
                165                 170                 175
```

<210> SEQ ID NO 39
<211> LENGTH: 1194
<212> TYPE: DNA
<213> ORGANISM: artificial
<220> FEATURE:
<223> OTHER INFORMATION: MA104-derived RV3 VP6

<400> SEQUENCE: 39

```
atggaggttc tgtattcatt gtcaaaaact cttaaagatg ctagggataa gattgttgaa     60

ggtacattat attctaatgt tagtgatctc attcagcaat ttaatcaaat gatagtaacc    120

atgaatggaa atgactttca aactggagga attggcaatt tacctattag aaattggaca    180

tttgactttg gtctactagg tactacgctg ttaaaccttg atgctaatta cgttgagacc    240

gcaagaacta caattaagta ttttattgac tttattgata atgtatgtat ggatgaaatg    300

gcaagagagt ctcaaagaaa tggagtagct ccacaatctg aggcattgag gaagctagcc    360

ggtattaaat ttaaaagaat aaattttaat aattcatcag aatatataga aaattggaat    420

ttacaaaata gaagacagcg taccggattt gttttccata aacctaatat atttccatac    480

tcagcatcat ttactttaaa taggtctcaa ccaatgcatg acaatttaat gggaaccatg    540

tggcttaacg ctggatcaga aattcaagtg gctggatttg actactcgtg tgccctaaat    600

gctccagcaa atattcagca gtttgaacat attgtccagc ttaggcgtgc gctaactaca    660

gctactataa ctttgctacc tgatgcagaa agatttagtt ttccaagagt tattaattca    720

gcagatggcg caaccacatg gttctttaat ccaattatcc taagaccaaa caatgtagag    780

gtagaatttt tactgaatgg acaaattatt aatacatatc aagctagatt tggcactatt    840

atcgcaagaa attttgatac aattcgtcta tcattccaat taatgcgtcc accaaacatg    900

acgccagccg taaatgcatt atttccgcaa gcacaacctt ttcaacatca tgcaacagtt    960

ggacttacgt tacgtattga gtctgcagtt tgtgaatcag tgcttgcgga tgcaaatgaa   1020

actttattgg cgaatgttac tgcagtacgt caagagtatg ctataccggt tggaccagta   1080

tttccaccag gcatgaattg gactgagctg attactaact attcaccatc cagggaagat   1140

aatttgcaac gtgtctttac agtagcctct atcagaagca tgttaattaa gtga         1194
```

<210> SEQ ID NO 40
<211> LENGTH: 397
<212> TYPE: PRT
<213> ORGANISM: artificial
<220> FEATURE:
<223> OTHER INFORMATION: MA104-derived RV3 VP6

<400> SEQUENCE: 40

```
Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
    50                  55                  60

Leu Leu Gly Thr Thr Leu Leu Asn Leu Asp Ala Asn Tyr Val Glu Thr
65                  70                  75                  80

Ala Arg Thr Thr Ile Lys Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asn Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Leu Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Ile Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Leu Ser Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365
```

```
Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395


<210> SEQ ID NO 41
<211> LENGTH: 1359
<212> TYPE: DNA
<213> ORGANISM: artificial
<220> FEATURE:
<223> OTHER INFORMATION: RV3-Vero VP6

<400> SEQUENCE: 41

ggcttttaaa cgaagaagtc ttcgacatgg aggttctgta ttcattgtca aaaactctta     60

aagatgctag ggataagatt gttgaaggta cattatattc taatgttagt gatctcattc    120

agcaatttaa tcaaatgata gtaaccatga atggaaatga ctttcaaact ggaggaattg    180

gcaatttacc tattagaaat tggacatttg actttggtct actaggtact acgctgttaa    240

accttgatgc taattacgtt gagaccgcaa gaactacaat taagtatttt attgacttta    300

ttgataatgt atgtatggat gaaatggcaa gagagtctca aagaaatgga gtagctccac    360

aatctgaggc attgaggaag ctagccggta ttaaatttaa aagaataaat tttaataatt    420

catcagaata tatagaaaat tggaatttac aaaatagaag acagcgtacc ggatttgttt    480

tccataaacc taatatattt ccatactcag catcatttac tttaaatagg tctcaaccaa    540

tgcatgacaa tttaatggga accatgtggc ttaacgctgg atcagaaatt caagtggctg    600

gatttgacta ctcgtgtgcc ctaaatgctc cagcaaatat tcagcagttt gaacatattg    660

tccagcttag gcgtgcgcta actacagcta ctataacttt gctacctgat gcagaaagat    720

ttagttttcc aagagttatt aattcagcag atggcgcaac cacatggttc tttaatccaa    780

ttatcctaag accaaacaat gtagaggtag aatttttact gaatggacaa attattaata    840

catatcaagc tagatttggc actattatcg caagaaattt tgatacaatt cgtctatcat    900

tccaattaat gcgtccacca aacatgacgc cagccgtaaa tgcattattt ccgcaagcac    960

aaccttttca acatcatgca acagttggac ttacgttacg tattgagtct gcagtttgtg   1020

aatcagtgct tgcggatgca aatgaaactt tattggcgaa tgttactgca gtacgtcaag   1080

agtatgctat accggttgga ccagtatttc caccaggcat gaattggact gagctgatta   1140

ctaactattc accatccagg gaagataatt tgcaacgtgt ctttacagta gcctctatca   1200

gaagcatgtt aattaagtga ggaccagact aaccatctgg tatccaatct taattagcat   1260

gtagctatgt caagtcattc agactctaca agtaaggaca tgatttcatg ttcgctacgt   1320

agagtaactg catgaatgat gtagtgagag gatgtgacc                          1359


<210> SEQ ID NO 42
<211> LENGTH: 397
<212> TYPE: PRT
<213> ORGANISM: artificial
<220> FEATURE:
<223> OTHER INFORMATION: RV3-Vero VP6

<400> SEQUENCE: 42

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30
```

```
Gln Phe Asn Gln Met Ile Val Thr Met Asn Gly Asn Asp Phe Gln Thr
        35                  40                  45

Gly Gly Ile Gly Asn Leu Pro Ile Arg Asn Trp Thr Phe Asp Phe Gly
    50                  55                  60

Leu Leu Gly Thr Thr Leu Leu Asn Leu Asp Ala Asn Tyr Val Glu Thr
65                  70                  75                  80

Ala Arg Thr Thr Ile Lys Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asn Asn Ser Ser Glu Tyr Ile Glu Asn Trp Asn Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Leu Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Ile Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
        275                 280                 285

Arg Leu Ser Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395
```

```
<210> SEQ ID NO 43
<211> LENGTH: 964
<212> TYPE: DNA
<213> ORGANISM: artificial
<220> FEATURE:
<223> OTHER INFORMATION: MA104-adapted RV3 NSP3

<400> SEQUENCE: 43
```

```
ttttaatgct tttcagtggt tgctgctcaa gatggagtct actcagcaga tggtaagctc      60

tattattaac acttcttttg aagctgcagt tgttgctgcc acttcaacat tagaattaat     120

gggtattcaa tatgattaca atgaagtatt tactagagtt aaaagtaaat ttgattatgt     180

gatggatgac tctggtgtta aaaacaatct tttgggtaaa gctataacta ttgatcaggc     240

gttaaatgga aagtttggct cagctattag aaatagaaat tggatgactg attctaaaac     300

ggttgctaaa ttagatgaag acgtgaataa acttagaatg acattatctt ctaaaggaat     360

cgaccaaaag atgagagtac ttaatgcttg ttttagtgta aaaagaatac caggaaaatc     420

atcatcaata attaaatgct ctagacttat gaaggataaa atagaacgtg gagaagttga     480

ggttgatgat tcatatgttg atgagaaaat ggaaattgat actattgatt ggaaatctcg     540

ttatgatcag ttagaaaaaa gatttgagtc actaaaacaa agagttaatg agaaatacaa     600

tacttgggta caaaaagcga agaaagtaaa tgaaaatatg tactctcttc agaatgtcat     660

ttcacaacag caaaaccaaa tagcagatct tcaacaatat tgtaataaat tggaagctga     720

tttgcaaggc aaatttagtt cattagtgtc atcagttgag tggtatctaa ggtctatgga     780

attgccaaat gatgtaaaga atgatattga acagcagtta aattcaattg atttaattaa     840

tcccattaat gctatagatg atatcgaatc attgattaga aatttaattc aagattatga     900

cagaacattt ttaatgttaa aaggactgtt gaagcaatgc aactatgaat atacatatga     960

gtag                                                                  964
```

<210> SEQ ID NO 44
<211> LENGTH: 310
<212> TYPE: PRT
<213> ORGANISM: artificial
<220> FEATURE:
<223> OTHER INFORMATION: MA104-derived RV3 NSP3

<400> SEQUENCE: 44

```
Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30

Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Asp Gln Ala Leu Asn Gly Lys Phe Gly Ser Ala Ile Arg
65                  70                  75                  80

Asn Arg Asn Trp Met Thr Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Ser Arg Leu Met Lys Asp Lys Ile
    130                 135                 140

Glu Arg Gly Glu Val Glu Val Asp Asp Ser Tyr Val Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Asn Glu Lys Tyr Asn Thr Trp
            180                 185                 190
```

```
Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Ala Asp Leu Gln Gly Lys Phe Ser Ser Leu Val Ser
225                 230                 235                 240

Ser Val Glu Trp Tyr Leu Arg Ser Met Glu Leu Pro Asn Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Ile Arg Asn Leu Ile Gln Asp
        275                 280                 285

Tyr Asp Arg Thr Phe Leu Met Leu Lys Gly Leu Leu Lys Gln Cys Asn
    290                 295                 300

Tyr Glu Tyr Thr Tyr Glu
305                 310
```

```
<210> SEQ ID NO 45
<211> LENGTH: 1070
<212> TYPE: DNA
<213> ORGANISM: artificial
<220> FEATURE:
<223> OTHER INFORMATION: RV3-Vero NSP3

<400> SEQUENCE: 45

ggcttttaat gcttttcagt ggttgctgct caagatggag tctactcagc agatggtaag     60

ctctattatt aacacttctt ttgaagctgc agttgttgct gccacttcaa cattagaatt    120

aatgggtatt caatatgatt acaatgaagt atttactaga gttaaaagta aatttgatta    180

tgtgatggat gactctggtg ttaaaaacaa tcttttgggt aaagctataa ctattgatca    240

ggcgttaaat ggaaagtttg gctcagctat tagaaataga aattggatga ctgattctaa    300

aacggttgct aaattagatg aagacgtgaa taaacttaga atgacattat cttctaaagg    360

aatcgaccaa aagatgagag tacttaatgc ttgttttagt gtaaaaagaa taccaggaaa    420

atcatcatca ataattaaat gctctagact tatgaaggat aaaatagaac gtggagaagt    480

tgaggttgat gattcatatg ttgatgagaa aatggaaatt gatactattg attggaaatc    540

tcgttatgat cagttagaaa aaagatttga gtcactaaaa caaagagtta atgagaaata    600

caatacttgg gtacaaaaag cgaagaaagt aaatgaaaat atgtactctc ttcagaatgt    660

catttcacaa cagcaaaacc aaatagcaga tcttcaacaa tattgtaata aattggaagc    720

tgatttgcaa ggcaaattta gttcattagt gtcatcagtt gagtggtatc taaggtctat    780

ggaattgcca aatgatgtaa agaatgatat tgaacagcag ttaaattcaa ttgatttaat    840

taatcccatt aatgctatag atgatatcga atcattgatt agaaatttaa ttcaagatta    900

tgacagaaca tttttaatgt taaaaggact gttgaagcaa tgcaactatg aatatacata    960

tgagtagtca cataattaaa agtattaacc atctacacat gaccctctat gagcacaata   1020

gttaaaagct aacactgtca aaaacctaaa tggctatagg ggcgttatgt              1070
```

```
<210> SEQ ID NO 46
<211> LENGTH: 310
<212> TYPE: PRT
<213> ORGANISM: artificial
<220> FEATURE:
<223> OTHER INFORMATION: RV3 Vero NSP3
```

<400> SEQUENCE: 46

```
Met Glu Ser Thr Gln Gln Met Val Ser Ser Ile Ile Asn Thr Ser Phe
1               5                   10                  15

Glu Ala Ala Val Val Ala Ala Thr Ser Thr Leu Glu Leu Met Gly Ile
            20                  25                  30

Gln Tyr Asp Tyr Asn Glu Val Phe Thr Arg Val Lys Ser Lys Phe Asp
        35                  40                  45

Tyr Val Met Asp Asp Ser Gly Val Lys Asn Asn Leu Leu Gly Lys Ala
    50                  55                  60

Ile Thr Ile Asp Gln Ala Leu Asn Gly Lys Phe Gly Ser Ala Ile Arg
65                  70                  75                  80

Asn Arg Asn Trp Met Thr Asp Ser Lys Thr Val Ala Lys Leu Asp Glu
                85                  90                  95

Asp Val Asn Lys Leu Arg Met Thr Leu Ser Ser Lys Gly Ile Asp Gln
            100                 105                 110

Lys Met Arg Val Leu Asn Ala Cys Phe Ser Val Lys Arg Ile Pro Gly
        115                 120                 125

Lys Ser Ser Ser Ile Ile Lys Cys Ser Arg Leu Met Lys Asp Lys Ile
    130                 135                 140

Glu Arg Gly Glu Val Glu Val Asp Asp Ser Tyr Val Asp Glu Lys Met
145                 150                 155                 160

Glu Ile Asp Thr Ile Asp Trp Lys Ser Arg Tyr Asp Gln Leu Glu Lys
                165                 170                 175

Arg Phe Glu Ser Leu Lys Gln Arg Val Asn Glu Lys Tyr Asn Thr Trp
            180                 185                 190

Val Gln Lys Ala Lys Lys Val Asn Glu Asn Met Tyr Ser Leu Gln Asn
        195                 200                 205

Val Ile Ser Gln Gln Gln Asn Gln Ile Ala Asp Leu Gln Gln Tyr Cys
    210                 215                 220

Asn Lys Leu Glu Ala Asp Leu Gln Gly Lys Phe Ser Ser Leu Val Ser
225                 230                 235                 240

Ser Val Glu Trp Tyr Leu Arg Ser Met Glu Leu Pro Asn Asp Val Lys
                245                 250                 255

Asn Asp Ile Glu Gln Gln Leu Asn Ser Ile Asp Leu Ile Asn Pro Ile
            260                 265                 270

Asn Ala Ile Asp Asp Ile Glu Ser Leu Ile Arg Asn Leu Ile Gln Asp
        275                 280                 285

Tyr Asp Arg Thr Phe Leu Met Leu Lys Gly Leu Leu Lys Gln Cys Asn
    290                 295                 300

Tyr Glu Tyr Thr Tyr Glu
305                 310
```

<210> SEQ ID NO 47
<211> LENGTH: 3267
<212> TYPE: DNA
<213> ORGANISM: artificial
<220> FEATURE:
<223> OTHER INFORMATION: MA104-adapted RV3 VP1

<400> SEQUENCE: 47

```
atggggaagt acaatctaat cttgtcagaa tatttatcat ttgtttataa ttcacaatct      60

gcagttcaaa taccaattta ttattcttcc aattcagaat tagaaaaaag atgtattgaa     120

tttcatgcta aatgtgttga cagttcaaaa aaaggtctat cattaaaacc tttattcgaa     180

aaatataaag atgtaataga taatgcaact ttactatctc tattatcata ttcttatgat     240
```

```
aaatacaacg ctgtagaaag gaaactagtc aattatgcta aaggtaaacc attagaggct    300
gatttaacgg caaacgagct tgattatgaa aataataaaa taacttctga attgtttcaa    360
tcagctgaag aatatactga ttcattaatg gatcctgcta tattaacttc gttatcttca    420
aatctaaatg cagtcatgtt ttggttagaa cgacactcaa atgacgttgc tgatgcaaac    480
aaaatttata aacgtagact ggatctattt accatagtag catctacaat aaataaatat    540
ggagtaccta gacataatga aaaatataga tatgaatacg aggtgatgaa ggataaaccg    600
tactacttag taacctgggc caactcatct atagaaatgc ttatgtcagt gttttcccat    660
gaagattatt taatagcaaa agagttaata atcttatcat attcaaatag atcaacgtta    720
gcaaaactag tttcatctcc aatgtcgata ttggttgcat taatagatat caatggtacg    780
tttattacaa atgaagagtt agaactcgag ttttcagata aatatgttaa ggcaattgtg    840
cctgatcaaa ttttcgatga attacaggaa atgatcgaca atatgaggaa agttggttta    900
gtagatatac caaaaatgat tcaagaatgg ttaattgatt gttcattaga gaaatttaca    960
ttgatgtcaa aaatttattc ttggtcattt catgttggtt ttagaaaaca aaagatgatt   1020
gatgcagcat tagaccaatt gaaaacagag tacactgaag atgtagataa tgagatgtat   1080
aatgagtata cgatgttaat tagagatgaa atagttaaaa tgctagaagt accagttaaa   1140
catgatgatc atctacttcg cgattcagaa ttagccggat tgttatcaat gtcatcagct   1200
tcaaatggtg aatcaaggca acttaaattt ggtcgtaaaa caatattttc aactaagaaa   1260
aatatgcatg tcatggatga tatcgcacat ggaaaatata ctccgggtgt cattcctcca   1320
gtaaatgtag atagaccaat tccactaggt cgtagagatg ttcctggacg aagaacaaga   1380
attatattca tattaccata tgaatacttt attgcgcagc acgctgtcgt agaaaaaatg   1440
ttatcatacg caaagcatac tagagagtac gcagaatttt attcgcagtc aaatcaattg   1500
ctatcatatg gtgatgttac aagattctta tccaataatt ctatggtatt atacacagac   1560
gtttcacaat gggattcgtc acaacataac acacaaccat ttagaaaagg aataattatg   1620
ggtttagata tgctatccaa tatgactaat gatccaaaag tagtacaaac gctaaattta   1680
tataaacaaa cacaaattaa tctcatggat tcatatgttc aaatacctga cggtaatgta   1740
ataaaaaaga ttcagtatgg tgctgttgct tcaggagaaa aacaaaccaa ggcagctaat   1800
tctatagcta atttggcact cattaaaacg gtattgtcaa gaattgcaaa taaatattct   1860
tttataacca aaataatcag agtcgatggt gatgataatt atgcagtact acaatttaat   1920
accgatgtca ctaaacaaat ggtccaagat gtgtcaaacg atgtgaggta tatatattct   1980
agaatgaatg ctaaagttaa agcactggta tctacagtcg gtatcgaaat agcaaaaaga   2040
tatatagcag gaggaaaaat atttttcaga gctggtataa acttattaaa taatgagaaa   2100
cgtggacaaa gtacacaatg ggatcaagca gctattttat actcaaacta cattgttaac   2160
aaattacgag gatttgagac tgatagagaa tttgtactaa ctaaaattat acaaatgaca   2220
tctatagcta ttactggatc actaaggcta tttccgtcag aacgagtgtt aactactaat   2280
tctacattca aagtatttga ctcagaagat ttcattatag agtatggaac aactgacgat   2340
gaagtatata tacaaagagc atttatgtca ttatctagtc aaaagtcagg aatagctgat   2400
gaaattgctt cttcacaaac atttaaaaat tatgtcaata aattatctga ccaactatta   2460
gtatcaaaaa acgtaattgt atctaaaggt atagctgtaa cagaaaaggc gaaattgaat   2520
tcatatgcac cagtttattt agaaaaacgt cgtgcacaaa tatcagcgct attaactatg   2580
```

```
ttgcagaaac cagtgtcatt taaatcaaat aaaattacta ttaatgacat tttgcgtgac   2640

ataaaaccat tttttgtcac ttctgaagct aatttgtcaa ttcaatacag aaaatttatg   2700

ccaacactac ctgataatgt ccaatatgtt atacaatgta taggatcgag gacgtaccag   2760

atagaagata gtgggtcaaa atcatcgatt tcgaagttaa tatcaaaata ttcagtttac   2820

aaaccatcga ttgaagaact atataaagtt atatctttaa gagaacaaga aatacagttg   2880

tatttagttt cattaggagt tccgctagtt gatgcaagca cgtacgtcgg gtcaagaata   2940

tattcgcaag ataaatataa aatattagaa tcttacgtat ataatttatt atcaattaat   3000

tatggatgtt atcaattatt cgattttaat tctccagatt tagagagact tatacgaatt   3060

ccttttaaag gtaagatacc agctgtaaca tttatattac atctttacgc taaacttgaa   3120

ataataaact atgctattaa gaacggagct tggatcagct tgttttgtaa ctatccaaaa   3180

tctgagatga ttaaattatg gaagaaaatg tggaatataa cagcattacg gtctccctat   3240

actagtgcga atttctttca agattag                                       3267
```

```
<210> SEQ ID NO 48
<211> LENGTH: 1088
<212> TYPE: PRT
<213> ORGANISM: artificial
<220> FEATURE:
<223> OTHER INFORMATION: MA104-adapted RV3 VP1

<400> SEQUENCE: 48

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Lys Arg Cys Ile Glu Phe His Ala Lys Cys Val Asp Ser
        35                  40                  45

Ser Lys Lys Gly Leu Ser Leu Lys Pro Leu Phe Glu Lys Tyr Lys Asp
    50                  55                  60

Val Ile Asp Asn Ala Thr Leu Leu Ser Leu Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Ile Leu Ser Tyr Ser Asn Arg Ser Thr Leu
225                 230                 235                 240
```

```
Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Ile Phe Asp Glu Leu
        275                 280                 285

Gln Glu Met Ile Asp Asn Met Arg Lys Val Gly Leu Val Asp Ile Pro
    290                 295                 300

Lys Met Ile Gln Glu Trp Leu Ile Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Glu Asp Val Asp Asn Glu Met Tyr Asn Glu Tyr Thr Met Leu Ile Arg
        355                 360                 365

Asp Glu Ile Val Lys Met Leu Glu Val Pro Val Lys His Asp Asp His
    370                 375                 380

Leu Leu Arg Asp Ser Glu Leu Ala Gly Leu Leu Ser Met Ser Ser Ala
385                 390                 395                 400

Ser Asn Gly Glu Ser Arg Gln Leu Lys Phe Gly Arg Lys Thr Ile Phe
                405                 410                 415

Ser Thr Lys Lys Asn Met His Val Met Asp Asp Ile Ala His Gly Lys
            420                 425                 430

Tyr Thr Pro Gly Val Ile Pro Pro Val Asn Val Asp Arg Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ser Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Met
    530                 535                 540

Leu Ser Asn Met Thr Asn Asp Pro Lys Val Val Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ala Asn Lys Tyr Ser Phe Ile Thr Lys
    610                 615                 620

Ile Ile Arg Val Asp Gly Asp Asp Asn Tyr Ala Val Leu Gln Phe Asn
625                 630                 635                 640

Thr Asp Val Thr Lys Gln Met Val Gln Asp Val Ser Asn Asp Val Arg
                645                 650                 655

Tyr Ile Tyr Ser Arg Met Asn Ala Lys Val Lys Ala Leu Val Ser Thr
```

```
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Val Leu Thr Lys Ile
                725                 730                 735

Ile Gln Met Thr Ser Ile Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Asn Lys Leu Ser
                805                 810                 815

Asp Gln Leu Leu Val Ser Lys Asn Val Ile Val Ser Lys Gly Ile Ala
            820                 825                 830

Val Thr Glu Lys Ala Lys Leu Asn Ser Tyr Ala Pro Val Tyr Leu Glu
        835                 840                 845

Lys Arg Arg Ala Gln Ile Ser Ala Leu Leu Thr Met Leu Gln Lys Pro
    850                 855                 860

Val Ser Phe Lys Ser Asn Lys Ile Thr Ile Asn Asp Ile Leu Arg Asp
865                 870                 875                 880

Ile Lys Pro Phe Phe Val Thr Ser Glu Ala Asn Leu Ser Ile Gln Tyr
                885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
        915                 920                 925

Ser Ile Ser Lys Leu Ile Ser Lys Tyr Ser Val Tyr Lys Pro Ser Ile
    930                 935                 940

Glu Glu Leu Tyr Lys Val Ile Ser Leu Arg Glu Gln Glu Ile Gln Leu
945                 950                 955                 960

Tyr Leu Val Ser Leu Gly Val Pro Leu Val Asp Ala Ser Thr Tyr Val
                965                 970                 975

Gly Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
        995                 1000                1005

Phe Asn  Ser Pro Asp Leu Glu  Arg Leu Ile Arg Ile  Pro Phe Lys
    1010                1015                1020

Gly Lys  Ile Pro Ala Val Thr  Phe Ile Leu His Leu  Tyr Ala Lys
    1025                1030                1035

Leu Glu  Ile Ile Asn Tyr Ala  Ile Lys Asn Gly Ala  Trp Ile Ser
    1040                1045                1050

Leu Phe  Cys Asn Tyr Pro Lys  Ser Glu Met Ile Lys  Leu Trp Lys
    1055                1060                1065

Lys Met  Trp Asn Ile Thr Ala  Leu Arg Ser Pro Tyr  Thr Ser Ala
    1070                1075                1080
```

```
Asn Phe  Phe Gln Asp
    1085

<210> SEQ ID NO 49
<211> LENGTH: 3322
<212> TYPE: DNA
<213> ORGANISM: artificial
<220> FEATURE:
<223> OTHER INFORMATION: Vero-adatped RV3 VP1

<400> SEQUENCE: 49

tgtaaaacga cggccagtgg ctattaaagc tgtacaatgg ggaagtacaa tctaatcttg     60

tcagaatatt tatcatttgt ttataattca caatctgcag ttcaaatacc aatttattat    120

tcttccaatt cagaattaga aaaaagatgt attgaatttc atgctaaatg tgttgacagt    180

tcaaaaaaag gtctatcatt aaaacccttta ttcgaaaaat ataaagatgt aatagataat    240

gcaactttac tatctctatt atcatattct tatgataaat acaacgctgt agaaaggaaa    300

ctagtcaatt atgctaaagg taaaccatta gaggctgatt taacggcaaa cgagcttgat    360

tatgaaaata ataaaataac ttctgaattg tttcaatcag ctgaagaata tactgattca    420

ttaatggatc ctgctatatt aacttcgtta tcttcaaatc taaatgcagt catgttttgg    480

ttagaacgac actcaaatga cgttgctgat gcaaacaaaa tttataaacg tagactggat    540

ctatttacca tagtagcatc tacaataaat aaatatggag tacctagaca taatgaaaaa    600

tatagatatg aatacgaggt gatgaaggat aaaccgtact acttagtaac ctgggccaac    660

tcatctatag aaatgcttat gtcagtgttt tcccatgaag attatttaat agcaaaagag    720

ttaataatct tatcatattc aaatagatca acgttagcaa aactagtttc atctccaatg    780

tcgatattgg ttgcattaat agatatcaat ggtacgttta ttacaaatga agagttagaa    840

ctcgagtttt cagataaata tgttaaggca attgtgcctg atcaaatttt cgatgaatta    900

caggaaatga tcgacaatat gaggaaagtt ggtttagtag atataccaaa aatgattcaa    960

gaatggttaa ttgattgttc attagagaaa tttacattga tgtcaaaaat ttattcttgg   1020

tcatttcatg ttggttttag aaaacaaaag atgattgatg cagcattaga ccaattgaaa   1080

acagagtaca ctgaagatgt agataatgag atgtataatg agtatacgat gttaattaga   1140

gatgaaatag ttaaaatgct agaagtacca gttaaacatg atgatcatct acttcgcgat   1200

tcagaattag ccggattgtt atcaatgtca tcagcttcaa atggtgaatc aaggcaactt   1260

aaatttggtc gtaaaacaat attttcaact aagaaaaata tgcatgtcat ggatgatatc   1320

gcacatggaa aatatactcc gggtgtcatt cctccagtaa atgtagatag accaattcca   1380

ctaggtcgta gagatgttcc tggacgaaga acaagaatta tattcatatt accatatgaa   1440

tactttattg cgcagcacgc tgtcgtagaa aaaatgttat catacgcaaa gcatactaga   1500

gagtacgcag aattttattc gcagtcaaat caattgctat catatggtga tgttacaaga   1560

ttcttatcca ataattctat ggtattatac acagacgttt cacaatggga ttcgtcacaa   1620

cataacacac aaccatttag aaaaggaata attatgggtt tagatatgct atccaatatg   1680

actaatgatc caaaagtagt acaaacgcta aatttatata aacaaacaca aattaatctc   1740

atggattcat atgttcaaat acctgacggt aatgtaataa aaaagattca gtatggtgct   1800

gttgcttcag gagaaaaaca aaccaaggca gctaattcta tagctaattt ggcactcatt   1860

aaaacggtat tgtcaagaat tgcaaataaa tattctttta taaccaaaat aatcagagtc   1920

gatggtgatg ataattatgc agtactacaa tttaataccg atgtcactaa acaaatggtc   1980
```

```
caagatgtgt caaacgatgt gaggtatata tattctagaa tgaatgctaa agttaaagca   2040

ctggtatcta cagtcggtat cgaaatagca aaaagatata tagcaggagg aaaaatattt   2100

ttcagagctg gtataaactt attaaataat gagaaacgtg gacaaagtac acaatgggat   2160

caagcagcta ttttatactc aaactacatt gttaacaaat tacgaggatt tgagactgat   2220

agagaatttg tactaactaa aattatacaa atgacatcta tagctattac tggatcacta   2280

aggctatttc cgtcagaacg agtgttaact actaattcta cattcaaagt atttgactca   2340

gaagatttca ttatagagta tggaacaact gacgatgaag tatatataca aagagcattt   2400

atgtcattat ctagtcaaaa gtcaggaata gctgatgaaa ttgcttcttc acaaacattt   2460

aaaaattatg tcaataaatt atctgaccaa ctattagtat caaaaaacgt aattgtatct   2520

aaaggtatag ctgtaacaga aaaggcgaaa ttgaattcat atgcaccagt ttatttagaa   2580

aaacgtcgtg cacaaatatc agcgctatta actatgttgc agaaaccagt gtcatttaaa   2640

tcaaataaaa ttactattaa tgacattttg cgtgacataa aaccattttt tttcacttct   2700

gaagctaatt tgtcaattca atacagaaaa tttatgccaa cactacctga taatgtccaa   2760

tatgttatac aatgtatagg atcgaggacg taccagatag aagatagtgg gtcaaaatca   2820

tcgatttcga agttaatatc aaaatattca gtttacaaac catcgattga agaactatat   2880

aaagttatat ctttaagaga acaagaaata cagttgtatt tagtttcatt aggagttccg   2940

ctagttgatg caagcacgta cgtcgggtca agaatatatt cgcaagataa atataaaata   3000

ttagaatctt acgtatataa tttattatca attaattatg gatgttatca attattcgat   3060

tttaattctc cagatttaga gagacttata cgaattcctt ttaaaggtaa gataccagct   3120

gtaacattta tattacatct ttacgctaaa cttgaaataa taaactatgc tattaagaac   3180

ggagcttgga tcagcttgtt ttgtaactat ccaaaatctg agatgattaa attatggaag   3240

aaaatgtgga atataacagc attacggtct ccctatacta gtgcgaattt ctttcaagat   3300

tagagcggct taggatgtga cc                                            3322
```

```
<210> SEQ ID NO 50
<211> LENGTH: 1088
<212> TYPE: PRT
<213> ORGANISM: artificial
<220> FEATURE:
<223> OTHER INFORMATION: Vero-adapted RV3 VP1

<400> SEQUENCE: 50

Met Gly Lys Tyr Asn Leu Ile Leu Ser Glu Tyr Leu Ser Phe Val Tyr
1               5                   10                  15

Asn Ser Gln Ser Ala Val Gln Ile Pro Ile Tyr Tyr Ser Ser Asn Ser
            20                  25                  30

Glu Leu Glu Lys Arg Cys Ile Glu Phe His Ala Lys Cys Val Asp Ser
        35                  40                  45

Ser Lys Lys Gly Leu Ser Leu Lys Pro Leu Phe Glu Lys Tyr Lys Asp
    50                  55                  60

Val Ile Asp Asn Ala Thr Leu Leu Ser Leu Leu Ser Tyr Ser Tyr Asp
65                  70                  75                  80

Lys Tyr Asn Ala Val Glu Arg Lys Leu Val Asn Tyr Ala Lys Gly Lys
                85                  90                  95

Pro Leu Glu Ala Asp Leu Thr Ala Asn Glu Leu Asp Tyr Glu Asn Asn
            100                 105                 110

Lys Ile Thr Ser Glu Leu Phe Gln Ser Ala Glu Glu Tyr Thr Asp Ser
```

```
        115                 120                 125

Leu Met Asp Pro Ala Ile Leu Thr Ser Leu Ser Ser Asn Leu Asn Ala
    130                 135                 140

Val Met Phe Trp Leu Glu Arg His Ser Asn Asp Val Ala Asp Ala Asn
145                 150                 155                 160

Lys Ile Tyr Lys Arg Arg Leu Asp Leu Phe Thr Ile Val Ala Ser Thr
                165                 170                 175

Ile Asn Lys Tyr Gly Val Pro Arg His Asn Glu Lys Tyr Arg Tyr Glu
            180                 185                 190

Tyr Glu Val Met Lys Asp Lys Pro Tyr Tyr Leu Val Thr Trp Ala Asn
        195                 200                 205

Ser Ser Ile Glu Met Leu Met Ser Val Phe Ser His Glu Asp Tyr Leu
    210                 215                 220

Ile Ala Lys Glu Leu Ile Ile Leu Ser Tyr Ser Asn Arg Ser Thr Leu
225                 230                 235                 240

Ala Lys Leu Val Ser Ser Pro Met Ser Ile Leu Val Ala Leu Ile Asp
                245                 250                 255

Ile Asn Gly Thr Phe Ile Thr Asn Glu Glu Leu Glu Leu Glu Phe Ser
            260                 265                 270

Asp Lys Tyr Val Lys Ala Ile Val Pro Asp Gln Ile Phe Asp Glu Leu
        275                 280                 285

Gln Glu Met Ile Asp Asn Met Arg Lys Val Gly Leu Val Asp Ile Pro
    290                 295                 300

Lys Met Ile Gln Glu Trp Leu Ile Asp Cys Ser Leu Glu Lys Phe Thr
305                 310                 315                 320

Leu Met Ser Lys Ile Tyr Ser Trp Ser Phe His Val Gly Phe Arg Lys
                325                 330                 335

Gln Lys Met Ile Asp Ala Ala Leu Asp Gln Leu Lys Thr Glu Tyr Thr
            340                 345                 350

Glu Asp Val Asp Asn Glu Met Tyr Asn Glu Tyr Thr Met Leu Ile Arg
        355                 360                 365

Asp Glu Ile Val Lys Met Leu Glu Val Pro Val Lys His Asp Asp His
    370                 375                 380

Leu Leu Arg Asp Ser Glu Leu Ala Gly Leu Leu Ser Met Ser Ser Ala
385                 390                 395                 400

Ser Asn Gly Glu Ser Arg Gln Leu Lys Phe Gly Arg Lys Thr Ile Phe
                405                 410                 415

Ser Thr Lys Lys Asn Met His Val Met Asp Asp Ile Ala His Gly Lys
            420                 425                 430

Tyr Thr Pro Gly Val Ile Pro Pro Val Asn Val Asp Arg Pro Ile Pro
        435                 440                 445

Leu Gly Arg Arg Asp Val Pro Gly Arg Arg Thr Arg Ile Ile Phe Ile
    450                 455                 460

Leu Pro Tyr Glu Tyr Phe Ile Ala Gln His Ala Val Val Glu Lys Met
465                 470                 475                 480

Leu Ser Tyr Ala Lys His Thr Arg Glu Tyr Ala Glu Phe Tyr Ser Gln
                485                 490                 495

Ser Asn Gln Leu Leu Ser Tyr Gly Asp Val Thr Arg Phe Leu Ser Asn
            500                 505                 510

Asn Ser Met Val Leu Tyr Thr Asp Val Ser Gln Trp Asp Ser Ser Gln
        515                 520                 525

His Asn Thr Gln Pro Phe Arg Lys Gly Ile Ile Met Gly Leu Asp Met
    530                 535                 540
```

```
Leu Ser Asn Met Thr Asn Asp Pro Lys Val Val Gln Thr Leu Asn Leu
545                 550                 555                 560

Tyr Lys Gln Thr Gln Ile Asn Leu Met Asp Ser Tyr Val Gln Ile Pro
                565                 570                 575

Asp Gly Asn Val Ile Lys Lys Ile Gln Tyr Gly Ala Val Ala Ser Gly
            580                 585                 590

Glu Lys Gln Thr Lys Ala Ala Asn Ser Ile Ala Asn Leu Ala Leu Ile
        595                 600                 605

Lys Thr Val Leu Ser Arg Ile Ala Asn Lys Tyr Ser Phe Ile Thr Lys
    610                 615                 620

Ile Ile Arg Val Asp Gly Asp Asp Asn Tyr Ala Val Leu Gln Phe Asn
625                 630                 635                 640

Thr Asp Val Thr Lys Gln Met Val Gln Asp Val Ser Asn Asp Val Arg
                645                 650                 655

Tyr Ile Tyr Ser Arg Met Asn Ala Lys Val Lys Ala Leu Val Ser Thr
            660                 665                 670

Val Gly Ile Glu Ile Ala Lys Arg Tyr Ile Ala Gly Gly Lys Ile Phe
        675                 680                 685

Phe Arg Ala Gly Ile Asn Leu Leu Asn Asn Glu Lys Arg Gly Gln Ser
    690                 695                 700

Thr Gln Trp Asp Gln Ala Ala Ile Leu Tyr Ser Asn Tyr Ile Val Asn
705                 710                 715                 720

Lys Leu Arg Gly Phe Glu Thr Asp Arg Glu Phe Val Leu Thr Lys Ile
                725                 730                 735

Ile Gln Met Thr Ser Ile Ala Ile Thr Gly Ser Leu Arg Leu Phe Pro
            740                 745                 750

Ser Glu Arg Val Leu Thr Thr Asn Ser Thr Phe Lys Val Phe Asp Ser
        755                 760                 765

Glu Asp Phe Ile Ile Glu Tyr Gly Thr Thr Asp Asp Glu Val Tyr Ile
    770                 775                 780

Gln Arg Ala Phe Met Ser Leu Ser Ser Gln Lys Ser Gly Ile Ala Asp
785                 790                 795                 800

Glu Ile Ala Ser Ser Gln Thr Phe Lys Asn Tyr Val Asn Lys Leu Ser
                805                 810                 815

Asp Gln Leu Leu Val Ser Lys Asn Val Ile Val Ser Lys Gly Ile Ala
            820                 825                 830

Val Thr Glu Lys Ala Lys Leu Asn Ser Tyr Ala Pro Val Tyr Leu Glu
        835                 840                 845

Lys Arg Arg Ala Gln Ile Ser Ala Leu Leu Thr Met Leu Gln Lys Pro
    850                 855                 860

Val Ser Phe Lys Ser Asn Lys Ile Thr Ile Asn Asp Ile Leu Arg Asp
865                 870                 875                 880

Ile Lys Pro Phe Phe Phe Thr Ser Glu Ala Asn Leu Ser Ile Gln Tyr
                885                 890                 895

Arg Lys Phe Met Pro Thr Leu Pro Asp Asn Val Gln Tyr Val Ile Gln
            900                 905                 910

Cys Ile Gly Ser Arg Thr Tyr Gln Ile Glu Asp Ser Gly Ser Lys Ser
        915                 920                 925

Ser Ile Ser Lys Leu Ile Ser Lys Tyr Ser Val Tyr Lys Pro Ser Ile
    930                 935                 940

Glu Glu Leu Tyr Lys Val Ile Ser Leu Arg Glu Gln Glu Ile Gln Leu
945                 950                 955                 960
```

```
Tyr Leu Val Ser Leu Gly Val Pro Leu Val Asp Ala Ser Thr Tyr Val
                965                 970                 975

Gly Ser Arg Ile Tyr Ser Gln Asp Lys Tyr Lys Ile Leu Glu Ser Tyr
            980                 985                 990

Val Tyr Asn Leu Leu Ser Ile Asn  Tyr Gly Cys Tyr Gln  Leu Phe Asp
        995                 1000                 1005

Phe Asn  Ser Pro Asp Leu Glu  Arg Leu Ile Arg Ile  Pro Phe Lys
    1010                 1015                 1020

Gly Lys  Ile Pro Ala Val Thr  Phe Ile Leu His Leu  Tyr Ala Lys
    1025                 1030                 1035

Leu Glu  Ile Ile Asn Tyr Ala  Ile Lys Asn Gly Ala  Trp Ile Ser
    1040                 1045                 1050

Leu Phe  Cys Asn Tyr Pro Lys  Ser Glu Met Ile Lys  Leu Trp Lys
    1055                 1060                 1065

Lys Met  Trp Asn Ile Thr Ala  Leu Arg Ser Pro Tyr  Thr Ser Ala
    1070                 1075                 1080

Asn Phe  Phe Gln Asp
    1085


<210> SEQ ID NO 51
<211> LENGTH: 2673
<212> TYPE: DNA
<213> ORGANISM: artificial
<220> FEATURE:
<223> OTHER INFORMATION: MA104-adapted RV3 VP2

<400> SEQUENCE: 51

atggcgtaca ggaagcgcgg agttaaacgt gaaaacttac cacaacaaaa tgaacgtctg     60

caagaaaaag aaactgaaaa taatacagac gtaaccatgg aaaataaaaa taacaataga    120

aggcagcaat tatctgacaa agtgttatca caaaaagagg aaataataac tgatgtacaa    180

gatgacatta aaatagctga tgaggttaaa aaatcatcaa aagaagagtc aaaacagtta    240

cttgaaatat taaaaacgaa agaagatcat cagaaagaag tacagtacga aattctacaa    300

aaaacaatac cgacttttga accaaaagaa tcaattttga aaaaattaga agatataaga    360

ccagaacaag ctaagaagca aatgaaattg tttagaatat ttgaaccaag acaattacca    420

atctatcgag caaatggtga gaaagagtta aggaatagat ggtattggaa attgaaaaag    480

gatacactgc cggacggaga ttatgacgta cgagagtatt ttttaaattt atatgatcaa    540

atactgatag aaatgccaga ttatttatta ctaaaagata tggctgtaga aaataaaaac    600

tctagagatg ctggtaaagt tgtagattct gagactgcaa gtatttgtga tgctatattt    660

caagatgagg agacagaggg agttattaga agattcatcg cagatatgag acaacaagtt    720

caagctgata gaaatattgt caattatcca tcaattttgc atccgattga tcacgcattt    780

aatgaatact tttgaatca tcaattagtt gaaccattga ataacgaaat tatttttaat    840

tatataccag aaagaataag gaatgatgtt aactatattt tgaatatgga tatgaatttg    900

ccatcaacag cgcgatatat tagaccaaat ctattgcaag atagactaaa tttacatgat    960

aattttgaat cattatggga cacgataact acatcaaatt acatattagc aagatcagtc   1020

gtgcctgatt tgaaggaaaa agaattagtt tcaactgaag ctcagatcca gaaaatgtct   1080

caagatttgc agcttgaagc tttaacaata caatctgaaa cgcagtttct ggccggtata   1140

aattcacaag cagcgaatga ttgttttaaa acactgatag cagctatgtt aagccaacgt   1200

acaatgtcat tagattttgt aactacgaat tatatgtcac ttatatctgg catgtggcta   1260
```

```
ttgactgtta taccaaatga tatgtttctt cgtgagtcgc tagtcgcatg cgaattggct   1320

ataataaata ctatagttta tccagcattt ggaatgcaaa gaatgcatta tagaaatggc   1380

gatcctcaga ctccatttca aatagcagaa caacagatac aaaattttca agtagctaat   1440

tggttacatt ttattaacaa taatagattt aggcaagttg ttattgatgg agtgttaaat   1500

caaacactta atgacaacat taggaatgga caagttatta atcaattaat ggaagcatta   1560

atgcagttat ctagacaaca atttccgacc atgccagttg attataaaag atcaatccag   1620

agaggaatat tgttattatc taacagatta ggtcagttgg ttgatttaac aagattatta   1680

tcatacaatt atgaaactct aatggcttgt ataactatga acatgcaaca tgttcaaact   1740

ctcactaccg aaaaattaca attaacttct gtcacatctt tatgtatgtt aattggaaat   1800

accacagtaa ttccaggtcc acaaacacta tttcactatt ataacgtaaa tgtaaatttt   1860

cattcaaatt ataacgaacg aattaatgat gctgtggcta ttattacggc tgctaataga   1920

ttaaacttat atcagaaaaa aatgaaatca atagttgagg attttttgaa aagattgcaa   1980

atttttgatg taccacgagt gccagatgac caaacgtaca ggttgagaga cagacttaga   2040

ttattgccag ttgaaagacg aagacttgat atatttaact taatattaat gaatatggag   2100

cagatcgaac gagcttcaga caaaattgct caaggagtaa taattgctta cagagatatg   2160

cagctagaaa gagatgagat gtatgggttt gttaacatcg ctaggaacct cgatggatat   2220

caacaaatca atttggaaga gttgatgaga actggggact atggtcaaat tactaatatg   2280

ctattaaaca accagcctgt agctttagta ggagcattac catttgtgac agattcatca   2340

gttatatcgc tcattgcaaa attggatgcc acagtttttg ctcaaatagt taaacttaga   2400

aaagtggaca ctttaaaacc aatattgtat aaaataaatt ctgattctaa tgatttctat   2460

ttagttgcaa attatgattg gataccaact tcaaccacaa aagtttataa gcaagtacca   2520

caaccttttg atttcagagc gtcaatgcat atgttaacgt ctaatttaac ttttactgtt   2580

tattccgatt tgctatcttt cgtttctgca gacacggttg aacctattaa cgcaattgct   2640

tttgacaata tgcgcattat gaacgaactg taa                                2673
```

```
<210> SEQ ID NO 52
<211> LENGTH: 890
<212> TYPE: PRT
<213> ORGANISM: artificial
<220> FEATURE:
<223> OTHER INFORMATION: MA104-adapted RV3 VP2

<400> SEQUENCE: 52

Met Ala Tyr Arg Lys Arg Gly Val Lys Arg Glu Asn Leu Pro Gln Gln
1               5                   10                  15

Asn Glu Arg Leu Gln Glu Lys Glu Thr Glu Asn Asn Thr Asp Val Thr
            20                  25                  30

Met Glu Asn Lys Asn Asn Asn Arg Arg Gln Gln Leu Ser Asp Lys Val
        35                  40                  45

Leu Ser Gln Lys Glu Glu Ile Ile Thr Asp Val Gln Asp Asp Ile Lys
    50                  55                  60

Ile Ala Asp Glu Val Lys Lys Ser Ser Lys Glu Glu Ser Lys Gln Leu
65                  70                  75                  80

Leu Glu Ile Leu Lys Thr Lys Glu Asp His Gln Lys Glu Val Gln Tyr
                85                  90                  95

Glu Ile Leu Gln Lys Thr Ile Pro Thr Phe Glu Pro Lys Glu Ser Ile
            100                 105                 110
```

```
Leu Lys Lys Leu Glu Asp Ile Arg Pro Glu Gln Ala Lys Lys Gln Met
        115                 120                 125

Lys Leu Phe Arg Ile Phe Glu Pro Arg Gln Leu Pro Ile Tyr Arg Ala
    130                 135                 140

Asn Gly Glu Lys Glu Leu Arg Asn Arg Trp Tyr Trp Lys Leu Lys Lys
145                 150                 155                 160

Asp Thr Leu Pro Asp Gly Asp Tyr Asp Val Arg Glu Tyr Phe Leu Asn
                165                 170                 175

Leu Tyr Asp Gln Ile Leu Ile Glu Met Pro Asp Tyr Leu Leu Leu Lys
            180                 185                 190

Asp Met Ala Val Glu Asn Lys Asn Ser Arg Asp Ala Gly Lys Val Val
        195                 200                 205

Asp Ser Glu Thr Ala Ser Ile Cys Asp Ala Ile Phe Gln Asp Glu Glu
    210                 215                 220

Thr Glu Gly Val Ile Arg Arg Phe Ile Ala Asp Met Arg Gln Gln Val
225                 230                 235                 240

Gln Ala Asp Arg Asn Ile Val Asn Tyr Pro Ser Ile Leu His Pro Ile
                245                 250                 255

Asp His Ala Phe Asn Glu Tyr Phe Leu Asn His Gln Leu Val Glu Pro
            260                 265                 270

Leu Asn Asn Glu Ile Ile Phe Asn Tyr Ile Pro Glu Arg Ile Arg Asn
        275                 280                 285

Asp Val Asn Tyr Ile Leu Asn Met Asp Met Asn Leu Pro Ser Thr Ala
    290                 295                 300

Arg Tyr Ile Arg Pro Asn Leu Leu Gln Asp Arg Leu Asn Leu His Asp
305                 310                 315                 320

Asn Phe Glu Ser Leu Trp Asp Thr Ile Thr Thr Ser Asn Tyr Ile Leu
                325                 330                 335

Ala Arg Ser Val Val Pro Asp Leu Lys Glu Lys Glu Leu Val Ser Thr
            340                 345                 350

Glu Ala Gln Ile Gln Lys Met Ser Gln Asp Leu Gln Leu Glu Ala Leu
        355                 360                 365

Thr Ile Gln Ser Glu Thr Gln Phe Leu Ala Gly Ile Asn Ser Gln Ala
    370                 375                 380

Ala Asn Asp Cys Phe Lys Thr Leu Ile Ala Ala Met Leu Ser Gln Arg
385                 390                 395                 400

Thr Met Ser Leu Asp Phe Val Thr Thr Asn Tyr Met Ser Leu Ile Ser
                405                 410                 415

Gly Met Trp Leu Leu Thr Val Ile Pro Asn Asp Met Phe Leu Arg Glu
            420                 425                 430

Ser Leu Val Ala Cys Glu Leu Ala Ile Ile Asn Thr Ile Val Tyr Pro
        435                 440                 445

Ala Phe Gly Met Gln Arg Met His Tyr Arg Asn Gly Asp Pro Gln Thr
    450                 455                 460

Pro Phe Gln Ile Ala Glu Gln Gln Ile Gln Asn Phe Gln Val Ala Asn
465                 470                 475                 480

Trp Leu His Phe Ile Asn Asn Asn Arg Phe Arg Gln Val Val Ile Asp
                485                 490                 495

Gly Val Leu Asn Gln Thr Leu Asn Asp Asn Ile Arg Asn Gly Gln Val
            500                 505                 510

Ile Asn Gln Leu Met Glu Ala Leu Met Gln Leu Ser Arg Gln Gln Phe
        515                 520                 525

Pro Thr Met Pro Val Asp Tyr Lys Arg Ser Ile Gln Arg Gly Ile Leu
```

```
    530                 535                 540

Leu Leu Ser Asn Arg Leu Gly Gln Leu Val Asp Leu Thr Arg Leu Leu
545                 550                 555                 560

Ser Tyr Asn Tyr Glu Thr Leu Met Ala Cys Ile Thr Met Asn Met Gln
                565                 570                 575

His Val Gln Thr Leu Thr Thr Glu Lys Leu Gln Leu Thr Ser Val Thr
            580                 585                 590

Ser Leu Cys Met Leu Ile Gly Asn Thr Thr Val Ile Pro Gly Pro Gln
        595                 600                 605

Thr Leu Phe His Tyr Tyr Asn Val Asn Val Asn Phe His Ser Asn Tyr
    610                 615                 620

Asn Glu Arg Ile Asn Asp Ala Val Ala Ile Ile Thr Ala Ala Asn Arg
625                 630                 635                 640

Leu Asn Leu Tyr Gln Lys Lys Met Lys Ser Ile Val Glu Asp Phe Leu
                645                 650                 655

Lys Arg Leu Gln Ile Phe Asp Val Pro Arg Val Pro Asp Asp Gln Thr
            660                 665                 670

Tyr Arg Leu Arg Asp Arg Leu Arg Leu Leu Pro Val Glu Arg Arg Arg
        675                 680                 685

Leu Asp Ile Phe Asn Leu Ile Leu Met Asn Met Glu Gln Ile Glu Arg
    690                 695                 700

Ala Ser Asp Lys Ile Ala Gln Gly Val Ile Ile Ala Tyr Arg Asp Met
705                 710                 715                 720

Gln Leu Glu Arg Asp Glu Met Tyr Gly Phe Val Asn Ile Ala Arg Asn
                725                 730                 735

Leu Asp Gly Tyr Gln Gln Ile Asn Leu Glu Glu Leu Met Arg Thr Gly
            740                 745                 750

Asp Tyr Gly Gln Ile Thr Asn Met Leu Leu Asn Asn Gln Pro Val Ala
        755                 760                 765

Leu Val Gly Ala Leu Pro Phe Val Thr Asp Ser Ser Val Ile Ser Leu
    770                 775                 780

Ile Ala Lys Leu Asp Ala Thr Val Phe Ala Gln Ile Val Lys Leu Arg
785                 790                 795                 800

Lys Val Asp Thr Leu Lys Pro Ile Leu Tyr Lys Ile Asn Ser Asp Ser
                805                 810                 815

Asn Asp Phe Tyr Leu Val Ala Asn Tyr Asp Trp Ile Pro Thr Ser Thr
            820                 825                 830

Thr Lys Val Tyr Lys Gln Val Pro Gln Pro Phe Asp Phe Arg Ala Ser
        835                 840                 845

Met His Met Leu Thr Ser Asn Leu Thr Phe Thr Val Tyr Ser Asp Leu
    850                 855                 860

Leu Ser Phe Val Ser Ala Asp Thr Val Glu Pro Ile Asn Ala Ile Ala
865                 870                 875                 880

Phe Asp Asn Met Arg Ile Met Asn Glu Leu
                885                 890


<210> SEQ ID NO 53
<211> LENGTH: 2717
<212> TYPE: DNA
<213> ORGANISM: artificial
<220> FEATURE:
<223> OTHER INFORMATION: Vero-adapted RV3 VP2

<400> SEQUENCE: 53

ggctattaaa ggttcaatgg cgtacaggaa gcgcggagtt aaacgtgaaa acttaccaca      60
```

```
acaaaatgaa cgtctgcaag aaaaagaaac tgaaaataat acagacgtaa ccatggaaaa    120
taaaaataac aatagaaggc agcaattatc tgacaaagtg ttatcacaaa aagaggaaat    180
aataactgat gtacaagatg acattaaaat agctgatgag gttaaaaaat catcaaaaga    240
agagtcaaaa cagttacttg aaatattaaa aacgaaagaa gatcatcaga aagaagtaca    300
gtacgaaatt ctacaaaaaa caataccgac ttttgaacca aaagaatcaa ttttgaaaaa    360
attagaagat ataagaccag aacaagctaa gaagcaaatg aaattgttta gaatatttga    420
accaagacaa ttaccaatct atcgagcaaa tggtgagaaa gagttaagga atagatggta    480
ttggaaattg aaaaaggata cactgccgga cggagattat gacgtacgag agtatttttt    540
aaatttatat gatcaaatac tgatagaaat gccagattat ttattactaa aagatatggc    600
tgtagaaaat aaaaactcta gagatgctgg taaagttgta gattctgaga ctgcaagtat    660
ttgtgatgct atatttcaag atgaggagac agagggagtt attagaagat tcatcgcaga    720
tatgagacaa caagttcaag ctgatagaaa tattgtcaat tatccatcaa ttttgcatcc    780
gattgatcac gcatttaatg aatacttttt gaatcatcaa ttagttgaac cattgaataa    840
cgaaattatt tttaattata taccagaaag aataaggaat gatgttaact atattttgaa    900
tatggatatg aatttgccat caacagcgcg atatattaga ccaaatctat tgcaagatag    960
actaaattta catgataatt ttgaatcatt atgggacacg ataactacat caaattacat   1020
attagcaaga tcagtcgtgc ctgatttgaa ggaaaaagaa ttagtttcaa ctgaagctca   1080
gatccagaaa atgtctcaag atttgcagct tgaagcttta acaatacaat ctgaaacgca   1140
gtttctggcc ggtataaatt cacaagcagc gaatgattgt tttaaaacac tgatagcagc   1200
tatgttaagc caacgtacaa tgtcattaga ttttgtaact acgaattata tgtcacttat   1260
atctggcatg tggctattga ctgttatacc aaatgatatg tttcttcgtg agtcgctagt   1320
cgcatgcgaa ttggctataa taaatactat agtttatcca gcatttggaa tgcaaagaat   1380
gcattataga aatggcgatc ctcagactcc atttcaaata gcagaacaac agatacaaaa   1440
ttttcaagta gctaattggt tacattttat taacaataat agatttaggc aagttgttat   1500
tgatggagtg ttaaatcaaa cacttaatga caacattagg aatggacaag ttattaatca   1560
attaatggaa gcattaatgc agttatctag acaacaattt ccgaccatgc cagttgatta   1620
taaaagatca atccagagag gaatattgtt attatctaac agattaggtc agttggttga   1680
tttaacaaga ttattatcat acaattatga aactctaatg gcttgtataa ctatgaacat   1740
gcaacatgtt caaactctca ctaccgaaaa attacaatta acttctgtca catctttatg   1800
tatgttaatt ggaaatacca cagtaattcc aggtccacaa acactatttc actattataa   1860
cgtaaatgta aattttcatt caaattataa cgaacgaatt aatgatgctg tggctattat   1920
tacggctgct aatagattaa acttatatca gaaaaaaatg aaatcaatag ttgaggattt   1980
tttgaaaaga ttgcaaattt ttgatgtacc acgagtgcca gatgaccaaa cgtacaggtt   2040
gagagacaga cttagattat tgccagttga aagacgaaga cttgatatat ttaacttaat   2100
attaatgaat atggagcaga tcgaacgagc ttcagacaaa attgctcaag gagtaataat   2160
tgcttacaga gatatgcagc tagaaagaga tgagatgtat gggtttgtta acatcgctag   2220
gaacctcgat ggatatcaac aaatcaattt ggaagagttg atgagaactg ggactatgg    2280
tcaaattact aatatgctat taaacaacca gcctgtagct ttagtaggag cattaccatt   2340
tgtgacagat tcatcagtta tatcgctcat tgcaaaattg gatgccacag tttttgctca   2400
```

```
aatagttaaa cttagaaaag tggacacttt aaaaccaata ttgtataaaa taaattctga   2460

ttctaatgat ttctatttag ttgcaaatta tgattggata ccaacttcaa ccacaaaagt   2520

ttataagcaa gtaccacaac cttttgattt cagagcgtca atgcatatgt taacgtctaa   2580

tttaactttt actgtttatt ccgatttgct atctttcgtt tctgcagaca cggttgaacc   2640

tattaacgca attgcttttg acaatatgcg cattatgaac gaactgtaaa cgccaacccc   2700

actgtggaga tatgacc                                                  2717


<210> SEQ ID NO 54
<211> LENGTH: 890
<212> TYPE: PRT
<213> ORGANISM: artificial
<220> FEATURE:
<223> OTHER INFORMATION: Vero-adapated RV3 VP2

<400> SEQUENCE: 54

Met Ala Tyr Arg Lys Arg Gly Val Lys Arg Glu Asn Leu Pro Gln Gln
1               5                   10                  15

Asn Glu Arg Leu Gln Glu Lys Glu Thr Glu Asn Asn Thr Asp Val Thr
            20                  25                  30

Met Glu Asn Lys Asn Asn Asn Arg Arg Gln Gln Leu Ser Asp Lys Val
        35                  40                  45

Leu Ser Gln Lys Glu Glu Ile Ile Thr Asp Val Gln Asp Asp Ile Lys
    50                  55                  60

Ile Ala Asp Glu Val Lys Lys Ser Ser Lys Glu Glu Ser Lys Gln Leu
65                  70                  75                  80

Leu Glu Ile Leu Lys Thr Lys Glu Asp His Gln Lys Glu Val Gln Tyr
                85                  90                  95

Glu Ile Leu Gln Lys Thr Ile Pro Thr Phe Glu Pro Lys Glu Ser Ile
            100                 105                 110

Leu Lys Lys Leu Glu Asp Ile Arg Pro Glu Gln Ala Lys Lys Gln Met
        115                 120                 125

Lys Leu Phe Arg Ile Phe Glu Pro Arg Gln Leu Pro Ile Tyr Arg Ala
    130                 135                 140

Asn Gly Glu Lys Glu Leu Arg Asn Arg Trp Tyr Trp Lys Leu Lys Lys
145                 150                 155                 160

Asp Thr Leu Pro Asp Gly Asp Tyr Asp Val Arg Glu Tyr Phe Leu Asn
                165                 170                 175

Leu Tyr Asp Gln Ile Leu Ile Glu Met Pro Asp Tyr Leu Leu Leu Lys
            180                 185                 190

Asp Met Ala Val Glu Asn Lys Asn Ser Arg Asp Ala Gly Lys Val Val
        195                 200                 205

Asp Ser Glu Thr Ala Ser Ile Cys Asp Ala Ile Phe Gln Asp Glu Glu
    210                 215                 220

Thr Glu Gly Val Ile Arg Arg Phe Ile Ala Asp Met Arg Gln Gln Val
225                 230                 235                 240

Gln Ala Asp Arg Asn Ile Val Asn Tyr Pro Ser Ile Leu His Pro Ile
                245                 250                 255

Asp His Ala Phe Asn Glu Tyr Phe Leu Asn His Gln Leu Val Glu Pro
            260                 265                 270

Leu Asn Asn Glu Ile Ile Phe Asn Tyr Ile Pro Glu Arg Ile Arg Asn
        275                 280                 285

Asp Val Asn Tyr Ile Leu Asn Met Asp Met Asn Leu Pro Ser Thr Ala
    290                 295                 300
```

```
Arg Tyr Ile Arg Pro Asn Leu Leu Gln Asp Arg Leu Asn Leu His Asp
305                 310                 315                 320

Asn Phe Glu Ser Leu Trp Asp Thr Ile Thr Thr Ser Asn Tyr Ile Leu
                325                 330                 335

Ala Arg Ser Val Val Pro Asp Leu Lys Glu Lys Glu Leu Val Ser Thr
            340                 345                 350

Glu Ala Gln Ile Gln Lys Met Ser Gln Asp Leu Gln Leu Glu Ala Leu
        355                 360                 365

Thr Ile Gln Ser Glu Thr Gln Phe Leu Ala Gly Ile Asn Ser Gln Ala
    370                 375                 380

Ala Asn Asp Cys Phe Lys Thr Leu Ile Ala Ala Met Leu Ser Gln Arg
385                 390                 395                 400

Thr Met Ser Leu Asp Phe Val Thr Thr Asn Tyr Met Ser Leu Ile Ser
                405                 410                 415

Gly Met Trp Leu Leu Thr Val Ile Pro Asn Asp Met Phe Leu Arg Glu
            420                 425                 430

Ser Leu Val Ala Cys Glu Leu Ala Ile Ile Asn Thr Ile Val Tyr Pro
        435                 440                 445

Ala Phe Gly Met Gln Arg Met His Tyr Arg Asn Gly Asp Pro Gln Thr
    450                 455                 460

Pro Phe Gln Ile Ala Glu Gln Gln Ile Gln Asn Phe Gln Val Ala Asn
465                 470                 475                 480

Trp Leu His Phe Ile Asn Asn Asn Arg Phe Arg Gln Val Val Ile Asp
                485                 490                 495

Gly Val Leu Asn Gln Thr Leu Asn Asp Asn Ile Arg Asn Gly Gln Val
            500                 505                 510

Ile Asn Gln Leu Met Glu Ala Leu Met Gln Leu Ser Arg Gln Gln Phe
        515                 520                 525

Pro Thr Met Pro Val Asp Tyr Lys Arg Ser Ile Gln Arg Gly Ile Leu
    530                 535                 540

Leu Leu Ser Asn Arg Leu Gly Gln Leu Val Asp Leu Thr Arg Leu Leu
545                 550                 555                 560

Ser Tyr Asn Tyr Glu Thr Leu Met Ala Cys Ile Thr Met Asn Met Gln
                565                 570                 575

His Val Gln Thr Leu Thr Thr Glu Lys Leu Gln Leu Thr Ser Val Thr
            580                 585                 590

Ser Leu Cys Met Leu Ile Gly Asn Thr Thr Val Ile Pro Gly Pro Gln
        595                 600                 605

Thr Leu Phe His Tyr Tyr Asn Val Asn Val Asn Phe His Ser Asn Tyr
    610                 615                 620

Asn Glu Arg Ile Asn Asp Ala Val Ala Ile Ile Thr Ala Ala Asn Arg
625                 630                 635                 640

Leu Asn Leu Tyr Gln Lys Lys Met Lys Ser Ile Val Glu Asp Phe Leu
                645                 650                 655

Lys Arg Leu Gln Ile Phe Asp Val Pro Arg Val Pro Asp Asp Gln Thr
            660                 665                 670

Tyr Arg Leu Arg Asp Arg Leu Arg Leu Leu Pro Val Glu Arg Arg Arg
        675                 680                 685

Leu Asp Ile Phe Asn Leu Ile Leu Met Asn Met Glu Gln Ile Glu Arg
    690                 695                 700

Ala Ser Asp Lys Ile Ala Gln Gly Val Ile Ile Ala Tyr Arg Asp Met
705                 710                 715                 720

Gln Leu Glu Arg Asp Glu Met Tyr Gly Phe Val Asn Ile Ala Arg Asn
```

```
                725                 730                 735

Leu Asp Gly Tyr Gln Gln Ile Asn Leu Glu Glu Leu Met Arg Thr Gly
            740                 745                 750

Asp Tyr Gly Gln Ile Thr Asn Met Leu Leu Asn Asn Gln Pro Val Ala
        755                 760                 765

Leu Val Gly Ala Leu Pro Phe Val Thr Asp Ser Ser Val Ile Ser Leu
    770                 775                 780

Ile Ala Lys Leu Asp Ala Thr Val Phe Ala Gln Ile Val Lys Leu Arg
785                 790                 795                 800

Lys Val Asp Thr Leu Lys Pro Ile Leu Tyr Lys Ile Asn Ser Asp Ser
                805                 810                 815

Asn Asp Phe Tyr Leu Val Ala Asn Tyr Asp Trp Ile Pro Thr Ser Thr
            820                 825                 830

Thr Lys Val Tyr Lys Gln Val Pro Gln Pro Phe Asp Phe Arg Ala Ser
        835                 840                 845

Met His Met Leu Thr Ser Asn Leu Thr Phe Thr Val Tyr Ser Asp Leu
    850                 855                 860

Leu Ser Phe Val Ser Ala Asp Thr Val Glu Pro Ile Asn Ala Ile Ala
865                 870                 875                 880

Phe Asp Asn Met Arg Ile Met Asn Glu Leu
                885                 890
```

<210> SEQ ID NO 55
<211> LENGTH: 2508
<212> TYPE: DNA
<213> ORGANISM: artificial
<220> FEATURE:
<223> OTHER INFORMATION: MA104-adapated RV3 VP3

<400> SEQUENCE: 55

```
atgaaagtat tagctttaag acacagtgtg gctcaggtgt atgcagatac tcaaacctat     60

ttgcatgatg attcaaaaga tgagtatgaa aatgcatttc tcatttctaa tctaactaca    120

cataatatat tatacctgaa ttacagcctt aaaacattaa aatattaaa tgaatcaggt    180

atagcagcag ttgaagtaca gtctccagat gaattatttg cgttaataag gtgtaatttt    240

acgtacgatt atgagaataa catagtttat ttacatgatt attcatatta tactaacaat    300

gaaataagaa cagatcaaca ttggataact aaaactgata taattgacta tctattacct    360

ggatggaaat taacatatgt aggctataat ggaaagaaca cacgaggtca ctatgatttt    420

tcatttatat gtcaaaatgc agctacagat gatgatataa taattgaata tatatactcc    480

aatgagttag actttcaaaa ctttctgtta agaaaaatta aagagagaat gaccacatct    540

cttccaattg ctagattatc aaatcgtgtg tttagagata aattatttcc atctattgta    600

aacatacata aaaaagtgat aaacgttggg ccaaggaatg aatctatgtt cacattctta    660

aattttccaa ctattaagca attttcaaac ggtgcgtata ttgtgaagca tactattaaa    720

ttgaagcagg agaaatggtt gggtaaaaga gtatcacaat ttgacatcgg acaatataaa    780

aacatgttaa atgtggttac tactatttac tattactata atttatacta ttcgaaacct    840

ataatataca tgcttggttc agctccatct tattggattt atgatattaa acagtattct    900

gattttacat ttgaaacatg ggatccatta gatactccat attctacaac acatcataaa    960

gaattatttt ttgataagga tgtcaataag cttaaagata attcagtttt atatatagac   1020

ataagaactg atagaggtaa tatggattgg aaagagtgga gaaaaatagt agaacaacaa   1080

actgttagca atctaaatat tgcgtataaa tatctatcaa caggaaaagc aaaggtgtgt   1140
```

```
tgtgttaaat taactgctat ggacctagaa ttaccaataa cagcaaaatt acttcatcat   1200
ccaactactg aagttagatc agaattttat gcaatattgg atgtatggga tattattacc   1260
attaaaagat ttataccaaa aggtgtattt tatgctttta taaataatgt aaccacagag   1320
aatgtgttta tacaacctcc tttcaaatta aaaacgtcac ctactgatta catagtggca   1380
ttgtatgctt tatccaatga cttcaactcg aggcaagatg ttattaattt gattaataaa   1440
caaaaacaat cactcattac tgttcgtata aataatactt ttaaagacga accaaaagta   1500
aattttaaaa atatttatga ttggacgttt ctgccaacag attttgaact taaagattcg   1560
ataattacat catatgatgg ttgtttaggc atattcggat tatcgatatc tttatcgtct   1620
aaacccactg gaaataatca tttatttata ataaatggaa ctgacaaata tgataaacta   1680
gaccaatatg caaatcatat gggtatttct agaagatcgc atcaaattag attctcagag   1740
tctgcgacat catattcggg atacattttt agagatcttt caaataataa tttcaatcta   1800
ataggtacta atgtggagaa ttcagtttca ggacatgtct ataatgcatt aatttactat   1860
agatataatt atgcgtttga tcttaaaaga tggatttatc tacattcaat tgggaaagtc   1920
gctgtagagg gtggaagata ttatgaacat gcaccaatcg aactgatata tgcatgccga   1980
tcagctaaag aatttgctat attacaagat gacttaacgg tattgagata cgctaatgaa   2040
attgaagggt atataagcaa agtgtacagt ataacctatg ctgacgatcc caattacttt   2100
ataggaatta aatttaatag tataccttat gaatacgatg ttaaaattcc acatttgacg   2160
ctaggagtat tatttatatc tgataatatg atacatgatg taatcacagt gttgaagaaa   2220
atgaagacag agctatttaa aatggaaatt agtactagtt atacttatat gctatctgat   2280
aatacgtatg tagcaaatgc tagtggtgtg ttatcaactt attttaaatt atataatatg   2340
ttctatagaa attatatcac gtttggacaa tcacgaatgt ttatcccaca cattacgctt   2400
agttttagca acaaacagac ggttagaata gaaagtacaa aactcagaat caattcaatt   2460
tacttaagaa agattaaagg tgaaaccgta tttgatatgt ctgagtga                2508
```

```
<210> SEQ ID NO 56
<211> LENGTH: 835
<212> TYPE: PRT
<213> ORGANISM: artificial
<220> FEATURE:
<223> OTHER INFORMATION: MA104-adapated RV3 VP3

<400> SEQUENCE: 56

Met Lys Val Leu Ala Leu Arg His Ser Val Ala Gln Val Tyr Ala Asp
1               5                   10                  15

Thr Gln Thr Tyr Leu His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Ser Leu Lys Thr Leu Lys Ile Leu Asn Glu Ser Gly Ile Ala Ala Val
    50                  55                  60

Glu Val Gln Ser Pro Asp Glu Leu Phe Ala Leu Ile Arg Cys Asn Phe
65                  70                  75                  80

Thr Tyr Asp Tyr Glu Asn Asn Ile Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asp Ile Ile Asp Tyr Leu Leu Pro Gly Trp Lys Leu Thr Tyr Val Gly
```

```
        115                 120                 125

Tyr Asn Gly Lys Asn Thr Arg Gly His Tyr Asp Phe Ser Phe Ile Cys
    130                 135                 140

Gln Asn Ala Ala Thr Asp Asp Asp Ile Ile Ile Glu Tyr Ile Tyr Ser
145                 150                 155                 160

Asn Glu Leu Asp Phe Gln Asn Phe Leu Leu Arg Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Pro Ser Ile Val Asn Ile His Lys Lys Val Ile Asn
        195                 200                 205

Val Gly Pro Arg Asn Glu Ser Met Phe Thr Phe Leu Asn Phe Pro Thr
    210                 215                 220

Ile Lys Gln Phe Ser Asn Gly Ala Tyr Ile Val Lys His Thr Ile Lys
225                 230                 235                 240

Leu Lys Gln Glu Lys Trp Leu Gly Lys Arg Val Ser Gln Phe Asp Ile
                245                 250                 255

Gly Gln Tyr Lys Asn Met Leu Asn Val Val Thr Thr Ile Tyr Tyr Tyr
            260                 265                 270

Tyr Asn Leu Tyr Tyr Ser Lys Pro Ile Ile Tyr Met Leu Gly Ser Ala
        275                 280                 285

Pro Ser Tyr Trp Ile Tyr Asp Ile Lys Gln Tyr Ser Asp Phe Thr Phe
    290                 295                 300

Glu Thr Trp Asp Pro Leu Asp Thr Pro Tyr Ser Thr Thr His His Lys
305                 310                 315                 320

Glu Leu Phe Phe Asp Lys Asp Val Asn Lys Leu Lys Asp Asn Ser Val
                325                 330                 335

Leu Tyr Ile Asp Ile Arg Thr Asp Arg Gly Asn Met Asp Trp Lys Glu
            340                 345                 350

Trp Arg Lys Ile Val Glu Gln Gln Thr Val Ser Asn Leu Asn Ile Ala
        355                 360                 365

Tyr Lys Tyr Leu Ser Thr Gly Lys Ala Lys Val Cys Cys Val Lys Leu
    370                 375                 380

Thr Ala Met Asp Leu Glu Leu Pro Ile Thr Ala Lys Leu Leu His His
385                 390                 395                 400

Pro Thr Thr Glu Val Arg Ser Glu Phe Tyr Ala Ile Leu Asp Val Trp
                405                 410                 415

Asp Ile Ile Thr Ile Lys Arg Phe Ile Pro Lys Gly Val Phe Tyr Ala
            420                 425                 430

Phe Ile Asn Asn Val Thr Thr Glu Asn Val Phe Ile Gln Pro Pro Phe
        435                 440                 445

Lys Leu Lys Thr Ser Pro Thr Asp Tyr Ile Val Ala Leu Tyr Ala Leu
    450                 455                 460

Ser Asn Asp Phe Asn Ser Arg Gln Asp Val Ile Asn Leu Ile Asn Lys
465                 470                 475                 480

Gln Lys Gln Ser Leu Ile Thr Val Arg Ile Asn Asn Thr Phe Lys Asp
                485                 490                 495

Glu Pro Lys Val Asn Phe Lys Asn Ile Tyr Asp Trp Thr Phe Leu Pro
            500                 505                 510

Thr Asp Phe Glu Leu Lys Asp Ser Ile Ile Thr Ser Tyr Asp Gly Cys
        515                 520                 525

Leu Gly Ile Phe Gly Leu Ser Ile Ser Leu Ser Ser Lys Pro Thr Gly
    530                 535                 540
```

```
Asn Asn His Leu Phe Ile Ile Asn Gly Thr Asp Lys Tyr Asp Lys Leu
545                 550                 555                 560

Asp Gln Tyr Ala Asn His Met Gly Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ala Phe Asp Leu Lys Arg Trp Ile Tyr Leu His Ser Ile Gly Lys Val
625                 630                 635                 640

Ala Val Glu Gly Gly Arg Tyr Tyr Glu His Ala Pro Ile Glu Leu Ile
                645                 650                 655

Tyr Ala Cys Arg Ser Ala Lys Glu Phe Ala Ile Leu Gln Asp Asp Leu
            660                 665                 670

Thr Val Leu Arg Tyr Ala Asn Glu Ile Glu Gly Tyr Ile Ser Lys Val
        675                 680                 685

Tyr Ser Ile Thr Tyr Ala Asp Asp Pro Asn Tyr Phe Ile Gly Ile Lys
    690                 695                 700

Phe Asn Ser Ile Pro Tyr Glu Tyr Asp Val Lys Ile Pro His Leu Thr
705                 710                 715                 720

Leu Gly Val Leu Phe Ile Ser Asp Asn Met Ile His Asp Val Ile Thr
                725                 730                 735

Val Leu Lys Lys Met Lys Thr Glu Leu Phe Lys Met Glu Ile Ser Thr
            740                 745                 750

Ser Tyr Thr Tyr Met Leu Ser Asp Asn Thr Tyr Val Ala Asn Ala Ser
        755                 760                 765

Gly Val Leu Ser Thr Tyr Phe Lys Leu Tyr Asn Met Phe Tyr Arg Asn
    770                 775                 780

Tyr Ile Thr Phe Gly Gln Ser Arg Met Phe Ile Pro His Ile Thr Leu
785                 790                 795                 800

Ser Phe Ser Asn Lys Gln Thr Val Arg Ile Glu Ser Thr Lys Leu Arg
                805                 810                 815

Ile Asn Ser Ile Tyr Leu Arg Lys Ile Lys Gly Glu Thr Val Phe Asp
            820                 825                 830

Met Ser Glu
        835
```

<210> SEQ ID NO 57
<211> LENGTH: 2591
<212> TYPE: DNA
<213> ORGANISM: artificial
<220> FEATURE:
<223> OTHER INFORMATION: Vero-adapated RV3 VP3

<400> SEQUENCE: 57

```
ggctattaaa gcagtaccag tagtgtgttt tacctctgat ggtgtaagca tgaaagtatt      60

agctttaaga cacagtgtgg ctcaggtgta tgcagatact caaacctatt tgcatgatga     120

ttcaaaagat gagtatgaaa atgcatttct catttctaat ctaactacac ataatatatt     180

atacctgaat tacagcctta aaacattaaa aatattaaat gaatcaggta tagcagcagt     240

tgaagtacag tctccagatg aattatttgc gttaataagg tgtaatttta cgtacgatta     300

tgagaataac atagtttatt tacatgatta ttcatattat accaacaatg aaataagaac     360
```

```
agatcaacat tggataacta aaactgatat aattgactat ctattacctg gatggaaatt    420
aacatatgta ggctataatg gaaagaacac acgaggtcac tatgattttt catttatatg    480
tcaaaatgca gctacagatg atgatataat aattgaatat atatactcca atgagttaga    540
ctttcaaaac tttctgttaa gaaaaattaa agagagaatg accacatctc ttccaattgc    600
tagattatca aatcgtgtgt ttagagataa attatttcca tctattgtaa acatacataa    660
aaaagtgata aacgttgggc caaggaatga atctatgttc acattcttaa attttccaac    720
tattaagcaa ttttcaaacg gtgcgtatat tgtgaagcat actattaaat tgaagcagga    780
gaaatggttg ggtaaaagag tatcacaatt tgacatcgga caatataaaa acatgttaaa    840
tgtggttact actatttact attactataa tttatactat tcgaaaccta taatatacat    900
gcttggttca gctccatctt attggattta tgatattaaa cagtattctg attttacatt    960
tgaaacatgg gatccattag atactccata ttctacaaca catcataaag aattattttt   1020
tgataaggat gtcaataagc ttaaagataa ttcagtttta tatatagaca taagaactga   1080
tagaggtaat atggattgga aagagtggag aaaaatagta gaacaacaaa ctgttagcaa   1140
tctaaatatt gcgtataaat atctatcaac aggaaaagca aaggtgtgtt gtgttaaatt   1200
aactgctatg gacctagaat taccaataac agcaaaatta cttcatcatc caactactga   1260
agttagatca gaattttatg caatattgga tgtatgggat attattacca ttaaaagatt   1320
tataccaaaa ggtgtatttt atgcttttat aaataatgta accacggaga atgtgtttat   1380
acaacctcct ttcaaattaa aaacgtcacc tactgattac atagtggcat tgtatgcttt   1440
atccaatgac ttcaactcga ggcaagatgt tattaatttg attaataaac aaaaacaatc   1500
actcattact gttcgtataa ataatacttt taaagacgaa ccaaaagtaa attttaaaaa   1560
tatttatgat tggacgtttc tgccaacaga ttttgaactt aaagattcga taattacatc   1620
atatgatggt tgtttaggca tattcggatt atcgatatct ttatcgtcta aacccactgg   1680
aaataatcat ttatttataa taaatggaac tgacaaatat gataaactag accaatatgc   1740
aaaccatatg ggtatttcta gaagatcgca tcaaattaga ttctcagagt ctgcgacatc   1800
atattcggga tacattttta gagatctttc aaataataat ttcaatctaa taggtactaa   1860
tgtggagaat tcagtttcag gacatgtcta taatgcatta atttactata gatataatta   1920
tgcgtttgat cttaaaagat ggatttatct acattcaatt gggaaagtcg ctgtaaaggg   1980
tggaagatat tatgaacatg caccaatcga actgatatat gcatgccgat cagctaaaga   2040
atttgctata ttacaagatg acttaacggt attgagatac gctaatgaaa ttgaagggta   2100
tataagcaaa gtgtacagta taacctatgc tgacgatccc aattacttta taggaattaa   2160
atttaatagt ataccttatg aatacgatgt taaaattcca catttgacgc taggagtatt   2220
atttatatct gataatatga tacatgatgt aatcacagtg ttgaagaaaa tgaagacaga   2280
gctatttaaa atggaaatta gtactagtta tacttatatg ctatctgata atacgtatgt   2340
agcaaatgct agtggtgtgt tatcaactta ttttaaatta tataatatgt tctatagaaa   2400
tcatatcacg tttggacaat cacgaatgtt tatcccacac attacgctta gttttagcaa   2460
caaacagacg gttagaatag aaagtacaaa actcagaatc aattcaattt acttaagaaa   2520
gattaaaggt gaaaccgtat ttgatatgtc tgagtgagct agaaacttaa cacactagtc   2580
atgatgtgac c                                                        2591
```

<210> SEQ ID NO 58

<211> LENGTH: 835
<212> TYPE: PRT
<213> ORGANISM: artificial
<220> FEATURE:
<223> OTHER INFORMATION: Vero-adapated RV3 VP3

<400> SEQUENCE: 58

```
Met Lys Val Leu Ala Leu Arg His Ser Val Ala Gln Val Tyr Ala Asp
1               5                   10                  15

Thr Gln Thr Tyr Leu His Asp Asp Ser Lys Asp Glu Tyr Glu Asn Ala
            20                  25                  30

Phe Leu Ile Ser Asn Leu Thr Thr His Asn Ile Leu Tyr Leu Asn Tyr
        35                  40                  45

Ser Leu Lys Thr Leu Lys Ile Leu Asn Glu Ser Gly Ile Ala Ala Val
    50                  55                  60

Glu Val Gln Ser Pro Asp Glu Leu Phe Ala Leu Ile Arg Cys Asn Phe
65                  70                  75                  80

Thr Tyr Asp Tyr Glu Asn Asn Ile Val Tyr Leu His Asp Tyr Ser Tyr
                85                  90                  95

Tyr Thr Asn Asn Glu Ile Arg Thr Asp Gln His Trp Ile Thr Lys Thr
            100                 105                 110

Asp Ile Ile Asp Tyr Leu Leu Pro Gly Trp Lys Leu Thr Tyr Val Gly
        115                 120                 125

Tyr Asn Gly Lys Asn Thr Arg Gly His Tyr Asp Phe Ser Phe Ile Cys
    130                 135                 140

Gln Asn Ala Ala Thr Asp Asp Asp Ile Ile Ile Glu Tyr Ile Tyr Ser
145                 150                 155                 160

Asn Glu Leu Asp Phe Gln Asn Phe Leu Leu Arg Lys Ile Lys Glu Arg
                165                 170                 175

Met Thr Thr Ser Leu Pro Ile Ala Arg Leu Ser Asn Arg Val Phe Arg
            180                 185                 190

Asp Lys Leu Phe Pro Ser Ile Val Asn Ile His Lys Lys Val Ile Asn
        195                 200                 205

Val Gly Pro Arg Asn Glu Ser Met Phe Thr Phe Leu Asn Phe Pro Thr
    210                 215                 220

Ile Lys Gln Phe Ser Asn Gly Ala Tyr Ile Val Lys His Thr Ile Lys
225                 230                 235                 240

Leu Lys Gln Glu Lys Trp Leu Gly Lys Arg Val Ser Gln Phe Asp Ile
                245                 250                 255

Gly Gln Tyr Lys Asn Met Leu Asn Val Val Thr Thr Ile Tyr Tyr Tyr
            260                 265                 270

Tyr Asn Leu Tyr Tyr Ser Lys Pro Ile Ile Tyr Met Leu Gly Ser Ala
        275                 280                 285

Pro Ser Tyr Trp Ile Tyr Asp Ile Lys Gln Tyr Ser Asp Phe Thr Phe
    290                 295                 300

Glu Thr Trp Asp Pro Leu Asp Thr Pro Tyr Ser Thr Thr His His Lys
305                 310                 315                 320

Glu Leu Phe Phe Asp Lys Asp Val Asn Lys Leu Lys Asp Asn Ser Val
                325                 330                 335

Leu Tyr Ile Asp Ile Arg Thr Asp Arg Gly Asn Met Asp Trp Lys Glu
            340                 345                 350

Trp Arg Lys Ile Val Glu Gln Gln Thr Val Ser Asn Leu Asn Ile Ala
        355                 360                 365

Tyr Lys Tyr Leu Ser Thr Gly Lys Ala Lys Val Cys Cys Val Lys Leu
    370                 375                 380
```

```
Thr Ala Met Asp Leu Glu Leu Pro Ile Thr Ala Lys Leu Leu His His
385                 390                 395                 400

Pro Thr Thr Glu Val Arg Ser Glu Phe Tyr Ala Ile Leu Asp Val Trp
                405                 410                 415

Asp Ile Ile Thr Ile Lys Arg Phe Ile Pro Lys Gly Val Phe Tyr Ala
            420                 425                 430

Phe Ile Asn Asn Val Thr Thr Glu Asn Val Phe Ile Gln Pro Pro Phe
        435                 440                 445

Lys Leu Lys Thr Ser Pro Thr Asp Tyr Ile Val Ala Leu Tyr Ala Leu
    450                 455                 460

Ser Asn Asp Phe Asn Ser Arg Gln Asp Val Ile Asn Leu Ile Asn Lys
465                 470                 475                 480

Gln Lys Gln Ser Leu Ile Thr Val Arg Ile Asn Asn Thr Phe Lys Asp
                485                 490                 495

Glu Pro Lys Val Asn Phe Lys Asn Ile Tyr Asp Trp Thr Phe Leu Pro
            500                 505                 510

Thr Asp Phe Glu Leu Lys Asp Ser Ile Ile Thr Ser Tyr Asp Gly Cys
        515                 520                 525

Leu Gly Ile Phe Gly Leu Ser Ile Ser Leu Ser Ser Lys Pro Thr Gly
    530                 535                 540

Asn Asn His Leu Phe Ile Ile Asn Gly Thr Asp Lys Tyr Asp Lys Leu
545                 550                 555                 560

Asp Gln Tyr Ala Asn His Met Gly Ile Ser Arg Arg Ser His Gln Ile
                565                 570                 575

Arg Phe Ser Glu Ser Ala Thr Ser Tyr Ser Gly Tyr Ile Phe Arg Asp
            580                 585                 590

Leu Ser Asn Asn Asn Phe Asn Leu Ile Gly Thr Asn Val Glu Asn Ser
        595                 600                 605

Val Ser Gly His Val Tyr Asn Ala Leu Ile Tyr Tyr Arg Tyr Asn Tyr
    610                 615                 620

Ala Phe Asp Leu Lys Arg Trp Ile Tyr Leu His Ser Ile Gly Lys Val
625                 630                 635                 640

Ala Val Lys Gly Gly Arg Tyr Tyr Glu His Ala Pro Ile Glu Leu Ile
                645                 650                 655

Tyr Ala Cys Arg Ser Ala Lys Glu Phe Ala Ile Leu Gln Asp Asp Leu
            660                 665                 670

Thr Val Leu Arg Tyr Ala Asn Glu Ile Glu Gly Tyr Ile Ser Lys Val
        675                 680                 685

Tyr Ser Ile Thr Tyr Ala Asp Asp Pro Asn Tyr Phe Ile Gly Ile Lys
    690                 695                 700

Phe Asn Ser Ile Pro Tyr Glu Tyr Asp Val Lys Ile Pro His Leu Thr
705                 710                 715                 720

Leu Gly Val Leu Phe Ile Ser Asp Asn Met Ile His Asp Val Ile Thr
                725                 730                 735

Val Leu Lys Lys Met Lys Thr Glu Leu Phe Lys Met Glu Ile Ser Thr
            740                 745                 750

Ser Tyr Thr Tyr Met Leu Ser Asp Asn Thr Tyr Val Ala Asn Ala Ser
        755                 760                 765

Gly Val Leu Ser Thr Tyr Phe Lys Leu Tyr Asn Met Phe Tyr Arg Asn
    770                 775                 780

His Ile Thr Phe Gly Gln Ser Arg Met Phe Ile Pro His Ile Thr Leu
785                 790                 795                 800
```

```
Ser Phe Ser Asn Lys Gln Thr Val Arg Ile Glu Ser Thr Lys Leu Arg
                805                 810                 815

Ile Asn Ser Ile Tyr Leu Arg Lys Ile Lys Gly Glu Thr Val Phe Asp
            820                 825                 830

Met Ser Glu
        835


<210> SEQ ID NO 59
<211> LENGTH: 2328
<212> TYPE: DNA
<213> ORGANISM: artificial
<220> FEATURE:
<223> OTHER INFORMATION: MA104-adapted RV3 VP4

<400> SEQUENCE: 59

atggcttcac tcatttatag acagctactc actaattcat acacagttga attatcagat     60

gagattaata cgattggatc agaaaaaagt caaaatgtaa cgattaatcc cggaccgttt    120

gctcaaccaa attatgcacg agtaacttgg agtcatgggg aagtgaatga ttcgacaaca    180

atagagccag tacttgatgg cccttatcaa tcaacaagtt ttaagccacc aagcgattac    240

tggatattat tgaatccaac taatcaacaa gttgtattag agggtaccaa taaaactgat    300

atttgggttg ccttattact tgttgaacca aacgtaacca atcaaagtag acaatacaca    360

ttatttggag aaacgaaaca aattactgta gaaaataaca caaacaaatg gaaattcttc    420

gaaatgttca gaagcagtgt tagtgccgaa tttcaacata agcgcacttt aacatcagac    480

actaaattag ctgggttttt aaaacattat aacagtgttt ggactttcca cggtgaaacg    540

ccacatgcta caactgatta ctcatcaact tcaaatttat ctgaagtaga aactacaata    600

catgttgagt tttatataat accaagatcg caggaatcta agtgtgttga atatataaat    660

actggattgc caccaatgca gaatacaagg aatatagttc cagttgcact atcatctaga    720

gcagtgactt atcaacgtgc tcaggttaat gaagatatca tcatatcaaa gacatcgttg    780

tggaaggaaa tgcaatataa cagagacatc gtaataaggt ttaaatttaa taatagtata    840

gtaaaacttg gtgggctagg ttataaatgg tcagaaattt cgtttaaagc tgctaattat    900

cagtacaatt acttgcgaga tggagaacaa gttacggcac atactacttg ttcagtcaat    960

ggtgtgaata acttcagtta taatggagga tcactgccaa ctgattttag tgtatcaaga   1020

tatgaagtga ttaaggagaa ttcttatgtc tatgttgatt attgggatga ttcacaagca   1080

tttaggaaca tggtatacgt caggtcattg gcagcaaatt taaattcagt aaagtgtagt   1140

ggaggaaatt atgattttca aataccagtt ggtgcatggc cagtgatgag tggaggtgcg   1200

gtatctttgc attttgcggg agtcacctta tccactcaat ttactgactt tgtatcactt   1260

aattcgttaa gatttagatt cagtttgacc gttgaagatc cacctttttc aatttcacgc   1320

acacgtgtgt caggattata cgggctacca gcatttaatc cgaatagcgg acatgaatat   1380

tatgaaatag ctggggggatt ttctcttatt tcattagtac cgtctaatga cgattatcaa   1440

actccaatca tgaattcagt tacagtgcga caagatcttg aacgtcaact aggtgattta   1500

agggaggaat tcaattctct atcacaagaa atagcgatga cgcaattgat agatttagca   1560

ttattaccgt tagatatgtt ttctatgttc tcaggtatta aaagcacaat tgacgcagct   1620

aaatcaatgg ccacaaaggt gatgaaaaag tttaagagat cgggattagc tacatcaatc   1680

tctgaattaa ctggatcatt atcaaacgct gcttcatcag tttccagaag ttcatctatt   1740

agatctaaca tatcatccat ttcagtgtgg acggatgttt ccgaacagat agcgggttcg   1800
```

```
tcagactctg tcaggaatat ttccacgcaa acgtcagcta ttagtagaag attgcgacta   1860

cgcgaaatta ctacacaaac tgaaggtatg aattttgatg atatttcagc ggcagttctt   1920

aaaactaaga tagataaatc aactcatata agcccagata cattaccaga cataataact   1980

gagtcatctg aaaaattcat accaaaacga gcttatagag ttctaaaaga tgatgaagtg   2040

atggaagctg acgtggatgg gaagttcttt gcatataagg ttgacacttt tgaagaagtg   2100

ccatttgacg tagataaatt tgtcgatttg gtaactgatt ctcctgtaat ttcagctata   2160

atcgatttta agacgttgaa gaatttaaac gacaattatg gtataacgcg atctcaagcg   2220

ttagacttaa tcagatctga tcccagagtt ttacgcgatt ttatcaatca gaataatcca   2280

attattaaaa atagaattga acagctaata ctgcaatgta gactgtga               2328
```

```
<210> SEQ ID NO 60
<211> LENGTH: 775
<212> TYPE: PRT
<213> ORGANISM: artificial
<220> FEATURE:
<223> OTHER INFORMATION: MA104-adapated RV3 VP4

<400> SEQUENCE: 60

Met Ala Ser Leu Ile Tyr Arg Gln Leu Leu Thr Asn Ser Tyr Thr Val
1               5                   10                  15

Glu Leu Ser Asp Glu Ile Asn Thr Ile Gly Ser Glu Lys Ser Gln Asn
            20                  25                  30

Val Thr Ile Asn Pro Gly Pro Phe Ala Gln Pro Asn Tyr Ala Arg Val
        35                  40                  45

Thr Trp Ser His Gly Glu Val Asn Asp Ser Thr Thr Ile Glu Pro Val
    50                  55                  60

Leu Asp Gly Pro Tyr Gln Ser Thr Ser Phe Lys Pro Pro Ser Asp Tyr
65                  70                  75                  80

Trp Ile Leu Leu Asn Pro Thr Asn Gln Gln Val Val Leu Glu Gly Thr
                85                  90                  95

Asn Lys Thr Asp Ile Trp Val Ala Leu Leu Leu Val Glu Pro Asn Val
            100                 105                 110

Thr Asn Gln Ser Arg Gln Tyr Thr Leu Phe Gly Glu Thr Lys Gln Ile
        115                 120                 125

Thr Val Glu Asn Asn Thr Asn Lys Trp Lys Phe Phe Glu Met Phe Arg
    130                 135                 140

Ser Ser Val Ser Ala Glu Phe Gln His Lys Arg Thr Leu Thr Ser Asp
145                 150                 155                 160

Thr Lys Leu Ala Gly Phe Leu Lys His Tyr Asn Ser Val Trp Thr Phe
                165                 170                 175

His Gly Glu Thr Pro His Ala Thr Thr Asp Tyr Ser Ser Thr Ser Asn
            180                 185                 190

Leu Ser Glu Val Glu Thr Thr Ile His Val Glu Phe Tyr Ile Ile Pro
        195                 200                 205

Arg Ser Gln Glu Ser Lys Cys Val Glu Tyr Ile Asn Thr Gly Leu Pro
    210                 215                 220

Pro Met Gln Asn Thr Arg Asn Ile Val Pro Val Ala Leu Ser Ser Arg
225                 230                 235                 240

Ala Val Thr Tyr Gln Arg Ala Gln Val Asn Glu Asp Ile Ile Ile Ser
                245                 250                 255

Lys Thr Ser Leu Trp Lys Glu Met Gln Tyr Asn Arg Asp Ile Val Ile
            260                 265                 270
```

```
Arg Phe Lys Phe Asn Asn Ser Ile Val Lys Leu Gly Gly Leu Gly Tyr
        275                 280                 285

Lys Trp Ser Glu Ile Ser Phe Lys Ala Ala Asn Tyr Gln Tyr Asn Tyr
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Gln Ala Phe Arg Asn Met Val Tyr Val Arg
        355                 360                 365

Ser Leu Ala Ala Asn Leu Asn Ser Val Lys Cys Ser Gly Gly Asn Tyr
    370                 375                 380

Asp Phe Gln Ile Pro Val Gly Ala Trp Pro Val Met Ser Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Glu
            420                 425                 430

Asp Pro Pro Phe Ser Ile Ser Arg Thr Arg Val Ser Gly Leu Tyr Gly
        435                 440                 445

Leu Pro Ala Phe Asn Pro Asn Ser Gly His Glu Tyr Tyr Glu Ile Ala
    450                 455                 460

Gly Gly Phe Ser Leu Ile Ser Leu Val Pro Ser Asn Asp Asp Tyr Gln
465                 470                 475                 480

Thr Pro Ile Met Asn Ser Val Thr Val Arg Gln Asp Leu Glu Arg Gln
                485                 490                 495

Leu Gly Asp Leu Arg Glu Glu Phe Asn Ser Leu Ser Gln Glu Ile Ala
            500                 505                 510

Met Thr Gln Leu Ile Asp Leu Ala Leu Leu Pro Leu Asp Met Phe Ser
        515                 520                 525

Met Phe Ser Gly Ile Lys Ser Thr Ile Asp Ala Ala Lys Ser Met Ala
    530                 535                 540

Thr Lys Val Met Lys Lys Phe Lys Arg Ser Gly Leu Ala Thr Ser Ile
545                 550                 555                 560

Ser Glu Leu Thr Gly Ser Leu Ser Asn Ala Ala Ser Ser Val Ser Arg
                565                 570                 575

Ser Ser Ser Ile Arg Ser Asn Ile Ser Ser Ile Ser Val Trp Thr Asp
            580                 585                 590

Val Ser Glu Gln Ile Ala Gly Ser Ser Asp Ser Val Arg Asn Ile Ser
        595                 600                 605

Thr Gln Thr Ser Ala Ile Ser Arg Arg Leu Arg Leu Arg Glu Ile Thr
    610                 615                 620

Thr Gln Thr Glu Gly Met Asn Phe Asp Asp Ile Ser Ala Ala Val Leu
625                 630                 635                 640

Lys Thr Lys Ile Asp Lys Ser Thr His Ile Ser Pro Asp Thr Leu Pro
                645                 650                 655

Asp Ile Ile Thr Glu Ser Ser Glu Lys Phe Ile Pro Lys Arg Ala Tyr
            660                 665                 670

Arg Val Leu Lys Asp Asp Glu Val Met Glu Ala Asp Val Asp Gly Lys
        675                 680                 685

Phe Phe Ala Tyr Lys Val Asp Thr Phe Glu Glu Val Pro Phe Asp Val
```

```
    690                 695                 700

Asp Lys Phe Val Asp Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ser Gln Ala Leu Asp Leu Ile Arg Ser Asp Pro Arg Val Leu Arg
            740                 745                 750

Asp Phe Ile Asn Gln Asn Asn Pro Ile Ile Lys Asn Arg Ile Glu Gln
        755                 760                 765

Leu Ile Leu Gln Cys Arg Leu
    770                 775


<210> SEQ ID NO 61
<211> LENGTH: 2378
<212> TYPE: DNA
<213> ORGANISM: artificial
<220> FEATURE:
<223> OTHER INFORMATION: Vero-adapated RV3 VP4

<400> SEQUENCE: 61

ggctataaaa tggcttcact catttataga cagctactca ctaattcata cacagttgaa     60

ttatcagatg agattaatac gattggatca gaaaaaagtc aaaatgtaac gattaatccc    120

ggaccgtttg ctcaaacaaa ttatgcacga gtaacttgga gtcatgggga agtgaatgat    180

tcgacaacaa tagagccagt acttgatggc ccttatcaat caacaagttt taagccacca    240

agcgattact ggatattatt gaatccaact aatcaacaag ttgtattaga gggtaccaat    300

aaaactgata tttgggttgc cttattactt gttgaaccaa acgtaaccaa tcaaagtaga    360

caatacacgt tatttggaga aacgaaacaa attactgtag aaaataacac aaacaaatgg    420

aaattcttcg aaatgttcag aagcagtgtt agtgccgaat ttcaacataa gcgcacttta    480

acatcagaca ctaaattagc tgggtttttta aaacattata acagtgtttg gactttccac    540

ggtgaaacgc cacatgctac aactgattac tcatcaactt caaatttatc tgaagtagaa    600

actacaatac atgttgagtt ttatataata ccaagatcgc aggaatctaa gtgtgttgaa    660

tatataaata ctggattgcc accaatgcag aatacaagga atatagttcc agttgcacta    720

tcatctagag cagtgactta tcaacgtgct caggttaatg aagatatcat catatcaaag    780

acatcgttgt ggaaggaaat gcaatataac agagacatcg taataaggtt taaatttaat    840

aatagtatag taaaacttgg tggctaggt tataaatggt cagaaatttc gtttaaagct    900

gctaattatc agtacaatta cttgcgagat ggagaacaag ttacggcaca tactacttgt    960

tcagtcaatg gtgtgaataa cttcagttat aatggaggat cactgccaac tgattttagt   1020

gtatcaagat atgaagtgat taaggagaat tcttatgtct atgttgatta ttgggatgat   1080

tcacaagcat ttaggaacat ggtatacgtc aggtcattgg cagcaaattc aaattcagta   1140

aagtgtagtg gaggaaatta taattttcaa ctaccagttg gtgcatggcc agtgatgagt   1200

ggaggtgcgg tatctttgca ttttgcggga gtcaccttat ccactcaatt tactgacttt   1260

gtatcactta attcgttaag atttagattc agtttgaccg ttgaagatcc accttttca    1320

atttcacgca cacatgtgtc aggattatac gggctaccag catttaatcc gaatagcgga   1380

catgaatatt atgaaatagc tgggggattt tctcttattt cattagtacc gtctaatgac   1440

gattatcaaa ctccaatcat gaattcagtt acagtgcgac aagatcttga acgtcaacta   1500

ggtgatttaa gggaggaatt caattctcta tcacaagaaa tagcgatgac gcaattgata   1560
```

```
gatttagcat tattaccgtt agatatgttt tctatgttct caggtattaa aagcacaatt   1620

gacgcagcta aatcaatggc cacaaaggtg atgaaaaagt ttaagagatc gggattagct   1680

acatcaatct ctgaattaac tggatcatta tcaaacgctg cttcatcagt ttccagaagt   1740

tcatctatta gatctaacat atcatccatt tcagtgtgga cggatgtttc cgaacagata   1800

gcgggttcgt cagactctgt caggaatatt tccacgcaaa cgtcagctat tagtagaaga   1860

ttgcgactac gcgaaattac tacacaaact gaaggtatga attttgatga tatttcagcg   1920

gcagttctta aaactaagat agataaatca actcatataa gcccagatac attaccagac   1980

ataataactg agtcatctga aaaattcata ccaaaacgag cttatagagt tctaaaagat   2040

gatgaagtga tggaagctga cgtggatggg aagttctttg catataaggt tgacactttt   2100

gaagaagtgc catttgacgt agataaattt gtcgatttgg taactgattc tcctgtaatt   2160

tcagctataa tcgattttaa gacgttgaag aatttaaacg acaattatgg tataacgcga   2220

tctcaagcgt tagacttaat cagatctgat cccagagttt tacgcgattt tatcattcag   2280

aataatccaa ttattaaaaa tagaattgaa cagctaatac tgcaatgtag actgtgagag   2340

ctccatcgag gaatgtgacc ggtcatagct gtttcctg                           2378
```

```
<210> SEQ ID NO 62
<211> LENGTH: 775
<212> TYPE: PRT
<213> ORGANISM: artificial
<220> FEATURE:
<223> OTHER INFORMATION: Vero-adapted RV3 VP4

<400> SEQUENCE: 62

Met Ala Ser Leu Ile Tyr Arg Gln Leu Leu Thr Asn Ser Tyr Thr Val
1               5                   10                  15

Glu Leu Ser Asp Glu Ile Asn Thr Ile Gly Ser Glu Lys Ser Gln Asn
            20                  25                  30

Val Thr Ile Asn Pro Gly Pro Phe Ala Gln Thr Asn Tyr Ala Arg Val
        35                  40                  45

Thr Trp Ser His Gly Glu Val Asn Asp Ser Thr Thr Ile Glu Pro Val
    50                  55                  60

Leu Asp Gly Pro Tyr Gln Ser Thr Ser Phe Lys Pro Pro Ser Asp Tyr
65                  70                  75                  80

Trp Ile Leu Leu Asn Pro Thr Asn Gln Gln Val Val Leu Glu Gly Thr
                85                  90                  95

Asn Lys Thr Asp Ile Trp Val Ala Leu Leu Leu Val Glu Pro Asn Val
            100                 105                 110

Thr Asn Gln Ser Arg Gln Tyr Thr Leu Phe Gly Glu Thr Lys Gln Ile
        115                 120                 125

Thr Val Glu Asn Asn Thr Asn Lys Trp Lys Phe Phe Glu Met Phe Arg
    130                 135                 140

Ser Ser Val Ser Ala Glu Phe Gln His Lys Arg Thr Leu Thr Ser Asp
145                 150                 155                 160

Thr Lys Leu Ala Gly Phe Leu Lys His Tyr Asn Ser Val Trp Thr Phe
                165                 170                 175

His Gly Glu Thr Pro His Ala Thr Thr Asp Tyr Ser Ser Thr Ser Asn
            180                 185                 190

Leu Ser Glu Val Glu Thr Thr Ile His Val Glu Phe Tyr Ile Ile Pro
        195                 200                 205

Arg Ser Gln Glu Ser Lys Cys Val Glu Tyr Ile Asn Thr Gly Leu Pro
    210                 215                 220
```

```
Pro Met Gln Asn Thr Arg Asn Ile Val Pro Val Ala Leu Ser Ser Arg
225                 230                 235                 240

Ala Val Thr Tyr Gln Arg Ala Gln Val Asn Glu Asp Ile Ile Ile Ser
                245                 250                 255

Lys Thr Ser Leu Trp Lys Glu Met Gln Tyr Asn Arg Asp Ile Val Ile
            260                 265                 270

Arg Phe Lys Phe Asn Asn Ser Ile Val Lys Leu Gly Gly Leu Gly Tyr
        275                 280                 285

Lys Trp Ser Glu Ile Ser Phe Lys Ala Ala Asn Tyr Gln Tyr Asn Tyr
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Gln Ala Phe Arg Asn Met Val Tyr Val Arg
        355                 360                 365

Ser Leu Ala Ala Asn Ser Asn Ser Val Lys Cys Ser Gly Gly Asn Tyr
    370                 375                 380

Asn Phe Gln Leu Pro Val Gly Ala Trp Pro Val Met Ser Gly Gly Ala
385                 390                 395                 400

Val Ser Leu His Phe Ala Gly Val Thr Leu Ser Thr Gln Phe Thr Asp
                405                 410                 415

Phe Val Ser Leu Asn Ser Leu Arg Phe Arg Phe Ser Leu Thr Val Glu
            420                 425                 430

Asp Pro Pro Phe Ser Ile Ser Arg Thr His Val Ser Gly Leu Tyr Gly
        435                 440                 445

Leu Pro Ala Phe Asn Pro Asn Ser Gly His Glu Tyr Tyr Glu Ile Ala
    450                 455                 460

Gly Gly Phe Ser Leu Ile Ser Leu Val Pro Ser Asn Asp Asp Tyr Gln
465                 470                 475                 480

Thr Pro Ile Met Asn Ser Val Thr Val Arg Gln Asp Leu Glu Arg Gln
                485                 490                 495

Leu Gly Asp Leu Arg Glu Glu Phe Asn Ser Leu Ser Gln Glu Ile Ala
            500                 505                 510

Met Thr Gln Leu Ile Asp Leu Ala Leu Leu Pro Leu Asp Met Phe Ser
        515                 520                 525

Met Phe Ser Gly Ile Lys Ser Thr Ile Asp Ala Ala Lys Ser Met Ala
    530                 535                 540

Thr Lys Val Met Lys Lys Phe Lys Arg Ser Gly Leu Ala Thr Ser Ile
545                 550                 555                 560

Ser Glu Leu Thr Gly Ser Leu Ser Asn Ala Ala Ser Ser Val Ser Arg
                565                 570                 575

Ser Ser Ser Ile Arg Ser Asn Ile Ser Ser Ile Ser Val Trp Thr Asp
            580                 585                 590

Val Ser Glu Gln Ile Ala Gly Ser Ser Asp Ser Val Arg Asn Ile Ser
        595                 600                 605

Thr Gln Thr Ser Ala Ile Ser Arg Arg Leu Arg Leu Arg Glu Ile Thr
    610                 615                 620

Thr Gln Thr Glu Gly Met Asn Phe Asp Asp Ile Ser Ala Ala Val Leu
625                 630                 635                 640
```

```
Lys Thr Lys Ile Asp Lys Ser Thr His Ile Ser Pro Asp Thr Leu Pro
                645                 650                 655

Asp Ile Ile Thr Glu Ser Ser Glu Lys Phe Ile Pro Lys Arg Ala Tyr
            660                 665                 670

Arg Val Leu Lys Asp Asp Glu Val Met Glu Ala Asp Val Asp Gly Lys
        675                 680                 685

Phe Phe Ala Tyr Lys Val Asp Thr Phe Glu Glu Val Pro Phe Asp Val
    690                 695                 700

Asp Lys Phe Val Asp Leu Val Thr Asp Ser Pro Val Ile Ser Ala Ile
705                 710                 715                 720

Ile Asp Phe Lys Thr Leu Lys Asn Leu Asn Asp Asn Tyr Gly Ile Thr
                725                 730                 735

Arg Ser Gln Ala Leu Asp Leu Ile Arg Ser Asp Pro Arg Val Leu Arg
            740                 745                 750

Asp Phe Ile Ile Gln Asn Asn Pro Ile Ile Lys Asn Arg Ile Glu Gln
        755                 760                 765

Leu Ile Leu Gln Cys Arg Leu
    770                 775
```

<210> SEQ ID NO 63
<211> LENGTH: 981
<212> TYPE: DNA
<213> ORGANISM: artificial
<220> FEATURE:
<223> OTHER INFORMATION: MA104-adapated RV3 VP7

<400> SEQUENCE: 63

```
atgtatggta ttgaatatac cacagttttg acctttttga tatcaattat attgttgaat     60

tacgtactca aatcattaac tagaataatg gactttatta tctacagatt tcttttgatt    120

atagttatac tgtcaccact ccttaatgca caaaattatg gaataaatct tccgattact    180

ggatcaatgg acacaccata tacgaactca acgcgagagg aagtattcct aacttcgact    240

ttatgtttgt attacccaac cgaagcagca acagaaataa atgataatgc atggaaggat    300

acactttctc aactattttt aactaaagga tggccgacag gatctattta ttttaaagat    360

tatactgata ttgcctcgtt ttcagttgat ccacaactgt actgtgatta taatttggta    420

ttaatgaaat acgacgctac actacaactg gacatgtctg aactagcaga tttgttactt    480

aatgagtggt tatgtaatcc tatggatatt actttgtatt attatcaaca aactgatgag    540

gcaaataaat ggatttcaat gggatcatct tgtaccataa aggtatgtcc actaaatacg    600

caaacattag gaattgggtg tctaactact gatacaaaca cgttcgaaga agttgcaaca    660

gctgaaaaat tagtgattac tgacgttgta gatggggtca atcataaatt gaacgtgacg    720

acaaacactt gtacgattag aaattgtaaa aaattaggac caagggaaaa cgtagcagtt    780

atacaggttg gtggctcaga tgtacttgac ataacagctg atcctacgac agcgccacga    840

acagaaagaa tgatgcgagt gaattggaag aaatggtggc aagtatttta tacaatagtt    900

gactacgtga atcaaattgt gcaagcgatg tccaaaagat cgagatcgtt aaattctgct    960

gcattttact acagggtata g                                              981
```

<210> SEQ ID NO 64
<211> LENGTH: 326
<212> TYPE: PRT
<213> ORGANISM: artificial
<220> FEATURE:
<223> OTHER INFORMATION: MA104-adapated RV3 VP7

<400> SEQUENCE: 64

```
Met Tyr Gly Ile Glu Tyr Thr Thr Val Leu Thr Phe Leu Ile Ser Ile
1               5                   10                  15

Ile Leu Leu Asn Tyr Val Leu Lys Ser Leu Thr Arg Ile Met Asp Phe
            20                  25                  30

Ile Ile Tyr Arg Phe Leu Leu Ile Ile Val Ile Leu Ser Pro Leu Leu
        35                  40                  45

Asn Ala Gln Asn Tyr Gly Ile Asn Leu Pro Ile Thr Gly Ser Met Asp
    50                  55                  60

Thr Pro Tyr Thr Asn Ser Thr Arg Glu Glu Val Phe Leu Thr Ser Thr
65                  70                  75                  80

Leu Cys Leu Tyr Tyr Pro Thr Glu Ala Ala Thr Glu Ile Asn Asp Asn
                85                  90                  95

Ala Trp Lys Asp Thr Leu Ser Gln Leu Phe Leu Thr Lys Gly Trp Pro
            100                 105                 110

Thr Gly Ser Ile Tyr Phe Lys Asp Tyr Thr Asp Ile Ala Ser Phe Ser
        115                 120                 125

Val Asp Pro Gln Leu Tyr Cys Asp Tyr Asn Leu Val Leu Met Lys Tyr
    130                 135                 140

Asp Ala Thr Leu Gln Leu Asp Met Ser Glu Leu Ala Asp Leu Leu Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Met Gly Ser Ser Cys Thr
            180                 185                 190

Ile Lys Val Cys Pro Leu Asn Thr Gln Thr Leu Gly Ile Gly Cys Leu
        195                 200                 205

Thr Thr Asp Thr Asn Thr Phe Glu Glu Val Ala Thr Ala Glu Lys Leu
    210                 215                 220

Val Ile Thr Asp Val Val Asp Gly Val Asn His Lys Leu Asn Val Thr
225                 230                 235                 240

Thr Asn Thr Cys Thr Ile Arg Asn Cys Lys Lys Leu Gly Pro Arg Glu
                245                 250                 255

Asn Val Ala Val Ile Gln Val Gly Gly Ser Asp Val Leu Asp Ile Thr
            260                 265                 270

Ala Asp Pro Thr Thr Ala Pro Arg Thr Glu Arg Met Met Arg Val Asn
        275                 280                 285

Trp Lys Lys Trp Trp Gln Val Phe Tyr Thr Ile Val Asp Tyr Val Asn
    290                 295                 300

Gln Ile Val Gln Ala Met Ser Lys Arg Ser Arg Ser Leu Asn Ser Ala
305                 310                 315                 320

Ala Phe Tyr Tyr Arg Val
                325
```

<210> SEQ ID NO 65
<211> LENGTH: 1062
<212> TYPE: DNA
<213> ORGANISM: artificial
<220> FEATURE:
<223> OTHER INFORMATION: Vero-adapated RV3 VP7

<400> SEQUENCE: 65

```
ggctttaaaa gagagaattt ccgtctggct agcggttagc tccttttaat gtatggtatt      60

gaatatacca cagttttgac ctttttgata tcaattatat tgttgaatta cgtactcaaa     120
```

```
tcattaacta gaataatgga ctttattatc tacagatttc ttttgattat agttatactg    180

tcaccactcc ttaatgcaca aaattatgga ataaatcttc cgattactgg atcaatggac    240

acaccatata cgaactcaac gcgagaggaa gtattcctaa cttcgacttt atgtttgtat    300

tacccaaccg aagcagcaac agaaataaat gataatgcat ggaaggatac actttctcaa    360

ctatttttaa ctaaaggatg gccgacagga tctatttatt ttaaagatta tactgatatt    420

gcctcgtttt cagttgatcc acaactgtac tgtgattata atttggtatt aatgaaatac    480

gacgctacac tacaactgga catgtctgaa ctagcagatt tgttacttaa tgagtggtta    540

tgtaatccta tggatattac tttgtattat tatcaacaaa ctgatgaggc aaataaatgg    600

atttcaatgg gatcatcttg taccataaag gtatgtccac taaatacgca aacattagga    660

attgggtgtc taactactga tacaaacacg ttcgaagaag ttgcaacagc tgaaaaatta    720

gtgattactg acgttgtaga tggggtcaat cataaattga acgtgacgac aaacacttgt    780

acgattagaa attgtaaaaa attaggacca agggaaaacg tagcagttat acaggttggt    840

ggctcagatg tacttgacat aacagctgat cctacgacag cgccacgaac agaaagaatg    900

atgcgagtga attggaagaa atggtggcaa gtattttata caatagttga ctacgtgaat    960

caaattgtgc aagcgatgtc caaaagatcg agatcgttaa attctgctgc attttactac   1020

agggtatagg tatagcttag attagaattg tatgatgtga cc                      1062
```

```
<210> SEQ ID NO 66
<211> LENGTH: 326
<212> TYPE: PRT
<213> ORGANISM: artificial
<220> FEATURE:
<223> OTHER INFORMATION: Vero-adapated RV3 VP7

<400> SEQUENCE: 66

Met Tyr Gly Ile Glu Tyr Thr Thr Val Leu Thr Phe Leu Ile Ser Ile
1               5                   10                  15

Ile Leu Leu Asn Tyr Val Leu Lys Ser Leu Thr Arg Ile Met Asp Phe
            20                  25                  30

Ile Ile Tyr Arg Phe Leu Leu Ile Ile Val Ile Leu Ser Pro Leu Leu
        35                  40                  45

Asn Ala Gln Asn Tyr Gly Ile Asn Leu Pro Ile Thr Gly Ser Met Asp
    50                  55                  60

Thr Pro Tyr Thr Asn Ser Thr Arg Glu Glu Val Phe Leu Thr Ser Thr
65                  70                  75                  80

Leu Cys Leu Tyr Tyr Pro Thr Glu Ala Ala Thr Glu Ile Asn Asp Asn
                85                  90                  95

Ala Trp Lys Asp Thr Leu Ser Gln Leu Phe Leu Thr Lys Gly Trp Pro
            100                 105                 110

Thr Gly Ser Ile Tyr Phe Lys Asp Tyr Thr Asp Ile Ala Ser Phe Ser
        115                 120                 125

Val Asp Pro Gln Leu Tyr Cys Asp Tyr Asn Leu Val Leu Met Lys Tyr
    130                 135                 140

Asp Ala Thr Leu Gln Leu Asp Met Ser Glu Leu Ala Asp Leu Leu Leu
145                 150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Trp Ile Ser Met Gly Ser Ser Cys Thr
            180                 185                 190

Ile Lys Val Cys Pro Leu Asn Thr Gln Thr Leu Gly Ile Gly Cys Leu
```

-continued

```
        195                 200                 205

Thr Thr Asp Thr Asn Thr Phe Glu Glu Val Ala Thr Ala Glu Lys Leu
    210                 215                 220

Val Ile Thr Asp Val Val Asp Gly Val Asn His Lys Leu Asn Val Thr
225                 230                 235                 240

Thr Asn Thr Cys Thr Ile Arg Asn Cys Lys Lys Leu Gly Pro Arg Glu
                245                 250                 255

Asn Val Ala Val Ile Gln Val Gly Gly Ser Asp Val Leu Asp Ile Thr
            260                 265                 270

Ala Asp Pro Thr Thr Ala Pro Arg Thr Glu Arg Met Met Arg Val Asn
        275                 280                 285

Trp Lys Lys Trp Trp Gln Val Phe Tyr Thr Ile Val Asp Tyr Val Asn
    290                 295                 300

Gln Ile Val Gln Ala Met Ser Lys Arg Ser Arg Ser Leu Asn Ser Ala
305                 310                 315                 320

Ala Phe Tyr Tyr Arg Val
                325
```

MODIFIED HUMAN ROTAVIRUSES AND USES THEREFOR

FILING DATA

This application is associated with and claims priority from Australian Provisional Patent Application No. 2012903702, filed on 27 Aug. 2012, entitled "Modified human rotaviruses and uses therefor", the entire contents of which, are incorporated herein by reference.

REFERENCE TO A SEQUENCE LISTING

The Sequence Listing in file SubstituteSequenceListing_50653-502N01US.txt, created on Dec. 3, 2016, 155,147 bytes, machine format IBM-PC, MS-Windows operating system, is hereby incorporated by reference in its entirety for all purposes.

FIELD

The present disclosure relates generally to the field of viral vaccines. Particularly, the present disclosure provides a modified human rotavirus strain and a culturing method to produce high titer virus, a rotavirus vaccine, vaccination protocols and diagnostic and prognostic assays.

BACKGROUND

Reference to any prior art in this specification is not, and should not be taken as, an acknowledgment or any form of suggestion that this prior art forms part of the common general knowledge in any country.

Bibliographic details of the publications referred to by author in this specification are collected alphabetically at the end of the description.

Worldwide, rotaviruses (RVs) are a major cause of diarrhea-associated morbidity and mortality in infants and young children. RV infection is responsible for more than 500,000 deaths annually, mainly in developing countries. The World Health Organization (WHO) has stated that development of a safe and effective vaccine is a priority (Bern and Glass (1994) *Impact of diarrheal diseases worldwide In Kapikian AZ (ed) Viral Infections of the gastrointestinal tract,* $2^{nd}$ edition, New York Marcel Dekker, Inc.:1-26; Jiang et al. (2002) *Clin Infect Dis* 34:1351-1361).

In particular, RV cause acute gastroenteritis, a disease that requires hospitalization of infants and young children. Studies in the U.S., Australia, and Japan have demonstrated that between 34 and 63% of hospitalizations of children for acute diarrheal disease are associated with RV infection. The incidence of hospitalization for RV gastroenteritis in a health maintenance organization in the U.S. was estimated to be 222 per 100,000 in children from 13 to 24 months of age, and 362 per 100,000 in those less than one year. Infection with RV was associated with 63% of all hospitalizations for acute diarrhea in this pediatric population. A review of mortality data in the U.S. from 1973 to 1983 indicated that 500 deaths per year occur in children less than 4 years old due to diarrheal diseases, and that 20 to 80% of excess winter deaths due to diarrhea in the U.S. are associated with RV infections. RVs are also responsible for a substantial proportion of the mortality associated with diarrheal diseases in third world countries. An effective RV vaccine would, therefore, have a major impact on the health of children in both the developed and developing areas of the world.

RVs are non-enveloped icoshedral viruses whose capsid is formed by three concentric layers of viral protein (VP). The innermost layer is formed by 60 dimers of VP2 that surrounds the viral genome which is composed of 11 segments of double-stranded RNA and 12 copies of each of VP1 (the RV polymerase) and VP3 (the virus copping enzyme). The second layer of protein is formed by 280 trimers of VP6 which is located on top of VP2 to form double-layered particles (DLPs). Finally, the addition of 280 trimers of the glycoprotein, VP7, which constitute the outermost layer of the RV and 60 dimeric spikes of the VP4 protein to the DLPs, serve to form the triple-layered particles (TLPs) which represent the mature, infectious RV.

VP7 is an outer capsid protein. It is a glycoprotein and interacts with VP4 and VP6. Another group of proteins is the "non-structural proteins" (NSPs). NSP5, for example, has been proposed to have a structural role together with NSP2 in the assembly of viroplasms and for virus replication.

Sato et al. (1981) *Arch. Virol.* 69:155-160, described successful cultivation of human RVs from fecal specimens using roller cultures of MA104 cells (fetal kidney cells from Rhesus monkeys). However, MA104 cells are relatively uncharacterized, at least for use as vehicles for generating viruses for a vaccine. There is a need to develop a protocol for cultivating RV in a well characterized cell system for use in the development of an RV vaccine. There is also a need for the virus to be of sufficient titer to produce a protective immunological and response in subjects.

SUMMARY

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

A culture method is provided for rotavirus (RV) in Vero cells. Reference to "Vero cells" includes Vero cell-derived cell lines. The RVs are referred to as "Vero-adapted" RVs or "RV3-Vero" or "RV3BB". The method involves trypsinization of an RV inoculum and culturing the trypsinized RV in Vero cells. This trypsin methodology uses much higher concentrations of trypsin to activate the virus to enable RV3 to grow in Vero cells, than is used in other RV production. Reference to "trypsinization" means treating the RV to a trypsin from any source including one or more of porcine, ruminant animal (e.g. bovine) and recombinant trypsin. On adaption to growth in continuous cell lines, the RV agents undergo a genomic modification, which is conveniently identified as an deduced amino acid change in one or both of the structural and non-structural proteins including VP1, VP3, VP4, NSP4, NSP5/6 and/or a nucleotide change in VP1, VP3, VP4, NSP2, NSP4 and/or NSP5/6. Genetic modifications leading to amino acid changes in other RV proteins or nucleotide changes in the RV genome are also contemplated by the present disclosure. The Vero-adapted RVs are proposed to be useful in vaccine development. Diagnostic and prognostic assays are also proposed to monitor RV infection, vaccine integrity and/or the efficacy of therapeutic or prophylactic protocols.

Hence, a Vero cell-adapted ("Vero-adapted") RV (also referred to as an RV-Vero or Vero-RV or RV3BB or Vero-adapted RV3BB) is provided comprising a mutation in VP1, VP3, VP4, NSP4 and/or NSP5/6 and/or in a gene encoding VP1, VP3, VP4, NSP2, NSP4 and/or NSP5/6, compared to the corresponding proteins in MA104-adapted RV.

For convenience, nucleotide and amino acid comparisons are made with reference to the MA104-adapted RV3 sequences published by Rippinger et al. (2010) *Virology* 405(1):1201-1213.

A method of culturing RV in Vero cells is also contemplated comprising trypsinizing an inoculum or aliquot of RV using a higher concentration of trypsin in relation to other RV activation protocols. Then culturing the RV in the presence of Vero cells for a time and under conditions sufficient for a genetic modification to occur resulting in at least an amino acid change in one or both of VP1, VP3, VP4, NSP4 and/or NSP5/6 and/or in a gene encoding VP1, VP3, VP4, NSP2, NSP4 and/or NSP5/6 such as when compared to MA104-adapted RV. As indicated above, the trypsin may be from any source such as a porcine trypsin, a ruminant animal trypsin or a recombinant trypsin. A ruminant animal trypsin includes a trypsin from cattle (bovine), sheep (ovine), goat (caprine), giraffe, yak, camel (camelus), llama, antelope or macropod. In an embodiment, the trypsin is porcine, bovine, ovine, caprine, camelus or recombinant trypsin.

In an embodiment, there is an amino acid or nucleotide change in a codon in NSP4 selected from 53, 76, 85, 162 and 165, a codon in NSP5/6 selected from 46 and 112, a codon in VP1 selected from 886, a codon in VP3 selected from 643 and 785, and a codon in VP4 selected from 43, 374, 385, 388, 442 and 756 and/or a nucleotide in NSP2 selected from 433, a nucleotide in NSP4 selected from 197, 267, 294, 525 and 534, a nucleotide in NSP5/6 selected from 158, 165 and 355, a nucleotide in VP1 selected from 2692, a nucleotide in VP3 selected from 343, 1366, 1744, 1976 and 2402 and/or a nucleotide in VP4 selected from 136, 369, 1130, 1162, 1171, 1334 and 2276.

Another aspect is directed to a composition comprising Vero-adapted RV3BB and one or more pharmaceutically acceptable carriers, diluents and/or excipients. Such a composition is considered a live attenuated RV vaccine or a killed RV vaccine.

Another aspect is directed to the use of a Vero-RV such as Vero-RV3 or a component thereof in the manufacture of a medicament in the treatment of RV infection or re-infection in a subject.

Diagnostic agents such as antibodies to Vero-adapted RV are also provided.

A nucleotide "change" includes a nucleotide substitution, addition, deletion or insertion. The change may or may not result in a corresponding amino acid change in a protein encoded by the nucleotide sequence carrying the change. Such nucleotide or amino acid changes are also useful for diagnostic purposes to monitor inter alia virus infection, load, therapeutic efficacy and evolution or adaptation. A summary of the differences in amino acid sequence and nucleotide sequence between Vero-adapted RV3 and MA104-adapted RV3 is shown in Table 2 and Table 5.

TABLE 1

Summary of sequence identifiers

| SEQUENCE ID NO: | DESCRIPTION |
|---|---|
| 1 | Primer - JCVI_VP1_5'UTR |
| 2 | Primer - GEN-VP1R |
| 3 | Primer - GEN-VP2F |
| 4 | Primer - GEN-VP2R |
| 5 | Primer - GEN-VP3F |
| 6 | Primer - GEN-VP3R |
| 7 | Primer - JP_1_For_g4_RV3 |
| 8 | Primer - JCVI_VP4_3'UTR |
| 9 | Primer - GEN-VP6F |
| 10 | Primer - GEN-VP6R |
| 11 | Primer - Beg9 |
| 12 | Primer - End9 |
| 13 | Primer - JCVI_NSP1_5'UTR |
| 14 | Primer - JCVI_NSP1_3'UTR |
| 15 | Primer - GEN-NSP2F |
| 16 | Primer - GEN-NSP2R |
| 17 | Primer - GEN-NSP3F |
| 18 | Primer - GEN-NSP3R |
| 19 | Primer - 10.1 |
| 20 | Primer - 10.2 |
| 21 | Primer - GEN-NSP5F |
| 22 | Primer - GEN-NSP5R |
| 23 | Nucleotide sequence MA104-derived RV3 NSP1 gene |
| 24 | Amino acid sequence of MA104-adapted RV3 NSP1 protein |
| 25 | Nucleotide sequence RV3-Vero NSP1 gene |
| 26 | Amino acid sequence of RV3-Vero NSP1 protein |
| 27 | Nucleotide sequence MA104-derived RV3 NSP5/6 gene |
| 28 | Amino acid sequence of MA104-adapted RV3 NSP5 protein |
| 29 | Nucleotide sequence RV3-Vero NSP5/6 gene |
| 30 | Amino acid sequence of RV3-Vero NSP5 protein |
| 31 | Nucleotide sequence MA104-derived RV3 NSP2 gene |
| 32 | Amino acid sequence of MA104-adapted RV3 NSP2 protein |
| 33 | Nucleotide sequence RV3-Vero NSP2 gene |
| 34 | Amino acid sequence of the coding region of RV3-Vero NSP2 protein |
| 35 | Nucleotide sequence MA104-derived RV3 NSP4 gene |
| 36 | Amino acid sequence of RV3 NSP4 protein |
| 37 | Nucleotide sequence RV3-Vero NSP4 gene |
| 38 | Amino acid sequence of RV3-Vero NSP4 protein |
| 39 | Nucleotide sequence MA104-derived RV3 VP6 gene |
| 40 | Amino acid sequence of MA104-derived RV3 VP6 protein |
| 41 | Nucleotide sequence RV3-Vero VP6 gene |
| 42 | Amino acid sequence of RV3-Vero VP6 protein |
| 43 | Nucleotide sequence MA104-adapted RV3 NSP3 gene |
| 44 | Amino acid sequence of MA104-derived RV3 NSP3 protein |
| 45 | Nucleotide sequence RV3-Vero NSP3 gene |
| 46 | Amino acid sequence of RV3 Vero NSP3 protein |
| 47 | Nucleotide sequence of MA104-adapted RV3 VP1 |
| 48 | Amino acid sequence of MA104-adapted RV3 VP1 |
| 49 | Nucleotide sequence of Vero-adapted RV3 VP1 |
| 50 | Amino acid sequence Vero-adapted RV3 VP1 |
| 51 | Nucleotide Sequence of MA104-adapted RV3 VP2 gene |
| 52 | Amino acid sequence of MA104-adapted RV3 VP2 protein |
| 53 | Nucleotide sequence of Vero-adapted RV3 VP2 gene |
| 54 | Amino acid sequence of Vero-adapted RV3 VP2 protein |
| 55 | Nucleotide sequence of MA104-adapted RV3 VP3 gene |
| 56 | Amino acid sequence of MA104-adapted RV3 VP7 protein |
| 57 | Nucleotide sequence of Vero-adapted RV3 VP3 gene |
| 58 | Amino acid sequence of Vero-adapted RV3 VP3 protein |
| 59 | Nucleotide sequence of MA104-adapted RV3 VP4 gene |
| 60 | Amino acid sequence of MA104-adapted RV3 VP4 gene |
| 61 | Nucleotide sequence of Vero-adapted RV3 VP4 gene |
| 62 | Amino acid sequence of Vero-adapted RV3 VP4 protein |
| 63 | Nucleotide sequence of MA104-adapted RV3 VP7 gene |
| 64 | Amino acid sequence of MA104-adapted RV3 VP7 protein |
| 65 | Nucleotide sequence of Vero-adapted RV3 VP7 gene |
| 66 | Amino acid sequence of Vero-adapted RV3 VP7 protein |

TABLE 2

Summary of differences between MA104-adapted RV3 and Vero-adapted RV3[1]

| Gene or Protein | MA104-adapted RV3 | Vero-adapted RV3 |
|---|---|---|
| NSP1 gene | — | — |
| NSP1 protein | — | — |
| NSP2 gene | 387G | 433A |

TABLE 2-continued

Summary of differences between MA104-adapted RV3 and Vero-adapted RV3[1]

| Gene or Protein | MA104-adapted RV3 | Vero-adapted RV3 |
| --- | --- | --- |
| NSP2 protein | — | — |
| NSP3 gene | — | — |
| NSP3 protein | — | — |
| NSP4 gene | 157G | 197A |
| | 227T | 267C |
| | 254G | 294A |
| | 485T | 525G |
| | 494C | 534T |
| NSP4 protein | 53A | 53T |
| | 76I | 76T |
| | 85C | 85Y |
| | 162V | 162G |
| | 165P | 165L |
| NSP5/6 gene | 137G | 158A |
| | 144T | 165C |
| | 334T | 355A |
| NSP5/6 protein | 46G | 46E |
| | 112L | 112I |
| VP1 gene | 2656G | 2692T |
| VP1 protein | 886V | 886F |
| VP2 gene | — | — |
| VP2 protein | — | — |
| VP3 gene | 294T | 343C |
| | 1317A | 1366G |
| | 1695T | 1744C |
| | 1927G | 1976A |
| | 2353T | 2402C |
| VP3 protein | 643E | 643K |
| | 785Y | 785H |
| VP4 gene | 127C | 136A |
| | 360A | 369G |
| | 1121T | 1130C |
| | 1153G | 1162A |
| | 1162A | 1171C |
| | 1325G | 1334A |
| | 2267A | 2276T |
| VP4 protein | 43P | 43T |
| | 374L | 374S |
| | 385D | 385N |
| | 388I | 388L |
| | 442R | 442H |
| | 756N | 756I |
| VP6 gene | — | — |
| VP6 protein | — | — |
| VP7 gene | — | — |
| VP7 protein | — | — |

[1]The nucleotide number or amino acid residue number is based on the numbering adopted by Rippinger et al, 2010 supra.

BRIEF DESCRIPTION OF THE FIGURES

FIG. 1 is a representation of the nucleotide sequence of MA104-adapted RV3 NSP1 gene (SEQ ID NO: 23).

FIG. 2 is a representation of the deduced amino acid sequence of MA104-adapted RV3 NSP1 protein (SEQ ID NO: 24).

FIG. 3 is a representation of the nucleotide sequence of Vero-adapted RV3 NSP1 gene (SEQ ID NO: 25).

FIG. 4 is a representation of the deduced amino acid sequence of Vero-adapted NSP1 protein (SEQ ID NO: 26).

FIGS. 5A and 5B are a representation of a comparison of the nucleotide sequence of MA104-adapted RV3 (SEQ ID NO: 23) and Vero-adapted RV3 (SEQ ID NO: 25) NSP1 genes.

FIG. 6 is a representation of a comparison of the deduced amino acid sequence of MA104-adapted RV3 (SEQ ID NO: 24) and Vero-adapted RV3 (SEQ ID NO: 26) NSP1 protein.

FIG. 7 is a representation of the nucleotide sequence of MA104-adapted RV3 NSP2 gene (SEQ ID NO: 31).

FIG. 8 is a representation of the deduced amino acid sequence MA104-adapted RV3 NSP2 protein (SEQ ID NO: 32).

FIG. 9 is a representation of the nucleotide sequence of Vero-adapted RV3 NSP2 gene (SEQ ID NO: 33).

FIG. 10 is a representation of the deduced amino acid sequence of Vero-adapted RV3 NSP2 protein (SEQ ID NO: 34).

FIG. 11 is a representation of a comparison of the nucleotide sequence of MA104-adapted RV3 (SEQ ID NO: 31) and Vero-adapted RV3 (SEQ ID NO: 33) NSP2 genes.

FIG. 12 is a representation of a comparison of the deduced amino acid sequence of MA104-adapted RV3 (SEQ ID NO: 32) and Vero-adapted RV3 (SEQ ID NO: 34) NSP2 proteins.

FIG. 13 is a representation of the nucleotide sequence of MA104-adapted RV3 NSP3 gene (SEQ ID NO: 43).

FIG. 14 is a representation of the deduced amino acid sequence of MA104-adapted RV3 NSP3 protein (SEQ ID NO: 44).

FIG. 15 is a representation of the nucleotide sequence of Vero-adapted RV3 NSP3 gene (SEQ ID NO: 45).

FIG. 16 is a representation of the deduced amino acid sequence of Vero-adapted RV3 NSP3 protein (SEQ ID NO: 46).

FIG. 17 is a representation of a comparison of the nucleotide sequence of MA104-adapted RV3 (SEQ ID NO: 43) and Vero-adapted RV3 (SEQ ID NO: 45) NSP3 genes.

FIG. 18 is a representation of a comparison of the deduced amino acid sequence of MA104-adapted RV3 (SEQ ID NO: 44) and Vero-adapted RV3 (SEQ ID NO: 46) NSP2 proteins.

FIG. 19 is a representation of the nucleotide sequence of MA104-adapted RV3 NSP4 gene (SEQ ID NO: 35).

FIG. 20 is a representation of the deduced amino acid sequence of MA104-adapted RV3 NSP4 protein (SEQ ID NO: 36).

FIG. 21 is a representation of the nucleotide sequence of Vero-adapted RV3 NSP4 gene (SEQ ID NO: 37).

FIG. 22 is a representation of the deduced amino acid sequence of Vero-adapted RV3 NSP4 protein (SEQ ID NO: 38).

FIG. 23 is a representation of a comparison of the nucleotide sequence of MA104-adapted RV3 (SEQ ID NO: 35) and Vero-derived RV3 (SEQ ID NO: 37) NSP4 genes.

FIG. 24 is a representation of a comparison of the deduced amino acid sequence of MA104-adapted RV3 (SEQ ID NO: 36) and Vero-adapted RV3 (SEQ ID NO: 38) NSP4 proteins.

FIG. 25 is a representation of the nucleotide sequence of MA104-adapted RV3 NSP5/6 gene (SEQ ID NO: 27).

FIG. 26 is a representation of the deduced amino acid sequence MA104-adapted RV3 NSP5 protein (SEQ ID NO: 28).

FIG. 27 is a representation of the nucleotide sequence of Vero-adapted RV3 NSP5/6 gene (SEQ ID NO: 29).

FIG. 28 is a representation of the deduced amino acid sequence of Vero-adapted RV3 NSP5 protein (SEQ ID NO: 30).

FIG. 29 is a representation of a comparison of the nucleotide sequence of MA104-adapted RV3 (SEQ ID NO: 27) and Vero-adapted RV3 (SEQ ID NO: 29) NSP5/6 genes.

FIG. 30 is a representation of a comparison of the deduced amino acid sequence of MA104-adapted RV3 (SEQ ID NO: 28) and Vero-adapted RV3 (SEQ ID NO: 30) NSP5 proteins.

FIG. 31 is a representation of the nucleotide sequence of MA104-adapted RV3 VP1 gene (SEQ ID NO: 47).

FIG. 32 is a representation of the amino acid sequence of MA104-adapted RV3 VP1 probe (SEQ ID NO: 48).

FIG. 33 is a representation of the nucleotide sequence of Vero-adapted RV3 VP1 gene (SEQ ID NO: 49).

FIG. 34 is a representation of the amino acid sequence of Vero-adapted RV3 VP1 protein (SEQ ID NO: 50).

FIGS. 35A-35D are a representation of a comparison of MA104-adapted RV3 (SEQ ID NO: 47) and Vero-adapted RV3 (SEQ ID NO: 49) VP1 genes.

FIG. 36 is a representation of a comparison of MA104-adapted RV3 (SEQ ID NO: 48) and Vero-adapted RV3 (SEQ ID NO: 50) VP1 proteins.

FIG. 37 is a representation of the nucleotide sequence of MA104-adapted RV3 VP2 gene (SEQ ID NO: 51).

FIG. 38 is a representation of the amino acid sequence of MA104-adapted RV3 VP2 protein (SEQ ID NO: 52).

FIG. 39 is a representation of the nucleotide sequence of Vero-adapted RV3 VP2 gene (SEQ ID NO: 53).

FIG. 40 is a representation of the amino acid sequence of Vero-adapted RV3 VP2 protein (SEQ ID NO: 54).

FIGS. 41A-41C are a representation of a comparison of MA104-adapted RV3 (SEQ ID NO: 51) and Vero-adapted RV3 (SEQ ID NO: 53) VP2 genes.

FIG. 42 is a representation of a comparison of MA104-adapted RV3 (SEQ ID NO: 52) and Vero-adapted RV3 (SEQ ID NO: 54) VP2 proteins.

FIG. 43 is a representation of the nucleotide sequence of MA104-adapted RV3 VP3 gene (SEQ ID NO: 55).

FIG. 44 is a representation of the deduced amino acid sequence MA104-adapted RV3 VP3 protein (SEQ ID NO: 56).

FIG. 45 is a representation of the nucleotide sequence of Vero-adapted RV3 VP3 gene (SEQ ID NO: 57).

FIG. 46 is a representation of the deduced amino acid sequence of Vero-adapted RV3 VP3 protein (SEQ ID NO: 58).

FIGS. 47A-47C are a representation of a comparison of the nucleotide sequence of MA104-adapted RV3 (SEQ ID NO: 55) and Vero-adapted RV3 (SEQ ID NO: 57) VP3 genes.

FIG. 48 is a representation of a comparison of the deduced amino acid sequence of MA104-adapted RV3 (SEQ ID NO: 56) and Vero-adapted RV3 (SEQ ID NO: 58) VP3 proteins.

FIG. 49 is a representation of the nucleotide sequence of MA104-adapted RV3 VP4 gene (SEQ ID NO: 59).

FIG. 50 is a representation of the amino acid sequence of MA104-adapted RV3 VP4 protein (SEQ ID NO: 60).

FIG. 51 is a representation of the nucleotide sequence of Vero-adapted RV3 VP4 gene (SEQ ID NO: 61).

FIG. 52 is a representation of the amino acid of Vero-adapted RV3 VP4 protein (SEQ ID NO: 62).

FIGS. 53A-53C are a representation of a comparison of MA104-adapted RV3 (SEQ ID NO: 59) and Vero-adapted RV3 (SEQ ID NO: 61) VP4 genes.

FIG. 54 is a representation of a comparison of MA104-adapted RV3 (SEQ ID NO: 60) and Vero-adapted RV3 (SEQ ID NO: 62) VP4 proteins.

FIG. 55 is a representation of the nucleotide sequence of MA104-adapted RV3 VP6 gene (SEQ ID NO: 39).

FIG. 56 is a representation of the amino acid sequence of MA104-adapted RV3 VP6 protein (SEQ ID NO: 40).

FIG. 57 is a representation of the nucleotide sequence of Vero-adapted RV3 VP6 gene (SEQ ID NO: 41).

FIG. 58 is a representation of the amino acid sequence of Vero-adapted RV3 VP6 protein (SEQ ID NO: 42).

FIGS. 59A and 59B are a representation of a comparison of MA104-adapted RV3 (SEQ ID NO: 39) and Vero-adapted RV3 (SEQ ID NO: 41) VP6 genes.

FIG. 60 is a representation of a comparison of MA104-adapted RV3 (SEQ ID NO: 40) and Vero-adapted RV3 (SEQ ID NO: 42) VP6 proteins.

FIG. 61 is a representation of the nucleotide sequence of MA104-adapted RV3 VP7 gene (SEQ ID NO: 63).

FIG. 62 is a representation of the amino acid sequence of MA104-adapted RV3 VP7 protein (SEQ ID NO: 64).

FIG. 63 is a representation of the nucleotide sequence of Vero-adapted RV3 VP7 gene (SEQ ID NO: 65).

FIG. 64 is a representation of the amino acid sequence of Vero-adapted RV3 VP7 protein (SEQ ID NO: 66).

FIG. 65 is a representation of a comparison of MA104-adapted RV3 (SEQ ID NO: 63) and Vero-adapted RV3 (SEQ ID NO: 65) VP7 genes.

FIG. 66 is a representation of a comparison of MA104-adapted RV3 (SEQ ID NO: 64) and Vero-adapted RV3 (SEQ ID NO: 66) VP7 proteins.

DETAILED DESCRIPTION

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

It must be noted that, as used in the subject specification, the singular forms "a", "an" and "the" include plural aspects unless the context clearly dictates otherwise. Thus, for example, reference to "a rotavirus" includes a single rotavirus, as well as two or more rotaviruses; reference to "an agent" includes a single agent, as well as two or more agents; reference to "the disclosure" includes a single reference to "the disclosure" includes a single and multiple aspects taught by the disclosure; and so forth. Aspects taught and enabled herein are encompassed by the term "invention". All such aspects are enabled within the width of the present invention.

A method is contemplated for culturing a strain of RV, the method comprising subjecting an aliquot or inoculum of RV to trypsinization using a higher concentration of trypsin relative to other RV activation protocols, then culturing the trypsinized RV in Vero cells or a Vero cell-derived cell line for a time and under conditions sufficient for the RV to undergo a genetic modification resulting in an amino acid change in at least one of VP1, VP3, VP4, NSP4 and/or NSP5/6 and/or a nucleotide change in at least one of VP1, VP3, VP4, NSP2, NSP4 and/or NSP5/6.

Reference to "change" includes an amino acid or nucleotide substitution, deletion, addition or insertion. Reference to "trypsinization" means treatment of the RV with a trypsin. The trypsin may be from any source and includes porcine trypsin, a ruminant animal trypsin and a recombinant trypsin. A ruminant animal trypsin may be from cattle (i.e. bovine animal), sheep (ovine), goat (caprine), giraffe, yak, camel (camelus), llama, antelope or a macropod. In an embodiment, the trypsin is porcine, bovine, ovine, caprine, camelus or recombinant trypsin. In an embodiment, the trypsin is porcine trypsin. In an embodiment, the trypsin is bovine trypsin. In an embodiment, the trypsin is porcine, bovine or recombinant trypsin. In an embodiment, the trypsin is a recombinant trypsin. A "recombinant trypsin" is a trypsin of any origin generated by expression of engineered genetic material in any cell type (e.g. a bacterial, insect, yeast or mammalian cell).

The RV strain is, in an embodiment, RV3. RVs produced are conveniently referred to as "Vero cell-adapted RV" or "Vero-adapted RV" or "Vero-RV" or "RV-Vero" or RV3BB. In a further aspect, the modified Vero-RVs are harvested, such as for use in a vaccine or for the generation of antibodies.

Hence, a method is contemplated for culturing a strain of RV3, the method comprising subjecting an aliquot or inoculum of RV3 to trypsinization using a higher concentration of trypsin relative to other RV3 activation protocols, then culturing the trypsinized RV in Vero cells or a Vero cell-derived cell line for a time and wider conditions sufficient for the RV to undergo a genetic modification resulting in an amino acid change in VP1, VP3, VP4, NSP4 and/or NSP5/6 and/or a nucleotide change in VP1, VP3, VP4, NSP2, NSP4 and/or NSP5/6 and then optionally harvesting the modified RV3.

Enabled herein is a method is contemplated for culturing a strain of RV3, the method comprising subjecting an aliquot or inoculum of RV3 to trypsinization using a higher concentration of porcine, ruminant animal or recombinant trypsin relative to other RV3 activation protocols, then culturing the trypsinized RV in Vero cells or a Vero cell-derived cell line for a time and under conditions sufficient for the RV to undergo a genetic modification resulting in an amino acid change in VP1, VP3, VP4, NSP4 and/or NSP5/6 and/or a nucleotide change in VP1, VP3, VP4, NSP2, NSP4 and/or NSP5/6 and then optionally harvesting the modified RV3.

Enabled herein is a method is contemplated for culturing a strain of RV3, the method comprising subjecting an aliquot or inoculum of RV3 to trypsinization using a higher concentration of porcine, bovine or recombinant trypsin relative to other RV3 activation protocols, then culturing the trypsinized RV in Vero cells or a Vero cell-derived cell line for a time and under conditions sufficient for the RV to undergo a genetic modification resulting in an amino acid change in VP1, VP3, VP4, NSP4 and/or NSP5/6 and/or a nucleotide change in VP1, VP3, VP4, NSP2, NSP4 and/or NSP5/6 and then optionally harvesting the modified RV3

In an embodiment, the RV is an R electropherotype such as RV1, RV2 or RV3. More particularly, the strain is RV3. In another embodiment, the RV is an M-electropherotype such as RV5 or a PA-electropherotype such as RV6 (see Rodger et al. (1981) *J. Clin. Microbiol* 13:272-278; Albert et al. (1983) *J. Clin. Microbiol* 17:162-164).

A method is therefore described herein for culturing a strain of RV in particular RV3BB to a high titer in Vero cells, the method comprising subjecting an aliquot or inoculum of RV to trypsinization using a higher concentration of trypsin relative to other RV activation protocols and then culturing the trypsinized RV in Vero cells or a Vero cell-derived cell line for a time and under conditions sufficient for the RV to undergo a genetic modification resulting in an amino acid change in VP1, VP3, VP4, NSP4 and/or NSP5/6 and/or a nucleotide change in VP1, VP3, VP4, NSP2, NSP4 and/or NSP5/6 and then optionally harvesting the modified RV.

The culturing protocol described herein enables the generation of live attenuated RV or a preparation of RV which can be killed or otherwise inactivated for use as a vaccine or to develop antibodies thereto or other diagnostic agents.

Hence, a method is provided for producing a live attenuated RV, the method comprising subjecting an aliquot or inoculum of an attenuated strain of RV to trypsinization using a higher concentration of trypsin relative to other RV activation protocols and then culturing the trypsinized RV in Vero cells or a Vero cell-derived cell line for a time an under conditions sufficient for the RV to undergo a genetic modification resulting in an amino acid change in VP1, VP3, VP4, NSP4 and/or NSP5/6 and/or a nucleotide change in VP1, VP3, VP4, NSP2, NSP4 and/or NSP5/6.

In an alternative embodiment, as indicated above RVs are cultured and harvested and then killed, hence, generating a killed RV preparation for use in a killed RV vaccine.

Reference to a "genetic modification" includes single or multiple nucleotide substitutions, additions, deletions and/or insertions. In a particular embodiment, the genetic modification leads to an amino acid alteration (i.e. a substitution, addition, deletion or insertion) in an encoded protein such NSP4, NSP5 or VP7. In another embodiment, the modification leads to a nucleotide substitution, addition, deletion and/or insertion to a gene encoding VP1, VP3, VP4, NSP2, NSP4 and/or NSP5/6. In another embodiment, the modification leads to an amino acid change in one or more of VP1, VP3, VP4, NSP4 and/or NSP5/6.

The genetic modification to the RV is conveniently compared to an RV cultured in MA104 cells (i.e. an MA104-adapted RV). This RV cultured in MA104 cells is not suitable for vaccine production as MA104 cells have not been fully qualified and their potential tumorgenecity profile is undetermined at this time.

A method is contemplated for culturing a strain of RV, the method comprising subjecting an aliquot or inoculum of RV to trypsinization using a higher concentration of trypsin relative to other RV activation protocols and then culturing the trypsinized RV in Vero cells or a Vero cell-derived cell line for a time and under conditions sufficient for the RV to undergo an amino acid medication in one or more of VP1, VP3, VP4, NSP4 and/or NSP5/6 and/or a nucleotide change in VP1, VP3, VP4, NSP2, NSP4 and/or NSP5/6.

A method is also described herein for culturing a strain of RV selected from the list consisting of RV1, RV2, RV3, RV5 and RV6, the method comprising subjecting an aliquot or inoculum of RV to trypsinization using a higher concentration of trypsin relative to other RV activation protocols and then culturing the trypsinized RV in Vero cells or a Vero cell-derived cell line for a time and under conditions sufficient for the RV to undergo an amino acid modification in one or more of VP1, VP3, VP4, NSP4 and/or NSP5/6 and/or a nucleotide change in VP1, VP3, VP4, NSP2, NSP4 and/or NSP5/6 in RV3 or its equivalent in RV1, RV2, RV5 or RV6 and then optionally harvesting the modified RV.

In relation to an embodiment, a method is contemplated for culturing a strain of RV3, the method comprising subjecting an aliquot or inoculum of RV3 to trypsinization using a higher concentration of trypsin relative to other RV activation protocols and then culturing the trypsinized RV3 in Vero cells or a Vero cell-derived cell line for a time and under conditions sufficient for the RV3 to undergo an amino acid change in VP1, VP3, VP4, NSP4 and/or NSP5/6 and/or a nucleotide change in VP1, VP3, VP4, NSP2, NSP4 and/or NSP5/6.

The harvested RVs are useful in the preparation of a live, attenuated RV composition including a vaccine composition. Alternatively, the harvested RVs are killed and used in a killed RV composition.

Hence, a method is provided for producing live attenuated RV, the method comprising subjecting an aliquot or inoculum of an attenuated strain of RV to trypsinization using a higher concentration of trypsin relative to other RV activation protocols and then culturing the trypsinized RV in Vero cells or a Vero cell-derived cell line for a time an under conditions sufficient for the RV to undergo an amino acid change in one or more of VP1, VP3, VP4, NSP4 and/or NSP5/6 and/or a nucleotide change in one or more of VP1, VP3, VP4, NSP2, NSP4 and/or NSP5/6.

In an embodiment, the RV is RV3, also referred to as RV3BB and the genetic modifications are those listed in Table 2 or Table 5. The present disclosure contemplates one or all mutations as listed in Table 2 or Table 5.

A method is therefore provided for culturing an RV in Vero cells, the method comprising subjecting the RV to trypsinization using a higher concentration of trypsin relative to other RV activation protocols and then culturing the trypsinized RV with Vero cells or a Vero cell-derived cell line for a time and under conditions sufficient for a genetic modification to occur at a site selected from the list a mutation listed in Table 2 or Table 5.

Reference to "equivalent" includes the corresponding nucleotide or amino acid in another strain of RV3 or another RV.

An isolated Vero-adapted RV is also described comprising a genetic modification in a gene or protein selected from the list consisting of VP1, VP3, VP4, NSP2, NSP4 and/or NSP5/6, the mutation selected from those in Table 2 or Table 5.

A method is contemplated herein for generating an attenuated RV3 in Vero cells, the method comprising trypsinizing an aliquot or inoculum of an attenuated RV3 and culturing the trypsinized RV3 with Vero cells or a Vero cell-derived cell line for a time and under conditions sufficient for a genetic modification to occur in a gene selected from the list set forth in Table 2 or Table 5 compared to MA104-adapted RV3.

The above-mentioned mutations are described using single amino acid codes as defined in Table 3.

TABLE 3

| Abbreviations | | |
|---|---|---|
| Amino Acid | Three-letter Abbreviation | One-letter Symbol |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalamine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present disclosure is instructional for a method for generating an attenuated RV3 in Vero cells the method comprising trypsinizing an aliquot or inoculum of an attenuated RV3 and culturing the trypsinized RV3 with Vero cells or a Vero cell-derived cell line for a time and under conditions sufficient for a genetic modification to occur selected from the list comprising nucleotide substitutions, deletions and/or additions at a codon in NSP4 selected from 53, 76, 85, 162 and 165, a codon in NSP5/6 selected from 46 and 112, a codon in VP1 selected from 886, a codon in VP3 selected from 643 and 785, and a codon in VP4 selected from 43, 374, 385, 388, 442 and 756 and/or a nucleotide in NSP2 selected from 433, a nucleotide in NSP4 selected from 197, 267, 294, 525 and 534, a nucleotide in NSP5/6 selected from 158, 165 and 355, a nucleotide in VP1 selected from 2692, a nucleotide in VP3 selected from 343, 1366, 1744, 1976 and 2402 and/or a nucleotide in VP4 selected from 136, 369, 1130, 1162, 1171, 1334 and 2276.

The production of a Vero-adapted RV and in particular a Vero-adapted RV3 enables its use as an attenuated live RV vaccine. Alternatively, the RV produced in Vero cells can be killed and used as a killed RV vaccine.

Taught herein, therefore, is an attenuated live or killed RV composition comprising an RV having one more mutations in VP1, VP3, VP4, NSP2, NSP4 and/or NSP5/6, the composition further comprising one or more pharmaceutically acceptable carriers, diluents and/or excipients.

In an embodiment, a composition is enabled comprising an attenuated or killed Vero-adapted RV having a genetic modification selected from one or more of a mutation in a codon in NSP4 selected from 53, 76, 85, 162 and 165, a codon in NSP5/6 selected from 46 and 112, a codon in VP1 selected from 886, a codon in VP3 selected from 643 and 785, and a codon in VP4 selected from 43, 374, 385, 388, 442 and 756 and/or a nucleotide in NSP2 selected from 433, a nucleotide in NSP4 selected from 197, 267, 294, 525 and 534, a nucleotide in NSP5/6 selected from 158, 165 and 355, a nucleotide in VP1 selected from 2692, a nucleotide in VP3 selected from 343, 1366, 1744, 1976 and 2402 and/or a nucleotide in VP4 selected from 136, 369, 1130, 1162, 1171, 1334 and 2276, compared to MA104-adapted RV3, the composition further comprising one or more pharmaceutically acceptable carriers, diluents and/or excipients.

A composition is provided comprising a live attenuated or killed RV3 comprising one or more mutations selected from the list in Table 2 or Table 5 compared to MA104-adapted RV3.

In an embodiment, the RV comprises one or more mutations listed in Table 2 or Table 5 including 1 to 38 mutations such as 1, 2, 3, 4, 5, 6, 7, 8, 9, 10, 11, 12, 13, 14, 15, 16, 17, 18, 19, 20, 21, 21, 23, 24, 25, 26, 27, 28, 29, 30, 31, 32, 33, 34, 35, 36, 37 or 38 mutation.

Preparation of the composition is conveniently undertaken to World Health Organization (WHO) standards. Generally, the composition is given orally before three months of age and as soon as practicable after birth. The composition may also be referred to as a vaccine, formulation, medicament and other like terms.

The desired immunological or physiological effect of the vaccine is the inhibition of RV infection, a prevention of re-infection by RV, clarification of RV from a target subject, or otherwise an amelioration of the symptoms of RV infection such as acute diarrhea and/or fluid loss (including dehydration). Specifically, the effect includes the generation of an immune response and in particular a humoral immune response against RV or an RV component such as a protein, carbohydrate or lipid.

The vaccine may also comprise two or more different strains of RV or two or more antigenic or immunogenic components thereof. A "combination" also includes multipart compositions such as a two-part composition where the viral agents are provided separately and given or dispensed separately or admixed together prior to dispenzation. For example, a multi-part pharmaceutical pack may have two or more live attenuated or killed RV agents or components thereof separately maintained.

The viral agents described herein may be maintained in a state referred to as a vaccine, formulation, medicament or composition or they may be in a dried, freeze dried, frozen or dehydrated form and what are reconstituted in a formulation prior to use. The term "vaccine" is not to regarded as limiting the formulation to agents which induce an immune response since the formulation may comprise RV-specific antibodies.

A method is enabled herein for vaccinating a human subject against RV infection, the method comprising administering to the subject an effective amount of a live, attenuated Vero-adapted RV3 or a killed Vero-adapted RV3 for a time and under conditions sufficient to generate an immune response against RV infection.

In particular, the immune response is a protective immune response. The immune response may be useful prior to, during or subsequent to infection or re-infection by a non-attenuated (virulent) strain of RV.

A method for treating a human subject with an RV infection or at risk of developing an RV infection or re-infection is taught by the present disclosure, the method comprising administering to the subject an effective amount of a live, attenuated Vero-adapted RV3 or a killed Vero-adapted RV3 for a time and under conditions sufficient to generate an immune response against RV infection. Such a method includes treating a human subject with diarrhea, caused by RV.

An "effective amount" includes a "therapeutically effective amount".

The terms "effective amount" and "therapeutically effective amount" of a vaccine or agent therein as used herein mean a sufficient amount of the agent (e.g. live attenuated RV or killed RV) to provide the desired therapeutic or physiological effect or outcome which is reduction in RV infection or generation of RV-specific antibodies. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the age and general condition of the subject, mode of administration and the like. Thus, it may not be possible to specify an exact "effective amount". However, an appropriate "effective amount" in any individual case may be determined by one of ordinary skill in the art using only routine experimentation.

Hence, as used herein, an "effective amount" refers to an amount of viral agent or component thereof that provides the desired effect of reducing RV infection, ameliorating symptoms of RV infection and/or generating RV-specific antibodies when administered according to a suitable dosing regime. Dosing may occur at intervals of several minutes, hours, days, weeks or months. Suitable dosage amounts and regimes can be determined by the attending physician or other care provider. For example, the administration of a live, attenuated RV includes $10^5$ to $10^8$ ffu/ml such as $10^5$, $10^6$, $10^7$ and $10^8$ ffu/ml.

By "pharmaceutically acceptable" carrier, excipient or diluent is meant a pharmaceutical vehicle comprised of a material that is not biologically or otherwise undesirable, i.e. the material may be administered to a subject along with the selected viral agent or component thereof without causing any or a substantial adverse reaction. Carriers may include excipients and other additives such as diluents, detergents, coloring agents, wetting or emulsifying agents, pH buffering agents, preservatives and the like.

The terms "treating" and "treatment" as used herein refer to reduction in severity and/or frequency of symptoms of RV infection, elimination of symptoms of RV infection, prevention of the occurrence of symptoms of RV infection and improvement or remediation or amelioration of symptoms following RV infection. Symptoms include acute or chronic diarrhea, fluid loss and/or fever.

"Treating" a subject may involve prevention of RV infection as well as treatment of a clinically symptomatic individual by ameliorating the symptoms of the condition. Treatment of a symptomatic subject is also contemplated. The term "treating" also applies to prophylaxis and induction of immunological memory against RV. The human subject may directly be treated or a pregnant mother may be treated with the desired immune response being passed onto the unborn infant.

A "subject" as used herein generally refers to a human who can benefit from the pharmaceutical formulations and methods described herein. A subject, may be referred to inter alia as an individual, patient, host or recipient.

Human subjects may be of any age. Examples of particular susceptible humans include from 0 to 5 years and over 50 years old such as 51 to 60, 61 to 70, 71 to 80, 81 to 90 and over 91 years old. Children of from 6 to 10, 11 to 15 and 16 to 20 are also contemplated as are humans from 21 to 50.

Experimental vaccinations or antibody production may also be in laboratory test animals. Examples of laboratory test animals include mice, rats, rabbits, simian animals, guinea pigs, hamsters and primates such as orangutans, gorillas, marmosets and Rhesus monkeys. Rabbits, rodent and simian animals provide a particularly convenient test system or animal model.

Compositions enabled herein include those suitable for oral administration and may be presented as discrete units such as liquids, capsules, sachets or tablets each containing a predetermined amount of the RV and/or a component thereof; as a powder or granules; as a solution or a suspension in an aqueous phase or non-aqueous liquid; or as an oil-in-water liquid emulsion or a water-in-oil emulsion. The active ingredient may also be presented as a bolus, electuary or paste.

The compositions may also be referred to as an antigenic composition.

For an antigenic composition to be useful as a vaccine, the composition must induce an immune response to the virus or component thereof. As used herein, an "antigenic composition" may comprise an antigen (e.g. VP1, VP3, VP4, NSP2, NSP4 and/or NSP5/6), a nucleic acid encoding an antigen (e.g. an antigen expression vector), or a cell expressing or presenting an antigen or a live attenuated or killed virus. In another embodiment, the composition is in a mixture that comprises an RV and an additional immunostimulatory agent or nucleic acids encoding such an agent. Immunostimulatory agents include but are not limited to an additional antigen or viral strains, an immunomodulator, an antigen presenting cell or an adjuvant.

In an embodiment, the composition or immunologically functional equivalent, is used as an effective vaccine in inducing a humoral and/or cell-mediated immune response in a human subject against RVs. One or more antigenic compositions or vaccines for use in both active and passive immunization embodiment's are contemplated herein.

A vaccine may vary in its composition. Of course, it will be understood that various compositions described herein may further comprise multiple components. For example, a vaccine may comprise one or more adjuvants. A vaccine may be prepared and/or administered by any method as would be known to one of ordinary skill in the art, in light of the present disclosure.

It is contemplated that immunomodulators may be included in the vaccine to augment a cell's or a patient's response. Immunomodulators can be included as purified proteins, nucleic acids encoding immunomodulators and/or cells that express immunomodulators in the vaccine composition. Non-limiting examples of immunomodulators contemplated herein include interleukins (Ls), cytokines, nucleic acids encoding interleukins or cytokines, and/or cells expressing such compounds. Interleukins and cytokines, include but are not limited to iIL-1, IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH-1, METH-2, tumor necrosis factor, TGFβ, LT and combinations thereof.

Chemokines, nucleic acids that encode for chemokines, and/or cells that express such also may be used as vaccine components. Chemokines generally act as chemoattractants to recruit immune effector cells to the site of chemokine expression. It may be advantageous to express a particular chemokine coding sequence in combination with, for example, a cytokine coding sequence; to enhance the recruitment of other immune system components to the site of treatment. Such chemokines include, for example, RANTES, MCAF, MIP1-alpha, MIP1-β, IP-10 and combinations thereof. The skilled artisan will recognize that certain cytokines are also known to have chemoattractant effects and could also be classified under the term chemokines.

It may be desirable to co-administer biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/m2) (Johnson/Mead, NJ), or a gene encoding a protein involved in one or more immune helper functions, such as B-7.

Immunization protocols are contemplated herein including those which use adjuvants to stimulate responses. Some adjuvants affect the way in which antigens are presented.

In certain embodiments, an adjuvant effect is achieved by use of an agent such as alum used in about 0.05 to about 0.1% w/v solution in phosphate buffered saline. Alternatively, the antigen is made as an admixture with synthetic polymers of sugars (Carbopol [Registered Trade Mark]) used as an about 0.25% w/v solution.

Some adjuvants, for example, are certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Various polysaccharide adjuvants may also be used. For example, pneumococcal polysaccharide adjuvants may be used. The doses that produce optimal responses, or that otherwise do not produce suppression, should be employed as indicated. Polyamine varieties of polysaccharides are particularly preferred, such as chitin and chitosan, including deacetylated chitin.

Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

Another adjuvant contemplated for use in the present disclosure is BCG. BCG (*bacillus* Calmette-Guerin, an attenuated strain of *Mycobacterium*) and BCG-cell wall skeleton (CWS) may also be used as adjuvants in the disclosure, with or without trehalose dimycolate. Trehalose dimycolate may be used itself. Trehalose dimycolate administration has been shown to correlate with augmented resistance to influenza virus infection in mice. Trehalose dimycolate may be prepared as described in U.S. Pat. No. 4,579,945.

BCG is an important clinical tool because of its immunostimulatory properties. BCG acts to stimulate the reticulo-endothelial system, activates natural killer cells and increases proliferation of hematopoietic stem cells. Cell wall extracts of BCG have proven to have excellent immune adjuvant activity. Molecular genetic tools and methods for mycobacteria have provided the means to introduce foreign genes into BCG.

Another aspect is directed to the use of a Vero-RV such as Vero-RV3 or a component thereof in the manufacture of a medicament in the treatment of RV infection/re-infection in a subject.

Antibodies to the Vero-adapted RV agents are also contemplated herein.

By "antibody" is meant a protein of the immunoglobulin family that is capable of combining, interacting or otherwise associating with an antigen (i.e. an RV agent or component thereof). An antibody is, therefore, an antigen-binding molecule. An "antibody" is an example of an immunointeractive molecule and includes a polyclonal or monoclonal antibody. Particular immunointeractive molecules are monoclonal antibodies for use in diagnostics or purification procedure or polyclonal antibodies when induced in a human subject. The term "antibody" also includes engineered antibodies such as bi-specific antibodies to two different RV antigens such as VP1, VP3, VP4, NSP2, NSP4 and/or NSP5/6.

The term "antigen" is used herein in its broadest sense to refer to a substance that is capable of reacting in and/or inducing an immune response. Reference to an "antigen" includes a whole virus or component thereof.

Immunization and subsequent production of monoclonal antibodies can be carried out using standard protocols as for example described by Köhler and Milstein (Kohler et al. (1975) *Nature* 256:495-499 and Kohler et al. (1976) *Eur. J. Immunol.* 6(7):511-519; Coligan et al (1991-1997) *Current Protocols in Immunology* or Toyama et al. (1987) *Monoclonal Antibody, Experiment Manual*, published by Kodansha Scientific). Essentially, an animal is immunized with Vero-adopted RV or an immunogenic fragment thereof by standard methods to produce antibody-producing cells, particularly antibody-producing somatic cells (e.g. B lymphocytes). These cells can then be removed from the immunized animal for immortalization. The antigen may need to first be associated with a carrier.

By "carrier" is meant any substance of typically high molecular weight to which a non- or poorly immunogenic substance (e.g. a hapten) is naturally or artificially linked to enhance its immunogenicity.

Immortalization of antibody-producing cells may be carried out using methods, which are well-known in the art. For example, the immortalization may be achieved by the transformation method using Epstein-Barr virus (EBV) [Kozbor et al. (1986) *Methods in Enzymology* 121:140]. In an embodiment, antibody-producing cells are immortalized using the cell fusion method (described in Coligan et al.

(1991-1997) supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In the exemplary embodiment, mice spleen cells are used. It would be possible, however, to use rat, rabbit, sheep or goat cells, or cells from other animal species instead.

Specialized myeloma cell lines have been developed from lymphocytic tumors for use in hybridoma-producing fusion procedures (Kohler et al. (1976) supra; Kozbor et al. (1986) supra; and Volk et al. (1982) *J. Virol.* 42(1):220-227). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumor cells to produce their own antibodies. To eliminate the production of tumor cell antibodies by the hybridomas, myeloma cell, lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4-1 (NS-1), Sp2/0-Ag14 and S194/5.XXO.Bu.1. The P3X63-Ag8 and NS-1 cell lines have been described by Köhler and Milstein (Kohler et al. (1976) supra). Shulman et al. (1978) *Nature* 276:269-270, developed the Sp2/0-Ag14 myeloma line. The S194/5.XXO.Bu.1 line was reported by Trowbridge (1982) *J. Exp. Med.* 148(1):220-227.

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Kohler et al. (1975) supra; Kohler et al. (1976) supra; Gefter et al. (1977) *Somatic Cell Genet.* 3:231-236; and Volk et al. (1982) supra). The fusion-promoting agents used by those investigators were Sendai virus and polyethylene glycol (PEG).

Because fusion procedures produce viable hybrids at very low frequency (e.g. when spleens are used as a source of somatic cells, only one hybrid is obtained for roughly every $1\times10^5$ spleen cells), it is useful to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The-somatic cells used in the fusion do not maintain long-term viability in vitro culture and hence do not pose a problem.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in U.S. Pat. No. 6,056,957.

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumors that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the virus or viral antigen of interest by any suitable immunodetection means. For example, cell lines can be aliquoted into a number of wells and incubated and the supernatant from each well is analyzed by enzyme-linked immunosorbant assay (ELISA), indirect fluorescent antibody technique, or the like. The cell line(s) producing a monoclonal antibody capable of recognizing the target antigen but which does not recognize non-target epitopes are identified and then directly cultured in vitro or injected into a histocompatible animal to form tumors and to produce, collect and purify the required antibodies.

Thus, polyclonal and monoclonal antibodies are provided which specifically interact with Vero-adapted RV such as Vero-adapted RV3 or components thereof, for use in diagnosis or prognosis or for use therapeutically to reducing RV infection, maintenance or assembly.

It is within the scope of this disclosure to include any second antibodies (monoclonal, polyclonal or fragments of antibodies or synthetic antibodies) directed to the first mentioned antibodies referred to above. Both the first and second antibodies may be used in detection assays or a first antibody may be used with a commercially available anti-immunoglobulin antibody. Hence, diagnostic and prognostic assays are provided herein to monitor RV infection, re-infection, history of infection, integrity of a vaccine and to monitor therapeutic intervention.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect, therefore, provides a method for detecting Vero-adapted RV such as RV3-Vero or a component thereof in a biological sample from a subject, the method comprising contacting the biological sample with an antibody specific for the RV or component thereof or its derivatives or homologs for a time and under conditions sufficient for an antibody-polypeptide complex to form, and then detecting the complex.

A biological sample includes a stool sample.

Hence, the presence of Vero-adapted RVs or antibodies thereto can be detected in a number of ways such as by Western blotting, ELISA procedures and RIP. A wide range of immunoassay techniques are available as can be seen by reference to U.S. Pat. Nos. 4,016,043, 4,424,279 and 4,018,653.

Sandwich assays are among the most useful and commonly used assays and are favoured for use in the present disclosure. A number of variations of the sandwich assay technique exist, and all are intended to be encompassed by the present disclosure. Briefly, in a typical forward assay, an unlabeled antibody is immobilized on a solid substrate and the sample to be tested for RV or an RV antigen (the "antigen") brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labeled antibody are added simultaneously to the bound antibody. These techniques are well known to those skilled in the art, including any minor variations as will be readily apparent. In accordance with the present disclosure the sample is one which might contain Vero-adapted RV or antibodies thereto including by tissue biopsy, stool sample, blood, synovial fluid and/or lymph. The sample is, therefore, generally a biological sample comprising biological fluid.

In the typical forward sandwich assay, a first antibody having specificity for RV or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing an RV antigen and then exposing the immobilized target to serum or plasma. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. The fluorescent labeled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

Genetic assays such as involving PCR analysis to detect Vero-adapted RV such as Vero-RV3 may also be conducted and are encompassed herein. Such genetic assays are useful for detecting nucleotide changes as contemplated herein.

Kits such as kits in compartmental forms wherein the compartments comprise reagents including antibodies, PCR components, substrates from reporter molecules and/or solid supports comprising immobilized antibodies or antigens are also provided. A set of instructions may also be included.

EXAMPLES

Aspects taught by the present disclosure are further described by the following non-limiting Examples.

Example 1

Procedure for Cultivation of Rotavirus Vaccine in Vero Cells

The following describes the method of adapting the rotavirus (RV3) to Vero cells.

1-1 Materials.

1. Virus Production Serum Free Medium (VP-SFM) GIBCO #11681.
2. L-Glutamine (0.2M) ICN Biomedicals Inc. #16-801-49 use @ 9 ml/liter.
3. Penicillin/Streptomycin (100×) CSL use @100 IU/ml/
4. Trypsin 1× Sigma Chemicals #T-7418 (use at 50 μg/ml for activation and 5 μg/ml for maintenance medium).
5. RV3 rotavirus: the RV3 strain of rotavirus is a serotype G3P2A[6], subgroup II, long electropherotype which was isolated from a neonate with asymptomatic infection. Suitable RV3 strains include Hu/Australia/10-25-10/77/L (ATCC identification number VR2104, deposit date: 1 Feb. 1985) and Hu/Australia/1-9-12/77/S (ATCC identification number R2105, deposit date: 1 Feb. 1985).
6. Vero cells 1-2 Preparation of Initial Virus Inoculum.

The RV3 was subject to trypsinization prior to infection of Vero cells. Briefly, 200 μl per tube of RV3 vaccine stock is incubated with 20 μl of 0.5 mg/ml trypsin for 30 mins at 37° C., then place at 4° C. until cell culture preparation is complete. This is at a higher concentration than is normally used to activate RV for infection into cells. Standard trypsin activation utilize between 5-15 μg/ml of porcine trypsin to cleave the rotavirus VP4 protein, which allows virus to become activated and ultimately bind to cells, enter and undergo replication. In this process, >3 times the standard amount to activate RV3BB is used.

1-3 Preparation of Vero Cells and Inoculation of Roller Tubes with RV3.

Vero cells in a flask were washed twice with PBS and placed into suspension following trypsinization using standard cell culture protocols. The trypsinized Vero cells were resuspended in 50 ml of PBS and centrifuged at 1700 rpm for 10 mins. The supernatant was removed and the pelleted Vero cells were washed and re-centrifuged as above in PBS. Cell count was performed and Vero cells were diluted in VP-SFM-T. (ie. VP-SFM+5 ug/ml Trypsin) to $7\times10^5$ cells/ml. A total of approximately $2\times10^6$ cells (2.5 mls of cell suspension) was placed into each sterile roller tissue culture tubes with either 200 ul of the trypsinized virus suspension, or as a control, "mock-infected" with media and trypsin (VP-SFM-T). Virus and cells, are incubated at 37° C./5% v/v $CO_2$/95% v/v air on a roller apparatus. After 24 hours, a further aliquot of trypsinized and washed Vero cells was added ($2\times10^6$ cells in 100 ul total volume VP-SFM). Infection was allowed to proceed and virus was harvested at 40 hours post-infection. To harvest RV3 virus, cells were lysed by two rounds of freezing (−70° C.) and thawing. The virus was centrifuged at a low speed to removed cellular debris and the clarified virus suspension was stored at −70° C.

Virus can be titrated to determine the number of infectious foci using standard procedures in MA104 cells.

Example 2

RNA Extraction and Method for RT-PCR Amplification and Sequencing

RNA Extraction.

Viral RNA was extracted from Vero-adapted RV-3 strain using the QIAamp Viral RNA minikit (QIAGEN, Westburg, Leusden, The Netherlands) according to the manufacturer's protocol.

RT-PCR.

Reverse transcriptase PCR (RT-PCR) was carried out using the Invitrogen one-step RT-PCR kit (Invitrogen, Carlsbad, Calif., USA). Primers used for the amplification of rotavirus genes are listed in Table 1. The RT-PCR was carried out with an initial reverse transcription step of 30 min at 45° C., followed by PCR activation at 95° C. for 15 min. Amplification consisted of 40 cycles at 45 sec at 94° C., 45 sec at 45° C. and 75 sec at 70° C. for VP6, VP7, NSP1-5 and 45 sec at 94° C., 45 sec at 45° C. and 3 min at 70° C. for VP1-4. The final extension was Performed at 7 min at 70° C. The amplicon was separated by electrophoresis and the appropriate DNA gel excised and purified using the QIAquick gel extraction kit (QIAGEN) according to the manufacturer's specification with the following modifications. Step 5, the addition of isopropanol to the emulsified gel DNA mixture was omitted and Step 9 the additional wash step to remove traces of agarose, labelled as optional by the manufacturer was included.

Sequencing.

Sequencing was carried out using Big Dye version 3.1 (ABI) according to the manufactures methods. The primers listed in Table 4 were used also for sequencing. Additional internal primers were used if required.

TABLE 4

Primers used for the amplification and sequencing of RV-3 viral genome

| Gene | Primer name | Primer sequence (5' to 3') | SEQ ID |
|---|---|---|---|
| VP1 | JCVI_VP1_5' UTR | TGTAAAACGACGGCCAGTGGCTATTAAAGCTGTAC | SEQ ID NO: 1 |
| | GEN-VP1R | GGTCACATCCTAAGCCGYTC | SEQ ID NO: 2 |
| VP2 | GEN-VP2F | GGCTATTRAAGGYTCAATGG | SEQ ID NO: 3 |
| | GEN-VP2R | GGTCATATCTCCACARTGG | SEQ ID NO: 4 |
| VP3 | GEN-VP3F | GGCTWTTAAAGCAGTACCA | SEQ ID NO: 5 |
| | GEN-VP3R | GGYCACATCATGACTAGTG | SEQ ID NO: 6 |
| VP4 | JP_1_For_g4_RV3 | GGCTATAAAATGGCTTCACTC | SEQ ID NO: 7 |
| | JCV1_VP4_3' UTR | CAGGAAACAGCTATGACCGGTCACATYCCTCRATR | SEQ ID NO: 8 |
| VP6 | GEN-VP6F | GGCTTTWAAACGAAGAAGTCTT | SEQ ID NO: 9 |
| | GEN-VP6R | GGT CAC ATC CTC TCA CT | SEQ ID NO: 10 |
| VP7 | Beg9 | GGCTTTAAAAGAGAGAATTTCCGTCTGG | SEQ ID NO: 11 |
| | End9 | GGTCACATCATACAATTCTAATCTAAG | SEQ ID NO: 12 |
| NSPI | JCVI_NSP1_5'UTR | TGTAAAACGACGGCCAGTTATGAAAAGTCTTGTGGAAGC | SEQ ID NO: 13 |
| | JCVI_NSP1_3'UTR | CAGGAAACAGCTATGACCCATTTTATGCTGCCTAGGCG | SEQ ID NO: 14 |

TABLE 4-continued

| Primers used for the amplification and sequencing of RV-3 viral genome | | | |
|---|---|---|---|
| Gene | Primer name | Primer sequence (5' to 3') | SEQ ID |
| NSP2 | GEN-NSP2F | GGCTTTTAAAGCGTCTCAG | SEQ ID NO: 15 |
| | GEN-NSP2R | GGTCACATAAGCGCTTTC | SEQ ID NO: 16 |
| NSP3 | GEN-NSP3F | GGCTTTTAATGCTTTTCAG TG | SEQ ID NO: 17 |
| | GEN-NSP3R | ACATAACGCCCCTATAGC | SEQ ID NO: 18 |
| NSP4 | 10.1 | GGCTTTTAAAAGTTCTGTCC | SEQ ID NO: 19 |
| | 10.2 | GGTCACACTAAGACCATTCC | SEQ ID NO: 20 |
| NSP5 | GEN-NSP5F | GGCTTTTAAAGCGCTACAG | SEQ ID NO: 21 |
| | GEN-NSPSR | GGTCACAAAACGGGAGT | SEQ ID NO: 22 |

Example 3

Identification of Nucleotide and Amino Acid Changes in RV3-Vero Compared to MA104 Adapted RV3

Unique nucleotide changes were identified in the RV3-Vero in comparison to the RV3 derived in MA104 cells (FIGS. 1 to 42 and Tables 2 and 5).

The unique nucleotide changes were located in a codon in NSP4 selected from 53, 76, 85, 162 and 165, a codon in NSP5/6 selected from 46 and 112, a codon in VP1 selected from 886, a codon in VP3 selected from 643 and 785, and a codon in VP4 selected from 43, 374, 385, 388, 442 and 756 and/or a nucleotide in NSP2 selected from 433, a nucleotide in NSP4 selected from 197, 267, 294, 525 and 534, a nucleotide in NSP5/6 selected from 158, 165 and 355, a nucleotide in VP1 selected from 2692, a nucleotide in VP3 selected from 343, 1366, 1744, 1976 and 2402 and/or a nucleotide in VP4 selected from 136, 369, 1130, 1162, 1171, 1334 and 2276. The specific nucleotide mutations in Vero-RV3 relative to MA104-RV3 are shown Tables 2 and 5.

TABLE 5

| Nucleotide and ammo acid differences between MA104-adapted RV3 and Vero-adapted RV3 | | | |
|---|---|---|---|
| Protein (bp-size) | nt region sequenced* | Nucleotide substitutions[1] | Amino acid substitutions |
| VP1 (3268 bp) | 37-3303 | Vaccine 2692 T to MA104 2656 G | Vaccine 886 F to MA104 886 V |
| VP2 (2717 bp) | 17-2686 | none | none |
| VP3 (2591 bp) | 50-2554 | Vaccine 343 C to MA104 294T<br>Vaccine 1366 G to MA104 1317 A<br>Vaccine 1744 C to MA104 1695 T<br>Vaccine 1976 A to MA104 1927 G<br>Vaccine 2402 C to MA104 2353 T | Vaccine 643 K to MA104 643 E<br>Vaccine 785 H to MA104 785 Y |
| VP4 (2359 bp) | 10-2334 | Vaccine 136 A to MA104 127C<br>Vaccine 369 G to MA104 360A<br>Vaccine 1130 C to MA104 1121T<br>Vaccine 1162 A to MA104 1153 G<br>Vaccine 1171 C to MA104 1162 A<br>Vaccine 1334 A to MA104 1325 G<br>Vaccine 2276 T to MA104 2267 A | Vaccine 43 T to MA104 43 P<br>Vaccine 374 S to MA104 374 L<br>Vaccine 385 N to MA104 385 D<br>Vaccine 388 L to MA104 388I<br>Vaccine 442 H to MA104 442 R<br>Vaccine 756I to MA104 756N |
| VP6 (1359 bp) | 27-1217 | none | none |
| VP7 ((1062 bp) | 49-1026 | none | none |
| NSP1 (1461 bp) | 47-1498 | none | none |
| NSP2 (1059 bp) | 47-997 | Vaccine 433 A to MA104 387 G | none |
| NPS3 (1070 bp) | 35-964 | none | none |
| NSP4 (750 bp) | 41-565 | Vaccine 197 A to MA104 157 G<br>Vaccine 267 C to MA104 227 T<br>Vaccine 294 A to MA104 254 G<br>Vaccine 525 G to MA104 485 T<br>Vaccine 534 T to MA104 494 C | Vaccine 53 T to MA104 53 A<br>Vaccine 76 T to MA104 761<br>Vaccine 85 Y to MA104 85 C<br>Vaccine 162 G to MA104 162 V<br>Vaccine 165 L to MA104 165P |
| NSP5/6 (664 bp) | 22-612 | Vaccine 158 A to MA104 137G<br>Vaccine 165 C to MA104 144 T<br>Vaccine 355 A to MA104 334 T | Vaccine 46 E to MA104 46 G<br>Vaccine 112 I to MA104 112 L |

[1]Nucleotide sequence for the coding region of each gene was compared to that of RV3 MA104-adpated virus published by Rippinger el al, 2010 supra.

Those skilled in the art will appreciate that aspects of the invention described herein are susceptible to variations and modifications other than those specifically described. It is to be understood that these aspects include all such variations and modifications. The disclosure teaches all of the steps, features, compositions and compounds referred to or indicated in this specification, individually or collectively, and any and all combinations of any two or more of the steps or features.

BIBLIOGRAPHY

Albert et al. (1983) *J. Clin. Microbiol* 17:162-164

Bern and Glass (1994) *Impact of diarrheal diseases worldwide In Kapikian AZ (ed) Viral Infections of the gastrointestinal tract*, 2nd edition, New York Marcel Dekker, Inc.:1-26

Coligan et al. (1991-1997) *Current Protocols in Immunology*

Gefter et al. (1977) *Somatic Cell Genet.* 3:231-236

Jiang et al. (2002) *Clin Infect Dis* 34:1351-1361

Kohler et al. (1975) *Nature* 256:495-499

Kohler et al (1976) *Eur. J. Immunol.* 6(7):511-519

Kozbor et al. 1986) *Methods in Enzymology* 121:140

Rippinger et al. (2010) *Virology* 405(1):1201-1213

Rodger et al. (1981) *J. Clin. Microbiol* 13:272-278

Sato et al. (1981) *Arch. Virol.* 69:155-160

Toyama et al. (1987) *Monoclonal Antibody, Experiment Manual*, published by Kodansha Scientific Trowbridge (1982) *J. Exp. Med.* 148(1):220-227

Volk et al. (1982) *J. Virol.* 42(1):220-227

The invention claimed is:

1. An isolated Vero-adapted rotavirus RV3 strain comprising at least one of a NSP2 nucleotide sequence comprising SEQ ID NO: 33, a NSP4 nucleotide sequence comprising SEQ ID NO: 37, a NSP5/6 nucleotide sequence comprising SEQ ID NO: 29, a VP1 nucleotide sequence comprising SEQ ID NO: 49, a VP3 nucleotide sequence comprising SEQ ID NO: 57, a VP4 nucleotide sequence comprising SEQ ID NO: 61, a NSP4 amino acid sequence comprising SEQ ID NO: 38, a NSP5 amino acid sequence comprising SEQ ID NO: 30, a VP1 amino acid sequence comprising SEQ ID NO: 50, a VP3 amino acid sequence comprising SEQ ID NO: 58, or a VP4 amino acid sequence comprising SEQ ID NO: 62.

2. The isolated Vero-adapted rotavirus RV3 strain of claim 1, comprising a NSP2 nucleotide sequence comprising SEQ ID NO: 33, a NSP4 nucleotide sequence comprising SEQ ID NO: 37, a NSP5/6 nucleotide sequence comprising SEQ ID NO: 29, a VP1 nucleotide sequence comprising SEQ ID NO: 49, a VP3 nucleotide sequence comprising SEQ ID NO: 57 and a VP4 nucleotide sequence comprising SEQ ID NO: 61; or comprising a NSP4 amino acid sequence comprising SEQ ID NO: 38, a NSP5 amino acid sequence comprising SEQ ID NO: 30, a VP1 amino acid sequence comprising SEQ ID NO: 50, a VP3 amino acid sequence comprising SEQ ID NO: 58 and a VP4 amino acid sequence comprising SEQ ID NO: 62.

3. An attenuated live or killed rotavirus (RV) composition comprising the isolated Vero-adapted rotavirus RV3 of claim 1 and one or more pharmaceutically acceptable carriers, diluents and/or excipients.

4. An attenuated live or killed rotavirus (RV) composition comprising the isolated Vero-adapted rotavirus RV3 of claim 2 and one or more pharmaceutically acceptable carriers, diluents and/or excipients.

* * * * *